(12) United States Patent
Rucker et al.

(10) Patent No.: US 12,049,502 B2
(45) Date of Patent: Jul. 30, 2024

(54) ANTIBODIES DIRECTED TO CLAUDIN 6, INCLUDING BISPECIFIC FORMATS THEREOF

(71) Applicant: Integral Molecular, Inc., Philadelphia, PA (US)

(72) Inventors: Joseph Rucker, Philadelphia, PA (US); Kyle Doolan, Philadelphia, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 0 days.

(21) Appl. No.: 18/523,196

(22) Filed: Nov. 29, 2023

(65) Prior Publication Data
US 2024/0174751 A1 May 30, 2024

Related U.S. Application Data

(60) Provisional application No. 63/591,924, filed on Oct. 20, 2023, provisional application No. 63/517,668, filed on Aug. 4, 2023, provisional application No. 63/506,533, filed on Jun. 6, 2023, provisional application No. 63/496,174, filed on Apr. 14, 2023, provisional application No. 63/385,535, filed on Nov. 30, 2022.

(51) Int. Cl.
*C07K 16/28* (2006.01)
*A61K 39/00* (2006.01)

(52) U.S. Cl.
CPC .......... *C07K 16/2809* (2013.01); *C07K 16/28* (2013.01); *A61K 39/00* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. |
| 4,699,880 A | 10/1987 | Goldstein |
| 4,816,567 A | 3/1989 | Cabilly et al. |
| 4,946,778 A | 8/1990 | Ladner et al. |
| 5,260,203 A | 11/1993 | Ladner et al. |
| 5,475,096 A | 12/1995 | Gold et al. |
| 5,831,012 A | 11/1998 | Nilsson et al. |
| 6,004,746 A | 12/1999 | Brent et al. |
| 6,005,079 A | 12/1999 | Casterman et al. |
| 6,794,144 B1 | 9/2004 | Saksela et al. |
| 6,818,418 B1 | 11/2004 | Lipovsek et al. |
| 6,994,982 B1 | 2/2006 | Watt et al. |
| 7,105,653 B2 | 9/2006 | Shanafelt et al. |
| 7,166,697 B1 | 1/2007 | Galanis et al. |
| 7,186,524 B2 | 3/2007 | Kolmar et al. |
| 7,250,297 B1 | 7/2007 | Beste et al. |
| 7,417,130 B2 | 8/2008 | Stumpp et al. |
| 7,763,258 B2 | 7/2010 | Doms et al. |
| 7,803,907 B2 | 9/2010 | Stemmer et al. |
| 7,838,629 B2 | 11/2010 | Fiedler et al. |
| 8,158,130 B2 | 4/2012 | Doms et al. |
| 8,377,691 B2 | 2/2013 | Doranz |
| 9,074,002 B2 | 7/2015 | Tonks et al. |
| 9,274,119 B2 | 3/2016 | Aburatani et al. |
| 9,428,567 B2 | 8/2016 | Garcia et al. |
| 9,580,486 B2 | 2/2017 | Gavin et al. |
| 9,616,106 B2 | 4/2017 | Basile |
| 10,053,511 B2 | 8/2018 | Santaguida et al. |
| 10,131,710 B2 | 11/2018 | Moore et al. |
| 10,336,818 B2 | 7/2019 | Chamberlain et al. |
| 10,604,568 B2 | 3/2020 | Sahin et al. |
| 10,968,276 B2 | 4/2021 | Moore et al. |
| 11,053,316 B2 | 7/2021 | Moore et al. |
| 11,248,046 B2* | 2/2022 | Chambers .......... A61K 47/6849 |
| 11,473,085 B2 | 10/2022 | Sahin et al. |
| 2004/0023334 A1 | 2/2004 | Prior |
| 2004/0132094 A1 | 7/2004 | Etzerodt et al. |
| 2004/0141980 A1 | 7/2004 | Ignijatovic et al. |
| 2004/0146938 A1 | 7/2004 | Nguyen et al. |
| 2004/0157209 A1 | 8/2004 | Yilmaz et al. |
| 2004/0209243 A1 | 10/2004 | Nixon et al. |
| 2005/0123563 A1 | 6/2005 | Doranz et al. |
| 2006/0269515 A1 | 11/2006 | Denis-Mize et al. |
| 2009/0215992 A1* | 8/2009 | Wu .................... C07K 16/2809 |
| | | | 530/391.1 |
| 2010/0119446 A1 | 5/2010 | Grabulovski et al. |
| 2010/0239633 A1 | 9/2010 | Stome et al. |

(Continued)

FOREIGN PATENT DOCUMENTS

| | | |
|---|---|---|
| CN | 103483449 A | 1/2014 |
| EA | 0171496 | 2/1986 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).
Kussie "A Single Engineered Amino Acid Substitution Changes Antibody Fine Specificity" J immunol 152(1):146-52 (Year: 1994).
Koenig "Mutational landscape of antibody variable domains reveals a switch modulating the interdomain conformational dynamics and antigen binding" PNAS E486-E495 (Year: 2017).
UniProtKB Accession No. A0A2V9M896_9BACT, Sialidase domain-containint protein, (2018).
Bird et al., "Single-Chain Antigen-Binding Proteins", Science, (1998) vol. 242, pp. 432-426.

(Continued)

*Primary Examiner* — Phuong Huynh
(74) *Attorney, Agent, or Firm* — Morgan, Lewis & Bockius LLP

(57) ABSTRACT

The disclosure is directed to an antibody specific for claudin 6 and CD3 and method of preparing and using the same. The present disclosure describes the isolation and characterization of antibodies, antibody fragments, and antibody variants specific for claudin 6 and CD3.

30 Claims, 64 Drawing Sheets

Specification includes a Sequence Listing.

(56) References Cited

U.S. PATENT DOCUMENTS

| | | |
|---|---|---|
| 2012/0195882 A1 | 8/2012 | Doms et al. |
| 2012/0301476 A1 | 11/2012 | Okano et al. |
| 2013/0183305 A1 | 7/2013 | Sahin et al. |
| 2014/0127219 A1 | 5/2014 | Sahin et al. |
| 2014/0286898 A1 | 9/2014 | Gavin et al. |
| 2017/0003712 A1 | 1/2017 | Funk et al. |
| 2017/0051029 A1 | 2/2017 | Greve |
| 2017/0355756 A1 | 12/2017 | Julien et al. |
| 2018/0044434 A1 | 2/2018 | Sato et al. |
| 2019/0083645 A1 | 3/2019 | Fong et al. |
| 2020/0199221 A1 | 6/2020 | Mitnacht-Kraus et al. |
| 2020/0026298 A1 | 8/2020 | Charpentier et al. |
| 2020/0291111 A1 | 9/2020 | Conklin et al. |
| 2022/0162299 A1 | 5/2022 | Conklin et al. |
| 2022/0395579 A1 | 12/2022 | Toda et al. |
| 2023/0220066 A1 | 7/2023 | Ishii et al. |

FOREIGN PATENT DOCUMENTS

| | | | |
|---|---|---|---|
| EP | 0125023 A1 | 11/1984 | |
| EP | 0173494 A2 | 3/1986 | |
| EP | 0184187 A2 | 6/1986 | |
| EP | 404097 A3 | 10/1991 | |
| WO | WO 1986/001533 | 3/1986 | |
| WO | WO 1987/002671 A1 | 5/1987 | |
| WO | WO 1988/01649 A1 | 3/1988 | |
| WO | WO 1993/011161 A1 | 6/1993 | |
| WO | WO 1994/004678 A1 | 3/1994 | |
| WO | WO 1994/025591 A1 | 11/1994 | |
| WO | WO 2008/068048 A2 | 6/2008 | |
| WO | WO 2009/025759 | 2/2009 | |
| WO | WO 2009/087978 A1 | 7/2009 | |
| WO | WO 2010/085495 A1 | 7/2010 | |
| WO | WO 2011/057788 A1 | 5/2011 | |
| WO | WO 2012/003956 A1 | 1/2012 | |
| WO | WO 2012/156018 A1 | 11/2012 | |
| WO | WO 2014/016737 | 1/2014 | |
| WO | WO-2014110601 A1 * | 7/2014 | ........... A61K 39/395 |
| WO | WO 2014/153111 A3 | 11/2014 | |
| WO | WO 2015/014376 A1 | 2/2015 | |
| WO | WO 2015/014870 A1 | 2/2015 | |
| WO | WO 2015/069794 A2 | 5/2015 | |
| WO | WO 2016/025385 A1 | 2/2016 | |
| WO | WO 2016/014428 A3 | 3/2016 | |
| WO | WO 2016/164937 A3 | 1/2017 | |
| WO | WO 2017/096163 A1 | 6/2017 | |
| WO | WO 2017/187186 A1 | 11/2017 | |
| WO | WO 2017/192567 A1 | 11/2017 | |
| WO | WO 2018/054484 A1 | 3/2018 | |
| WO | WO 2018/067198 | 4/2018 | |
| WO | WO 2019/048040 A1 | 3/2019 | |
| WO | WO 2019/048489 A1 | 3/2019 | |
| WO | WO 2019/056023 A2 | 3/2019 | |
| WO | WO 2020/075325 A1 | 4/2020 | |
| WO | WO 2020/168059 A1 | 8/2020 | |
| WO | WO 2020/191342 A1 | 9/2020 | |
| WO | WO 2021/006328 A1 | 1/2021 | |
| WO | WO 2022/096700 A1 | 3/2022 | |
| WO | WO 2022/192403 A1 | 9/2022 | |
| WO | WO 2023/053282 A1 | 4/2023 | |
| WO | WO 2023/054421 A1 | 4/2023 | |

OTHER PUBLICATIONS

Better et al., "*Escherichia coli* Secretion of an Active Chimeric Antibody Fragment", Science (1988) 240 (4855, 1041-1043.

Liu et al., "Production of a mouse-human chimeric monoclonal antibody to CD20 with potent Fc-dependent biologic activity", J. Immunolo. (1987) 139(10):3521-6.

Nishibori, et al., "Humanization of chicken monoclonal antibody using phage-display system", Molecular Immunology (2006) 43 pp. 634-642.

Tsurushita, et al., "Humanization of a chicken anti-IL-12 monoclonal antibody", Journal of Immunological Methods, 2004) 295, pp. 9-19.

Almagro, "Identification of differences in the specificity-determining residues of antibodies that recognize antigens of differencet size: implications for the rational design of antibody repertoires", J. Mol. Reconit. (2004); 17:132-143.

Sahagan, et al., "A genetically engineered murine/human chimeric antibody retains specificity for human tumor-associated antigen.", J. Immunol. (1986) 137:pp. 1066-1074.

Ward et al., "Binding activities of a repertoire of single immunoglobulin variable domains secreted from *Escherichia coli*", Nature (1989) vol. 341 pp. 544-546.

Kohler, et al., "Continuous cultures of fused cells secreting antibody of predefined specificity", Nature (1975) Vo. 256: pp. 495 497.

Neuberger, et al., "A hapten-specific chimaeric IgE antibody with human physiological effector function", Nature (1985) vol. 314 pp. 268-270.

Hodgson et al., "Making Monoclonais in Microbes", BioTechnology (1991) 9:421-425.

Boulianne, et al., "Production of functional chimaeric mouse/human antibody", Nature (1984) 312:643 646.

Kozbor, et al., "The production of monoclonal antibodies from human lymphocytes", Immunol. Today (1983) 4:72 79.

Cabilly, et al., "Generation of antibody activity from immunoglobutin polypeptide chaings produced in *Escherichia coli*", (1984) Proc. Natl. Acad. Sci USA 81:3273-3277.

Morrison, et al., "Chimeric human antibody molecules: Mouse antigen-binding domains wiht humane constant region domains", (1984) Proc. Natl. Acad. Sci. USA 81:6851-6855.

Liu, et al., "Chimeric mouse-human IgG1 antibody that can mediate lysis of cancer cells", Proc. Nationl. Acad. Sci. (1987) 84:3439-3433.

Sun, et al., "Chimeric antibody with human constant regions and mouse variable regions directed against carcinoma-associated antigen 7-1A", Proc. Natil. Acad. Sci. (1987) 84:214-218.

Queen, et al., "A humanized antibody that binds to the interleukin 2 receptor", Proc. Natil. Acad. Sci (1989), 86:10029-10032.

Riechmann, et al., "Reshaping human antibodies for therapy", Nature (1968) 332 (6162), vol. pp. 323-327.

Wu et al., "An analysis of the sequences of the variable regions of bence jones proteins and myeloma light chains and their implications for anti-body complementarily", Journal of Experimental Medicine (1970) 132: pp. 211-250.

Chothia, et al., "Canonical Structures for the Hypervariable Regions of Immunoglobutins", Mol. Biol. (1987) 196:901-917.

Lefrance et al., "IMGT unique numbering for immunoglobulin and T cell receptor variable domains and lg superfamily v-like domains" Developmental & Comparative Immunology (2003) 27:55-77.

Huston et al., "Protein engineering of antibody binding sites Recovery of specific activity in an anti-digoxin single-chain Fv analogue produced in *Escherichia coli*", Proc. Nat. Acad. Sci. (1988) 85:5879-5883.

Wahl et al., "Improved Radioimingin and Tumor Localization with Monoclonal F(ab')2.", J. Nucl. Med. (1983) 24:316 325.

Lathe et al., "Synthetic oligonucleotide probes deduced from amine acid sequence data. Theroetical and practical consideratiosn", J. Molec. Biol. (1985) 183:1-12.

Muller et al., "Determination of Affinity and Specificity of Anti-Haplen Antibodies by Competitive Radioimmunoassay", Meth. Enzymol. (1983) 92:589-601.

Baert, et al., "Influence of Immunogenicity on the Long-Term Efficacy of infliximab in Crohn's Disease ", New Engl. J. Med. (2003) 348:601-608.

Holliger at al., "Engineered Antibody Fragments and the Rise of Single Domains", Nat. Biotechnol. (2005) 23:1126-1135.

Holliger et al. "Diabodies", Small bivalent and bispecific antibody fragments, Proc Nall. Acad. Sci. USA (1993) 90:6444-5448.

Mitgrom et al., "Treatment of Allergic Asthma with Monoclonal Anti-IgE Antibody", (1999) New Engl. J. Med. 341:1966-1973.

Stamon et al. "Use of Chemotherapy Plus a Monoclonal Antibody Against HER2 for Metastatic Breast Cancer that Overexpresses HER2", New Engl. J. Med. (2001) 344:783-792.

Storz et al., "Intellectual property protection Strategies for future antibody inventions", MAbs. (2011) 3(3): 310-317.

(56) References Cited

OTHER PUBLICATIONS

Reichmann et al., "Single domain antibodies: comparison of camel VH and camelised human VH domains", J. Immunol Method (1999) 231:25.

* cited by examiner

FIG. 5

| Name | Format | CLDN6 | CD3 | Affinity Purification | Efficacy of Integral produced material | | Production, Purification and Polish | | | | | | Developability Panel 2 | | | | | | | |
|---|---|---|---|---|---|---|---|---|---|---|---|---|---|---|---|---|---|---|---|---|
| | | | | | EC50 (nM) - HEK-CLDN6 | EC50 (nM) - OV90 | Large-scale yield (mg) | % Monomer (protein A) | Polish Yield (mg) | % Monomer (post-SEC) | % Monomer (pre-FT) | % Monomer (Post 3F/T) | Mode Diameter DLS (nm) | Tm1 (°C) | Tm2 (°C) | Tagg 266 (°C) | Tagg 473 (°C) | # charge variants (cIEF) | pI of major peak | Mass Spec/PTM (only high % modifications) |
| IMC-16-3 | Fab-scFv (#16) | 1HEP | SP34-1 | Protein A | 0.015 | 0.28 | 240 | 93 | 180 | 100.0 | 100.0 | 99.5 | 9.62 | 67.5 | – | 65.0 | 65.5 | 9 | 9.2 | C-terminal lysine cleavage (HC), high % deamidation (1) and oxidation (1) sites |
| IMC-16-15 | Fab-scFv (#16) | 1HFJ | SP34-1 | Protein A | 0.065 | 0.88 | 184 | 96 | 116 | 99.5 | 100.0 | 99.4 | 9.62 | 67.5 | – | 65.2 | 65.8 | 10 | 9.2 | C-terminal lysine cleavage (HC), high % deamidation (2) and oxidation (1) sites |
| IMC-21-1 | bi-(Fab-scFv) (#21) | 1HEP | Nanobody | Protein A | 0.026 | 0.24 | 96 | 92 | 66 | 99.7 | 98.5 | 98.7 | 11.25 | 69.0 | – | 63.8 | 65.3 | 6 | 9.2 | high % deamidation (2) and oxidation (1) sites |
| IMC-2-7 | BiTE (#2) | 1HEP | SP34-1 | IMAC | 0.95 | 4.9 | 180 | 77 | 75 | 91.9 | 91.3 | 91.5 | 7.03 | 62.9 | – | 52.7 | 52.2 | 5 | 9.8 | No major modifications, low level glycosylation |

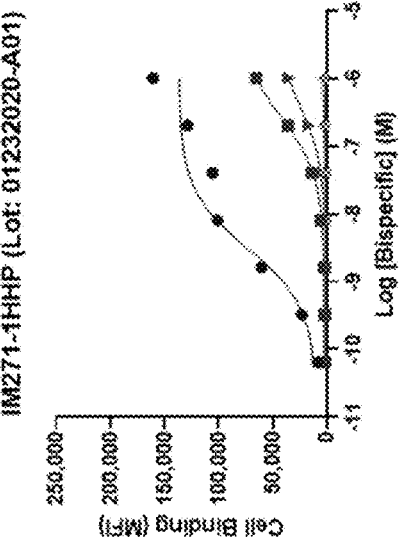
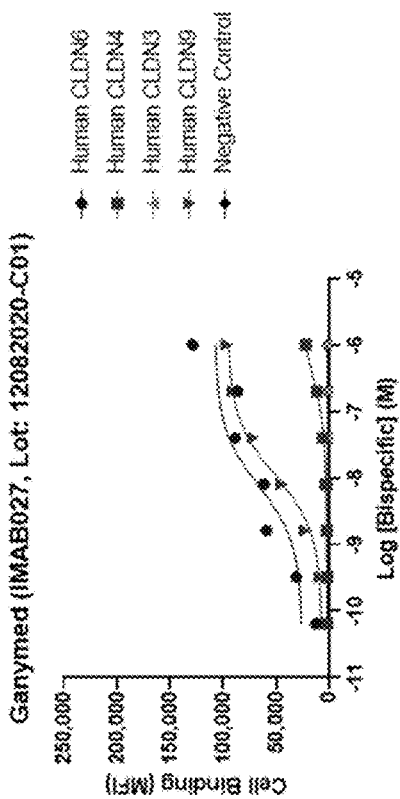
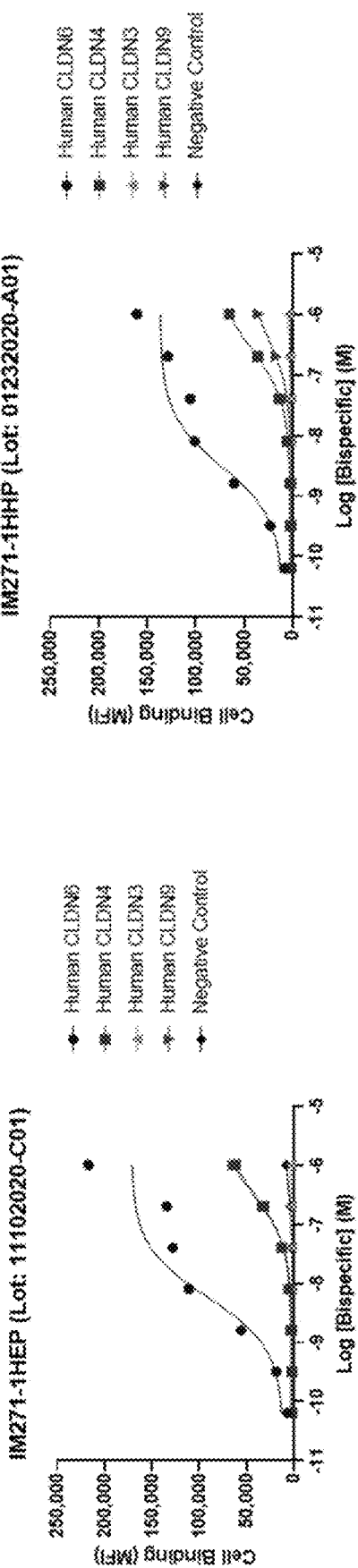
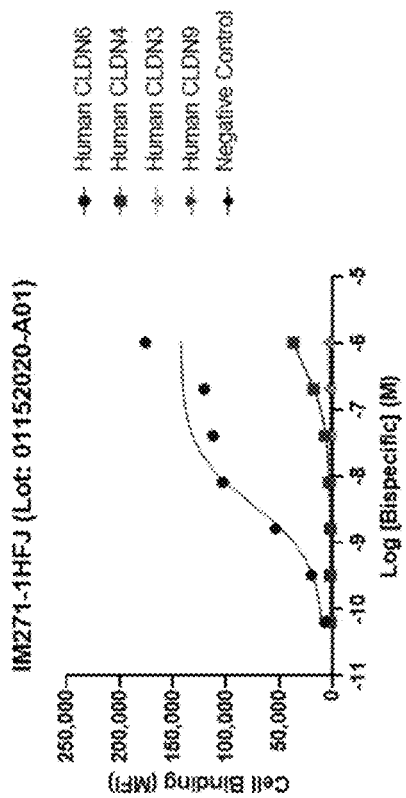

IMC-2-7 (Lot: TP44331F)

IMC-16-15 (Lot: TP44321F)

IMC-16-3 (Lot: TP44320F)

IMC-21-1 (Lot: TP44324F)

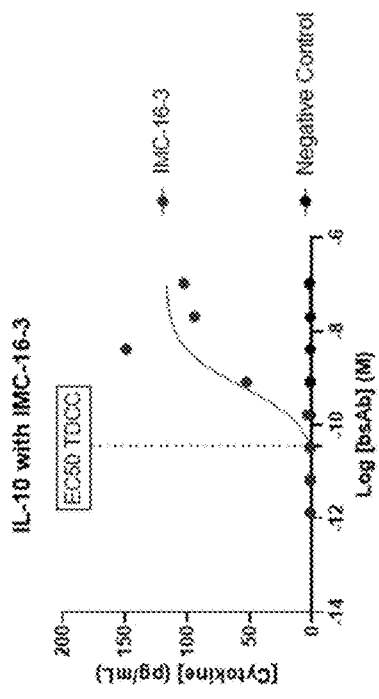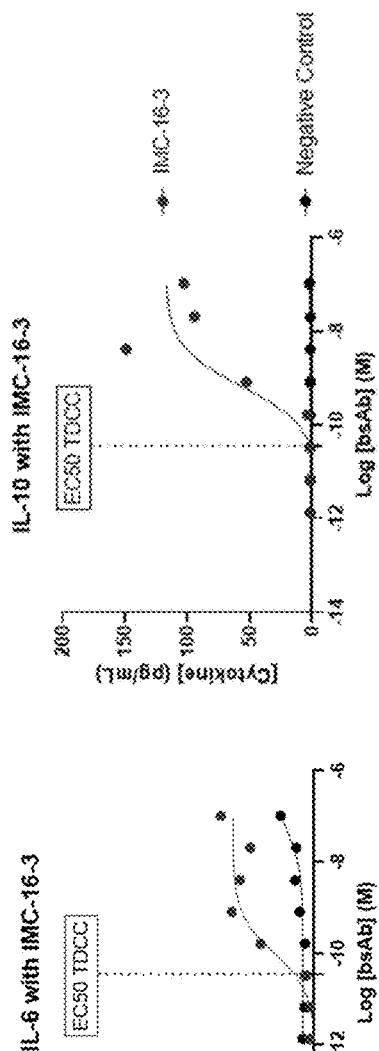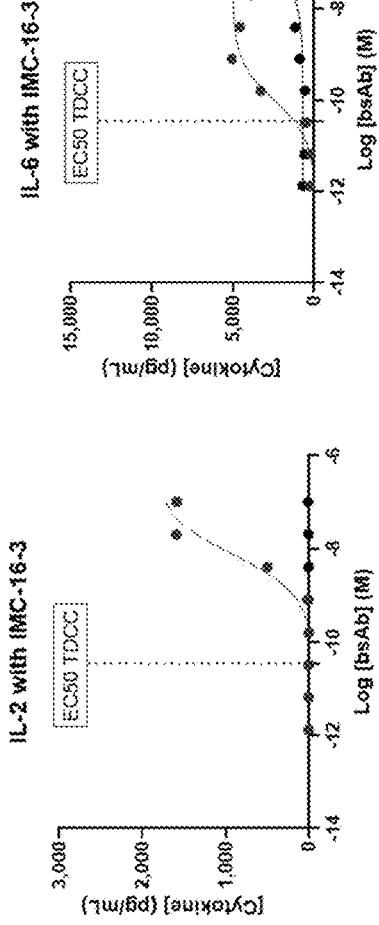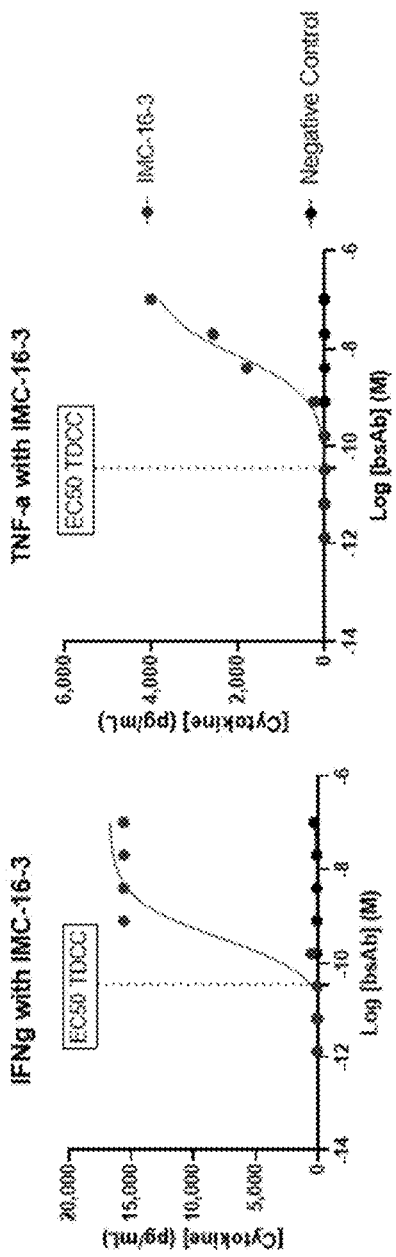
FIG. 14A  FIG. 14B  FIG. 14C  FIG. 14D  FIG. 14E

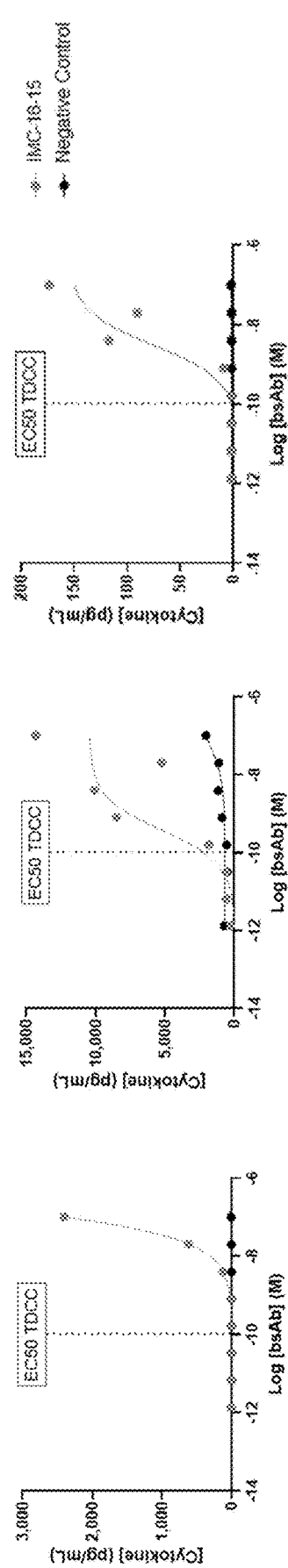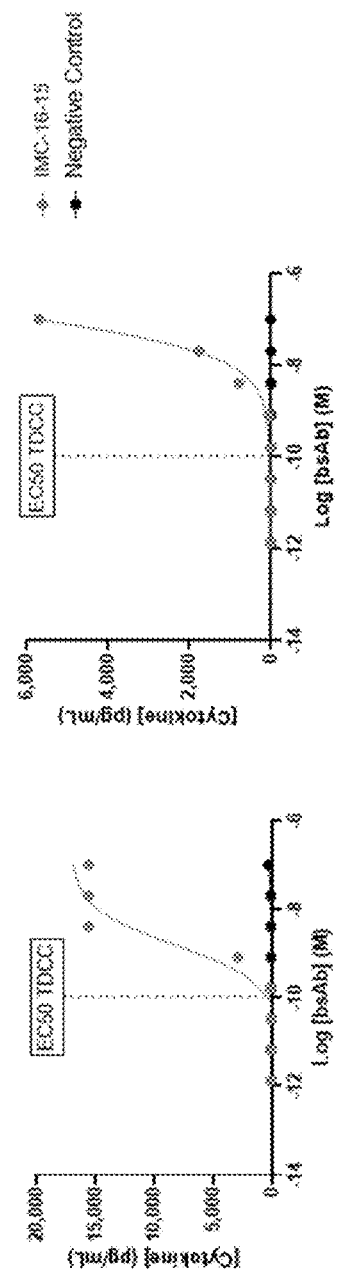

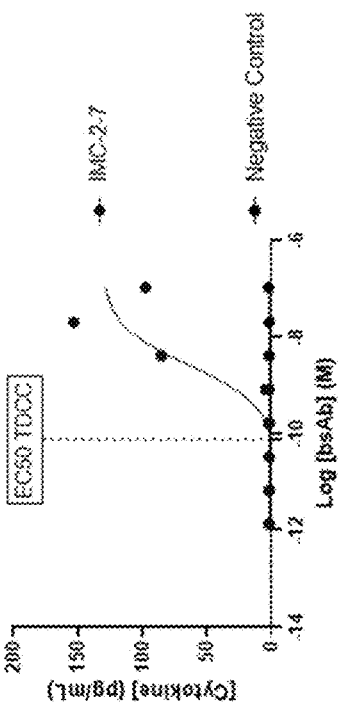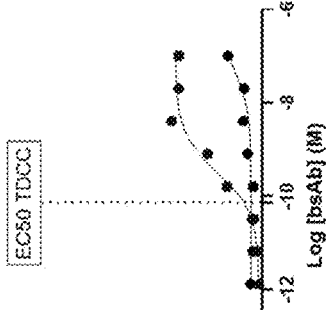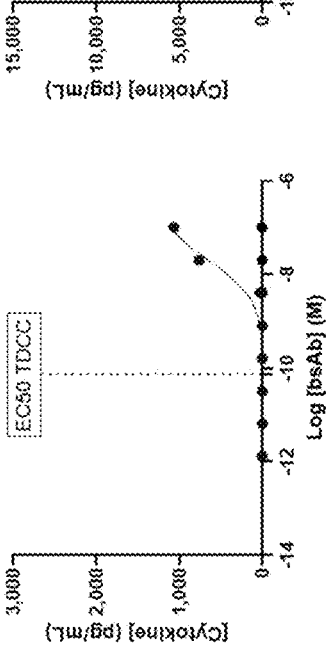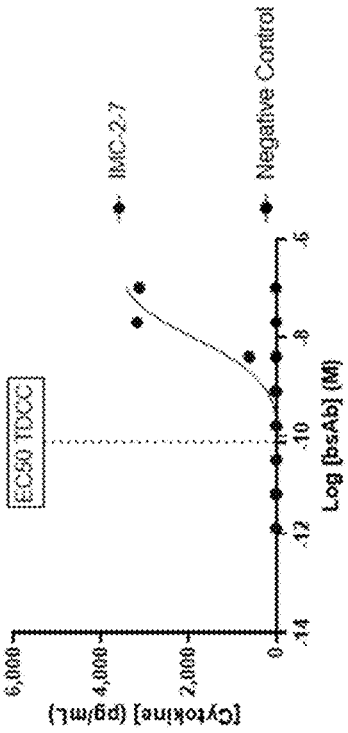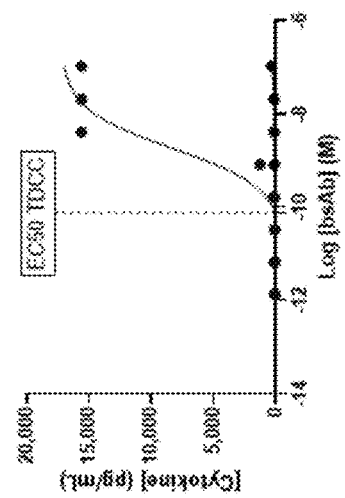

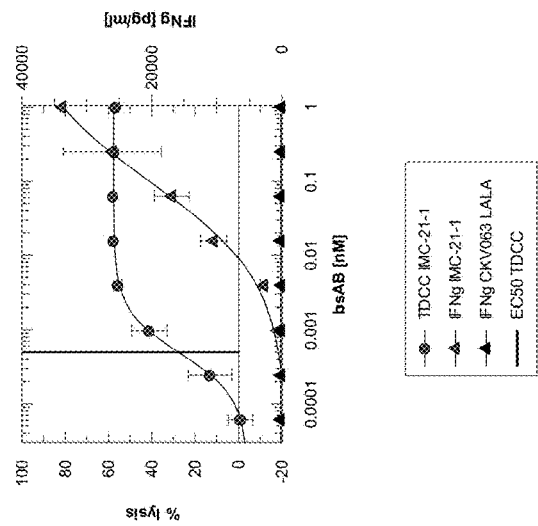
FIG. 20C  FIG. 20D  FIG. 20E
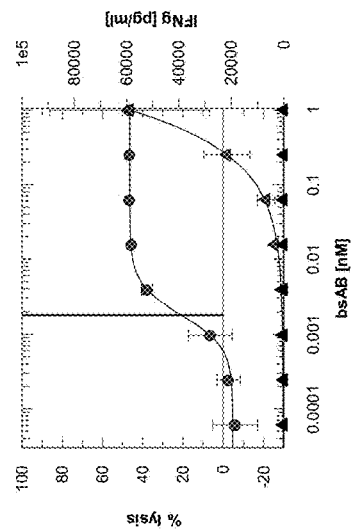
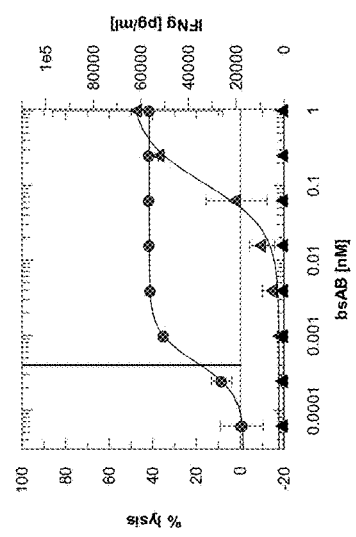

48hrs

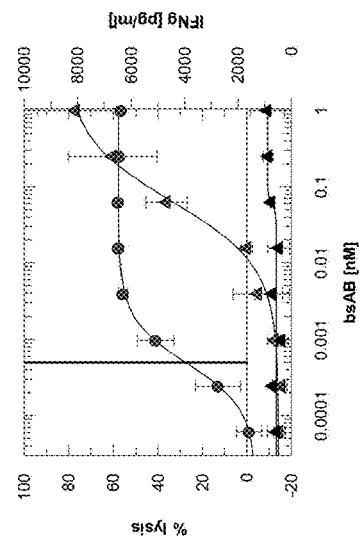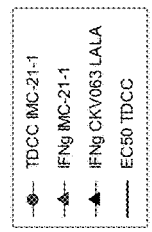
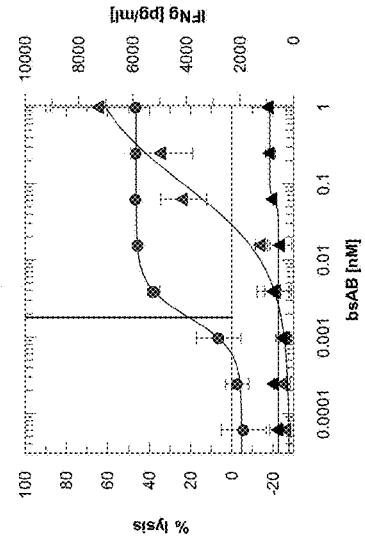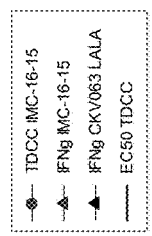
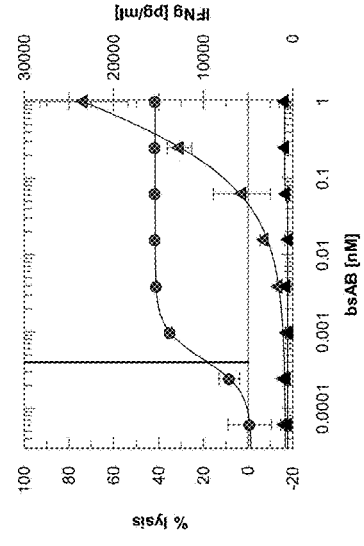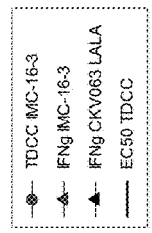
FIG. 20H, FIG. 20I, FIG. 20J

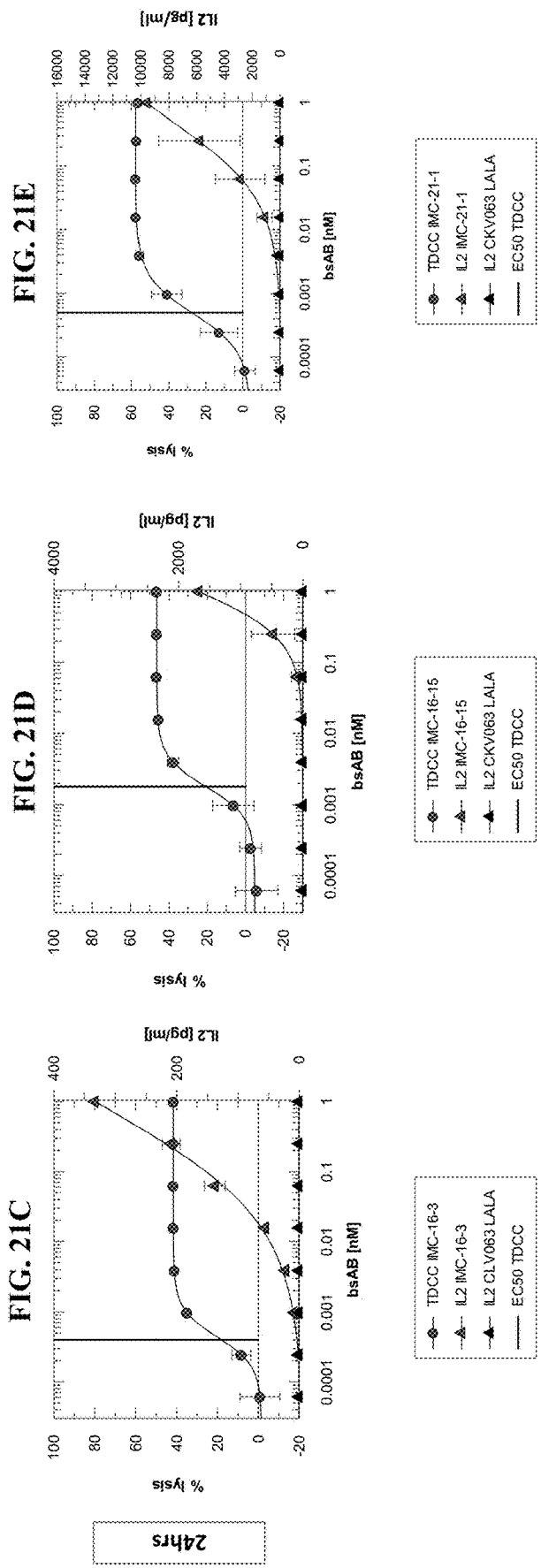

48hrs

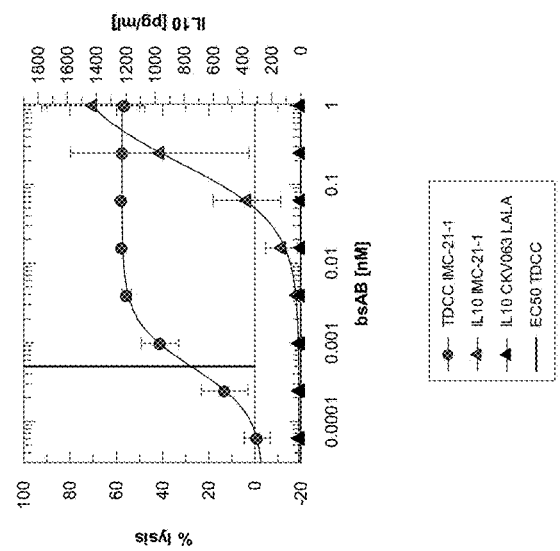
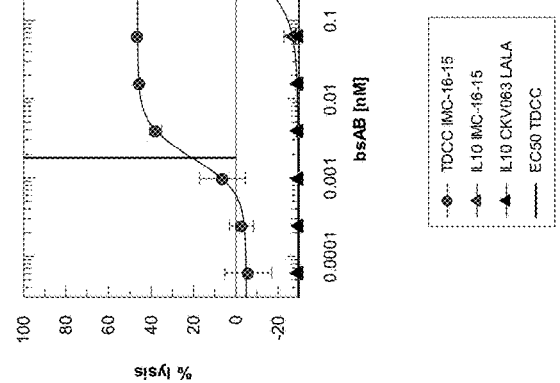
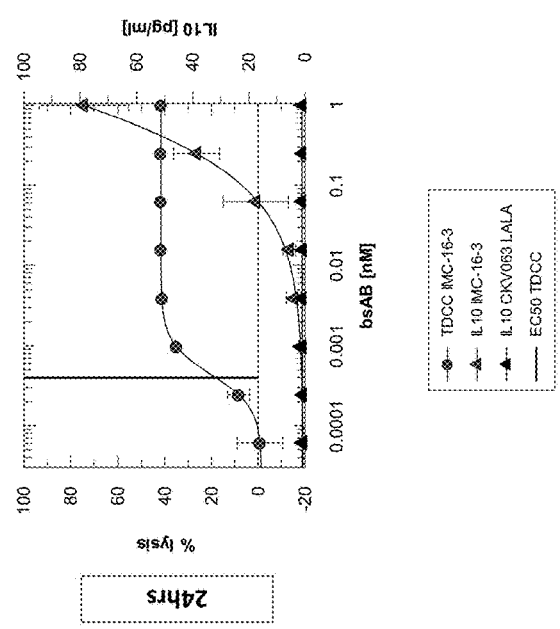

48hrs

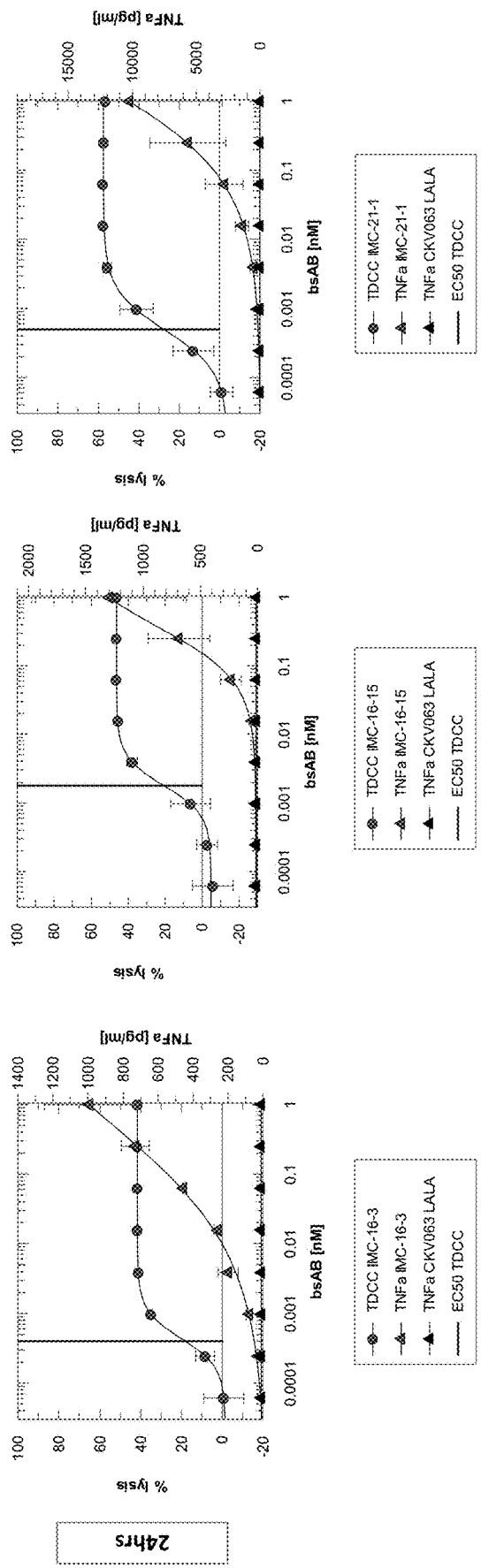

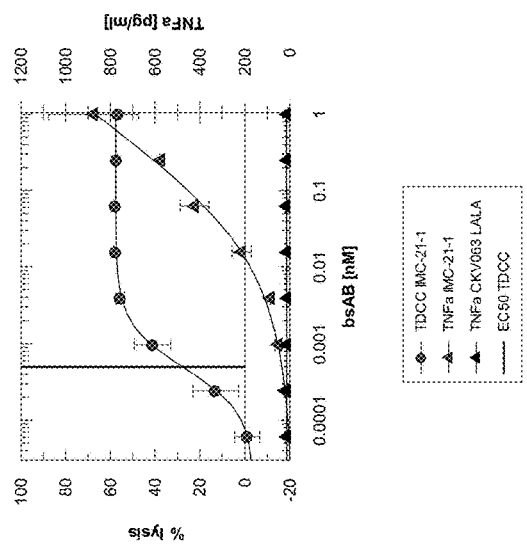
FIG. 23H  FIG. 23I  FIG. 23J
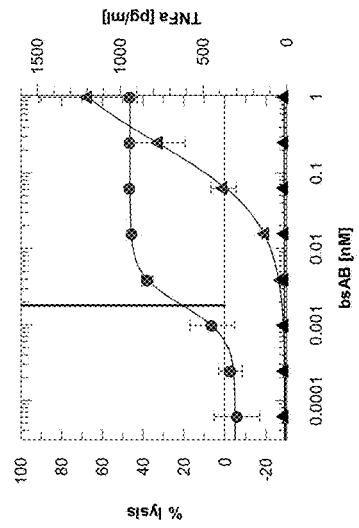
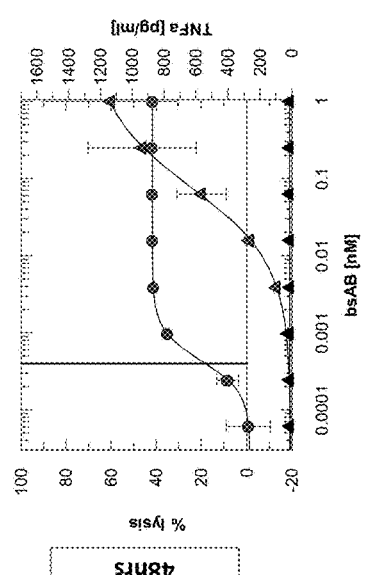

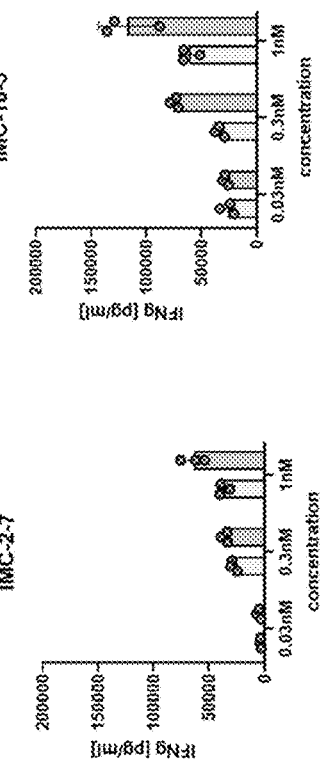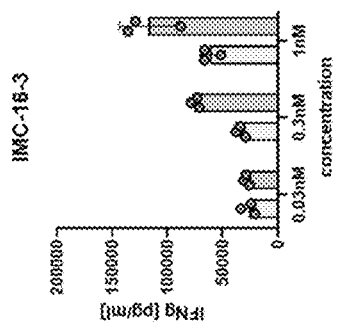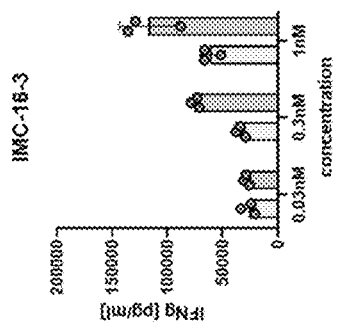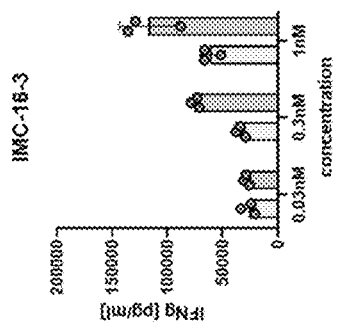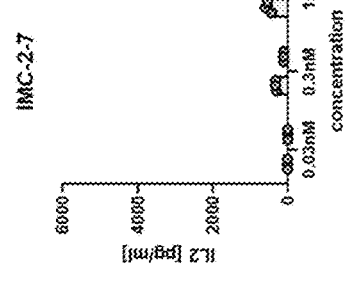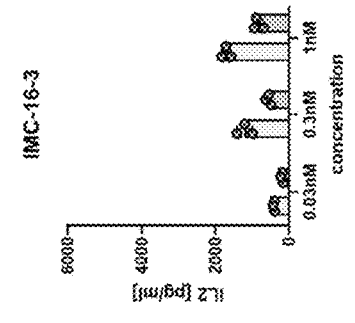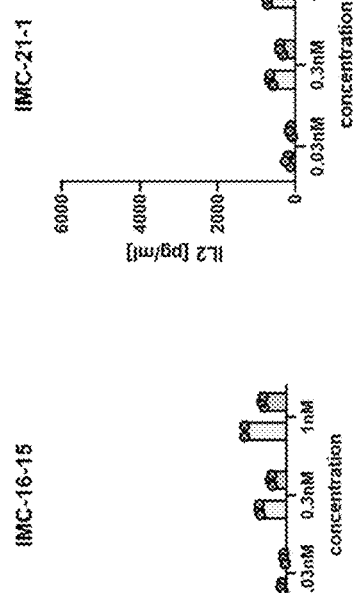

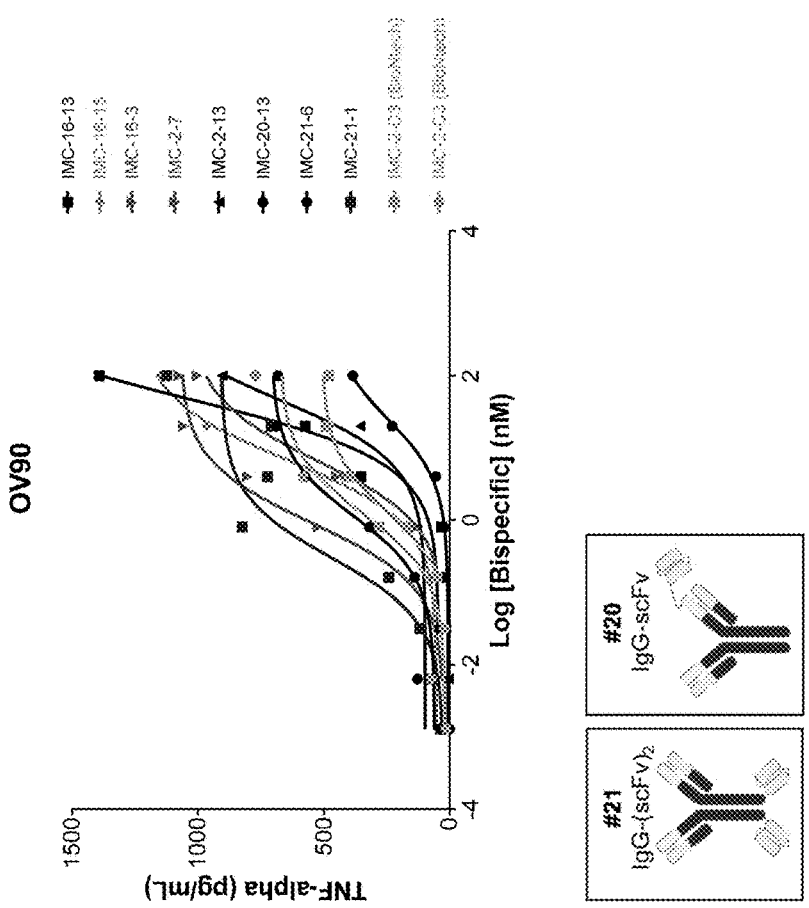
FIG. 26A
FIG. 26B
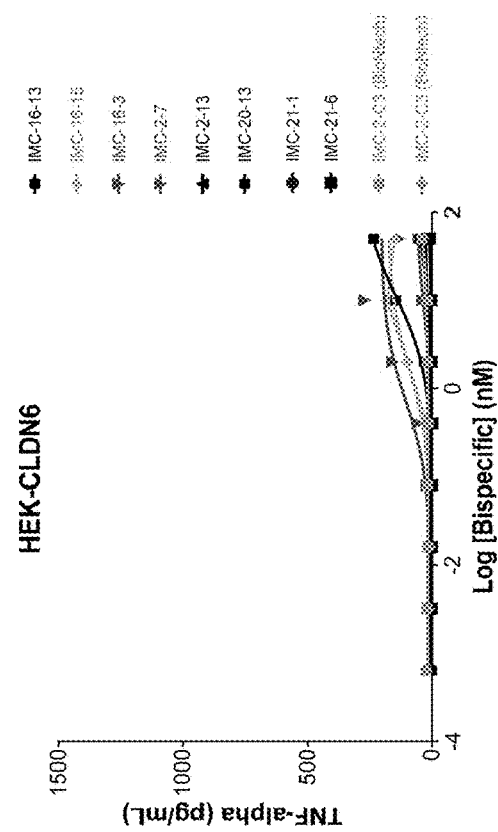

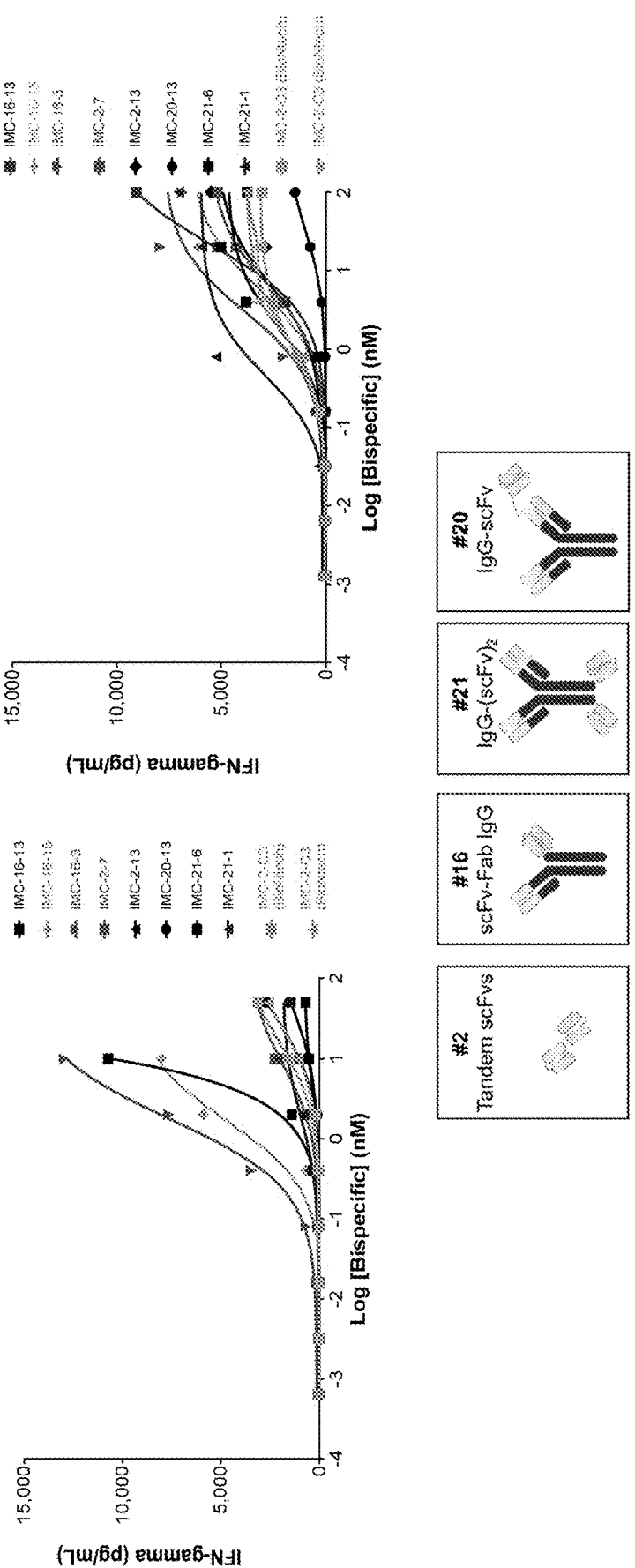
FIG. 27A HEK-CLDN6
FIG. 27B OV90

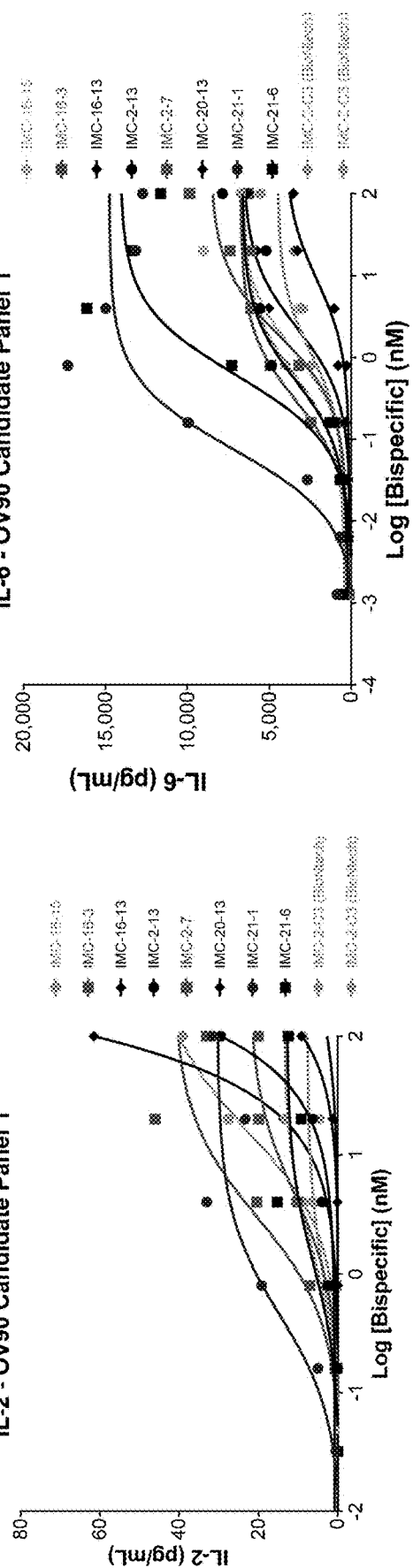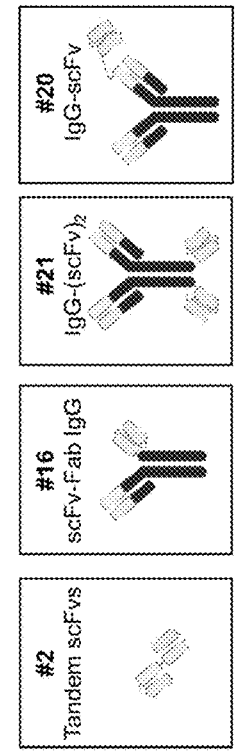
FIG. 28B
FIG. 28A

IMC-16-3

IMC-16-15

IMC-21-1

IMC-2-7

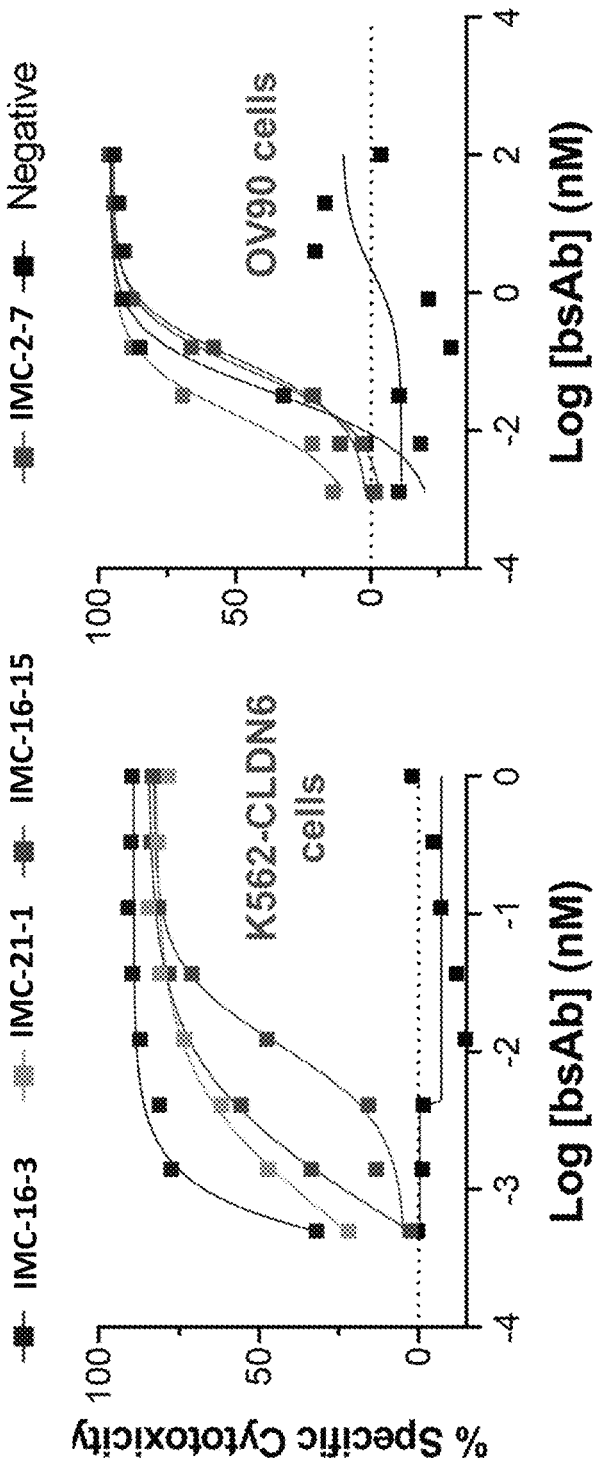
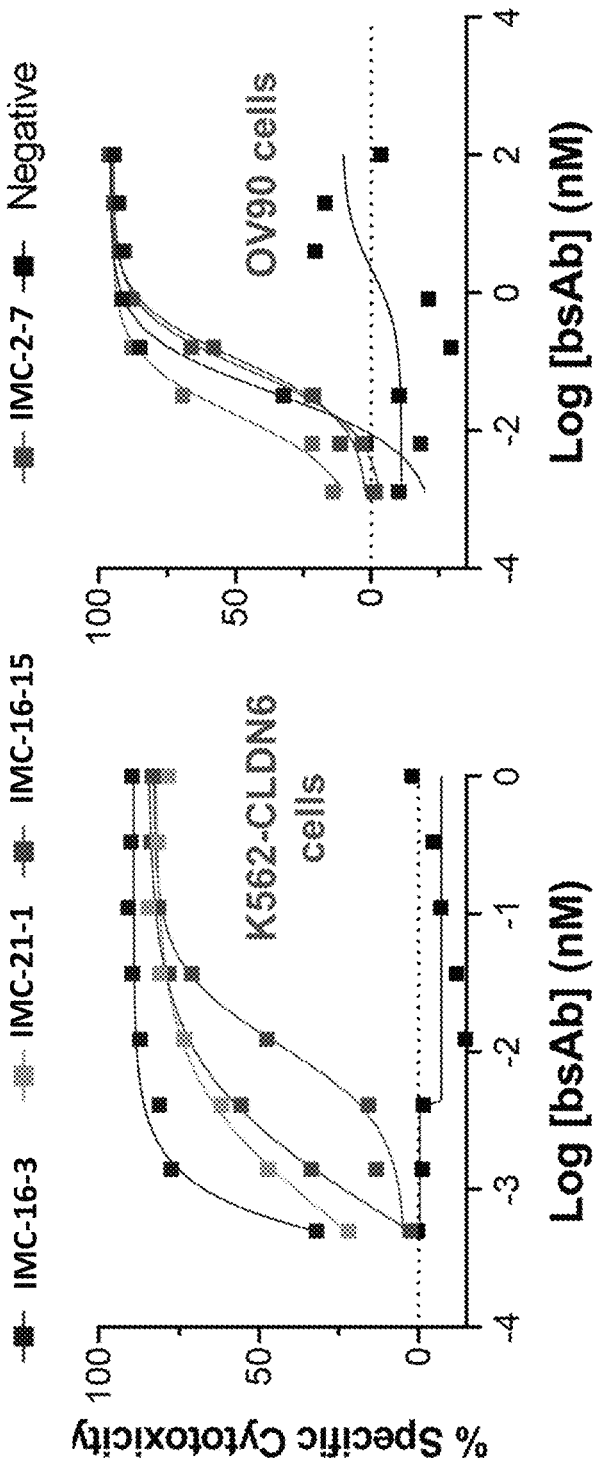
FIG. 30A
FIG. 30B

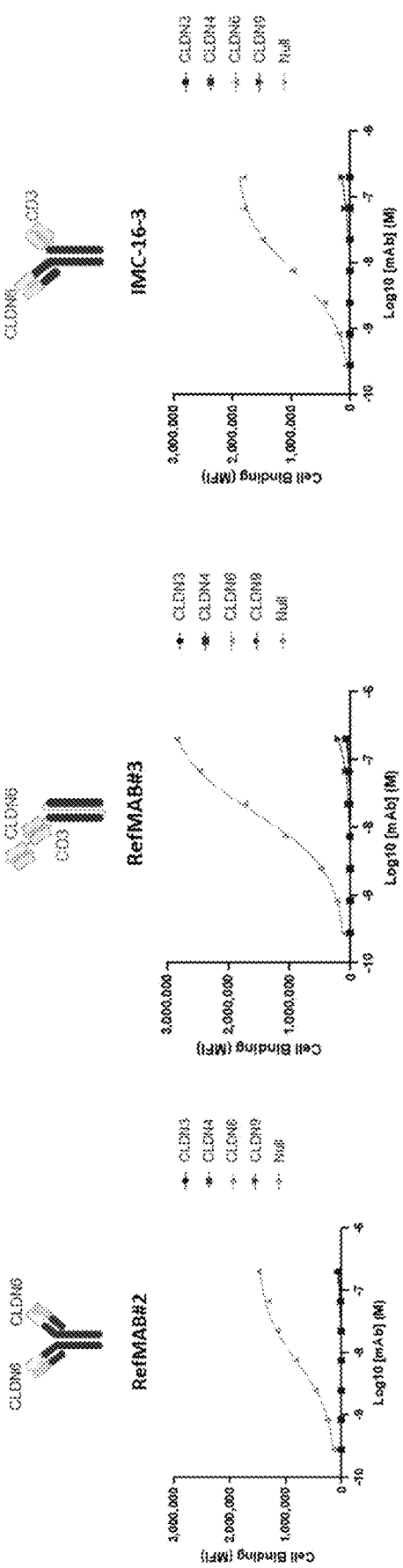

SEQUENCE LISTING

```
Sequence total quantity: 131
SEQ ID NO: 1            moltype = AA  length = 8
FEATURE                 Location/Qualifiers
source                  1..8
                        mol_type = protein
                        organism = synthetic construct
SEQUENCE: 1
SAGSGLYG                                                                8

SEQ ID NO: 2            moltype = AA  length = 7
FEATURE                 Location/Qualifiers
source                  1..7
                        mol_type = protein
                        organism = synthetic construct
SEQUENCE: 2
GTNKRPS                                                                 7

SEQ ID NO: 3            moltype = AA  length = 11
FEATURE                 Location/Qualifiers
source                  1..11
                        mol_type = protein
                        organism = synthetic construct
SEQUENCE: 3
GSADSSTNAG I                                                           11
```

-continued

```
SEQ ID NO: 4                 moltype = AA   length = 5
FEATURE                      Location/Qualifiers
source                       1..5
                             mol_type = protein
                             organism = synthetic construct
SEQUENCE: 4
SYAMN                                                                         5

SEQ ID NO: 5                 moltype = AA   length = 17
FEATURE                      Location/Qualifiers
source                       1..17
                             mol_type = protein
                             organism = synthetic construct
SEQUENCE: 5
GISSSGRYTG YADSVKG                                                           17

SEQ ID NO: 6                 moltype = AA   length = 18
FEATURE                      Location/Qualifiers
source                       1..18
                             mol_type = protein
                             organism = synthetic construct
SEQUENCE: 6
SVGSGVSWSG YVATSLDA                                                          18

SEQ ID NO: 7                 moltype = AA   length = 5
FEATURE                      Location/Qualifiers
source                       1..5
                             mol_type = protein
                             organism = synthetic construct
SEQUENCE: 7
RYTMH                                                                         5

SEQ ID NO: 8                 moltype = AA   length = 17
FEATURE                      Location/Qualifiers
source                       1..17
                             mol_type = protein
                             organism = synthetic construct
SEQUENCE: 8
YINPSRGYTN YNQKFKD                                                           17

SEQ ID NO: 9                 moltype = AA   length = 10
FEATURE                      Location/Qualifiers
source                       1..10
                             mol_type = protein
                             organism = synthetic construct
SEQUENCE: 9
YDDHYCLDY                                                                    10

SEQ ID NO: 10                moltype = AA   length = 10
FEATURE                      Location/Qualifiers
source                       1..10
                             mol_type = protein
                             organism = synthetic construct
SEQUENCE: 10
RASSSVSYMN                                                                   10

SEQ ID NO: 11                moltype = AA   length = 7
FEATURE                      Location/Qualifiers
source                       1..7
                             mol_type = protein
                             organism = synthetic construct
SEQUENCE: 11
DTSKVAS                                                                       7

SEQ ID NO: 12                moltype = AA   length = 9
FEATURE                      Location/Qualifiers
source                       1..9
                             mol_type = protein
                             organism = synthetic construct
SEQUENCE: 12
QQWSSNPLT                                                                     9

SEQ ID NO: 13                moltype = AA   length = 8
FEATURE                      Location/Qualifiers
source                       1..8
                             mol_type = protein
                             organism = synthetic construct
SEQUENCE: 13
SGGSGSYG                                                                      8
```

```
SEQ ID NO: 14            moltype = AA   length = 7
FEATURE                  Location/Qualifiers
source                   1..7
                         mol_type = protein
                         organism = synthetic construct
SEQUENCE: 14
GTYKRPS                                                                    7

SEQ ID NO: 15            moltype = AA   length = 18
FEATURE                  Location/Qualifiers
source                   1..18
                         mol_type = protein
                         organism = synthetic construct
SEQUENCE: 15
SVGSGVSWSG YVATSLDV                                                       18

SEQ ID NO: 16            moltype = AA   length = 5
FEATURE                  Location/Qualifiers
source                   1..5
                         mol_type = protein
                         organism = synthetic construct
SEQUENCE: 16
GYSMG                                                                      5

SEQ ID NO: 17            moltype = AA   length = 17
FEATURE                  Location/Qualifiers
source                   1..17
                         mol_type = protein
                         organism = synthetic construct
SEQUENCE: 17
AIVWSGGNTY YEDSVKG                                                        17

SEQ ID NO: 18            moltype = AA   length = 15
FEATURE                  Location/Qualifiers
source                   1..15
                         mol_type = protein
                         organism = synthetic construct
SEQUENCE: 18
KIRPYIFKIA GQYDY                                                          15

SEQ ID NO: 19            moltype = AA   length = 5
FEATURE                  Location/Qualifiers
source                   1..5
                         mol_type = protein
                         organism = synthetic construct
SEQUENCE: 19
KYAMN                                                                      5

SEQ ID NO: 20            moltype = AA   length = 19
FEATURE                  Location/Qualifiers
source                   1..19
                         mol_type = protein
                         organism = synthetic construct
SEQUENCE: 20
RIRSKYNNYA TYYADSVKD                                                      19

SEQ ID NO: 21            moltype = AA   length = 14
FEATURE                  Location/Qualifiers
source                   1..14
                         mol_type = protein
                         organism = synthetic construct
SEQUENCE: 21
HGNFGNSYIS YWAY                                                           14

SEQ ID NO: 22            moltype = AA   length = 14
FEATURE                  Location/Qualifiers
source                   1..14
                         mol_type = protein
                         organism = synthetic construct
SEQUENCE: 22
GSSTGAVTSG NYPN                                                           14

SEQ ID NO: 23            moltype = AA   length = 7
FEATURE                  Location/Qualifiers
source                   1..7
                         mol_type = protein
                         organism = synthetic construct
SEQUENCE: 23
```

```
GTKFLAP                                                                              7

SEQ ID NO: 24          moltype = AA  length = 9
FEATURE                Location/Qualifiers
source                 1..9
                       mol_type = protein
                       organism = synthetic construct
SEQUENCE: 24
VLWYSNRWV                                                                            9

SEQ ID NO: 25          moltype = AA  length = 5
FEATURE                Location/Qualifiers
source                 1..5
                       mol_type = protein
                       organism = synthetic construct
SEQUENCE: 25
TYAMN                                                                                5

SEQ ID NO: 26          moltype = AA  length = 19
FEATURE                Location/Qualifiers
source                 1..19
                       mol_type = protein
                       organism = synthetic construct
SEQUENCE: 26
RIRSKYNNYA TYYADSVKG                                                                19

SEQ ID NO: 27          moltype = AA  length = 14
FEATURE                Location/Qualifiers
source                 1..14
                       mol_type = protein
                       organism = synthetic construct
SEQUENCE: 27
HGNFGDSYVS WFAY                                                                     14

SEQ ID NO: 28          moltype = AA  length = 14
FEATURE                Location/Qualifiers
source                 1..14
                       mol_type = protein
                       organism = synthetic construct
SEQUENCE: 28
GSSTGAVTTS NYAN                                                                     14

SEQ ID NO: 29          moltype = AA  length = 7
FEATURE                Location/Qualifiers
source                 1..7
                       mol_type = protein
                       organism = synthetic construct
SEQUENCE: 29
GTNKRAP                                                                              7

SEQ ID NO: 30          moltype = AA  length = 9
FEATURE                Location/Qualifiers
source                 1..9
                       mol_type = protein
                       organism = synthetic construct
SEQUENCE: 30
ALWYSNHWV                                                                            9

SEQ ID NO: 31          moltype = AA  length = 19
FEATURE                Location/Qualifiers
source                 1..19
                       mol_type = protein
                       organism = synthetic construct
SEQUENCE: 31
RIRSKYNNYA TYYADSVKS                                                                19

SEQ ID NO: 32          moltype = AA  length = 14
FEATURE                Location/Qualifiers
source                 1..14
                       mol_type = protein
                       organism = synthetic construct
SEQUENCE: 32
HGNFGNSYVS WFAY                                                                     14

SEQ ID NO: 33          moltype = AA  length = 14
FEATURE                Location/Qualifiers
source                 1..14
                       mol_type = protein
                       organism = synthetic construct
```

```
SEQUENCE: 33
RSSTGAVTTS NYAN                                                          14

SEQ ID NO: 34              moltype = AA  length = 7
FEATURE                    Location/Qualifiers
source                     1..7
                           mol_type = protein
                           organism = synthetic construct
SEQUENCE: 34
GANKRAP                                                                  7

SEQ ID NO: 35              moltype = AA  length = 9
FEATURE                    Location/Qualifiers
source                     1..9
                           mol_type = protein
                           organism = synthetic construct
SEQUENCE: 35
ALWYSNLWV                                                                9

SEQ ID NO: 36              moltype = AA  length = 17
FEATURE                    Location/Qualifiers
source                     1..17
                           mol_type = protein
                           organism = synthetic construct
SEQUENCE: 36
YINPSRGYTN YNQKVKD                                                       17

SEQ ID NO: 37              moltype = AA  length = 10
FEATURE                    Location/Qualifiers
source                     1..10
                           mol_type = protein
                           organism = synthetic construct
SEQUENCE: 37
SASSSVSYMN                                                               10

SEQ ID NO: 38              moltype = AA  length = 7
FEATURE                    Location/Qualifiers
source                     1..7
                           mol_type = protein
                           organism = synthetic construct
SEQUENCE: 38
DTSKLAS                                                                  7

SEQ ID NO: 39              moltype = AA  length = 9
FEATURE                    Location/Qualifiers
source                     1..9
                           mol_type = protein
                           organism = synthetic construct
SEQUENCE: 39
QQWSSNPFT                                                                9

SEQ ID NO: 40              moltype = AA  length = 5
FEATURE                    Location/Qualifiers
source                     1..5
                           mol_type = protein
                           organism = synthetic construct
SEQUENCE: 40
GYTMN                                                                    5

SEQ ID NO: 41              moltype = AA  length = 17
FEATURE                    Location/Qualifiers
source                     1..17
                           mol_type = protein
                           organism = synthetic construct
SEQUENCE: 41
LINPYKGVST YNQKVKG                                                       17

SEQ ID NO: 42              moltype = AA  length = 13
FEATURE                    Location/Qualifiers
source                     1..13
                           mol_type = protein
                           organism = synthetic construct
SEQUENCE: 42
SGYYGDSDWY FDV                                                           13

SEQ ID NO: 43              moltype = AA  length = 11
FEATURE                    Location/Qualifiers
source                     1..11
                           mol_type = protein
```

```
                          -continued organism = synthetic construct
SEQUENCE: 43
RASQDIRNYL N                                                            11

SEQ ID NO: 44         moltype = AA  length = 7
FEATURE               Location/Qualifiers
source                1..7
                      mol_type = protein
                      organism = synthetic construct
SEQUENCE: 44
YTSRLHS                                                                 7

SEQ ID NO: 45         moltype = AA  length = 9
FEATURE               Location/Qualifiers
source                1..9
                      mol_type = protein
                      organism = synthetic construct
SEQUENCE: 45
QQGNTLPWT                                                               9

SEQ ID NO: 46         moltype = AA  length = 6
FEATURE               Location/Qualifiers
source                1..6
                      mol_type = protein
                      organism = synthetic construct
SEQUENCE: 46
HHHHHH                                                                  6

SEQ ID NO: 47         moltype = AA  length = 18
FEATURE               Location/Qualifiers
source                1..18
                      mol_type = protein
                      organism = synthetic construct
SEQUENCE: 47
SMGSGVSWSG YVATSIDV                                                     18

SEQ ID NO: 48         moltype = AA  length = 13
FEATURE               Location/Qualifiers
source                1..13
                      mol_type = protein
                      organism = synthetic construct
SEQUENCE: 48
RSSTGAVTTS NYA                                                          13

SEQ ID NO: 49         moltype = AA  length = 13
FEATURE               Location/Qualifiers
source                1..13
                      mol_type = protein
                      organism = synthetic construct
SEQUENCE: 49
GSSTGAVTSG NYP                                                          13

SEQ ID NO: 50         moltype = AA  length = 15
FEATURE               Location/Qualifiers
source                1..15
                      mol_type = protein
                      organism = synthetic construct
SEQUENCE: 50
GGGGSGGGGS GGGGS                                                        15

SEQ ID NO: 51         moltype = AA  length = 5
FEATURE               Location/Qualifiers
source                1..5
                      mol_type = protein
                      organism = synthetic construct
SEQUENCE: 51
GGGGS                                                                   5

SEQ ID NO: 52         moltype = AA  length = 16
FEATURE               Location/Qualifiers
source                1..16
                      mol_type = protein
                      organism = synthetic construct
SEQUENCE: 52
GGSGGSGGSG GSGGVD                                                       16

SEQ ID NO: 53         moltype = AA  length = 20
FEATURE               Location/Qualifiers
source                1..20
```

```
                          mol_type = protein
                          organism = synthetic construct
SEQUENCE: 53
GKPGSGKPGS GKPGSGKPGS                                                       20

SEQ ID NO: 54             moltype = AA  length = 5
FEATURE                   Location/Qualifiers
source                    1..5
                          mol_type = protein
                          organism = synthetic construct
REPEAT                    1..5
                          note = sequence is present 1, 2, 3, or 4 times
SEQUENCE: 54
GGGGS                                                                       5

SEQ ID NO: 55             moltype = AA  length = 8
FEATURE                   Location/Qualifiers
source                    1..8
                          mol_type = protein
                          organism = synthetic construct
SEQUENCE: 55
GGGGGGGG                                                                    8

SEQ ID NO: 56             moltype = AA  length = 6
FEATURE                   Location/Qualifiers
source                    1..6
                          mol_type = protein
                          organism = synthetic construct
SEQUENCE: 56
GGGGGG                                                                      6

SEQ ID NO: 57             moltype = AA  length = 5
FEATURE                   Location/Qualifiers
source                    1..5
                          mol_type = protein
                          organism = synthetic construct
REPEAT                    1..5
                          note = Sequence is present 1, 2, or 3 times
SEQUENCE: 57
EAAAK                                                                       5

SEQ ID NO: 58             moltype = AA  length = 7
FEATURE                   Location/Qualifiers
source                    1..7
                          mol_type = protein
                          organism = synthetic construct
REPEAT                    2..6
                          note = Sequence is repeated 2, 3, 4, or 5 times
SEQUENCE: 58
AEAAAKA                                                                     7

SEQ ID NO: 59             moltype = AA  length = 12
FEATURE                   Location/Qualifiers
source                    1..12
                          mol_type = protein
                          organism = synthetic construct
SEQUENCE: 59
AEAAAKEAAA KA                                                               12

SEQ ID NO: 60             moltype = AA  length = 16
FEATURE                   Location/Qualifiers
source                    1..16
                          mol_type = protein
                          organism = synthetic construct
REPEAT                    11..15
                          note = Sequence is repeated 4 times
REPEAT                    2..6
                          note = Sequence is repeated 4 times
SEQUENCE: 60
AEAAAKALEA EAAAKA                                                           16

SEQ ID NO: 61             moltype = AA  length = 5
FEATURE                   Location/Qualifiers
source                    1..5
                          mol_type = protein
                          organism = synthetic construct
SEQUENCE: 61
PAPAP                                                                       5
```

```
SEQ ID NO: 62           moltype = AA   length = 18
FEATURE                 Location/Qualifiers
source                  1..18
                        mol_type = protein
                        organism = synthetic construct
SEQUENCE: 62
KESGSVSSEQ LAQFRSLD                                                    18

SEQ ID NO: 63           moltype = AA   length = 14
FEATURE                 Location/Qualifiers
source                  1..14
                        mol_type = protein
                        organism = synthetic construct
SEQUENCE: 63
EGKSSGSGSE SKST                                                        14

SEQ ID NO: 64           moltype = AA   length = 12
FEATURE                 Location/Qualifiers
source                  1..12
                        mol_type = protein
                        organism = synthetic construct
SEQUENCE: 64
GSAGSAAGSG EF                                                          12

SEQ ID NO: 65           moltype = AA   length = 211
FEATURE                 Location/Qualifiers
source                  1..211
                        mol_type = protein
                        organism = synthetic construct
SEQUENCE: 65
SYELTQPPSV SVSPGQTARI TCSAGSGLYG WYQQKPGQAP VLVIYGTNKR PSGIPERFSG       60
SSSGTTVTLT ISGVQAEDEA DYYCGSADSS TNAGIFGGGT KLTVLGQPKA APSVTLFPPS      120
SEELQANKAT LVCLISDFYP GAVTVAWKAD SSPVKAGVET TTPSKQSNNK YAASSYLSLT      180
PEQWKSHRSY SCQVTHEGST VEKTVAPTEC S                                    211

SEQ ID NO: 66           moltype = AA   length = 211
FEATURE                 Location/Qualifiers
source                  1..211
                        mol_type = protein
                        organism = synthetic construct
SEQUENCE: 66
SYELTQPPSV SVSPGQTARI TCSGGSGSYG WYQQKPGQAP VLVIYGTYKR PSGIPERFSG       60
SSSGTTVTLT ISGVQAEDEA DYYCGSADSS TNAGIFGGGT KLTVLGQPKA APSVTLFPPS      120
SEELQANKAT LVCLISDFYP GAVTVAWKAD SSPVKAGVET TTPSKQSNNK YAASSYLSLT      180
PEQWKSHRSY SCQVTHEGST VEKTVAPTEC S                                    211

SEQ ID NO: 67           moltype = AA   length = 211
FEATURE                 Location/Qualifiers
source                  1..211
                        mol_type = protein
                        organism = synthetic construct
SEQUENCE: 67
SYELTQPPSV SVSPGQTARI TCSAGSGLYG WYQQKPGQAP VLVIYGTNKR PSGIPERFSG       60
SSSGTTVTLT ISGVQAEDEA DYYCGSADSS TNAGIFGGGT KLTVLGQPKA APSVTLFPPS      120
SEELQANKAT LVCLISDFYP GAVTVAWKAD SSPVKAGVET TTPSKQSNNK YAASSYLSLT      180
PEQWKSHRSY SCQVTHEGST VEKTVAPTEC S                                    211

SEQ ID NO: 68           moltype = AA   length = 105
FEATURE                 Location/Qualifiers
source                  1..105
                        mol_type = protein
                        organism = synthetic construct
SEQUENCE: 68
SYELTQPPSV SVSPGQTARI TCSAGSGLYG WYQQKPGQAP VLVIYGTNKR PSGIPERFSG       60
SSSGTTVTLT ISGVQAEDEA DYYCGSADSS TNAGIFGGGT KLTVL                     105

SEQ ID NO: 69           moltype = AA   length = 127
FEATURE                 Location/Qualifiers
source                  1..127
                        mol_type = protein
                        organism = synthetic construct
SEQUENCE: 69
EVQLLESGGG LVQPGGSLRL SCAASGFTFS SYAMNWVRQA PGKGLEWVAG ISSSGRYTGY       60
ADSVKGRFTI SRDNSKNTLY LQMNSLRAED TAVYYCAKSV GSGVSWSGYV ATSLDAWGQG      120
TLVTVSS                                                               127

SEQ ID NO: 70           moltype = AA   length = 125
FEATURE                 Location/Qualifiers
source                  1..125
```

```
                        mol_type = protein
                        organism = synthetic construct
SEQUENCE: 70
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSS                                                              125

SEQ ID NO: 71           moltype = AA   length = 109
FEATURE                 Location/Qualifiers
source                  1..109
                        mol_type = protein
                        organism = synthetic construct
SEQUENCE: 71
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVL               109

SEQ ID NO: 72           moltype = AA   length = 106
FEATURE                 Location/Qualifiers
source                  1..106
                        mol_type = protein
                        organism = synthetic construct
SEQUENCE: 72
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 73           moltype = AA   length = 330
FEATURE                 Location/Qualifiers
source                  1..330
                        mol_type = protein
                        organism = synthetic construct
SEQUENCE: 73
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLWC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 74           moltype = AA   length = 233
FEATURE                 Location/Qualifiers
source                  1..233
                        mol_type = protein
                        organism = synthetic construct
SEQUENCE: 74
ASPKSSDKTH TCPPCPAPEA AGGPSVFLFP PKPKDTLMIS RTPEVTCVVV DVSHEDPEVK    60
FNWYVDGVEV HNAKTKPREE QYNSTYRVVS VLTVLHQDWL NGKEYKCKVS NKALPAPIEK   120
TISKAKGQPR EPQVYTLPPS REEMTKNQVS LSCAVKGFYP SDIAVEWESN GQPENNYKTT   180
PPVLDSDGSF FLVSKLTVDK SRWQQGNVFS CSVMHEALHN HYTQKSLSLS PGK          233

SEQ ID NO: 75           moltype = AA   length = 124
FEATURE                 Location/Qualifiers
source                  1..124
                        mol_type = protein
                        organism = synthetic construct
SEQUENCE: 75
EVQLVESGGG PVQAGGSLRL SCAASGRTYR GYSMGWFRQA PGKEREFVAA IVWSGGNTYY    60
EDSVKGRFTI SRDNAKNTMY LQMTSLKPED SATYYCAAKI RPYIFKIAGQ YDYWGQGTQV   120
TVSS                                                               124

SEQ ID NO: 76           moltype = AA   length = 457
FEATURE                 Location/Qualifiers
source                  1..457
                        mol_type = protein
                        organism = synthetic construct
SEQUENCE: 76
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDAWGQG   120
TLVTVSSAST KGPSVPPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLWCLVK GFYPSDIAVE WESNGQPENN YKTTPPVLDS DGSFFLYSKL   420
TVDKSRWQQG NVFSCSVMHE ALHNHYTQKS LSLSPGK                            457

SEQ ID NO: 77           moltype = AA   length = 211
FEATURE                 Location/Qualifiers
source                  1..211
                        mol_type = protein
                        organism = synthetic construct
```

```
SEQUENCE: 77
SYELTQPPSV SVSPGQTARI TCSAGSGLYG WYQQKPGQAP VLVIYGTNKR PSGIPERFSG     60
SSSGTTVTLT ISGVQAEDEA DYYCGSADSS TNAGIFGGGT KLTVLGQPKA APSVTLFPPS    120
SEELQANKAT LVCLISDFYP GAVTVAWKAD SSPVKAGVET TTPSKQSNNK YAASSYLSLT    180
PEQWKSHRSY SCQVTHEGST VEKTVAPTEC S                                   211

SEQ ID NO: 78            moltype = AA   length = 357
FEATURE                  Location/Qualifiers
source                   1..357
                         mol_type = protein
                         organism = synthetic construct
SEQUENCE: 78
EVQLVESGGG PVQAGGSLRL SCAASGRTYR GYSMGWFRQA PGKEREFVAA IVWSGGNTYY     60
EDSVKGRFTI SRDNAKNTMY LQMTSLKPED SATYYCAAKI RPYIFKIAGQ YDYWGQGTQV    120
TVSSASPKSS DKTHTCPPCP APEAAGGPSV FLFPPKPKDT LMISRTPEVT CVVVDVSHED    180
PEVKFNWYVD GVEVHNAKTK PREEQYNSTY RVVSVLTVLH QDWLNGKEYK CKVSNKALPA    240
PIEKTISKAK GQPREPQVYT LPPSREEMTK NQVSLSCAVK GFYPSDIAVE WESNGQPENN    300
YKTTPPVLDS DGSFFLVSKL TVDKSRWQQG NVFSCSVMHE ALHNHYTQKS LSLSPGK       357

SEQ ID NO: 79            moltype = AA   length = 457
FEATURE                  Location/Qualifiers
source                   1..457
                         mol_type = protein
                         organism = synthetic construct
SEQUENCE: 79
EVQLLESGGG LVQPGGSLRL SCAASGFTFS SYAMNWVRQA PGKGLEWVAG ISSSGRYTGY     60
ADSVKGRFTI SRDNSKNTLY LQMNSLRAED TAVYYCAKSV GSGVSWSGYV ATSLDAWGQG    120
TLVTVSSAST KGPSVFPLAP SSKSTSGGTA ALGCLVKDYF PEPVTVSWNS GALTSGVHTF    180
PAVLQSSGLY SLSSVVTVPS SSLGTQTYIC NVNHKPSNTK VDKKVEPKSC DKTHTCPPCP    240
APEAAGGPSV FLFPPKPKDT LMISRTPEVT CVVVDVSHED PEVKFNWYVD GVEVHNAKTK    300
PREEQYNSTY RVVSVLTVLH QDWLNGKEYK CKVSNKALPA PIEKTISKAK GQPREPQVYT    360
LPPSREEMTK NQVSLWCLVK GFYPSDIAVE WESNGQPENN YKTTPPVLDS DGSFFLYSKL    420
TVDKSRWQQG NVFSCSVMHE ALHNHYTQKS LSLSPGK                             457

SEQ ID NO: 80            moltype = AA   length = 357
FEATURE                  Location/Qualifiers
source                   1..357
                         mol_type = protein
                         organism = synthetic construct
SEQUENCE: 80
EVQLVESGGG PVQAGGSLRL SCAASGRTYR GYSMGWFRQA PGKEREFVAA IVWSGGNTYY     60
EDSVKGRFTI SRDNAKNTMY LQMTSLKPED SATYYCAAKI RPYIFKIAGQ YDYWGQGTQV    120
TVSSASPKSS DKTHTCPPCP APEAAGGPSV FLFPPKPKDT LMISRTPEVT CVVVDVSHED    180
PEVKFNWYVD GVEVHNAKTK PREEQYNSTY RVVSVLTVLH QDWLNGKEYK CKVSNKALPA    240
PIEKTISKAK GQPREPQVYT LPPSREEMTK NQVSLSCAVK GFYPSDIAVE WESNGQPENN    300
YKTTPPVLDS DGSFFLVSKL TVDKSRWQQG NVFSCSVMHE ALHNHYTQKS LSLSPGK       357

SEQ ID NO: 81            moltype = AA   length = 454
FEATURE                  Location/Qualifiers
source                   1..454
                         mol_type = protein
                         organism = synthetic construct
SEQUENCE: 81
EVQLLESGGG LVQPGGSLRL SCAASGFTYR GYSMGWVRQA PGKGLEFVAA IVWSGGNTYY     60
EDSVKGRFTI SRDNSKNTLY LQMNSLRAED TAVYYCAAKI RPYIFKIAGQ YDYWGQGTLV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSNTKVDK KVEPKSCDKT HTCPPCPAPE    240
AAGGPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPIE KTISKAKGQP REPQVYTLPP    360
SREEMTKNQV SLSCAVKGFY PSDIAVEWES NGQPENNYKT TPPVLDSDGS FFLVSKLTVD    420
KSRWQQGNVF SCSVMHEALH NHYTQKSLSL SPGK                                454

SEQ ID NO: 82            moltype = AA   length = 495
FEATURE                  Location/Qualifiers
source                   1..495
                         mol_type = protein
                         organism = synthetic construct
SEQUENCE: 82
SYELTQPPSV SVSPGQTARI TCSAGSGLYG WYQQKPGQAP VLVIYGTNKR PSGIPERFSG     60
SSSGTTVTLT ISGVQAEDEA DYYCGSADSS TNAGIFGGGT KLTVLGGGGS GGGGSGGGGS    120
EVQLLESGGG LVQPGGSLRL SCAASGFTFS SYAMNWVRQA PGKGLEWVAG ISSSGRYTGY    180
ADSVKGRFTI SRDNSKNTLY LQMNSLRAED TAVYYCAKSV GSGVSWSGYV ATSLDAWGQG    240
TLVTVSSGGG GSDIKLQQSG AELARPGASV KMSCKTSGYT FTRYTMHWVK QRPGQGLEWI    300
GYINPSRGYT NYNQKFKDKA TLTTDKSSST AYMQLSSLTS EDSAVYYCAR YDDHYCLDY    360
WGQGTTLTVS SVEGGSGGSG GSGGSGGVDD IQLTQSPAIM SASPGEKVTM TCRASSSVSY    420
MNWYQQKSGT SPKRWIYDTS KVASGVPYRF SGSGSGTSYS LTISSMEAED AATYYCQQWS    480
SNPLTFGAGT KLELK                                                     495

SEQ ID NO: 83            moltype = AA   length = 495
```

```
FEATURE                 Location/Qualifiers
source                  1..495
                        mol_type = protein
                        organism = synthetic construct
SEQUENCE: 83
SYELTQPPSV SVSPGQTARI TCSGGSGSYG WYQQKPGQAP VLVIYGTYKR PSGIPERFSG  60
SSSGTTVTLT ISGVQAEDEA DYYCGSADSS TNAGIFGGGT KLTVLGGGGS GGGGSGGGGS 120
EVQLLESGGG LVQPGGSLRL SCAASGFTFS SYAMNWVRQA PGKGLEWVAG ISSSGRYTGY 180
ADSVKGRFTI SRDNSKNTLY LQMNSLRAED TAVYYCAKSV GSGVSWSGYV ATSLDVWGQG 240
TLVTVSSGGG GSDIKLQQSG AELARPGASV KMSCKTSGYT FTRYTMHWVK QRPGQGLEWI 300
GYINPSRGYT NYNQKFKDKA TLTTDKSSST AYMQLSSLTS EDSAVYYCAR YYDDHYCLDY 360
WGQGTTLTVS SVEGGSGGSG GSGGSGGVDD IQLTQSPAIM SASPGEKVTM TCRASSSVSY 420
MNWYQQKSGT SPKRWIYDTS KVASGVPYRF SGSGSGTSYS LTISSMEAED AATYYCQQWS 480
SNPLTFGAGT KLELK                                                  495

SEQ ID NO: 84           moltype = AA  length = 376
FEATURE                 Location/Qualifiers
source                  1..376
                        mol_type = protein
                        organism = synthetic construct
SEQUENCE: 84
SYELTQPPSV SVSPGQTARI TCSAGSGLYG WYQQKPGQAP VLVIYGTNKR PSGIPERFSG  60
SSSGTTVTLT ISGVQAEDEA DYYCGSADSS TNAGIFGGGT KLTVLGGGGS GGGGSGGGGS 120
EVQLLESGGG LVQPGGSLRL SCAASGFTFS SYAMNWVRQA PGKGLEWVAG ISSSGRYTGY 180
ADSVKGRFTI SRDNSKNTLY LQMNSLRAED TAVYYCAKSV GSGVSWSGYV ATSLDAWGQG 240
TLVTVSSGGG GSEVQLVESG GGPVQAGGSL RLSCAASGRT YRGYSMGWFR QAPGKEREFV 300
AAIVWSGGNT YYEDSVKGRF TISRDNAKNT MYLQMTSLKP EDSATYYCAA KIRPYIFKIA 360
GQYDYWGQGT QVTVSS                                                 376

SEQ ID NO: 85           moltype = AA  length = 376
FEATURE                 Location/Qualifiers
source                  1..376
                        mol_type = protein
                        organism = synthetic construct
SEQUENCE: 85
SYELTQPPSV SVSPGQTARI TCSGGSGSYG WYQQKPGQAP VLVIYGTYKR PSGIPERFSG  60
SSSGTTVTLT ISGVQAEDEA DYYCGSADSS TNAGIFGGGT KLTVLGGGGS GGGGSGGGGS 120
EVQLLESGGG LVQPGGSLRL SCAASGFTFS SYAMNWVRQA PGKGLEWVAG ISSSGRYTGY 180
ADSVKGRFTI SRDNSKNTLY LQMNSLRAED TAVYYCAKSV GSGVSWSGYV ATSLDVWGQG 240
TLVTVSSGGG GSEVQLVESG GGPVQAGGSL RLSCAASGRT YRGYSMGWFR QAPGKEREFV 300
AAIVWSGGNT YYEDSVKGRF TISRDNAKNT MYLQMTSLKP EDSATYYCAA KIRPYIFKIA 360
GQYDYWGQGT QVTVSS                                                 376

SEQ ID NO: 86           moltype = AA  length = 596
FEATURE                 Location/Qualifiers
source                  1..596
                        mol_type = protein
                        organism = synthetic construct
SEQUENCE: 86
EVQLLESGGG LVQPGGSLRL SCAASGFTFS SYAMNWVRQA PGKGLEWVAG ISSSGRYTGY  60
ADSVKGRFTI SRDNSKNTLY LQMNSLRAED TAVYYCAKSV GSGVSWSGYV ATSLDVWGQG 120
TLVTVSSAST KGPSVFPLAP SSKSTSGGTA ALGCLVKDYF PEPVTVSWNS GALTSGVHTF 180
PAVLQSSGLY SLSSVVTVPS SSLGTQTYIC NVNHKPSNTK VDKKVEPKSC DKTHTCPPCP 240
APEAAGGPSV FLFPPKPKDT LMISRTPEVT CVVVDVSHED PEVKFNWYVD GVEVHNAKTK 300
PREEQYNSTY RVVSVLTVLH QDWLNGKEYK CKVSNKALPA PIEKTISKAK GQPREPQVYT 360
LPPSRDELTK NQVSLTCLVK GFYPSDIAVE WESNGQPENN YKTTPPVLDS DGSFFLYSKL 420
TVDKSRWQQG NVFSCSVMHE ALHNHYTQKS LSLSPGKGGG GSGGGGTGGG GSEVQLVESG 480
GGPVQAGGSL RLSCAASGRT YRGYSMGWFR QAPGKEREFV AAIVWSGGNT YYEDSVKGRF 540
TISRDNAKNT MYLQMTSLKP EDSATYYCAA KIRPYIFKIA GQYDYWGQGT QVTVSS     596

SEQ ID NO: 87           moltype = AA  length = 596
FEATURE                 Location/Qualifiers
source                  1..596
                        mol_type = protein
                        organism = synthetic construct
SEQUENCE: 87
EVQLLESGGG LVQPGGSLRL SCAASGFTFS SYAMNWVRQA PGKGLEWVAG ISSSGRYTGY  60
ADSVKGRFTI SRDNSKNTLY LQMNSLRAED TAVYYCAKSV GSGVSWSGYV ATSLDVWGQG 120
TLVTVSSAST KGPSVFPLAP SSKSTSGGTA ALGCLVKDYF PEPVTVSWNS GALTSGVHTF 180
PAVLQSSGLY SLSSVVTVPS SSLGTQTYIC NVNHKPSNTK VDKKVEPKSC DKTHTCPPCP 240
APEAAGGPSV FLFPPKPKDT LMISRTPEVT CVVVDVSHED PEVKFNWYVD GVEVHNAKTK 300
PREEQYNSTY RVVSVLTVLH QDWLNGKEYK CKVSNKALPA PIEKTISKAK GQPREPQVYT 360
LPPSRDELTK NQVSLTCLVK GFYPSDIAVE WESNGQPENN YKTTPPVLDS DGSFFLYSKL 420
TVDKSRWQQG NVFSCSVMHE ALHNHYTQKS LSLSPGKGGG GSGGGGTGGG GSEVQLVESG 480
GGPVQAGGSL RLSCAASGRT YRGYSMGWFR QAPGKEREFV AAIVWSGGNT YYEDSVKGRF 540
TISRDNAKNT MYLQMTSLKP EDSATYYCAA KIRPYIFKIA GQYDYWGQGT QVTVSS     596

SEQ ID NO: 88           moltype = AA  length = 457
FEATURE                 Location/Qualifiers
```

```
source                  1..457
                        mol_type = protein
                        organism = synthetic construct
SEQUENCE: 88
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLWCLVK GFYPSDIAVE WESNGQPENN YKTTPPVLDS DGSFFLYSKL   420
TVDKSRWQQG NVFSCSVMHE ALHNHYTQKS LSLSPGK                            457

SEQ ID NO: 89           moltype = AA  length = 487
FEATURE                 Location/Qualifiers
source                  1..487
                        mol_type = protein
                        organism = synthetic construct
SEQUENCE: 89
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGGKPG SGKPGSGKPG SGKPGSQAVV TQEPSLTVSP GGTVTLTCGS STGAVTTSNYA   180
NWVQQKPGKS PRGLIGGTNK RAPGVPARFS GSLLGGKAAL TISGAQPEDE ADYYCALWYS   240
NHWVFGGGTK LTVLASPKSS DKTHTCPPCP APEAAGGPSV FLFPPKPKDT LMISRTPEVT   300
CVVVDVSHED PEVKFNWYVD GVEVHNAKTK PREEQYNSTY RVVSVLTVLH QDWLNGKEYK   360
CKVSNKALPA PIEKTISKAK GQPREPQVYT LPPSREEMTK NQVSLSCAVK GFYPSDIAVE   420
WESNGQPENN YKTTPPVLDS DGSFFLVSKL TVDKSRWQQG NVFSCSVMHE ALHNHYTQKS   480
LSLSPGK                                                             487

SEQ ID NO: 90           moltype = AA  length = 485
FEATURE                 Location/Qualifiers
source                  1..485
                        mol_type = protein
                        organism = synthetic construct
SEQUENCE: 90
EVQLVESGGG LVQPGGSLRL SCAASGFTFN TYAMNWVRQA PGKGLEWVAR IRSKYNNYAT    60
YYADSVKSRT TISDDSKNTL YLQMNSLRAE DTAVYYCVRH GNFGNSYVSW FAYWGQTTVT   120
VSSGGGGSGG GGSGGGGSGG GGSEIVVTQS PATLSVSPGE RATLSCRSST GAVTTSNYAN   180
WVQEPGQAFR GLIGGANKRA PGVPARFSGS LSGDEATLTI SSLQSEDFAV YYCALWYSNL   240
WVFGQGTKLE IKASPKSSDK THTCPPCPAP EAAGGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREEMTKNQ VSLSCAVKGF YPSDIAVEWE   420
SNGQPENNYK TTPPVLDSDG SFFLVSKLTV DKSRWQQGNV FSCSVMHEAL HNHYTQKSLS   480
LSPGK                                                               485

SEQ ID NO: 91           moltype = AA  length = 482
FEATURE                 Location/Qualifiers
source                  1..482
                        mol_type = protein
                        organism = synthetic construct
SEQUENCE: 91
EVQLVESGGG LVQPGGSLKL SCAASGFTFN KYAMNWVRQA PGKGLEWVAR IRSKYNNYAT    60
YYADSVKDRF TISRDDSKNT AYLQMNNLKT EDTAVYYCVR HGNFGNSYIS YWAYWGQGTL   120
VTVSSGGGGS GGGGSGGGGS QTVVTQEPSL TVSPGGTVTL TCGSSTGAVT SGNYPNWVQQ   180
KPGQAPRGLI GGTKFLAPGT PARFSGSLLG GKAALTLSGV QPEDEAEYYC VLWYSNRWVF   240
GGGTKLTVLA SPKSSDKTHT CPPCPAPEAA GGPSVFLFPP KPKDTLMISR TPEVTCVVVD   300
VSHEDPEVKF NWYVDGVEVH NAKTKPREEQ YNSTYRVVSV LTVLHQDWLN GKEYKCKVSN   360
KALPAPIEKT ISKAKGQPRE PQVYTLPPSR EEMTKNQVSL SCAVKGFYPS DIAVEWESNG   420
QPENNYKTTP PVLDSDGSFF LVSKLTVDKS RWQQGNVFSC SVMHEALHNH YTQKSLSLSP   480
GK                                                                  482

SEQ ID NO: 92           moltype = AA  length = 474
FEATURE                 Location/Qualifiers
source                  1..474
                        mol_type = protein
                        organism = synthetic construct
SEQUENCE: 92
QVQLVQSGGG VVQPGRSLRL SCKASGYTFT RYTMHWVRQA PGKGLEWIGY INPSRGYTNY    60
NQKVKDRFTI STDKSKSTAF LQMDSLRPED TAVYYCARYY DDHYCLDYWG QGTTLTVSSG   120
GGGSGGGGSG GGGSDIQMTQ SPSSLSASVG DRVTITCSAS SSVSYMNWYQ QTPGKAPKRW   180
IYDTSKLASG VPSRFSGSGS GTDYTFTISS LQPEDIATYY CQQWSSNPFT FGQGTKLQIT   240
RASPKSSDKT HTCPPCPAPE AAGGPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVYTLPP SREEMTKNQV SLSCAVKGFY PSDIAVEWES NGQPENNYKT   420
TPPVLDSDGS FFLVSKLTVD KSRWQQGNVF SCSVMHEALH NHYTQKSLSL SPGK         474

SEQ ID NO: 93           moltype = AA  length = 501
FEATURE                 Location/Qualifiers
source                  1..501
```

```
                        mol_type = protein
                        organism = synthetic construct
SEQUENCE: 93
SYELTQPPSV SVSPGQTARI TCSAGSGLYG WYQQKPGQAP VLVIYGTNKR PSGIPERFSG      60
SSSGTTVTLT ISGVQAEDEA DYYCGSADSS TNAGIFGGGT KLTVLGGGGS GGGGSGGGGS     120
EVQLLESGGG LVQPGGSLRL SCAASGFTFS SYAMNWVRQA PGKGLEWVAG ISSSGRYTGY     180
ADSVKGRFTI SRDNSKNTLY LQMNSLRAED TAVYYCAKSV GSGVSWSGYV ATSLDAWGQG     240
TLVTVSSGGG GSEVQLVESG GGLVQPGGSL KLSCAASGFT FNKYAMNWVR QAPGKGLEWV     300
ARIRSKYNNY ATYYADSVKD RFTISRDDSK NTAYLQMNNL KTEDTAVYYC VRHGNFGNSY     360
ISYWAYWGQG TLVTVSSGGG GSGGGGSGGG GSQTVVTQEP SLTVSPGGTV TLTCGSSTGA     420
VTSGNYPNWV QQKPGQAPRG LIGGTKFLAP GTPARFSGSL LGGKAALTLS GVQPEDEAEY     480
YCVLWYSNRW VFGGGTKLTV L                                               501

SEQ ID NO: 94           moltype = AA  length = 501
FEATURE                 Location/Qualifiers
source                  1..501
                        mol_type = protein
                        organism = synthetic construct
SEQUENCE: 94
SYELTQPPSV SVSPGQTARI TCSGGSGSYG WYQQKPGQAP VLVIYGTYKR PSGIPERFSG      60
SSSGTTVTLT ISGVQAEDEA DYYCGSADSS TNAGIFGGGT KLTVLGGGGS GGGGSGGGGS     120
EVQLLESGGG LVQPGGSLRL SCAASGFTFS SYAMNWVRQA PGKGLEWVAG ISSSGRYTGY     180
ADSVKGRFTI SRDNSKNTLY LQMNSLRAED TAVYYCAKSV GSGVSWSGYV ATSLDVWGQG     240
TLVTVSSGGG GSEVQLVESG GGLVQPGGSL KLSCAASGFT FNKYAMNWVR QAPGKGLEWV     300
ARIRSKYNNY ATYYADSVKD RFTISRDDSK NTAYLQMNNL KTEDTAVYYC VRHGNFGNSY     360
ISYWAYWGQG TLVTVSSGGG GSGGGGSGGG GSQTVVTQEP SLTVSPGGTV TLTCGSSTGA     420
VTSGNYPNWV QQKPGQAPRG LIGGTKFLAP GTPARFSGSL LGGKAALTLS GVQPEDEAEY     480
YCVLWYSNRW VFGGGTKLTV L                                               501

SEQ ID NO: 95           moltype = AA  length = 506
FEATURE                 Location/Qualifiers
source                  1..506
                        mol_type = protein
                        organism = synthetic construct
SEQUENCE: 95
SYELTQPPSV SVSPGQTARI TCSAGSGLYG WYQQKPGQAP VLVIYGTNKR PSGIPERFSG      60
SSSGTTVTLT ISGVQAEDEA DYYCGSADSS TNAGIFGGGT KLTVLGGGGS GGGGSGGGGS     120
EVQLLESGGG LVQPGGSLRL SCAASGFTFS SYAMNWVRQA PGKGLEWVAG ISSSGRYTGY     180
ADSVKGRFTI SRDNSKNTLY LQMNSLRAED TAVYYCAKSV GSGVSWSGYV ATSLDAWGQG     240
TLVTVSSGGG GSEVQLVESG GGLVQPGGSL RLSCAASGFT FSTYAMNWVR QAPGKGLEWV     300
GRIRSKYNNY ATYYADSVKG RFTISRDDSK NTLYLQMNSL RAEDTAVYYC VRHGNFGDSY     360
VSWFAYWGQG TLVTVSSGKP GSGKPGSGKP GSGKPGSQAV VTQEPSLTVS PGGTVTLTCG     420
SSTGAVTTSN YANWVQQKPG KSPRGLIGGT NKRAPGVPAR FSGSLLGGKA ALTISGAQPE     480
DEADYYCALW YSNHWVFGGG TKLTVL                                          506

SEQ ID NO: 96           moltype = AA  length = 506
FEATURE                 Location/Qualifiers
source                  1..506
                        mol_type = protein
                        organism = synthetic construct
SEQUENCE: 96
SYELTQPPSV SVSPGQTARI TCSGGSGSYG WYQQKPGQAP VLVIYGTYKR PSGIPERFSG      60
SSSGTTVTLT ISGVQAEDEA DYYCGSADSS TNAGIFGGGT KLTVLGGGGS GGGGSGGGGS     120
EVQLLESGGG LVQPGGSLRL SCAASGFTFS SYAMNWVRQA PGKGLEWVAG ISSSGRYTGY     180
ADSVKGRFTI SRDNSKNTLY LQMNSLRAED TAVYYCAKSV GSGVSWSGYV ATSLDVWGQG     240
TLVTVSSGGG GSEVQLVESG GGLVQPGGSL RLSCAASGFT FSTYAMNWVR QAPGKGLEWV     300
GRIRSKYNNY ATYYADSVKG RFTISRDDSK NTLYLQMNSL RAEDTAVYYC VRHGNFGDSY     360
VSWFAYWGQG TLVTVSSGKP GSGKPGSGKP GSGKPGSQAV VTQEPSLTVS PGGTVTLTCG     420
SSTGAVTTSN YANWVQQKPG KSPRGLIGGT NKRAPGVPAR FSGSLLGGKA ALTISGAQPE     480
DEADYYCALW YSNHWVFGGG TKLTVL                                          506

SEQ ID NO: 97           moltype = AA  length = 504
FEATURE                 Location/Qualifiers
source                  1..504
                        mol_type = protein
                        organism = synthetic construct
SEQUENCE: 97
SYELTQPPSV SVSPGQTARI TCSAGSGLYG WYQQKPGQAP VLVIYGTNKR PSGIPERFSG      60
SSSGTTVTLT ISGVQAEDEA DYYCGSADSS TNAGIFGGGT KLTVLGGGGS GGGGSGGGGS     120
EVQLLESGGG LVQPGGSLRL SCAASGFTFS SYAMNWVRQA PGKGLEWVAG ISSSGRYTGY     180
ADSVKGRFTI SRDNSKNTLY LQMNSLRAED TAVYYCAKSV GSGVSWSGYV ATSLDAWGQG     240
TLVTVSSGGG GSEVQLVESG GGLVQPGGSL RLSCAASGFT FNTYAMNWVR QAPGKGLEWV     300
ARIRSKYNNY ATYYADSVKS RTTISDDSKN TLYLQMNSLA EDTAVYYC RHGNFGNSYV       360
SWFAYWGQTT VTVSSGGGGS GGGGSGGGGS GGGGSEIVVT QSPATLSVSP GERATLSCRS     420
STGAVTTSNY ANWVQEPGQA FRGLIGGANK RAPGVPARFS GSLSGDEATL TISSLQSEDF     480
AVYYCALWYS NLWVFGQGTK LEIK                                            504

SEQ ID NO: 98           moltype = AA  length = 504
FEATURE                 Location/Qualifiers
```

```
source                      1..504
                            mol_type = protein
                            organism = synthetic construct
SEQUENCE: 98
SYELTQPPSV SVSPGQTARI TCSGGSGSYG WYQQKPGQAP VLVIYGTYKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSV GSGVSWSGYV ATSLDVWGQG   240
TLVTVSSGGG GSEVQLVESG GGLVQPGGSL RLSCAASGFT FNTYAMNWVR QAPGKGLEWV   300
ARIRSKYNNY ATYYADSVKS RTTISDDSKN TLYLQMNSLR AEDTAVYYCV RHGNFGNSYV   360
SWFAYWGQTT VTVSSGGGGS GGGGSGGGGS GGGGSEIVVT QSPATLSVSP GERATLSCRS   420
STGAVTTSNY ANWVQEPGQA FRGLIGGANK RAPGVPARFS GSLSGDEATL TISSLQSEDF   480
AVYYCALWYS NLWVFGQGTK LEIK                                         504

SEQ ID NO: 99               moltype = AA    length = 493
FEATURE                     Location/Qualifiers
source                      1..493
                            mol_type = protein
                            organism = synthetic construct
SEQUENCE: 99
SYELTQPPSV SVSPGQTARI TCSAGSGLYG WYQQKPGQAP VLVIYGTNKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSV GSGVSWSGYV ATSLDAWGQG   240
TLVTVSSGGG GSQVQLVQSG GGVVQPGRSL RLSCKASGYT FTRYTMHWVR QAPGKGLEWI   300
GYINPSRGYT NYNQKVKDRF TISTDKSKST AFLQMDSLRP EDTAVYYCAR YYDDHYCLDY   360
WGQGTTLTVS SGGGGSGGGG SGGGGSDIQM TQSPSSLSAS VGDRVTITCS ASSSVSYMNW   420
YQQTPGKAPK RWIYDTSKLA SGVPSRFSGS GSGTDYTFTI SSLQPEDIAT YYCQQWSSNP   480
FTFGQGTKLQ ITR                                                     493

SEQ ID NO: 100              moltype = AA    length = 493
FEATURE                     Location/Qualifiers
source                      1..493
                            mol_type = protein
                            organism = synthetic construct
SEQUENCE: 100
SYELTQPPSV SVSPGQTARI TCSGGSGSYG WYQQKPGQAP VLVIYGTYKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSV GSGVSWSGYV ATSLDVWGQG   240
TLVTVSSGGG GSQVQLVQSG GGVVQPGRSL RLSCKASGYT FTRYTMHWVR QAPGKGLEWI   300
GYINPSRGYT NYNQKVKDRF TISTDKSKST AFLQMDSLRP EDTAVYYCAR YYDDHYCLDY   360
WGQGTTLTVS SGGGGSGGGG SGGGGSDIQM TQSPSSLSAS VGDRVTITCS ASSSVSYMNW   420
YQQTPGKAPK RWIYDTSKLA SGVPSRFSGS GSGTDYTFTI SSLQPEDIAT YYCQQWSSNP   480
FTFGQGTKLQ ITR                                                     493

SEQ ID NO: 101              moltype = AA    length = 713
FEATURE                     Location/Qualifiers
source                      1..713
                            mol_type = protein
                            organism = synthetic construct
SEQUENCE: 101
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDAWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSQVQLVQSG   480
GGVVQPGRSL RLSCKASGYT FTRYTMHWVR QAPGKGLEWI GYINPSRGYT NYNQKVKDRF   540
TISTDKSKST AFLQMDSLRP EDTAVYYCAR YYDDHYCLDY WGQGTTLTVS SGGGGSGGGG   600
SGGGGSDIQM TQSPSSLSAS VGDRVTITCS ASSSVSYMNW YQQTPGKAPK RWIYDTSKLA   660
SGVPSRFSGS GSGTDYTFTI SSLQPEDIAT YYCQQWSSNP FTFGQGTKLQ ITR          713

SEQ ID NO: 102              moltype = AA    length = 713
FEATURE                     Location/Qualifiers
source                      1..713
                            mol_type = protein
                            organism = synthetic construct
SEQUENCE: 102
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSQVQLVQSG   480
```

```
GGVVQPGRSL RLSCKASGYT FTRYTMHWVR QAPGKGLEWI GYINPSRGYT NYNQKVKDRF   540
TISTDKSKST AFLQMDSLRP EDTAVYYCAR YYDDHYCLDY WGQGTTLTVS SGGGGSGGGG   600
SGGGGSDIQM TQSPSSLSAS VGDRVTITCS ASSSVSYMNW YQQTPGKAPK RWIYDTSKLA   660
SGVPSRFSGS GSGTDYTFTI SSLQPEDIAT YYCQQWSSNP FTFGQGTKLQ ITR          713

SEQ ID NO: 103              moltype = AA   length = 726
FEATURE                     Location/Qualifiers
source                      1..726
                            mol_type = protein
                            organism = synthetic construct
SEQUENCE: 103
EVQLLESGGG LVQPGGSLRL SCAASGFTFS SYAMNWVRQA PGKGLEWVAG ISSSGRYTGY   60
ADSVKGRFTI SRDNSKNTLY LQMNSLRAED TAVYYCAKSV GSGVSWSGYV ATSLDAWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
GGLVQPGGSL RLSCAASGFT FSTYAMNWVR QAPGKGLEWV GRIRSKYNNY ATYYADSVKG   540
RFTISRDDSK NTLYLQMNSL RAEDTAVYYC VRHGNFGDSY VSWFAYWGQG TLVTVSSGKP   600
GSGKPGSGKP GSGKPGSQAV VTQEPSLTVS PGGTVTLTCG SSTGAVTTSN YANWVQQKPG   660
KSPRGLIGGT NKRAPGVPAR FSGSLLGGKA ALTISGAQPE DEADYYCALW YSNHWVFGGG   720
TKLTVL                                                              726

SEQ ID NO: 104              moltype = AA   length = 726
FEATURE                     Location/Qualifiers
source                      1..726
                            mol_type = protein
                            organism = synthetic construct
SEQUENCE: 104
EVQLLESGGG LVQPGGSLRL SCAASGFTFS SYAMNWVRQA PGKGLEWVAG ISSSGRYTGY   60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
GGLVQPGGSL RLSCAASGFT FSTYAMNWVR QAPGKGLEWV GRIRSKYNNY ATYYADSVKG   540
RFTISRDDSK NTLYLQMNSL RAEDTAVYYC VRHGNFGDSY VSWFAYWGQG TLVTVSSGKP   600
GSGKPGSGKP GSGKPGSQAV VTQEPSLTVS PGGTVTLTCG SSTGAVTTSN YANWVQQKPG   660
KSPRGLIGGT NKRAPGVPAR FSGSLLGGKA ALTISGAQPE DEADYYCALW YSNHWVFGGG   720
TKLTVL                                                              726

SEQ ID NO: 105              moltype = AA   length = 724
FEATURE                     Location/Qualifiers
source                      1..724
                            mol_type = protein
                            organism = synthetic construct
SEQUENCE: 105
EVQLLESGGG LVQPGGSLRL SCAASGFTFS SYAMNWVRQA PGKGLEWVAG ISSSGRYTGY   60
ADSVKGRFTI SRDNSKNTLY LQMNSLRAED TAVYYCAKSV GSGVSWSGYV ATSLDAWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
GGLVQPGGSL RLSCAASGFT FNTYAMNWVR QAPGKGLEWV ARIRSKYNNY ATYYADSVKS   540
RTTISDDSKN TLYLQMNSLR AEDTAVYYCV RHGNFGNSYV SWFAYWGQTT VTVSSGGGGS   600
GGGGSGGGGS GGGGSEIVVT QSPATLSVSP GERATLSCRS STGAVTTSNY ANWVQEPGQA   660
FRGLIGGANK RAPGVPARFS GSLSGDEATL TISSLQSEDF AVYYCALWYS NLWVFGQGTK   720
LEIK                                                                724

SEQ ID NO: 106              moltype = AA   length = 724
FEATURE                     Location/Qualifiers
source                      1..724
                            mol_type = protein
                            organism = synthetic construct
SEQUENCE: 106
EVQLLESGGG LVQPGGSLRL SCAASGFTFS SYAMNWVRQA PGKGLEWVAG ISSSGRYTGY   60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
```

```
GGLVQPGGSL RLSCAASGFT FNTYAMNWVR QAPGKGLEWV ARIRSKYNNY ATYYADSVKS   540
RTTISDDSKN TLYLQMNSLR AEDTAVYYCV RHGNFGNSYV SWFAYWGQTT VTVSSGGGGS   600
GGGGSGGGGS GGGGSEIVVT QSPATLSVSP GERATLSCRS STGAVTTSNY ANWVQEPGQA   660
FRGLIGGANK RAPGVPARFS GSLSGDEATL TISSLQSEDF AVYYCALWYS NLWVFGQGTK   720
LEIK                                                                724

SEQ ID NO: 107            moltype = AA  length = 721
FEATURE                   Location/Qualifiers
source                    1..721
                          mol_type = protein
                          organism = synthetic construct
SEQUENCE: 107
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDAWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
GGLVQPGGSL KLSCAASGFT FNKYAMNWVR QAPGKGLEWV ARIRSKYNNY ATYYADSVKD   540
RFTISRDDSK NTAYLQMNNL KTEDTAVYYC VRHGNFGNSY ISYWAYWGQG TLVTVSSGGG   600
GSGGGGSGGG GSQTVVTQEP SLTVSPGGTV TLTCGSSTGA VTSGNYPNWV QQKPGQAPRG   660
LIGGTKFLAP GTPARFSGSL LGGKAALTLS GVQPEDEAEY YCVLWYSNRW VFGGGTKLTV   720
L                                                                  721

SEQ ID NO: 108            moltype = AA  length = 721
FEATURE                   Location/Qualifiers
source                    1..721
                          mol_type = protein
                          organism = synthetic construct
SEQUENCE: 108
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLVESG   480
GGLVQPGGSL KLSCAASGFT FNKYAMNWVR QAPGKGLEWV ARIRSKYNNY ATYYADSVKD   540
RFTISRDDSK NTAYLQMNNL KTEDTAVYYC VRHGNFGNSY ISYWAYWGQG TLVTVSSGGG   600
GSGGGGSGGG GSQTVVTQEP SLTVSPGGTV TLTCGSSTGA VTSGNYPNWV QQKPGQAPRG   660
LIGGTKFLAP GTPARFSGSL LGGKAALTLS GVQPEDEAEY YCVLWYSNRW VFGGGTKLTV   720
L                                                                  721

SEQ ID NO: 109            moltype = AA  length = 496
FEATURE                   Location/Qualifiers
source                    1..496
                          mol_type = protein
                          organism = synthetic construct
SEQUENCE: 109
SYELTQPPSV SVSPGQTARI TCSAGSGLYG WYQQKPGQAP VLVIYGTNKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSV GSGVSWSGYV ATSLDAWGQG   240
TLVTVSSGGG GSEVQLLESG GGLVQPGGSL RLSCAASGFS FTGYTMNWVR QAPGKGLEWM   300
GLINPYKGVS TYNQKVKGRF TISRDNSKNT LYLQMNSLRA EDTAVYYCAR SGYYGDSDWY   360
FDVWGQGTLV TVSSGGGGSG GGSGGGGSSD IQMTQSPSSL SASVGDRVTI TCRASQDIRN   420
YLNWYQQTPG KAPKRWIYYT SRLHSGVPSR FSGSGSGTDY TFTYSSLQPE DIATYYCQQG   480
NTLPWTFGQG TKLEIK                                                   496

SEQ ID NO: 110            moltype = AA  length = 496
FEATURE                   Location/Qualifiers
source                    1..496
                          mol_type = protein
                          organism = synthetic construct
SEQUENCE: 110
SYELTQPPSV SVSPGQTARI TCSGGSGSYG WYQQKPGQAP VLVIYGTYKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSV GSGVSWSGYV ATSLDVWGQG   240
TLVTVSSGGG GSEVQLLESG GGLVQPGGSL RLSCAASGFS FTGYTMNWVR QAPGKGLEWM   300
GLINPYKGVS TYNQKVKGRF TISRDNSKNT LYLQMNSLRA EDTAVYYCAR SGYYGDSDWY   360
FDVWGQGTLV TVSSGGGGSG GGSGGGGSSD IQMTQSPSSL SASVGDRVTI TCRASQDIRN   420
YLNWYQQTPG KAPKRWIYYT SRLHSGVPSR FSGSGSGTDY TFTYSSLQPE DIATYYCQQG   480
NTLPWTFGQG TKLEIK                                                   496

SEQ ID NO: 111            moltype = AA  length = 477
```

```
FEATURE                 Location/Qualifiers
source                  1..477
                        mol_type = protein
                        organism = synthetic construct
SEQUENCE: 111
EVQLLESGGG LVQPGGSLRL SCAASGFSFT GYTMNWVRQA PGKGLEWMGL INPYKGVSTY    60
NQKVKGRFTI SRDNSKNTLY LQMNSLRAED TAVYYCARSG YYGDSDWYFD VWGQGTLVTV   120
SSGGGGSGGG GSGGGGSDIQ MTQSPSSLSA SVGDRVTITC RASQDIRNYL NWYQQTPGKA   180
PKRWIYYTSR LHSGVPSRFS GSGSGTDYTF TYSSLQPEDI ATYYCQQGNT LPWTFGQGTK   240
LEIKASPKSS DKTHTCPPCP APEAAGGPSV FLFPPKPKDT LMISRTPEVT CVVVDVSHED   300
PEVKFNWYVD GVEVHNAKTK PREEQYNSTY RVVSVLTVLH QDWLNGKEYK CKVSNKALPA   360
PIEKTISKAK GQPREPQVYT LPPSREEMTK NQVSLSCAVK GFYPSDIAVE WESNGQPENN   420
YKTTPPVLDS DGSFFLVSKL TVDKSRWQQG NVFSCSVMHE ALHNHYTQKS LSLSPGK     477

SEQ ID NO: 112          moltype = AA  length = 716
FEATURE                 Location/Qualifiers
source                  1..716
                        mol_type = protein
                        organism = synthetic construct
SEQUENCE: 112
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDAWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLLESG   480
GGLVQPGGSL RLSCAASGFS FTGYTMNWVR QAPGKGLEWM GLINPYKGVS TYNQKVKGRF   540
TISRDNSKNT LYLQMNSLRA EDTAVYYCAR SGYYGDSDWY FDVWGQGTLV TVSSGGGGSG   600
GGGSGGGGSD IQMTQSPSSL SASVGDRVTI TCRASQDIRN YLNWYQQTPG KAPKRWIYYT   660
SRLHSGVPSR FSGSGSGTDY TFTYSSLQPE DIATYYCQQG NTLPWTFGQG TKLEIK      716

SEQ ID NO: 113          moltype = AA  length = 716
FEATURE                 Location/Qualifiers
source                  1..716
                        mol_type = protein
                        organism = synthetic construct
SEQUENCE: 113
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSV GSGVSWSGYV ATSLDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGKGGG GSGGGGTGGG GSEVQLLESG   480
GGLVQPGGSL RLSCAASGFS FTGYTMNWVR QAPGKGLEWM GLINPYKGVS TYNQKVKGRF   540
TISRDNSKNT LYLQMNSLRA EDTAVYYCAR SGYYGDSDWY FDVWGQGTLV TVSSGGGGSG   600
GGGSGGGGSD IQMTQSPSSL SASVGDRVTI TCRASQDIRN YLNWYQQTPG KAPKRWIYYT   660
SRLHSGVPSR FSGSGSGTDY TFTYSSLQPE DIATYYCQQG NTLPWTFGQG TKLEIK      716

SEQ ID NO: 114          moltype = AA  length = 457
FEATURE                 Location/Qualifiers
source                  1..457
                        mol_type = protein
                        organism = synthetic construct
SEQUENCE: 114
EVQLLESGGG LVQPGGSLRL SCAASGFTFS SYAMNWVRQA PGKGLEWVAG ISSSGRYTGY    60
ADSVKGRFTI SRDNSKNTLY LQMNSLRAED TAVYYCAKSM GSGVSWSGYV ATSIDVWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APEAAGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLWCLVK GFYPSDIAVE WESNGQPENN YKTTPPVLDS DGSFFLYSKL   420
TVDKSRWQQG NVFSCSVMHE ALHNHYTQKS LSLSPGK                           457

SEQ ID NO: 115          moltype = AA  length = 495
FEATURE                 Location/Qualifiers
source                  1..495
                        mol_type = protein
                        organism = synthetic construct
SEQUENCE: 115
SYELTQPPSV SVSPGQTARI TCSAGSGLYG WYQQKPGQAP VLVIYGTNKR PSGIPERFSG    60
SSSGTTVTLT ISGVQAEDEA DYYCGSADSS TNAGIFGGGT KLTVLGGGGS GGGGSGGGGS   120
EVQLLESGGG LVQPGGSLRL SCAASGFTFS SYAMNWVRQA PGKGLEWVAG ISSSGRYTGY   180
ADSVKGRFTI SRDNSKNTLY LQMNSLRAED TAVYYCAKSM GSGVSWSGYV ATSIDVWGQG   240
TLVTVSSGGG GSDIKLQQSG AELARPGASV KMSCKTSGYT FTRYTMHWVK QRPGQGLEWI   300
GYINPSRGYT NYNQKFKDKA TLTTDKSSST AYMQLSSLTS EDSAVYYCAR YYDDHYCLDY   360
```

```
WGQGTTLTVS SVEGGSGGSG GSGGSGGVDD IQLTQSPAIM SASPGEKVTM TCRASSSVSY  420
MNWYQQKSGT SPKRWIYDTS KVASGVPYRF SGSGSGTSYS LTISSMEAED AATYYCQQWS  480
SNPLTFGAGT KLELK                                                  495

SEQ ID NO: 116          moltype = AA  length = 596
FEATURE                 Location/Qualifiers
source                  1..596
                        mol_type = protein
                        organism = synthetic construct
SEQUENCE: 116
EVQLVESGGG PVQAGGSLRL SCAASGRTYR GYSMGWFRQA PGKEREFVAA IVWSGGNTYY  60
EDSVKGRFTI SRDNAKNTMY LQMTSLKPED SATYYCAAKI RPYIFKIAGQ YDYWGQGTQV  120
TVSSGGGGSG GGGSGGGGSE VQLLESGGGL VQPGGSLRLS CAASGFTFSS YAMNWVRQAP  180
GKGLEWVAGI SSSGRYTGYA DSVKGRFTIS RDNSKNTLYL QMNSLRAEDT AVYYCAKSMG  240
SGVSWSGYVA TSIDVWGQGT LVTVSSASTK GPSVFPLAPS SKSTSGGTAA LGCLVKDYFP  300
EPVTVSWNSG ALTSGVHTFP AVLQSSGLYS LSSVVTVPSS SLGTQTYICN VNHKPSNTKV  360
DKKVEPKSCD KTHTCPPCPA PEAAGGPSVF LFPPKPKDTL MISRTPEVTC VVVDVSHEDP  420
EVKFNWYVDG VEVHNAKTKP REEQYNSTYR VVSVLTVLHQ DWLNGKEYKC KVSNKALPAP  480
IEKTISKAKG QPREPQVYTL PPSREEMTKN QVSLSCAVKG FYPSDIAVEW ESNGQPENNY  540
KTTPPVLDSD GSFFLVSKLT VDKSRWQQGN VFSCSVMHEA LHNHYTQKSL SLSPGK     596

SEQ ID NO: 117          moltype = AA  length = 596
FEATURE                 Location/Qualifiers
source                  1..596
                        mol_type = protein
                        organism = synthetic construct
SEQUENCE: 117
EVQLLESGGG LVQPGGSLRL SCAASGFTFS SYAMNWVRQA PGKGLEWVAG ISSSGRYTGY  60
ADSVKGRFTI SRDNSKNTLY LQMNSLRAED TAVYYCAKSV GSGVSWSGYV ATSLDAWGQG  120
TLVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APEAAGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLSCAVK GFYPSDIAVE WESNGQPENN YKTTPPVLDS DGSFFLVSKL  420
TVDKSRWQQG NVFSCSVMHE ALHNHYTQKS LSLSPGKGGG GSGGGGTGGG GSEVQLVESG  480
GGPVQAGGSL RLSCAASGRT YRGYSMGWFR QAPGKEREFV AAIVWSGGNT YYEDSVKGRF  540
TISRDNAKNT MYLQMTSLKP EDSATYYCAA KIRPYIFKIA GQYDYWGQGT QVTVSS     596

SEQ ID NO: 118          moltype = AA  length = 596
FEATURE                 Location/Qualifiers
source                  1..596
                        mol_type = protein
                        organism = synthetic construct
SEQUENCE: 118
EVQLVESGGG PVQAGGSLRL SCAASGRTYR GYSMGWFRQA PGKEREFVAA IVWSGGNTYY  60
EDSVKGRFTI SRDNAKNTMY LQMTSLKPED SATYYCAAKI RPYIFKIAGQ YDYWGQGTQV  120
TVSSGGGGSG GGTGGGGSE VQLLESGGGL VQPGGSLRLS CAASGFTFSS YAMNWVRQAP  180
GKGLEWVAGI SSSGRYTGYA DSVKGRFTIS RDNSKNTLYL QMNSLRAEDT AVYYCAKSVG  240
SGVSWSGYVA TSLDAWGQGT LVTVSSASTK GPSVFPLAPS SKSTSGGTAA LGCLVKDYFP  300
EPVTVSWNSG ALTSGVHTFP AVLQSSGLYS LSSVVTVPSS SLGTQTYICN VNHKPSNTKV  360
DKKVEPKSCD KTHTCPPCPA PEAAGGPSVF LFPPKPKDTL MISRTPEVTC VVVDVSHEDP  420
EVKFNWYVDG VEVHNAKTKP REEQYNSTYR VVSVLTVLHQ DWLNGKEYKC KVSNKALPAP  480
IEKTISKAKG QPREPQVYTL PPSREEMTKN QVSLSCAVKG FYPSDIAVEW ESNGQPENNY  540
KTTPPVLDSD GSFFLVSKLT VDKSRWQQGN VFSCSVMHEA LHNHYTQKSL SLSPGK     596

SEQ ID NO: 119          moltype = AA  length = 596
FEATURE                 Location/Qualifiers
source                  1..596
                        mol_type = protein
                        organism = synthetic construct
SEQUENCE: 119
EVQLLESGGG LVQPGGSLRL SCAASGFTFS SYAMNWVRQA PGKGLEWVAG ISSSGRYTGY  60
ADSVKGRFTI SRDNSKNTLY LQMNSLRAED TAVYYCAKSV GSGVSWSGYV ATSLDVWGQG  120
TLVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APEAAGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLSCAVK GFYPSDIAVE WESNGQPENN YKTTPPVLDS DGSFFLVSKL  420
TVDKSRWQQG NVFSCSVMHE ALHNHYTQKS LSLSPGKGGG GSGGGGTGGG GSEVQLVESG  480
GGPVQAGGSL RLSCAASGRT YRGYSMGWFR QAPGKEREFV AAIVWSGGNT YYEDSVKGRF  540
TISRDNAKNT MYLQMTSLKP EDSATYYCAA KIRPYIFKIA GQYDYWGQGT QVTVSS     596

SEQ ID NO: 120          moltype = AA  length = 596
FEATURE                 Location/Qualifiers
source                  1..596
                        mol_type = protein
                        organism = synthetic construct
SEQUENCE: 120
EVQLVESGGG PVQAGGSLRL SCAASGRTYR GYSMGWFRQA PGKEREFVAA IVWSGGNTYY  60
```

```
EDSVKGRFTI SRDNAKNTMY LQMTSLKPED SATYYCAAKI RPYIFKIAGQ YDYWGQGTQV  120
TVSSGGGGSG GGGTGGGGSE VQLLESGGGL VQPGGSLRLS CAASGFTFSS YAMNWVRQAP  180
GKGLEWVAGI SSSGRYTGYA DSVKGRFTIS RDNSKNTLYL QMNSLRAEDT AVYYCAKSVG  240
SGVSWSGYVA TSLDVWGQGT LVTVSSASTK GPSVFPLAPS SKSTSGGTAA LGCLVKDYFP  300
EPVTVSWNSG ALTSGVHTFP AVLQSSGLYS LSSVVTVPSS SLGTQTYICN VNHKPSNTKV  360
DKKVEPKSCD KTHTCPPCPA PEAAGGPSVF LFPPKPKDTL MISRTPEVTC VVVDVSHEDP  420
EVKFNWYVDG VEVHNAKTKP REEQYNSTYR VVSVLTVLHQ DWLNGKEYKC KVSNKALPAP  480
IEKTISKAKG QPREPQVYTL PPSREEMTKN QVSLSCAVKG FYPSDIAVEW ESNGQPENNY  540
KTTPPVLDSD GSFFLVSKLT VDKSRWQQGN VFSCSVMHEA LHNHYTQKSL SLSPGK      596

SEQ ID NO: 121          moltype = AA  length = 455
FEATURE                 Location/Qualifiers
source                  1..455
                        mol_type = protein
                        organism = synthetic construct
SEQUENCE: 121
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLSCAVKGF YPSDIAVEWE SNGQPENNYK TTPPVLDSDG SFFLVSKLTV  420
DKSRWQQGNV FSCSVMHEAL HNHYTQKSLS LSPGK                             455

SEQ ID NO: 122          moltype = AA  length = 215
FEATURE                 Location/Qualifiers
source                  1..215
                        mol_type = protein
                        organism = synthetic construct
SEQUENCE: 122
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 123          moltype = AA  length = 453
FEATURE                 Location/Qualifiers
source                  1..453
                        mol_type = protein
                        organism = synthetic construct
SEQUENCE: 123
EVQLVESGGG LVQPGGSLRL SCAASGFTFN TYAMNWVRQA PGKGLEWVAR IRSKYNNYAT   60
YYADSVKSRT TISDDSKNTL YLQMNSLRAE DTAVYYCVRH GNFGNSYVSW FAYWGQTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LSCAVKGFYP SDIAVEWESN GQPENNYKTT PPVLDSDGSF FLVSKLTVDK  420
SRWQQGNVFS CSVMHEALHN HYTQKSLSLS PGK                               453

SEQ ID NO: 124          moltype = AA  length = 215
FEATURE                 Location/Qualifiers
source                  1..215
                        mol_type = protein
                        organism = synthetic construct
SEQUENCE: 124
EIVVTQSPAT LSVSPGERAT LSCRSSTGAV TTSNYANWVQ EPGQAFRGLI GGANKRAPGV   60
PARFSGSLSG DEATLTISSL QSEDFAVYYC ALWYSNLWVF GQGTKLEIKT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 125          moltype = AA  length = 455
FEATURE                 Location/Qualifiers
source                  1..455
                        mol_type = protein
                        organism = synthetic construct
SEQUENCE: 125
EVQLVESGGG LVQPGGSLKL SCAASGFTFN KYAMNWVRQA PGKGLEWVAR IRSKYNNYAT   60
YYADSVKDRF TISRDDSKNT AYLQMNNLKT EDTAVYYCVR HGNFGNSYIS YWAYWGQGTL  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSREEMTKNQ VSLSCAVKGF YPSDIAVEWE SNGQPENNYK TTPPVLDSDG SFFLVSKLTV  420
DKSRWQQGNV FSCSVMHEAL HNHYTQKSLS LSPGK                             455

SEQ ID NO: 126          moltype = AA  length = 216
FEATURE                 Location/Qualifiers
```

```
source                  1..216
                        mol_type = protein
                        organism = synthetic construct
SEQUENCE: 126
EQTVVTQEPS LTVSPGGTVT LTCGSSTGAV TSGNYPNWVQ QKPGQAPRGL IGGTKFLAPG    60
TPARFSGSLL GGKAALTLSG VQPEDEAEYY CVLWYSNRWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 127          moltype = AA  length = 449
FEATURE                 Location/Qualifiers
source                  1..449
                        mol_type = protein
                        organism = synthetic construct
SEQUENCE: 127
QVQLVQSGGG VVQPGRSLRL SCKASGYTFT RYTMHWVRQA PGKGLEWIGY INPSRGYTNY    60
NQKVKDRFTI STDKSKSTAF LQMDSLRPED TAVYYCARYY DDHYCLDYWG QGTTLTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPGK                                    449

SEQ ID NO: 128          moltype = AA  length = 214
FEATURE                 Location/Qualifiers
source                  1..214
                        mol_type = protein
                        organism = synthetic construct
SEQUENCE: 128
DIQMTQSPSS LSASVGDRVT ITCSASSSVS YMNWYQQTPG KAPKRWIYDT SKLASGVPSR    60
FSGSGSGTDY TFTISSLQPE DIATYYCQQW SSNPFTFGQG TKLQITRRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 129          moltype = AA  length = 452
FEATURE                 Location/Qualifiers
source                  1..452
                        mol_type = protein
                        organism = synthetic construct
SEQUENCE: 129
EVQLLESGGG LVQPGGSLRL SCAASGFSFT GYTMNWVRQA PGKGLEWMGL INPYKGVSTY    60
NQKVKGRFTI SRDNSKNTLY LQMNSLRAED TAVYYCARSG YYGDSDWYFD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL SCAVKGFYPS DIAVEWESNG QPENNYKTTP PVLDSDGSFF LVSKLTVDKS   420
RWQQGNVFSC SVMHEALHNH YTQKSLSLSP GK                                452

SEQ ID NO: 130          moltype = AA  length = 213
FEATURE                 Location/Qualifiers
source                  1..213
                        mol_type = protein
                        organism = synthetic construct
SEQUENCE: 130
DIQMTQSPSS LSASVGDRVT ITCRASQDIR NYLNWYQQTP GKAPKRWIYY TSRLHSGVPS    60
RFSGSGSGTD YTFTYSSLQP EDIATYYCQQ GNTLPWTFGQ GTKLEIKTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                               213

SEQ ID NO: 131          moltype =    length =
SEQUENCE: 131
000
```

ANTIBODIES DIRECTED TO CLAUDIN 6, INCLUDING BISPECIFIC FORMATS THEREOF

CROSS REFERENCE TO RELATED APPLICATIONS

This application claims the benefit of U.S. Provisional Application No. 63/385,535 filed Nov. 30, 2022, U.S. Provisional Application No. 63/496,174 filed Apr. 14, 2023, U.S. Provisional Application No. 63/506,533 filed Jun. 6, 2023, U.S. Provisional Application No. 63/517,668 filed Aug. 4, 2023, and U.S. Provisional Application No. 63/591,924 filed Oct. 20, 2023, the contents of each of which are hereby incorporated by reference in their entirety.

SEQUENCE LISTING SUBMISSION VIA EFS-WEB

The instant application contains a sequence listing, which has been submitted in XML format via EFS-Web. The contents of the XML copy named "INM-001US_122086-5001 Sequence Listing", which was created on Nov. 29, 2023 and is 142,000 bytes in size, the contents of which are incorporated herein by reference in their entirety.

FIELD OF THE DISCLOSURE

The disclosure is directed to compositions that bind Claudin 6, and related methods.

BACKGROUND

Cell adhesion proteins are critical for maintaining tissue integrity, as well as regulating diverse cellular events in a wide variety of physiological and pathological processes. Among cell adhesion proteins, some members of the claudin (CLDN) family are often aberrantly expressed in various cancers. Clinical application of CLDN therapeutics has been difficult because of lack of antibody specificity for particular CLDN proteins and widespread expression of closely related CLDN family members in normal cells. Thus, there remains a significant need for improved compositions and methods that can modulate the activity of CLDN family members to treat various cancers and diseases.

SUMMARY

Accordingly, in various aspects, the present disclosure relates to a composition that specifically binds to claudin 6 and CD3. The present disclosure describes the isolation and characterization of antibodies, antibody fragments, and antibody variants specific for claudin 6 and CD3. In some embodiments, the antibody specific for claudin 6 and CD3 is a tandem single-chain variable fragment (scFv). In some embodiments, the antibody specific for claudin 6 and CD3 is a scFv-Fab Fc antibody specific for claudin 6 and CD3. In some embodiments, the antibody specific for claudin 6 and CD3 is an IgG-(scFv)$_2$ antibody specific for claudin 6 and CD3. In some embodiments, the antibody specific for claudin 6 and CD3 is a scFv-Fab Fc specific for claudin 6 and CD3. In some embodiments, the antibody specific for claudin 6 and CD3 binds claudin 6 and CD3 contemporaneously.

In some embodiments, disclosed herein is a composition comprising a scFv-Fab Fc antibody specific for claudin 6 and CD3 comprising:

(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or
(ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof,
(b) a second heavy chain selected from:
(i.) SEQ ID NO: 80,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or
(ii.) SEQ ID NO: 89,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or
a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, or
(iii.) SEQ ID NO: 90,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or
a heavy chain variable region comprising heavy chain CDR1, CDR2, and CDR3 sequences, wherein the heavy chain CDR1 comprises an amino acid sequence of SEQ ID NO: 48, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, or
(iv.) SEQ ID NO: 91,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of ID NO: 21, or a variant thereof, or
a heavy chain variable region comprising heavy chain CDR1, CDR2, and CDR3 sequences, wherein the heavy chain CDR1 comprises an amino acid sequence of SEQ ID NO: 49, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, or
(v.) SEQ ID NO: 92,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or
a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, or
(vi.) SEQ ID NO: 111,
an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or
a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof,
and
(c) a first light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of ID NO: 3, or a variant thereof,
or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or
wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.
In some embodiments, the Fc is from IgG.
In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are selected from:
(a) T366Y and Y407T or T366Y/F405A and T394W/Y407T in human IgG1, or
(b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V, in human IgG1.

In some embodiments, the human IgG Fc comprises one or mutations to reduce or eliminate the effector function of the Fc domains. In some embodiments, the mutations are L234A and L235A (LALA) substitutions in human IgG1.

In some embodiments, the human IgG Fc comprises one or mutations to stabilize a hinge region in the Fc domain. In some embodiments, the mutation is S228P.

In some embodiments, disclosed herein is a composition comprising a scFv-Fab Fc antibody specific for claudin 6 and CD3 comprising:
(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof, (b) a second heavy chain selected from:
SEQ ID NO: 81,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
and
(c) a light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or
wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, mutations are:

(a) T366Y and Y407T or T366Y/F405A and T394W/ Y407T in human IgG1 or
(b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V, in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, mutation is S228P.

In some embodiments, disclosed herein is a composition comprising a scFv-Fab Fc antibody specific for claudin 6 and CD3 comprising:

(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof, (b) a second heavy chain selected from:
(i.) SEQ ID NO: 117,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
(ii.) SEQ ID NO: 119,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
(iii.) SEQ ID NO: 118,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(iv.) SEQ ID NO: 120,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, and (c) a light chain selected from:

(i) SEQ ID NO: 67, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66 an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are:

(a) T366Y and Y407T or T366Y/F405A and T394W/Y407T in human IgG1 or (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V, in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, the mutation is S228P.

In some embodiments, disclosed herein is a composition comprising a scFv-Fab Fc antibody specific for claudin 6 and CD3 comprising:

(a) a first heavy chain selected from:

(i) SEQ ID NO: 79, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or (ii) SEQ ID NO: 88, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or (iii) SEQ ID NO: 114, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof, (b) a second heavy chain selected from:

(i) SEQ ID NO: 121, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, (ii) SEQ ID NO: 123, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, (iii) SEQ ID NO: 125, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, (iv) SEQ ID NO: 127, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or (v) SEQ ID NO: 129, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, and (c) a first light chain selected from:

(i) SEQ ID NO: 67, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, and (d) a second light chain selected from:

(i) SEQ ID NO: 122, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 28, or a variant thereof, the light chain CDR2 comprises an amino acid sequence of SEQ ID NO: 29, or a variant thereof, and the light chain CDR3 comprises an amino acid sequence of SEQ ID NO: 30, or a variant thereof, or (ii) SEQ ID NO: 124, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 33, or a variant thereof, the light chain CDR2 comprises an amino acid sequence of SEQ ID NO: 34, or a variant thereof, and the light chain CDR3 comprises an amino acid sequence of SEQ ID NO: 35, or a variant thereof, or (iii) SEQ ID NO: 126, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of ID NO: 22, or a variant thereof, the light chain CDR2 comprises an amino acid sequence of SEQ ID NO: 23, or a variant thereof, and the light chain CDR3 comprises an amino acid sequence of SEQ ID NO: 24, or a variant thereof, or (iv) SEQ ID NO: 128,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 37, or a variant thereof, the light chain CDR2 comprises an amino acid sequence of SEQ ID NO: 38, or a variant thereof, and the light chain CDR3 comprises an amino acid sequence of SEQ ID NO: 39, or a variant thereof, or
(v) SEQ ID NO: 130,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 43, or a variant thereof, the light chain CDR2 comprises an amino acid sequence of SEQ ID NO: 44, or a variant thereof, and the light chain CDR3 comprises an amino acid sequence of SEQ ID NO: 45, or a variant thereof, or
wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

In some embodiments, disclosed herein is a bispecific antibody, wherein the bispecific antibody comprises three polypeptides (e.g., a first polypeptide, a second polypeptide, and a third polypeptide) that form a first antigen binding domain that binds to CLDN6, and a second antigen binding domain that binds to CD3. In some embodiments, the first polypeptide comprises a first light chain comprising a first variable light chain region (first $V_L$), wherein the first variable light chain region comprises a CDR1 sequence comprising the amino acid sequence of SEQ ID NO: 1, a CDR2 sequence comprising the amino acid sequence of SEQ ID NO: 2, and a CDR3 sequence comprising the amino acid sequence of SEQ ID NO: 3. In some embodiments, the second polypeptide comprises a first heavy chain comprising a first variable region heavy chain region (first $V_H$), wherein the first variable heavy chain region comprises a CDR1 sequence comprising the amino acid sequence of SEQ ID NO: 4, a CDR2 sequence comprising the amino acid sequence of SEQ ID NO: 5, and a CDR3 sequence comprising the amino acid sequence of SEQ ID NO: 6. In some embodiments, the third polypeptide comprises a second heavy chain and a second a light chain, wherein the second heavy chain comprises a second variable heavy chain region (second $V_H$) comprising a CDR1 sequence comprising the amino acid sequence of SEQ ID NO: 25, a CDR2 sequence comprising the amino acid sequence of SEQ ID NO: 26, and a CDR3 sequence comprising the amino acid sequence of SEQ ID NO: 27; wherein the second light chain comprises a second variable light chain region (second $V_L$) comprising a CDR1 sequence comprising the amino sequence of SEQ ID NO: 28, a CDR2 sequence comprising the amino acid sequence of SEQ ID NO: 29, and a CDR3 sequence comprising the amino acid sequence of SEQ ID NO: 30. In some embodiments, the second heavy chain and the second light chain are linked by a peptide linker. In some embodiments, the peptide linker is as described herein. In some embodiments, the peptide linker comprises the amino acid sequence of (GKPGSGKPGSGKPGSGKPGS) SEQ ID NO: 53. In some embodiments, the peptide linker comprising one or more glycines and serines is replaced with another peptide linker or functionally equivalent variation thereof. In some embodiments, the first $V_L$ and the first $V_H$ interact to form the antigen binding domain that binds to CLDN6. In some embodiments, the second VI, and the second Vu interact to form the antigen binding domain that binds to CD3. In some embodiments, the second VI, and the second VI are in a scFv format. In some embodiments, the first $V_L$ and the first $V_H$ are in a Fab format, or a fragment thereof.

In some embodiments, the first variable light chain region of the first polypeptide comprises the amino acid sequence of SEQ ID NO: 68, or an amino acid sequence having at least about 90%, or about 93%, or about 95%, or about 97%, or about 98%, or about 99% identity thereto.

In some embodiments, the first variable heavy chain region of the second polypeptide comprises the amino acid sequence of SEQ ID NO: 69, or an amino acid sequence having at least about 90%, or about 93%, or about 95%, or about 97%, or about 98%, or about 99% identity thereto.

In some embodiments, the second variable heavy chain region of the third polypeptide comprises the amino acid sequence of SEQ ID NO: 70, or an amino acid sequence having at least about 90%, or about 93%, or about 95%, or about 97%, or about 98%, or about 99% identity thereto.

In some embodiments, the second variable light chain region of the third polypeptide comprises the amino acid sequence of SEQ ID NO: 71, or an amino acid sequence having at least about 90%, or about 93%, or about 95%, or about 97%, or about 98%, or about 99% identity thereto.

In some embodiments, the first polypeptide compromising the light chain comprises the first variable light chain region and a light chain constant domain, which can be referred to as the first light chain constant domain. In some embodiments, the first light chain constant domain comprises the amino acid sequence of SEQ ID NO: 72, or an amino acid sequence having at least about 90%, or about 93%, or about 95%, or about 97%, or about 98%, or about 99% identity thereto.

In some embodiments, the first polypeptide comprises the amino acid sequence of SEQ ID NO: 67, or an amino acid sequence having at least about 90%, or about 93%, or about 95%, or about 97%, or about 98%, or about 99% identity thereto.

In some embodiments, the second polypeptide compromising the first heavy chain comprises the first variable heavy chain region and a heavy chain constant domain, which can be referred to as the first heavy chain constant domain. In some embodiments, the first heavy chain constant domain comprises the amino acid sequence of SEQ ID NO: 73, or an amino acid sequence having at least about 90%, or about 93%, or about 95%, or about 97%, or about 98%, or about 99% identity thereto.

In some embodiments, the second polypeptide comprises the amino acid sequence of SEQ ID NO: 79, or an amino acid sequence having at least about 90%, or about 93%, or about 95%, or about 97%, or about 98%, or about 99% identity thereto.

In some embodiments, the third polypeptide comprises a constant domain. In some embodiments, the constant domain is linked to the C-terminus of the second variable light chain region. In some embodiments, there is no peptide linker between the C-terminus of the second variable light chain region and the constant domain. In some embodiments, the constant domain present in the third polypeptide comprises the amino acid sequence of SEQ ID NO: 74, or an amino acid sequence having at least about 90%, or about 93%, or about 95%, or about 97%, or about 98%, or about 99% identity thereto.

In some embodiments, the third polypeptide comprises the amino acid sequence of SEQ ID NO: 89, or an amino acid sequence having at least about 90%, or about 93%, or about 95%, or about 97%, or about 98%, or about 99% identity thereto.

In some embodiments, the first polypeptide comprises the amino acid sequence of SEQ ID NO: 67; the second polypeptide comprises the amino acid sequence of SEQ ID NO: 79; and the third polypeptide comprises the amino acid sequence of SEQ ID NO: 89.

As used herein, the term constant domain refers to the Fc domain. The constant domains exemplified above are optional embodiments and other constant domains can be substituted for the constant domains described herein.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are:

(a) T366Y and Y407T or T366Y/F405A and T394W/Y407T in human IgG1 or (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V, in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, the mutation is S228P.

In some embodiments, the composition binds claudin 6 and CD3 contemporaneously.

In some embodiments, the composition binds claudin 6 with an affinity of less than 10 nM and with at least 100 fold greater affinity than claudin 9, claudin 3, and/or claudin 4.

In some embodiments, disclosed herein is a pharmaceutical composition comprising an isolated antibody of any one of the preceding embodiments, or a nucleic acid molecule encoding the same. In some embodiments, the composition is an injectable pharmaceutical composition. In some embodiments, the composition is sterile. In some embodiments, the composition is pyrogen free.

In some embodiments, disclosed herein is a nucleic acid molecule encoding an antibody or an amino acid sequence of any of the preceding embodiments.

In some embodiments, disclosed herein is a vector comprising the nucleic acid molecule of any of the preceding embodiments.

In some embodiments, disclosed herein is a cell comprising the nucleic acid molecule of any of the preceding embodiments, or the vector of any of the preceding embodiments.

In some embodiments, disclosed herein is a method for modulating and/or targeting claudin 6 and CD3 in a biological cell, comprising contacting the cell with a composition of any of the preceding embodiments.

In some embodiments, disclosed herein is a method for modulating claudin 6 activity in a biological cell comprising contacting a cell expressing claudin 6 with a composition of any of the preceding embodiments.

In some embodiments, disclosed herein is a method for inhibiting the function of claudin 6 in a biological cell comprising contacting a cell expressing claudin 6 with a composition of any of the preceding embodiments.

In some embodiments, disclosed herein is a method for treating or preventing cancer comprising administering an effective amount of the composition of any of the preceding embodiments to a subject in need thereof.

In some embodiments, disclosed herein is a use of the composition of any of the preceding embodiments for the preparation of a medicament for the treatment of prevention of cancer.

In some embodiments, disclosed herein is a method or use of any one of the preceding embodiments, wherein the cancer is selected form one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer: esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; lymphoma including Hodgkin's and non-Hodgkin's lymphoma, as well as B-cell lymphoma (including low grade/follicular non-Hodgkin's lymphoma (NHL): small lymphocytic (SL) NHL; intermediate grade/follicular NHL: intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses; edema (e.g. that associated with brain tumors); and Meigs' syndrome.

In some embodiments, disclosed herein is an isolated antibody comprising one or more of the sequences disclosed herein.

The details of one or more examples of the disclosure are set forth in the description below: Other features or advantages of the present disclosure will be apparent from the following drawings, detailed description of several examples, and also from the appended claims. The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

BRIEF DESCRIPTION OF THE DRAWINGS

FIG. 5 is a chart showing an overview of the data related to the four selected antibodies.

FIG. 11A, FIG. 11B, FIG. 11C, and FIG. 11D are graphs showing parental and benchmark antibody binding data from flow cytometry experiments. FIG. 11A is a graph showing binding of IM271-1HEP antibody to human CLDN6 (circle shapes), human CLDN4 (square shapes), human CLDN3 (triangle shapes), human CLDN9 (inverted triangle shapes), and a negative control (diamond shapes). FIG. 11B is a graph showing binding of IM271-1HHP antibody to human CLDN6 (circle shapes), human CLDN4 (square shapes), human CLDN3 (triangle shapes), human CLDN9 (inverted triangle shapes), and a negative control (diamond shapes). FIG. 11C is a graph showing binding of IM271-1HFJ antibody to human CLDN6 (circle shapes), human CLDN4 (square shapes), human CLDN3 (triangle shapes), human CLDN9 (inverted triangle shapes), and a negative control (diamond shapes). FIG. 11D is a graph showing binding of an antibody to human CLDN6 (circle shapes), human CLDN4 (square shapes), human CLDN3 (triangle shapes), human CLDN9 (inverted triangle shapes), and a negative control (diamond shapes).

FIG. 12A is a graph showing binding of the IMC-2-7 tandem scFv antibody to human CLDN6 (circle shapes), human CLDN4 (square shapes), human CLDN3 (triangle shapes), human CLDN9 (inverted triangle shapes), and a negative control (diamond shapes). FIG. 12B is a graph showing binding of the IMC-16-3 scFv-Fab IgG antibody to human CLDN6 (circle shapes), human CLDN4 (square shapes), human CLDN3 (triangle shapes), human CLDN9 (inverted triangle shapes), and a negative control (diamond shapes). FIG. 12C is a graph showing binding of the IMC-16-15 scFv-Fab IgG antibody to human CLDN6 (circle shapes), human CLDN4 (square shapes), human CLDN3 (triangle shapes), human CLDN9 (inverted triangle shapes), and a negative control (diamond shapes). FIG. 12D is a graph showing binding of the IMC-21-1 IgG-(scFv)$_2$ antibody to human CLDN6 (circle shapes), human CLDN4 (square shapes), human CLDN3 (triangle shapes), human CLDN9 (inverted triangle shapes), and a negative control (diamond shapes).

FIG. 14A, FIG. 14B, FIG. 14C, FIG. 14D, and FIG. 14E are graphs showing the production of cytokines by human PBMCs co-cultured with CLDN6 positive OV-90 cells in the presence or absence of the IMC-16-3 scFv-Fab IgG antibody. FIG. 14A illustrates the results for IL-2 production, FIG. 14B illustrates the results for IL-6 production, FIG. 14C illustrates the results for IL-10 production, FIG. 14D illustrates the results for IFN-γ production, and FIG. 14E illustrates the results for TNF-α production.

FIG. 15A, FIG. 15B, FIG. 15C, FIG. 15D, and FIG. 15E are graphs showing the production of cytokines by human PBMCs co-cultured with CLDN6 positive OV-90 cells in the presence or absence of the IMC-16-15 scFv-Fab IgG. FIG. 15A illustrates the results for IL-2 production, FIG. 15B illustrates the results for IL-6 production, FIG. 15C illustrates the results for IL-10 production, FIG. 15D illustrates the results for IFN-γ production, and FIG. 15E illustrates the results for TNF-α production.

FIG. 16A illustrates the results for IL-2 production, FIG. 16B illustrates the results for IL-6 production, FIG. 16C illustrates the results for IL-10 production, FIG. 16D illustrates the results for IFN-γ production, and FIG. 16E illustrates the results for TNF-α production.

FIG. 17A, FIG. 17B, FIG. 17C, FIG. 17D, and FIG. 17E are graphs showing the production of cytokines by human PBMCs co-cultured with CLDN6 positive OV-90 cells in the presence or absence of the IMC-2-7 tandem scFv antibody. FIG. 17A illustrates the results for IL-2 in production, FIG. 17B illustrates the results for IL-6 in production, FIG. 17C illustrates the results for IL-10 in production, FIG. 17D illustrates the results for IFN-γ in production, and FIG. 17E illustrates the results for TNF-α in production.

FIG. 18 shows cytotoxicity data of the IMC-2-7 tandem scFv antibody, IMC-16-3 scFv-Fab IgG antibody, IMC-16-15 scFv-Fab IgG antibody, IMC-21-1 IgG-(scFv)$_2$ antibody, and a negative control (CKV063 LALA) in K562 cells. The table to the right of FIG. 18 shows EC50 values for cellular toxicity.

FIG. 19A shows cellular toxicity and IFN-γ release data of the IMC-16-3 scFv-Fab IgG antibody at 24 hours. FIG. 19B shows cellular toxicity and IFN-γ release data of the IMC-16-15 scFv-Fab IgG antibody at 24 hours. FIG. 19C shows cellular toxicity and IFN-γ release data of the IMC-21-1 IgG-(scFv)$_2$ antibody at 24 hours. FIG. 19D shows cellular toxicity and IFN-γ release data of the IMC-2-7 tandem scFv antibody at 24 hours. FIG. 19E shows cellular toxicity and IFN-γ release data of the IMC-16-3 scFv-Fab IgG antibody at 48 hours. FIG. 19F shows cellular toxicity and IFN-γ release data of the IMC-16-15 scFv-Fab IgG antibody at 48 hours. FIG. 19G shows cellular toxicity and IFN-γ release data of the IMC-21-1 IgG-(scFv)$_2$ antibody at 48 hours. FIG. 19H shows cellular toxicity and IFN-γ release data of the IMC-2-7 tandem scFv antibody at 48 hours. The CKV063 LALA antibody is a negative control in each experiment.

FIG. 20A, FIG. 20B, FIG. 20C, FIG. 20D, FIG. 20E, FIG. 20F, FIG. 20G, FIG. 20H, FIG. 20I, and FIG. 20J are graphs showing cellular toxicity and IFN-γ release potency data at 24 hours and 48 hours from cellular cytotoxicity experiments. FIG. 20A shows cellular toxicity and IFN-γ release data of the IMC-16-7 antibody (SEQ ID NOs: 79, 67, and 91) at 24 hours. FIG. 20B shows cellular toxicity and IFN-γ release data of the IMC-2-7 tandem scFv antibody at 24 hours. FIG. 20C shows cellular toxicity and IFN-γ release data of the IMC-16-3 scFv-Fab IgG antibody at 24 hours. FIG. 20D shows cellular toxicity and IFN-γ release data of the IMC-16-15 scFv-Fab IgG antibody at 24 hours. FIG. 20E shows cellular toxicity and IFN-γ release data of the IMC-21-1 IgG-(scFv)$_2$ antibody at 24 hours. FIG. 20F shows cellular toxicity and IFN-γ release data of the IMC-16-7 antibody at 48 hours. FIG. 20G shows cellular toxicity and IFN-γ release data of the IMC-2-7 tandem scFv antibody at 48 hours. FIG. 20H shows cellular toxicity and IFN-γ release data of the IMC-16-3 scFv-Fab IgG antibody at 48 hours. FIG. 20I shows cellular toxicity and IFN-γ release data of the IMC-16-15 scFv-Fab IgG antibody at 48 hours. FIG. 20J shows cellular toxicity and IFN-γ release data of the IMC-21-1 IgG-(scFv)$_2$ antibody at 48 hours. The CKV063 LALA antibody is a negative control in each experiment.

FIG. 21A, FIG. 21B, FIG. 21C, FIG. 21D, FIG. 21E, FIG. 21F, FIG. 21G, FIG. 21H, FIG. 21I, and FIG. 21J are graphs showing cellular toxicity and IL-2 release potency data at 24 hours and 48 hours from cellular cytotoxicity experiments. FIG. 21A shows cellular toxicity and IL-2 release data of the IMC-16-7 antibody (SEQ ID NOs: 79, 67, and 91) at 24 hours. FIG. 21B shows cellular toxicity and IL-2 release data of the IMC-2-7 tandem scFv antibody at 24 hours. FIG. 21C shows cellular toxicity and IL-2 release data of the IMC-16-3 scFv-Fab IgG antibody at 24 hours. FIG. 21D shows cellular toxicity and IL-2 release data of the IMC-16-15 scFv-Fab IgG antibody at 24 hours. FIG. 21E shows cellular toxicity and IL-2 release data of the MC-21-1 antibody at 24 hours. FIG. 21F shows cellular toxicity and IL-2 release data of the IMC-16-7 antibody at 48 hours. FIG. 21G shows cellular toxicity and IL-2 release data of the IMC-2-7 tandem scFv antibody at 48 hours. FIG. 21H shows cellular toxicity and IL-2 release data of the IMC-16-3 scFv-Fab IgG antibody at 48 hours. FIG. 21I shows cellular toxicity and IL-2 release data of the IMC-16-15 scFv-Fab IgG antibody at 48 hours. FIG. 21J shows cellular toxicity and IL-2 release data of the IMC-21-1 IgG-(scFv)$_2$ antibody at 48 hours. The CKV063 LALA antibody is a negative control in each experiment.

FIG. 22A, FIG. 22B, FIG. 22C, FIG. 22D, FIG. 22E, FIG. 22F, FIG. 22G, FIG. 22H, FIG. 22I, and FIG. 22J are graphs showing cellular toxicity and IL-10 release potency data at 24 hours and 48 hours from cytotoxicity experiments. FIG. 22A shows cellular toxicity and IL-10 release data of the IMC-16-7 antibody at 24 hours. FIG. 22B shows cellular toxicity and IL-10 release data of the IMC-2-7 tandem scFv antibody at 24 hours. FIG. 22C shows cellular toxicity and IL-10 release data of the IMC-16-3 scFv-Fab IgG antibody at 24 hours. FIG. 22D shows cellular toxicity and IL-10 release data of the IMC-16-15 scFv-Fab IgG antibody at 24 hours. FIG. 22E shows cellular toxicity and IL-10 release data of the IMC-21-1 IgG-(scFv)$_2$ antibody at 24 hours. FIG. 22F shows cellular toxicity and IL-10 release data of the IMC-16-7 antibody at 48 hours. FIG. 22G shows cellular toxicity and IL-10 release data of the IMC-2-7 tandem scFv antibody at 48 hours. FIG. 22H shows cellular toxicity and IL-10 release data of the IMC-16-3 scFv-Fab IgG antibody at 48 hours. FIG. 22I shows cellular toxicity and IL-10 release data of the IMC-16-15 scFv-Fab IgG antibody at 48 hours. FIG. 22J shows cellular toxicity and IL-10 release data of the IMC-21-1 IgG-(scFv)$_2$ antibody at 48 hours. The CKV063 LALA antibody is a negative control in each experiment.

FIG. 23A, FIG. 23B, FIG. 23C, FIG. 23D, FIG. 23E, FIG. 23F, FIG. 23G, FIG. 23H, FIG. 23I, and FIG. 23J are graphs showing cellular toxicity and TNF-α release potency data at 24 hours and 48 hours from cytotoxicity experiments. FIG. 23A shows cellular toxicity and TNF-α release data of the IMC-16-7 antibody at 24 hours. FIG. 23B shows cellular toxicity and TNF-α release data of the IMC-2-7 tandem scFv antibody at 24 hours. FIG. 23C shows cellular toxicity and TNF-α release data of the IMC-16-3 scFv-Fab IgG antibody at 24 hours. FIG. 23D shows cellular toxicity and TNF-α release data of the IMC-16-15 scFv-Fab IgG antibody at 24 hours. FIG. 23E shows cellular toxicity and TNF-α release data of the IMC-21-1 IgG-(scFv)$_2$ antibody at 24 hours. FIG. 23F shows cellular toxicity and TNF-α release data of the IMC-16-7 antibody at 48 hours. FIG. 23G shows cellular toxicity and TNF-α release data of the IMC-2-7 tandem scFv antibody at 48 hours. FIG. 23H shows cellular toxicity and TNF-α release data of the IMC-16-3 scFv-Fab IgG antibody at 48 hours. FIG. 23I shows cellular toxicity and TNF-α release data of the IMC-16-15 scFv-Fab IgG antibody at 48 hours. FIG. 23J shows cellular toxicity and TNF-α release data of the IMC-21-1 IgG-(scFv)₂ antibody at 48 hours. The CKV063 LALA antibody is a negative control in each experiment.

FIG. 24A, FIG. 24B, FIG. 24C, FIG. 24D, FIG. 24E, FIG. 24F, FIG. 24G, and FIG. 24H are graphs showing cytokine analysis of IFN-γ and IL-2 at 24 hours and 48 hours. FIG. 24A is a graph showing IFN-γ levels at 24 hours and 48 hours for the IMC-2-7 tandem scFv antibody. FIG. 24B is a graph showing IFN-γ levels at 24 hours and 48 hours for the IMC-16-3 scFv-Fab IgG antibody. FIG. 24C is a graph showing IFN-γ levels at 24 hours and 48 hours for the IMC-16-15 scFv-Fab IgG antibody. FIG. 24D is a graph showing IFN-γ levels at 24 hours and 48 hours for the IMC-21-1 IgG-(scFv)₂ antibody. FIG. 24E is a graph showing IL-2 levels at 24 hours and 48 hours for the IMC-2-7 tandem scFv antibody. FIG. 24F is a graph showing IL-2 levels at 24 hours and 48 hours for the IMC-16-3 scFv-Fab IgG antibody. FIG. 24G is a graph showing IL-2 levels at 24 hours and 48 hours for the IMC-16-15 scFv-Fab IgG antibody. FIG. 24H is a graph showing IL-2 levels at 24 hours and 48 hours for the IMC-21-1 IgG-(scFv)₂ antibody.

FIG. 25A is a graph showing IL-10 levels at 24 hours and 48 hours for the IMC-16-7 antibody. FIG. 25B is a graph showing IL-10 levels at 24 hours and 48 hours for the IMC-2-7 tandem scFv antibody. FIG. 25C is a graph showing IL-10 levels at 24 hours and 48 hours for the IMC-16-3 scFv-Fab IgG antibody. FIG. 25D is a graph showing IL-10 levels at 24 hours and 48 hours for the IMC-16-15 scFv-Fab IgG antibody. FIG. 25E is a graph showing IL-10 levels at 24 hours and 48 hours for the IMC-21-1 IgG-(scFv)₂ antibody. FIG. 25F is a graph showing TNF-α levels at 24 hours and 48 hours for the IMC-16-7 antibody. FIG. 25G is a graph showing TNF-α levels at 24 hours and 48 hours for the IMC-2-7 tandem scFv antibody. FIG. 25H is a graph showing TNF-α levels at 24 hours and 48 hours for the IMC-16-3 scFv-Fab IgG antibody. FIG. 25I is a graph showing TNF-α levels at 24 hours and 48 hours for the IMC-16-15 scFv-Fab IgG antibody. FIG. 25J is a graph showing TNF-α levels at 24 hours and 48 hours for the IMC-21-1 IgG-(scFv)₂ antibody.

FIG. 26A and FIG. 26B are graphs showing the production of TNF-α by human PBMCs co-cultured with either claudin 6 expressing HEK cells or OV-90 cells. FIG. 26A shows antibody induced TNF-α levels for the IMC-16-13 scFv-Fab IgG antibody (SEQ ID NOs: 114, 65, and 80). IMC-16-15 scFv-Fab IgG antibody. IMC-16-3 scFv-Fab IgG antibody. IMC-2-7 tandem scFv antibody. IMC-2-13 tandem scFv antibody (SEQ ID NO: 115). IMC-20-13 IgG-scFv antibody (SEQ ID NOs: 114, 65, and 116). IMC-21-1 IgG-(scFv)₂ antibody. IMC-21-6 IgG-(scFv)₂ antibody (SEQ ID NOs: 104 and 66), and the IMC-2-3 tandem scFv antibody (SEQ ID NO: 84) in the PBMC:HEK-CLDN6 co-culture. FIG. 26B shows antibody induced TNF-α levels for the IMC-16-13 scFv-Fab IgG antibody. IMC-16-15 scFv-Fab IgG antibody. IMC-16-3 scFv-Fab IgG antibody. IMC-2-7 tandem scFv antibody. IMC-2-13 tandem scFv antibody. IMC-20-13 IgG-scFv antibody. IMC-21-1 IgG-(scFv)₂ antibody, IMC-21-6 IgG-(scFv)₂ antibody, and the IMC-2-3 tandem scFv antibody in the PBMC:OV-90 co-culture.

FIG. 27A and FIG. 27B are graphs showing the production of IFN-γ by human PBMCs co-cultured with either claudin 6 expressing HEK cells or OV-90 cells. FIG. 27A shows antibody induced IFN-γ levels for the IMC-16-13 scFv-Fab IgG antibody. IMC-16-15 scFv-Fab IgG antibody. IMC-16-3 scFv-Fab IgG antibody. IMC-2-7 tandem scFv antibody. IMC-2-13 tandem scFv antibody. IMC-20-13 IgG-scFv antibody. IMC-21-1 IgG-(scFv)₂ antibody. IMC-21-6 IgG-(scFv)₂ antibody, and the IMC-2-3 tandem scFv antibody in the PBMC:HEK-CLDN6 co-culture. FIG. 27B shows antibody induced IFN-γ levels for the IMC-16-13 scFv-Fab IgG antibody. IMC-16-15 scFv-Fab IgG antibody, IMC-16-3 scFv-Fab IgG antibody, IMC-2-7 tandem scFv antibody, IMC-2-13 tandem scFv antibody, IMC-20-13 IgG-scFv antibody, IMC-21-1 IgG-(scFv)₂ antibody. IMC-21-6 IgG-(scFv)₂ antibody, and the IMC-2-3 tandem scFv antibody in the PBMC:OV-90 co-culture.

FIG. 28A and FIG. 28B are graphs showing the production of IL-2 (FIG. 28A) and IL-6 levels (FIG. 28B) in by human PBMCs co-cultured with OV-90 cells. FIG. 28A shows antibody induced IL-2 levels for the IMC-16-13 scFv-Fab IgG antibody. IMC-16-15 scFv-Fab IgG antibody. IMC-16-3 scFv-Fab IgG antibody. IMC-2-7 tandem scFv antibody. IMC-2-13 tandem scFv antibody. IMC-20-13 IgG-scFv antibody. IMC-21-1 IgG-(scFv)₂ antibody, IMC-21-6 IgG-(scFv)₂ antibody, and the IMC-2-3 tandem scFv antibody in the PBMC:OV-90 co-culture. FIG. 28B shows antibody induced IL-6 levels for the IMC-16-13 scFv-Fab IgG antibody, IMC-16-15 scFv-Fab IgG antibody, IMC-16-3 scFv-Fab IgG antibody, IMC-2-7 tandem scFv antibody, IMC-2-13 tandem scFv antibody, IMC-20-13 IgG-scFv antibody, IMC-21-1 IgG-(scFv)2 antibody, IMC-21-6 IgG-(scFv)2 antibody, and the IMC-2-3 tandem scFv antibody in the PBMC: OV-90 co-culture.

FIG. 30A and FIG. 30B are graphs of cellular toxicity data from human T-cell dependent cellular cytotoxicity experiments. FIG. 30A shows cytotoxicity data of the IMC-16-3 scFv-Fab IgG antibody, IMC-21-1 IgG-(scFv)₂ antibody, IMC-16-15 scFv-Fab IgG antibody, IMC-2-7 tandem scFv antibody, and a negative control (CKV063 LALA) versus K562 CLDN6 expressing cells. FIG. 30B shows cytotoxicity data of the IMC-16-3 scFv-Fab IgG antibody, IMC-21-1 IgG-(scFv)₂ antibody, IMC-16-15 scFv-Fab IgG antibody, IMC-2-7 scFv antibody, and a negative control (CKV063 LALA) versus OV-90 cells.

The experiments in FIG. 31A and FIG. 31B show cytokine analysis data of the IMC-16-3 scFv-Fab IgG antibody (FIG. 31A), and the IMC-2-7 tandem scFv antibody (FIG. 31B) by human T cells co-cultured with K562 CLDN6 expressing cells.

FIG. 33A shows binding data of the IMC-16-3 scFv-Fab IgG antibody, IMC-16-15 scFv-Fab IgG antibody, IMC-21-1 IgG-(scFv)₂ antibody, and IMC-2-7 tandem scFv antibody to HEK293-F cells transiently expressing CLDN6. FIG. 33B shows binding data of the IMC-16-3 scFv-Fab IgG antibody, IMC-16-15 scFv-Fab IgG antibody, IMC-21-1 IgG-(scFv)₂ antibody, and IMC-2-7 tandem scFv antibody to HEK293-F cells transiently expressing CLDN9.

FIG. 38A illustrates the percent internalization of the antibodies in a K562 cell line with high expression of CLDN6. FIG. 38B illustrates the percent internalization of the antibodies in OV-90 cells with moderate expression of CLDN6.

FIG. 41A, FIG. 41B, and FIG. 41C illustrate the comparative selectivity of RefMAB #2 (FIG. 41A), RefMAB #3 (FIG. 41B), and IMC-16-3 (FIG. 41C) for various claudin proteins.

FIG. 42A illustrates the results when using a 12.5:1 E:T ratio. FIG. 42B illustrates the results when using a 2.5:1 E:T ratio.

FIG. 43A illustrates IL-6 production. FIG. 43B illustrates IL-2 production. FIG. 43C illustrates TNF-α production. FIG. 43D illustrates IL-8 production.

FIG. 44A illustrates the results versus cells expressing high levels of CLDN6. FIG. 44B illustrates the results versus cells expressing moderate levels of CLDN6. FIG. 44C illustrates the results versus cells expressing no CLDN6 (but which have a high rate of nonspecific pinocytosis).

DETAILED DESCRIPTION

Figure 1:
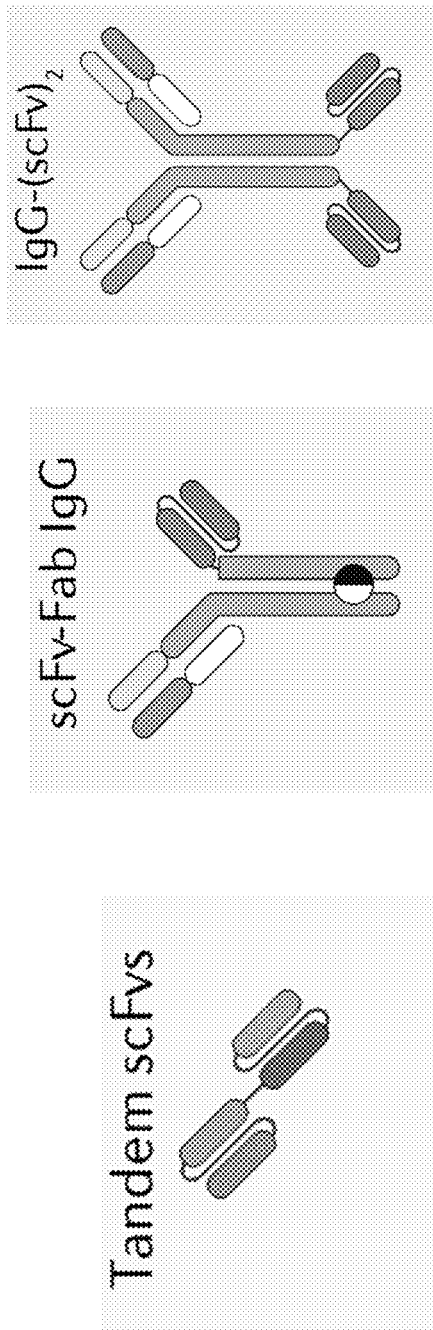
FIG. 1 shows images of illustrative bispecific formats, including a tandem scFv (left), a scFv-Fab IgG (middle), and an IgG-(scFv)$_2$ (right).

The present disclosure is based, in part, on the surprising discovery of an antibody specific for claudin 6 and CD3. The present disclosure describes the isolation and characterization of antibodies, antibody fragments, and antibody variants specific for claudin 6 and CD3. In some embodiments, the antibody specific for claudin 6 and CD3 is a tandem single-chain variable fragment (scFv). In some embodiments, the antibody specific for claudin 6 and CD3 is a scFv-Fab Fc antibody specific for claudin 6 and CD3. In some embodiments, the antibody specific for claudin 6 and CD3 is an IgG-(scFV)₂ antibody specific for claudin 6 and CD3. In some embodiments, the antibody specific for claudin 6 and CD3 is a scFv-Fab Fc specific for claudin 6 and CD3. In some embodiments, the antibody specific for claudin 6 and CD3 binds claudin 6 and CD3 contemporaneously.

For example, in some embodiments, the antibody specific for claudin 6 and CD3 is a tandem scFv selected from an amino acid sequence of SEQ ID NO: 82, SEQ ID NO: 83, SEQ ID NO: 84, SEQ ID NO: 85, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 109, SEQ ID NO: 110, or 115, or an amino acid sequence having at least about 90%, or about 93%, or about 95%, or about 97%, or about 98%, or about 99% identity thereto.

In some embodiments, the antibody specific for claudin 6 and CD3 is a scFv-Fab Fc antibody comprising a first heavy chain sequence, a second heavy chain sequence, and a light chain sequence. For example, the antibody specific for claudin 6 and CD3 is selected from a first heavy chain having an amino acid sequence of SEQ ID NO: 79, SEQ ID NO: 114, or SEQ ID NO: 88, a second heavy chain having an amino acid sequence of SEQ ID NO: 80, SEQ ID NO: 89, SEQ ID NO: 90, SEQ ID NO: 91, SEQ ID NO: 92, SEQ ID NO: 111, or SEQ ID NO: 116, and a light chain having an amino acid sequence of SEQ ID NO: 67, SEQ ID NO: 65, or SEQ ID NO: 66. In some embodiments, the first heavy chain comprises an amino acid sequence of SEQ ID NO: 79, SEQ ID NO: 114, or SEQ ID NO: 88, or an amino acid sequence having at least about 90%, or about 93%, or about 95%, or about 97%, or about 98%, or about 99% identity thereto. In some embodiments, the second heavy comprises an amino acid sequence of SEQ ID NO: 80, SEQ ID NO: 89, SEQ ID NO: 90, SEQ ID NO: 91, SEQ ID NO: 92, SEQ ID NO: 111, or SEQ ID NO: 116, or an amino acid sequence having at least about 90%, or about 93%, or about 95%, or about 97%, or about 98%, or about 99% identity thereto. In some embodiments, the light chain comprises an amino acid sequence of SEQ ID NO: 67. SEQ ID NO: 65, or SEQ ID NO: 66, or an amino acid sequence having at least about 90%, or about 93%, or about 95%, or about 97%, or about 98%, or about 99% identity thereto.

In some embodiments, the antibody specific for claudin 6 and CD3 is an IgG-(scFV)₂ antibody comprising a heavy chain selected from an amino acid sequence of SEQ ID NO: 86. SEQ ID NO: 87, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 112, or SEQ ID NO: 113, and a light chain selected from an amino acid sequence of SEQ ID NO: 67, SEQ ID NO: 65, or SEQ ID NO: 66. In some embodiments, the heavy chain comprises an amino acid sequence of SEQ ID NO: 86, SEQ ID NO: 87, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 112, or SEQ ID NO: 113, or an amino acid sequence having at least about 90%, or about 93%, or about 95%, or about 97%, or about 98%, or about 99% identity thereto. In some embodiments, the light chain comprises an amino acid sequence of SEQ ID NO: 67, SEQ ID NO: 65, or SEQ ID NO: 66, or an amino acid sequence having at least about 90%, or about 93%, or about 95%, or about 97%, or about 98%, or about 99% identity thereto.

In some embodiments, the antibody specific for claudin 6 and CD3 is a scFv-Fab Fc antibody comprising a first heavy chain selected from an amino acid sequence of SEQ ID NO: 79, SEQ ID NO: 114, or SEQ ID NO: 88, a second heavy chain selected from an amino acid sequence of SEQ ID NO: 81, and a light chain selected from an amino acid sequence of SEQ ID NO: 67, SEQ ID NO: 65, or SEQ ID NO: 66. In some embodiments, the antibody comprises a first heavy chain amino acid sequence of SEQ ID NO: 79, SEQ ID NO: 114, or SEQ ID NO: 88, or an amino acid sequence having at least about 90%, or about 93%, or about 95%, or about 97%, or about 98%, or about 99% identity thereto. In some embodiments, the antibody comprises a second heavy chain amino acid sequence of SEQ ID NO: 81, or an amino acid sequence having at least about 90%, or about 93%, or about 95%, or about 97%, or about 98%, or about 99% identity thereto. In some embodiments, the antibody comprises a light chain amino acid sequence of SEQ ID NO: 67, SEQ ID NO: 65, or SEQ ID NO: 66, or an amino acid sequence having at least about 90%, or about 93%, or about 95%, or about 97%, or about 98%, or about 99% identity thereto.

In some embodiments, the antibody specific for claudin 6 and CD3 is a scFv-Fab Fc antibody comprising a first heavy chain selected from an amino acid sequence of SEQ ID NO: 79, SEQ ID NO: 114, or SEQ ID NO: 88, a second heavy chain selected from an amino acid sequence of SEQ ID NO: 117, SEQ ID NO: 119, SEQ ID NO: 118, or SEQ ID NO: 120, and a light chain selected from an amino acid sequence of SEQ ID NO: 67, SEQ ID NO: 65, or SEQ ID NO: 66. In some embodiments, the antibody comprises a first heavy chain amino acid sequence of SEQ ID NO: 79, SEQ ID NO: 114, or SEQ ID NO: 88, or an amino acid sequence having at least about 90%, or about 93%, or about 95%, or about 97%, or about 98%, or about 99% identity thereto. In some embodiments, the antibody comprises a second heavy chain amino acid sequence of SEQ ID NO: 117, SEQ ID NO: 119, SEQ ID NO: 118, or SEQ ID NO: 120, or an amino acid sequence having at least about 90%, or about 93%, or about 95%, or about 97%, or about 98%, or about 99% identity thereto. In some embodiments, the antibody comprises a light chain amino acid sequence of SEQ ID NO: 67, SEQ ID NO: 65, or SEQ ID NO: 66, or an amino acid sequence having at least about 90%, or about 93%, or about 95%, or about 97%, or about 98%, or about 99% identity thereto.

In some embodiments, the antibody specific for claudin 6 and CD3 is a scFv-Fab Fc antibody comprising a first heavy chain selected from an amino acid sequence of SEQ ID NO: 79, SEQ ID NO: 114, or SEQ ID NO: 88, a second heavy chain selected from an amino acid sequence of SEQ ID NO: 121, SEQ ID NO: 123, SEQ ID NO: 125, SEQ ID NO: 127. SEQ ID NO: 129, a first light selected from an chain amino acid sequence of SEQ ID NO: 67. SEQ ID NO: 65, or SEQ ID NO: 66, and a second light chain selected from an amino acid sequence of SEQ ID NO: 122, SEQ ID NO: 124, SEQ ID NO: 126, SEQ ID NO: 128, or SEQ ID NO: 130. In some embodiments, the antibody comprises a first heavy chain selected from an amino acid sequence of SEQ ID NO: 79, SEQ ID NO: 114, or SEQ ID NO: 88, or an amino acid sequence having at least about 90%, or about 93%, or about 95%, or about 97%, or about 98%, or about 99% identity thereto. In some embodiments, the antibody comprises a second heavy chain selected from an amino acid sequence of SEQ ID NO: 121, SEQ ID NO: 123, SEQ ID NO: 125, SEQ ID NO: 127, SEQ ID NO: 129, or an amino acid sequence having at least about 90%, or about 93%, or about 95%, or about 97%, or about 98%, or about 99% identity thereto. In some embodiments, the antibody comprises a first light selected from an chain amino acid sequence of SEQ ID NO: 67, SEQ ID NO: 65, or SEQ ID NO: 66, or an amino acid sequence having at least about 90%, or about 93%, or about 95%, or about 97%, or about 98%, or about 99% identity thereto. In some embodiments, the antibody comprises a second light chain selected from an amino acid sequence of SEQ ID NO: 122, SEQ ID NO: 124, SEQ ID NO: 126, SEQ ID NO: 128, or SEQ ID NO: 130, or an amino acid sequence having at least about 90%, or about 93%, or about 95%, or about 97%, or about 98%, or about 99% identity thereto.

In various embodiments, the antibody (e.g., a tandem scFv antibody, scFv-Fab Fc antibody, IgG-(scFV)$_2$ antibody, and a scFv-Fab Fc antibody), or fragment thereof, or variant thereof, may comprise an amino acid sequence having one or more amino acid mutations (e.g., substitutions or deletions) relative to any of the sequences disclosed herein. In some embodiments, the one or more amino acid mutations may be independently selected from substitutions, insertions, deletions, and truncations. In embodiments, the antibody (e.g. a tandem scFv antibody, scFv-Fab Fc antibody, IgG-(scFV)$_2$ antibody, and a scFv-Fab Fc antibody), or fragment thereof, or variant thereof, comprises a sequence that has about 1, 2, 3, 4, 5, 6, 7, 8, 9, or 10 or more amino acid mutations with respect to any one of the amino acid sequences disclosed herein.

In various embodiments, the antibody or antibody format (e.g. a tandem scFv antibody, scFv-Fab Fc antibody, IgG-(scFV)$_2$ antibody, and a scFv-Fab Fc antibody), or fragment thereof, or variant thereof, may comprise an amino acid sequence having at least about 50%, about 60%, about 70%, about 80%, about 90%, about 95%, about 96%, about 97%, about 98%, about 99% sequence homology to the amino acid sequences disclosed herein.

In various embodiments, disclosed herein are variants or fragments comprising any of the sequences described herein, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with any of the sequences disclosed herein.

In some embodiments, variants are those that have conservative amino acid substitutions made at one or more predicted non-essential amino acid residues. For example, a "conservative amino acid substitution" is one in which the amino acid residue is replaced with an amino acid residue having a similar side chain.

In embodiments, the amino acid mutations are amino acid substitutions, and may include conservative and/or non-conservative substitutions. Throughout the present disclosure, the term "mutation" and "substitution" may be used interchangeably when the context allows. For example, a substitution of threonine at position 366 of a protein to a serine may be referred to as a T366S substitution or a T366S mutation. The skilled artisan would readily understand that "T366S" connotes a substitution of threonine for serine at position 366, and thus the skilled artisan would readily understand that "T366S mutation" refers to a substitution.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

As disclosed herein, the term "antibody" refers to a broad sense and includes immunoglobulin or antibody molecules including polyclonal antibodies, monoclonal antibodies including murine, human, humanized and chimeric monoclonal antibodies and antibody fragments, such as ScFv (PLOS Biology|DOI:10.1371/journal.pbio.1002344 Jan. 6, 2016, which is hereby incorporated by reference in its entirety).

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end: the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD. IgE, IgG and IgM, depending on the heavy chain constant domain amino acid sequence. IgA and IgG are further sub-classified as the isotypes IgA1, IgA2, IgG1, IgG2, IgG3 and IgG4.

As disclosed herein, the term "antibody fragment" refers to an intact antibody, generally the antigen binding or variable region of the intact antibody. Examples of antibody fragments include Fab. Fab', F(ab')2 and Fv fragments, diabodies, single chain antibody molecules and multispecific antibodies formed from at least two intact antibodies or fragments thereof.

As disclosed herein, the term "antigen" refers to any molecule that has the ability to generate antibodies either directly or indirectly.

As disclosed herein, the term "specific binding" or "immunospecific binding" or "binds immunospecifically" refers to antibody binding to a predetermined antigen (e.g., Claudin 6) or epitope present on the antigen. In some embodiments, the antibody binds with a dissociation constant (KD) of about $10^{-10}$ M or less, of about $10^{-9}$ M or less, of about $10^{-8}$ M or less, of about $10^{-7}$ M or less, of about $10^{-6}$ M or less, of about $10^{-5}$ M or less, and binds to the predetermined antigen with a KD that is at least two-fold less than its KD for binding to a non-specific antigen (e.g., BSA, casein, or another non-specific polypeptide) other than the predetermined antigen. The phrases "an antibody recognizing Claudin 6" and "an antibody specific for Claudin 6" are used interchangeably herein with the term "an antibody which binds immunospecifically to Claudin 6." Reference in the present disclosure may be made to Claudin 6. In some embodiments, the antibody is specific for Claudin 6 and does not specifically bind to claudin 3, claudin 4, and/or claudin 9.

"CDRs" are referred to as the complementarity determining region amino acid sequences of an antibody which are the hypervariable regions of immunoglobulin heavy and light chains. See, e.g., Kabat et al., *Sequences of Proteins of Immunological Interest.* 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity, as the CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived. In some embodiments, the antibody is a chimeric antibody. In some embodiments, the antibody is a humanized antibody.

CDRs are based on sequence variability (Wu and Kabat, J. Exp. Med. 132:211-250, 1970). There are six CDRs—three in the variable heavy chain, or VH, and are typically designated H-CDR1, H-CDR2, and H-CDR3, and three CDRs in the variable light chain, or VL, and are typically designated L-CDR1, L-CDR2, and L-CDR3 (Kabat et al., Sequences of Proteins of Immunological Interest, 5th Ed. Public Health Service, National Institutes of Health, Bethesda, Md., 1991). "Hypervariable region", "HVR", or "HV" refer to the regions of an antibody variable domain which are variable in structure as defined by Chothia and Lesk (Chothia and Lesk, Mol. Biol. 196:901-917, 1987). There are six HVRs, three in VH (H1, H2, H3) and three in VL (L1, L2, L3). Chothia and Lesk refer to structurally conserved HVs as "canonical structures." Another method of describing the regions that form the antigen-binding site has been proposed by Lefranc (Lefranc et al., Developmental & Comparative Immunology 27:55-77, 2003) based on the comparison of V domains from immunoglobulins and T-cell receptors (Lefranc et al., Developmental & Comparative Immunology 27:55-77, 2003). The antigen-binding site can also be delineated based on "Specificity Determining Residue Usage (SDRU)", according to Almagro (Almagro, Mol. Recognit. 17:132-43, 2004), where SDRU refers to amino acid residues of an immunoglobulin that are directly involved in antigen contact.

An "isolated antibody," as used herein, refers to an antibody that is substantially free of other antibodies having different antigenic specificities (e.g., an isolated antibody that specifically binds Claudin 6 is substantially free of antibodies that specifically bind antigens other than Claudin 6). Moreover, an isolated antibody may be substantially free of other cellular material and/or chemicals. An isolated antibody can also be sterile or pyrogen free or formulated as injectable pharmaceutical as described herein.

In some embodiments, the source for the DNA encoding a non-human antibody include cell lines which produce antibody, such as hybrid cell lines commonly known as hybridomas.

Claudin 6/CD3 Binders

In some embodiments, the antibody specific for claudin 6 and CD3 (e.g. a tandem scFv antibody, scFv-Fab Fc antibody, IgG-(scFV)₂ antibody, and a scFv-Fab Fc antibody), or fragment thereof, or variant thereof, is selected from one of the following amino acid sequences. Bold font refers to a CDR based on Kabat designations, and the underline formatting refers to a linker.

>SEQ ID NO: 82
(SEQ ID NO: 82)
SYELTQPPSVSVSPGQTARITCSAGSGLYGWYQQKPGQAPVLV

IYGTNKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI

SSSGRYTGYADSVKGRFTISRDNSKNTLYLQMNSLRAEDTAV

YYCAKSVGSGVSWSGYVATSLDAWGQGTLVTVSS<u>GGGGS</u>DI

KLQQSGAELARPGASVKMSCKTSGYTFTRYTMHWVKQRPGQ

GLEWIGYINPSRGYTNYNQKFKDKATLTTDKSSSTAYMQLSS

LTSEDSAVYYCARYYDDHYCLDYWGQGTTLTVSSVE<u>GGSGGS</u>

<u>GGSGGSGGV</u>DDIQLTQSPAIMSASPGEKVTMTCRASSSVSYMN

WYQQKSGTSPKRWIYDTSKVASGVPYRFSGSGSGTSYSLTISS

MEAEDAATYYCQQWSSNPLTFGAGTKLELK

>SEQ ID NO: 83
(SEQ ID NO: 83)
SYELTQPPSVSVSPGQTARITCSGGSGSYGWYQQKPGQAPVLV

IYGTYKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI

SSSGRYTGYADSVKGRFTISRDNSKNTLYLQMNSLRAEDTAV

YYCAKSVGSGVSWSGYVATSLDVWGQGTLVTVSS<u>GGGGS</u>DI

KLQQSGAELARPGASVKMSCKTSGYTFTRYTMHWVKQRPGQ

GLEWIGYINPSRGYTNYNQKFKDKATLTTDKSSSTAYMQLSS

LTSEDSAVYYCARYYDDHYCLDYWGQGTTLTVSSVE<u>GGSGGS</u>

<u>GGSGGS</u>GGVDDIQLTQSPAIMSASPGEKVTMTCRASSSVSYMN

WYQQKSGTSPKRWIYDTSKVASGVPYRFSGSGSGTSYSLTISS

MEAEDAATYYCQQWSSNPLTFGAGTKLELK

>SEQ ID NO: 84
(SEQ ID NO: 84)
SYELTQPPSVSVSPGQTARITCSAGSGLYGWYQQKPGQAPVLV

IYGTNKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI

SSSGRYTGYADSVKGRFTISRDNSKNTLYLQMNSLRAEDTAV

YYCAKSVGSGVSWSGYVATSLDAWGQGTLVTVSS<u>GGGGS</u>EV

QLVESGGGPVQAGGSLRLSCAASGRTYRGYSMGWFRQAPGK

EREFVAAIVWSGGNTYYEDSVKGRFTISRDNAKNTMYLQMTS

LKPEDSATYYCAAKIRPYIFKIAGQYDYWGQGTQVTVSS

>SEQ ID NO: 85
(SEQ ID NO: 85)
SYELTQPPSVSVSPGQTARITCSGGSGSYGWYQQKPGQAPVLV

IYGTYKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI

SSSGRYTGYADSVKGRFTISRDNSKNTLYLQMNSLRAEDTAV

YYCAKSVGSGVSWSGYVATSLDVWGQGTLVTVSS<u>GGGGS</u>EV

QLVESGGGPVQAGGSLRLSCAASGRTYRGYSMGWFRQAPGK

EREFVAAIVWSGGNTYYEDSVKGRFTISRDNAKNTMYLQMTS

LKPEDSATYYCAAKIRPYIFKIAGQYDYWGQGTQVTVSS

>SEQ ID NO: 93
(SEQ ID NO: 93)
SYELTQPPSVSVSPGQTARITCSAGSGLYGWYQQKPGQAPVLV

IYGTNKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI

SSSGRYTGYADSVKGRFTISRDNSKNTLYLQMNSLRAEDTAV

YYCAKSVGSGVSWSGYVATSLDAWGQGTLVTVSS<u>GGGGS</u>EV

QLVESGGGLVQPGGSLKLSCAASGFTFNKYAMNWVRQAPGK

GLEWVARIRSKYNNYATYYADSVKDRFTISRDDSKNTAYLQM

NNLKTEDTAVYYCVRHGNFGNSYISYWAYWGQGTLVTVSS<u>G</u>

<u>GGGSGGGGSGGGGS</u>QTVVTQEPSLTVSPGGTVTLTCGSSTGAV

TSGNYPNWVQQKPGQAPRGLIGGTKFLAPGTPARFSGSLLGG

KAALTLSGVQPEDEAEYYCVLWYSNRWVFGGGTKLTVL

>SEQ ID NO: 94
(SEQ ID NO: 94)
SYELTQPPSVSVSPGQTARITCSGGSGSYGWYQQKPGQAPVLV

IYGTYKRPSGIPERFSGSSSGTTVTLTISGVQAEDEADYYCGSA

DSSTNAGIFGGGTKLTVL<u>GGGGSGGGGSGGGGS</u>EVQLLESGG

GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDVWGQGTLVTVSS<u>GGGGSEV</u>
QLVESGGGLVQPGGSLKLSCAASGFTFNKYAMNWVRQAPGK
GLEWVARIRSKYNNYATYYADSVKDRFTISRDDSKNTAYLQM
NNLKTEDTAVYYCVRHGNFGNSYISYWAYWGQGTLVTVSS<u>G</u>
<u>GGGSGGGGSGGGGS</u>QTVVTQEPSLTVSPGGTVTLTCGSSTGAV
TSGNYPNWVQQKPGQAPRGLIGGTKFLAPGTPARFSGSLLGG
KAALTLSGVQPEDEAEYYCVLWYSNRWVFGGGTKLTVL
>SEQ ID NO: 95
                               (SEQ ID NO: 95)
SYELTQPPSVSVSPGQTARITCSAGSGLYGWYQQKPGQAPVLV
IYGTNKRPSGIPERFSGSSSGTTVTLTISGVQAEDEADYYCGSA
DSSTNAGIFGGGTKLTVL<u>GGGGSGGGGSGGGGS</u>EVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDAWGQGTLVTVSS<u>GGGGSEV</u>
QLVESGGGLVQPGGSLRLSCAASGFTFSTYAMNWVRQAPGKG
LEWVGRIRSKYNNYATYYADSVKGRFTISRDDSKNTLYLQMN
SLRAEDTAVYYCVRHGNFGDSYVSWFAYWGQGTLVTVSS<u>GK</u>
<u>PGSGKPGSGKPGSGKPGS</u>QAVVTQEPSLTVSPGGTVTLTCGSST
GAVTTSNYANWVQQKPGKSPRGLIGGTNKRAPGVPARFSGSL
LGGKAALTISGAQPEDEADYYCALWYSNHWVFGGGTKLTVL
>SEQ ID NO: 115
                              (SEQ ID NO: 115)
SYELTQPPSVSVSPGQTARITCSAGSGLYGWYQQKPGQAPVLVIYGT
NKRPSGIPERFSGSSSGTTVTLTISGVQAEDEADYYCGSADSSTNAGIF
GGGTKLTVL<u>GGGGSGGGGSGGGGS</u>EVQLLESGGGLVQPGGSLRLSCA
ASGFTFSSYAMNWVRQAPGKGLEWVAGISSSGRYTGYADSVKGRFT
ISRDNSKNTLYLQMNSLRAEDTAVYYCAKSMGSGVSWSGYVATSID
VWGQGTLVTVSS<u>GGGGSD</u>IKLQQSGAELARPGASVKMSCKTSGYTFT
RYTMHWVKQRPGQGLEWIGYINPSRGYTNYNQKFKDKATLTTDKS
SSTAYMQLSSLTSEDSAVYYCARYYDDHYCLDYWGQGTTLTVSSVE
<u>GGSGGSGGSGGSGGV</u>DDIQLTQSPAIMSASPGEKVTMTCRASSSVSY
MNWYQQKSGTSPKRWIYDTSKVASGVPYRFSGSGSGTSYSLTISSME
AEDAATYYCQQWSSNPLTFGAGTKLELK
>SEQ ID NO: 96
                             (SEQ ID NO: 96)
SYELTQPPSVSVSPGQTARITCSGGSGSYGWYQQKPGQAPVLV
IYGTYKRPSGIPERFSGSSSGTTVTLTISGVQAEDEADYYCGSA
DSSTNAGIFGGGTKLTVL<u>GGGGSGGGGSGGGGS</u>EVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDVWGQGTLVTVSS<u>GGGGSEV</u>

QLVESGGGLVQPGGSLRLSCAASGFTFSTYAMNWVRQAPGKG
LEWVGRIRSKYNNYATYYADSVKGRFTISRDDSKNTLYLQMN
SLRAEDTAVYYCVRHGNFGDSYVSWFAYWGQGTLVTVSS<u>GK</u>
<u>PGSGKPGSGKPGSGKPGS</u>QAVVTQEPSLTVSPGGTVTLTCGSST
GAVTTSNYANWVQQKPGKSPRGLIGGTNKRAPGVPARFSGSL
LGGKAALTISGAQPEDEADYYCALWYSNHWVFGGGTKLTVL
>SEQ ID NO: 97
                             (SEQ ID NO: 97)
SYELTQPPSVSVSPGQTARITCSAGSGLYGWYQQKPGQAPVLV
IYGTNKRPSGIPERFSGSSSGTTVTLTISGVQAEDEADYYCGSA
DSSTNAGIFGGGTKLTVL<u>GGGGSGGGGGGGGS</u>EVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDAWGQGTLVTVSS<u>GGGGSEV</u>
QLVESGGGLVQPGGSLRLSCAASGFTFNTYAMNWVRQAPGKG
LEWVARIRSKYNNYATYYADSVKSRTTISDDSKNTLYLQMNS
LRAEDTAVYYCVRHGNFGNSYVSWFAYWGQTTVTVSS<u>GGGG</u>
<u>SGGGGSGGGGSGGGGS</u>EIVVTQSPATLSVSPGERATLSCRSSTG
AVTTSNYANWVQEPGQAFRGLIGGANKRAPGVPARFSGSLSG
DEATLTISSLQSEDFAVYYCALWYSNLWVFGQGTKLEIK
>SEQ ID NO: 98
                             (SEQ ID NO: 98)
SYELTQPPSVSVSPGQTARITCSGGSGSYGWYQQKPGQAPVLV
IYGTYKRPSGIPERFSGSSSGTTVTLTISGVQAEDEADYYCGSA
DSSTNAGIFGGGTKLTVL<u>GGGGSGGGGSGGGGS</u>EVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDVWGQGTLVTVSS<u>GGGGSEV</u>
QLVESGGGLVQPGGSLRLSCAASGFTFNTYAMNWVRQAPGKG
LEWVARIRSKYNNYATYYADSVKSRTTISDDSKNTLYLQMNS
LRAEDTAVYYCVRHGNFGNSYVSWFAYWGQTTVTVSS<u>GGGG</u>
<u>SGGGGSGGGGSGGGGS</u>EIVVTQSPATLSVSPGERATLSCRSSTG
AVTTSNYANWVQEPGQAFRGLIGGANKRAPGVPARFSGSLSG
DEATLTISSLQSEDFAVYYCALWYSNLWVFGQGTKLEIK
>SEQ ID NO: 99
                             (SEQ ID NO: 99)
SYELTQPPSVSVSPGQTARITCSAGSGLYGWYQQKPGQAPVLV
IYGTNKRPSGIPERFSGSSSGTTVTLTISGVQAEDEADYYCGSA
DSSTNAGIFGGGTKLTVL<u>GGGGSGGGGSGGGGS</u>EVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDAWGQGTLVTVSS<u>GGGGSQV</u>
QLVQSGGGVVQPGRSLRLSCKASGYTFTRYTMHWVRQAPGK

```
GLEWIGYINPSRGYTNYNQKVKDRFTISTDKSKSTAFLQMDSL
RPEDTAVYYCARYYDDHYCLDYWGQGTTLTVSSGGGGSGGG
GSGGGGSDIQMTQSPSSLSASVGDRVTITCSASSSVSYMNWYQ
QTPGKAPKRWIYDTSKLASGVPSRFSGSGSGTDYTFTISSLQPE
DIATYYCQQWSSNPFTFGQGTKLQITR
>SEQ ID NO: 100
                                    (SEQ ID NO: 100)
SYELTQPPSVSVSPGQTARITCSGGSGSYGWYQQKPGQAPVLV
IYGTYKRPSGIPERFSGSSSGTTVTLTISGVQAEDEADYYCGSA
DSSTNAGIFGGGTKLTVLGGGGSGGGGSGGGGSEVQLLESGG
GLVQPGGSLRLSCAASGFTFSSYAMNWVRQAPGKGLEWVAGI
SSSSGRYTGYADSVKGRFTISRDNSKNTLYLQMNSLRAEDTAV
YYCAKSVGSGVSWSGYVATSLDVWGQGTLVTVSSGGGGSQV
QLVQSGGGVVQPGRSLRLSCKASGYTFTRYTMHWVRQAPGK
GLEWIGYINPSRGYTNYNQKVKDRFTISTDKSKSTAFLQMDSL
RPEDTAVYYCARYYDDHYCLDYWGQGTTLTVSSGGGGSGGG
GSGGGGSDIQMTQSPSSLSASVGDRVTITCSASSSVSYMNWYQ
QTPGKAPKRWIYDTSKLASGVPSRFSGSGSGTDYTFTISSLQPE
DIATYYCQQWSSNPFTFGQGTKLQITR
>SEQ ID NO: 109
                                    (SEQ ID NO: 109)
SYELTQPPSVSVSPGQTARITCSAGSGLYGWYQQKPGQAPVLV
IYGTNKRPSGIPERFSGSSSGTTVTLTISGVQAEDEADYYCGSA
DSSTNAGIFGGGTKLTVLGGGGSGGGGSGGGGSEVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDAWGQGTLVTVSSGGGGSEV
QLLESGGGLVQPGGSLRLSCAASGFSFTGYTMNWVRQAPGKG
LEWMGLINPYKGVSTYNQKVKGRFTISRDNSKNTLYLQMNSL
RAEDTAVYYCARSGYYGDSDWYFDVWGQGTLVTVSSGGGGS
GGGGSGGGGSDIQMTQSPSSLSASVGDRVTITCRASQDIRNYL
NWYQQTPGKAPKRWIYYTSRLHSGVPSRFSGSGSGTDYTFTYS
SLQPEDIATYYCQQGNTLPWTFGQGTKLEIK
>SEQ ID NO: 110
                                    (SEQ ID NO: 110)
SYELTQPPSVSVSPGQTARITCSGGSGSYGWYQQKPGQAPVLV
IYGTYKRPSGIPERFSGSSSGTTVTLTISGVQAEDEADYYCGSA
DSSTNAGIFGGGTKLTVLGGGGSGGGGSGGGGSEVQLLESGG
GLVQPGGSLRLSCAASGFTFSSYAMNWVRQAPGKGLEWVAGI
SSSGRYTGYADSVKGRFTISRDNSKNTLYLQMNSLRAEDTAV
YYCAKSVGSGVSWSGYVATSLDVWGQGTLVTVSSGGGGSEV
QLLESGGGLVQPGGSLRLSCAASGFSFTGYTMNWVRQAPGKG
LEWMGLINPYKGVSTYNQKVKGRFTISRDNSKNTLYLQMNSL
RAEDTAVYYCARSGYYGDSDWYFDVWGQGTLVTVSSGGGGS

GGGGSGGGGSDIQMTQSPSSLSASVGDRVTITCRASQDIRNYL
NWYQQTPGKAPKRWIYYTSRLHSGVPSRFSGSGSGTDYTFTYS
SLQPEDIATYYCQQGNTLPWTFGQGTKLEIK
>SEQ ID NO: 79
                                    (SEQ ID NO: 79)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDAWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSREEMTKNQVSLWCLVKGFYPS
DIAVEWESNGQPENNYKTTPPVLDSDGSFFLYSKLTVDKSRWQ
QGNVFSCSVMHEALHNHYTQKSLSLSPGK
>SEQ ID NO: 88
                                    (SEQ ID NO: 88)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDVWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSREEMTKNQVSLWCLVKGFYPS
DIAVEWESNGQPENNYKTTPPVLDSDGSFFLYSKLTVDKSRWQ
QGNVFSCSVMHEALHNHYTQKSLSLSPGK
>SEQ ID NO: 114
                                    (SEQ ID NO: 114)
EVQLLESGGGLVQPGGSLRLSCAASGFTFSSYAMNWVRQAPGKGLE
WVAGISSSGRYTGYADSVKGRFTISRDNSKNTLYLQMNSLRAEDTAV
YYCAKSMGSGVSWSGYVATSIDVWGQGTLVTVSSASTKGPSVFPLA
PSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHT
CPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSREEMTKNQVSLWC
LVKGFYPSDIAVEWESNGQPENNYKTTPPVLDSDGSFFLYSKLTVDKS
RWQQGNVFSCSVMHEALHNHYTQKSLSLSPGK
>SEQ ID NO: 80
                                    (SEQ ID NO: 80)
EVQLVESGGGPVQAGGSLRLSCAASGRTYRGYSMGWFRQAP
```

GKEREFVAAIVWSGGNTYYEDSVKGRFTISRDNAKNTMYLQ
MTSLKPEDSATYYCAAKIRPYIFKIAGQYDYWGQGTQVTVSS
ASPKSSDKTHTCPPCPAPEAAGGPSVFLFPPKPKDTLMISRTPEV
TCVVVDVSHEDPEVKFNWYVDGVEVHNAKTKPREEQYNSTY
RVVSVLTVLHQDWLNGKEYKCKVSNKALPAPIEKTISKAKGQP
REPQVYTLPPSREEMTKNQVSLSCAVKGFYPSDIAVEWESNGQ
PENNYKTTPPVLDSDGSFFLVSKLTVDKSRWQQGNVFSCSVMH
EALHNHYTQKSLSLSPGK

>SEQ ID NO: 89 (SEQ ID NO: 89)
EVQLVESGGGLVQPGGSLRLSCAASGFTFSTYAMNWVRQAPG
KGLEWVGRIRSKYNNYATYYADSVKGRFTISRDDSKNTLYLQ
MNSLRAEDTAVYYCVRHGNFGDSYVSWFAYWGQGTLVTVSS
<u>GKPGSGKPGSGKPGSGKPGS</u>QAVVTQEPSLTVSPGGTVTLTC**G
SSTGAVTTSNYANWVQQKPGKSPRGLIGGTNKRAP**GVPARFS
GSLLGGKAALTISGAQPEDEADYYCALWYSNHWVFGGGTKL
TVLASPKSSDKTHTCPPCPAPEAAGGPSVFLFPPKPKDTLMISRT
PEVTCVVVDVSHEDPEVKFNWYVDGVEVHNAKTKPREEQYNS
TYRVVSVLTVLHQDWLNGKEYKCKVSNKALPAPIEKTISKAKG
QPREPQVYTLPPSREEMTKNQVSLSCAVKGFYPSDIAVEWESN
GQPENNYKTTPPVLDSDGSFFLVSKLTVDKSRWQQGNVFSCSV
MHEALHNHYTQKSLSLSPGK

>SEQ ID NO: 90 (SEQ ID NO: 90)
EVQLVESGGGLVQPGGSLRLSCAASGFTFNTYAMNWVRQAPG
KGLEWVARIRSKYNNYATYYADSVKSRTTISDDSKNTLYLQM
NSLRAEDTAVYYCVRHGNFGNSYVSWFAYWGQTTVTVSS<u>GG
GGSGGGGSGGGGSGGGGS</u>EIVVTQSPATLSVSPGERATLSC**RSS
TGAVTTSNYANWVQEPGQAFRGLIGGANKRAP**GVPARFSGSL
SGDEATLTISSLQSEDFAVYYCALWYSNLWVFGQGTKLEIKAS
PKSSDKTHTCPPCPAPEAAGGPSVFLFPPKPKDTLMISRTPEVTC
VVVDVSHEDPEVKFNWYVDGVEVHNAKTKPREEQYNSTYRV
VSVLTVLHQDWLNGKEYKCKVSNKALPAPIEKTISKAKGQPRE
PQVYTLPPSREEMTKNQVSLSCAVKGFYPSDIAVEWESNGQPE
NNYKTTPPVLDSDGSFFLVSKLTVDKSRWQQGNVFSCSVMHE
ALHNHYTQKSLSLSPGK

>SEQ ID NO: 91 (SEQ ID NO: 91)
EVQLVESGGGLVQPGGSLKLSCAASGFTFNKYAMNWVRQAP
GKGLEWVARIRSKYNNYATYYADSVKDRFTISRDDSKNTAYL
QMNNLKTEDTAVYYCVRHGNFGNSYISYWAYWGQGTLVTV
SS<u>GGGGSGGGGSGGGGS</u>QTVVTQEPSLTVSPGGTVTLTC**GSST
GAVTSGNYPNWVQQKPGQAPRGLIGGTKFLAP**GTPARFSGSL
LGGKAALTLSGVQPEDEAEYYCVLWYSNRWVFGGGTKLTVL

ASPKSSDKTHTCPPCPAPEAAGGPSVFLFPPKPKDTLMISRTPEV
TCVVVDVSHEDPEVKFNWYVDGVEVHNAKTKPREEQYNSTY
RVVSVLTVLHQDWLNGKEYKCKVSNKALPAPIEKTISKAKGQP
REPQVYTLPPSREEMTKNQVSLSCAVKGFYPSDIAVEWESNGQ
PENNYKTTPPVLDSDGSFFLVSKLTVDKSRWQQGNVFSCSVMH
EALHNHYTQKSLSLSPGK

>SEQ ID NO: 116 (SEQ ID NO: 116)
EVQLVESGGGPVQAGGSLRLSCAASGRTYRGYSMGWFRQAPG
KEREFVAAIVWSGGNTYYEDSVKGRFTISRDNAKNTMYLQMT
SLKPEDSATYYCAAKIRPYIFKIAGQYDYWGQGTQVTVSSGGG
GSGGGGSGGGGSEVQLLESGGGLVQPGGSLRLSCAASGFTFSS
YAMNWVRQAPGKGLEWVAGISSSGRYTGYADSVKGRFTISRD
NSKNTLYLQMNSLRAEDTAVYYCAKSMGSGVSWSGYVATSID
VWGQGTLVTVSSASTKGPSVFPLAPSSKSTSGGTAALGCLVKD
YFPEPVTVSWNSGALTSGVHTFPAVLQSSGLYSLSSVVTVPSSS
LGTQTYICNVNHKPSNTKVDKKVEPKSCDKTHTCPPCPAPEAA
GGPSVFLFPPKPKDTLMISRTPEVTCVVVDVSHEDPEVKFNWY
VDGVEVHNAKTKPREEQYNSTYRVVSVLTVLHQDWLNGKEY
KCKVSNKALPAPIEKTISKAKGQPREPQVYTLPPSREEMTKNQV
SLSCAVKGFYPSDIAVEWESNGQPENNYKTTPPVLDSDGSFFLV
SKLTVDKSRWQQGNVFSCSVMHEALHNHYTQKSLSLSPGK

>SEQ ID NO: 92 (SEQ ID NO: 92)
QVQLVQSGGGVVQPGRSLRLSCKASGYTFTRYTMHWVRQAP
GKGLEWIGYINPSRGYTNYNQKVKDRFTISTDKSKSTAFLQM
DSLRPEDTAVYYCARYYDDHYCLDYWGQGTTLTVSS<u>GGGGS
GGGGSGGGGS</u>DIQMTQSPSSLSASVGDRVTITCSASSSVSYMN
WYQQTPGKAPKRWIYDTSKLASGVPSRFSGSGSGTDYTFTISSL
QPEDIATYYCQQWSSNPFTFGQGTKLQITRASPKSSDKTHTCPP
CPAPEAAGGPSVFLFPPKPKDTLMISRTPEVTCVVVDVSHEDPE
VKFNWYVDGVEVHNAKTKPREEQYNSTYRVVSVLTVLHQDW
LNGKEYKCKVSNKALPAPIEKTISKAKGQPREPQVYTLPPSREE
MTKNQVSLSCAVKGFYPSDIAVEWESNGQPENNYKTTPPVLDS
DGSFFLVSKLTVDKSRWQQGNVFSCSVMHEALHNHYTQKSLS
LSPGK

>SEQ ID NO: 111 (SEQ ID NO: 111)
EVQLLESGGGLVQPGGSLRLSCAASGFSFTGYTMNWVRQAPG
KGLEWMGLINPYKGVSTYNQKVKGRFTISRDNSKNTLYLQM
NSLRAEDTAVYYCARSGYYGDSDWYFDVWGQGTLVTVSS<u>GG
GGSGGGGSGGGGS</u>DIQMTQSPSSLSASVGDRVTITC**RASQDIR
NYLNWYQQTPGKAPKRWIYYTSRLHS**GVPSRFSGSGSGTDYT

FTYSSLQPEDIATYYCQQGNTLPWTFGQGTKLEIKASPKSSDK
THTCPPCPAPEAAGGPSVFLFPPKPKDTLMISRTPEVTCVVVDV
SHEDPEVKFNWYVDGVEVHNAKTKPREEQYNSTYRVVSVLTV
LHQDWLNGKEYKCKVSNKALPAPIEKTISKAKGQPREPQVYTL
PPSREEMTKNQVSLSCAVKGFYPSDIAVEWESNGQPENNYKTT
PPVLDSDGSFFLVSKLTVDKSRWQQGNVFSCSVMHEALHNHY
TQKSLSLSPGK

>SEQ ID NO: 67                                    (SEQ ID NO: 67)
SYELTQPPSVSVSPGQTARITCAGSGLYGWYQQKPGQAPVLV
IYGTNKRPSGIPERFSGSSSGTTVTLTISGVQAEDEADYYCGSA
DSSTNAGIFGGGTKLTVLGQPKAAPSVTLFPPSSEELQANKATL
VCLISDFYPGAVTVAWKADSSPVKAGVETTTPSKQSNNKYAAS
SYLSLTPEQWKSHRSYSCQVTHEGSTVEKTVAPTECS

>SEQ ID NO: 65                                    (SEQ ID NO: 65)
SYELTQPPSVSVSPGQTARITCSAGSGLYGWYQQKPGQAPVLVIYGT
NKRPSGIPERFSGSSSGTTVTLTISGVQAEDEADYYCGSADSSTNAGIF
GGGTKLTVLGQPKAAPSVTLFPPSSEELQANKATLVCLISDFYPGAVT
VAWKADSSPVKAGVETTTPSKQSNNKYAASSYLSLTPEQWKSHRSYS
CQVTHEGSTVEKTVAPTECS

>SEQ ID NO: 66                                    (SEQ ID NO: 66)
SYELTQPPSVSVSPGQTARITCSGGSGSYGWYQQKPGQAPVLV
IYGTYKRPSGIPERFSGSSSGTTVTLTISGVQAEDEADYYCGSA
DSSTNAGIFGGGTKLTVLGQPKAAPSVTLFPPSSEELQANKATL
VCLISDFYPGAVTVAWKADSSPVKAGVETTTPSKQSNNKYAAS
SYLSLTPEQWKSHRSYSCQVTHEGSTVEKTVAPTECS

>SEQ ID NO: 86                                    (SEQ ID NO: 86)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDAWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK<u>GGGGSGGGGTGGG</u>
<u>GS</u>EVQLVESGGGPVQAGGSLRLSCAASGRTYRGYSMGWFRQ
APGKEREFVAAIVWSGGNTYYEDSVKGRFTISRDNAKNTMYL
QMTSLKPEDSATYYCAAKIRPYIFKIAGQYDYWGQGTQVTVS
S

>SEQ ID NO: 87                                    (SEQ ID NO: 87)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDVWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK<u>GGGGSGGGGTGGG</u>
<u>GS</u>EVQLVESGGGPVQAGGSLRLSCAASGRTYRGYSMGWFRQ
APGKEREFVAAIVWSGGNTYYEDSVKGRFTISRDNAKNTMYL
QMTSLKPEDSATYYCAAKIRPYIFKIAGQYDYWGQGTQVTVS
S

>SEQ ID NO: 101                                   (SEQ ID NO: 101)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDAWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK<u>GGGGSGGGGTGGG</u>
<u>GS</u>QVQLVQGGGVVQPGRSLRLSCKASGYTFTRYTMHWVRQ
APGKGLEWIGYINPSRGYTNYNQKVKDRFTISTDKSKSTAFLQ
MDSLRPEDTAVYYCARYYDDHYCLDYWGQGTTLTVSS<u>GGGG</u>
<u>SGGGGSGGGGS</u>DIQMTQSPSSLSASVGDRVTITCSASSSVSYMN
WYQQTPGKAPKRWIYDTSKLASGVPSRFSGSGSTDYTFTISSL
QPEDIATYYCQQWSSNPFTFGQGTKLQITR

>SEQ ID NO: 102                                   (SEQ ID NO: 102)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDVWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN

```
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGKGGGGSGGGGTGGG
GSQVQLVQSGGGVVQPGRSLRLSCKASGYTFTRYTMHWVRQ
APGKGLEWIGYINPSRGYTNYNQKVKDRFTISTDKSKSTAFLQ
MDSLRPEDTAVYYCARYYDDHYCLDYWGQGTTLTVSSGGGG
SGGGGSGGGGSDIQMTQSPSSLSASVGDRVTITCSASSSVSYMN
WYQQTPGKAPKRWIYDTSKLASGVPSRFSGSGSGTDYTFTISSL
QPEDIATYYCQQWSSNPFTFGQGTKLQITR
>SEQ ID NO: 103
                                        (SEQ ID NO: 103)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDAWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGKGGGGSGGGGTGGG
GSEVQLVESGGGLVQPGGSLRLSCAASGFTFSTYAMNWVRQA
PGKGLEWVGRIRSKYNNYATYYADSVKGRFTISRDDSKNTLY
LQMNSLRAEDTAVYYCRHGNFGDSYVSWFAYWGQGTLVT
VSSGKPGSGKPGSGKPGSGKPGSQAVVTQEPSLTVSPGGTVTLT
CGSSTGAVTTSNYANWVQQKPGKSPRGLIGGTNKRAPGVPA
RFSGSLLGGKAALTISGAQPEDEADYYCALWYSNHWVFGGGT
KLTVL
>SEQ ID NO: 104
                                        (SEQ ID NO: 104)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDVWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGKGGGGSGGGGTGGG
GSEVQLVESGGGLVQPGGSLRLSCAASGFTFSTYAMNWVRQA
PGKGLEWVGRIRSKYNNYATYYADSVKGRFTISRDDSKNTLY
LQMNSLRAEDTAVYYCRHGNFGDSYVSWFAYWGQGTLVT
VSSGKPGSGKPGSGKPGSGKPGSQAVVTQEPSLTVSPGGTVTLT
CGSSTGAVTTSNYANWVQQKPGKSPRGLIGGTNKRAPGVPA
RFSGSLLGGKAALTISGAQPEDEADYYCALWYSNHWVFGGGT
KLTVL
>SEQ ID NO: 105
                                        (SEQ ID NO: 105)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDAWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGKGGGGSGGGGTGGG
GSEVQLVESGGGLVQPGGSLRLSCAASGFTFNTYAMNWVRQA
PGKGLEWVARIRSKYNNYATYYADSVKSRTTISDDSKNTLYL
QMNSLRAEDTAVYYCRHGNFGNSYVSWFAYWGQTTVTVSS
GGGGSGGGGSGGGGSGGGGSEIVVTQSPATLSVSPGERATLSC
RSSTGAVTTSNYANWVQEPGQAFRGLIGGANKRAPGVPARFS
GSLSGDEATLTISSLQSEDFAVYYCALWYSNLWVFGQGTKLEI
K
>SEQ ID NO: 106
                                        (SEQ ID NO: 106)
EVQLLESGGGLVQPGGSLRLSCAASGFTFSSYAMNWVRQAPG
KGLEWVAGISSSGRYTGYADSVKGRFTISRDNSKNTLYLQMN
SLRAEDTAVYYCAKSVGSGVSWSGYVATSLDVWGQGTLVTV
SSASTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKKVEPKSCDKTHTCPPCPAPEAAGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGKGGGGSGGGGTGGG
```

-continued

GSEVQLVESGGGLVQPGGSLRLSCAASGFTFNTYAMNWVRQA

PGKGLEWVARIRSKYNNYATYYADSVKSRTTISDDSKNTLYL

QMNSLRAEDTAVYYCVRHGNFGNSYVSWFAYWGQTTVTVSS

GGGGSGGGGSGGGGSGGGGSEIVVTQSPATLSVSPGERATLSC

RSSTGAVTTSNYANWVQEPGQAFRGLIGGANKRAPGVPARFS

GSLSGDEATLTISSLQSEDFAVYYCALWYSNLWVFGQGTKLEI

K

>SEQ ID NO: 107 (SEQ ID NO: 107)
EVQLLESGGGLVQPGGSLRLSCAASGFTFSSYAMNWVRQAPG

KGLEWVAGISSSGRYTGYADSVKGRFTISRDNSKNTLYLQMN

SLRAEDTAVYYCAKSVGSGVSWSGYVATSLDAWGQTLVTV

SSASTKGPSVFPLAPSSKSTSGGTAALGCLVKDYFPEPVTVSWN

SGALTSGVHTFPAVLQSSGLYSLSSVVTVPSSSLGTQTYICNVN

HKPSNTKVDKKVEPKSCDKTHTCPPCPAPEAAGGPSVFLFPPKP

KDTLMISRTPEVTCVVVDVSHEDPEVKFNWYVDGVEVHNAKT

KPREEQYNSTYRVVSVLTVLHQDWLNGKEYKCKVSNKALPAP

IEKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK GGGGSGGGGTGGG

GSEVQLVESGGGLVQPGGSLKLSCAASGFTFNKYAMNWVRQ

APGKGLEWVARIRSKYNNYATYYADSVKDRFTISRDDSKNTA

YLQMNNLKTEDTAVYYCVRHGNFGNSYISYWAYWGQGTLV

TVSSGGGGSGGGGSGGGGSQTVVTQEPSLTVSPGGTVTLTCGS

STGAVTSGNYPNWVQQKPGQAPRGLIGGTKFLAPGTPARFSG

SLLGGKAALTLSGVQPEDEAEYYCVLWYSNRWVFGGGTKLT

VL

>SEQ ID NO: 109 (SEQ ID NO: 109)
EVQLLESGGGLVQPGGSLRLSCAASGFTFSSYAMNWVRQAPG

KGLEWVAGISSSGRYTGYADSVKGRFTISRDNSKNTLYLQMN

SLRAEDTAVYYCAKSVGSGVSWSGYVATSLDVWGQTLVTV

SSASTKGPSVFPLAPSSKSTSGGTAALGCLVKDYFPEPVTVSWN

SGALTSGVHTFPAVLQSSGLYSLSSVVTVPSSSLGTQTYICNVN

HKPSNTKVDKKVEPKSCDKTHTCPPCPAPEAAGGPSVFLFPPKP

KDTLMISRTPEVTCVVVDVSHEDPEVKFNWYVDGVEVHNAKT

KPREEQYNSTYRVVSVLTVLHQDWLNGKEYKCKVSNKALPAP

IEKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK GGGGSGGGGTGGG

GSEVQLVESGGGLVQPGGSLKLSCAASGFTFNKYAMNWVRQ

APGKGLEWVARIRSKYNNYATYYADSVKDRFTISRDDSKNTA

YLQMNNLKTEDTAVYYCVRHGNFGNSYISYWAYWGQGTLV

-continued

TVSSGGGGSGGGGSGGGGSQTVVTQEPSLTVSPGGTVTLTCGS

STGAVTSGNYPNWVQQKPGQAPRGLIGGTKFLAPGTPARFSG

SLLGGKAALTLSGVQPEDEAEYYCVLWYSNRWVFGGGTKLT

VL

>SEQ ID NO: 112 (SEQ ID NO: 112)
EVQLLESGGGLVQPGGSLRLSCAASGFTFSSYAMNWVRQAPG

KGLEWVAGISSSGRYTGYADSVKGRFTISRDNSKNTLYLQMN

SLRAEDTAVYYCAKSVGSGVSWSGYVATSLDAWGQTLVTV

SSASTKGPSVFPLAPSSKSTSGGTAALGCLVKDYFPEPVTVSWN

SGALTSGVHTFPAVLQSSGLYSLSSVVTVPSSSLGTQTYICNVN

HKPSNTKVDKKVEPKSCDKTHTCPPCPAPEAAGGPSVFLFPPKP

KDTLMISRTPEVTCVVVDVSHEDPEVKFNWYVDGVEVHNAKT

KPREEQYNSTYRVVSVLTVLHQDWLNGKEYKCKVSNKALPAP

IEKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK GGGGSGGGGTGGG

GSEVQLLESGGGLVQPGGSLRLSCAASGFSFTGYTMNWVRQA

PGKGLEWMGLINPYKGVSTYNQKVKGRFTISRDNSKNTLYLQ

MNSLRAEDTAVYYCARSGYYGDSDWYFDVWGQGTLVTVSS

GGGGSGGGGSGGGGSDIQMTQSPSSLSASVGDRVTITCRASQD

IRNYLNWYQQTPGKAPKRWIYYTSRLHSGVPSRFSGSGSGTD

YTFTYSSLQPEDIATYYCQQGNTLPWTFGQGTKLEIK

>SEQ ID NO: 113 (SEQ ID NO: 113)
EVQLLESGGGLVQPGGSLRLSCAASGFTFSSYAMNWVRQAPG

KGLEWVAGISSSGRYTGYADSVKGRFTISRDNSKNTLYLQMN

SLRAEDTAVYYCAKSVGSGVSWSGYVATSLDVWGQTLVTV

SSASTKGPSVFPLAPSSKSTSGGTAALGCLVKDYFPEPVTVSWN

SGALTSGVHTFPAVLQSSGLYSLSSVVTVPSSSLGTQTYICNVN

HKPSNTKVDKKVEPKSCDKTHTCPPCPAPEAAGGPSVFLFPPKP

KDTLMISRTPEVTCVVVDVSHEDPEVKFNWYVDGVEVHNAKT

KPREEQYNSTYRVVSVLTVLHQDWLNGKEYKCKVSNKALPAP

IEKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK GGGGSGGGGTGGG

GSEVQLLESGGGLVQPGGSLRLSCAASGFSFTGYTMNWVRQA

PGKGLEWMGLINPYKGVSTYNQKVKGRFTISRDNSKNTLYLQ

MNSLRAEDTAVYYCARSGYYGDSDWYFDVWGQGTLVTVSS

GGGGSGGGGSGGGGSDIQMTQSPSSLSASVGDRVTITCRASQD

IRNYLNWYQQTPGKAPKRWIYYTSRLHSGVPSRFSGSGSGTD

YTFTYSSLQPEDIATYYCQQGNTLPWTFGQGTKLEIK

>SEQ ID NO: 81
(SEQ ID NO: 81)
EVQLLESGGGLVQPGGSLRLSCAASGFTYRGYSMGWVRQAPG

KGLEFVAAIVWSGGNTYYEDSVKGRFTISRDNSKNTLYLQMN

SLRAEDTAVYYCAAKIRPYIFKIAGQYDYWGQGTLVTVSSAS

TKGPSVFPLAPSSKSTSGGTAALGCLVKDYFPEPVTVSWNSGA

LTSGVHTFPAVLQSSGLYSLSSVVTVPSSSLGTQTYICNVNHKP

SNTKVDKKVEPKSCDKTHTCPPCPAPEAAGGPSVFLFPPKPKDT

LMISRTPEVTCVVVDVSHEDPEVKFNWYVDGVEVHNAKTKPR

EEQYNSTYRVVSVLTVLHQDWLNGKEYKCKVSNKALPAPIEK

TISKAKGQPREPQVYTLPPSREEMTKNQVSLSCAVKGFYPSDIA

VEWESNGQPENNYKTTPPVLDSDGSFFLVSKLTVDKSRWQQG

NVFSCSVMHEALHNHYTQKSLSLSPGK

>SEQ ID NO: 121
(SEQ ID NO: 121)
EVQLVESGGGLVQPGGSLRLSCAASGFTFSTYAMNWVRQAPG

KGLEWVGRIRSKYNNYATYYADSVKGRFTISRDDSKNTLYLQ

MNSLRAEDTAVYYCVRHGNFGDSYVSWFAYWGQGTLVTVSS

ASTKGPSVFPLAPSSKSTSGGTAALGCLVKDYFPEPVTVSWNSG

ALTSGVHTFPAVLQSSGLYSLSSVVTVPSSSLGTQTYICNVNHK

PSNTKVDKKVEPKSCDKTHTCPPCPAPEAAGGPSVFLFPPKPKD

TLMISRTPEVTCVVVDVSHEDPEVKFNWYVDGVEVHNAKTKP

REEQYNSTYRVVSVLTVLHQDWLNGKEYKCKVSNKALPAPIE

KTISKAKGQPREPQVYTLPPSREEMTKNQVSLSCAVKGFYPSDI

AVEWESNGQPENNYKTTPPVLDSDGSFFLVSKLTVDKSRWQQ

GNVFSCSVMHEALHNHYTQKSLSLSPGK

>SEQ ID NO: 123
(SEQ ID NO: 123)
EVQLVESGGGLVQPGGSLRLSCAASGFTFNTYAMNWVRQAPG

KGLEWVARIRSKYNNYATYYADSVKSRTTISDDSKNTLYLQM

NSLRAEDTAVYYCVRHGNFGNSYVSWFAYWGQTTVTVSSAS

TKGPSVFPLAPSSKSTSGGTAALGCLVKDYFPEPVTVSWNSGA

LTSGVHTFPAVLQSSGLYSLSSVVTVPSSSLGTQTYICNVNHKP

SNTKVDKKVEPKSCDKTHTCPPCPAPEAAGGPSVFLFPPKPKDT

LMISRTPEVTCVVVDVSHEDPEVKFNWYVDGVEVHNAKTKPR

EEQYNSTYRVVSVLTVLHQDWLNGKEYKCKVSNKALPAPIEK

TISKAKGQPREPQVYTLPPSREEMTKNQVSLSCAVKGFYPSDIA

VEWESNGQPENNYKTTPPVLDSDGSFFLVSKLTVDKSRWQQG

NVFSCSVMHEALHNHYTQKSLSLSPGK

>SEQ ID NO: 125
(SEQ ID NO: 125)
EVQLVESGGGLVQPGGSLKLSCAASGFTFNKYAMNWVRQAP

GKGLEWVARIRSKYNNYATYYADSVKDRFTISRDDSKNTAYL

QMNNLKTEDTAVYYCVRHGNFGNSYISYWAYWGQGTLVTV

SSASTKGPSVFPLAPSSKSTSGGTAALGCLVKDYFPEPVTVSWN

SGALTSGVHTFPAVLQSSGLYSLSSVVTVPSSSLGTQTYICNVN

HKPSNTKVDKKVEPKSCDKTHTCPPCPAPEAAGGPSVFLFPPKP

KDTLMISRTPEVTCVVVDVSHEDPEVKFNWYVDGVEVHNAKT

KPREEQYNSTYRVVSVLTVLHQDWLNGKEYKCKVSNKALPAP

IEKTISKAKGQPREPQVYTLPPSREEMTKNQVSLSCAVKGFYPS

DIAVEWESNGQPENNYKTTPPVLDSDGSFFLVSKLTVDKSRWQ

QGNVFSCSVMHEALHNHYTQKSLSLSPGK

>SEQ ID NO: 127
(SEQ ID NO: 127)
QVQLVQSGGGVVQPGRSLRLSCKASGYTFTRYTMHWVRQAP

GKGLEWIGYINPSRGYTNYNQKVKDRFTISTDKSKSTAFLQM

DSLRPEDTAVYYCARYYDDHYCLDYWGQGTTLTVSSASTKGP

SVFPLAPSSKSTSGGTAALGCLVKDYFPEPVTVSWNSGALTSG

VHTFPAVLQSSGLYSLSSVVTVPSSSLGTQTYICNVNHKPSNTK

VDKKVEPKSCDKTHTCPPCPAPEAAGGPSVFLFPPKPKDTLMIS

RTPEVTCVVVDVSHEDPEVKFNWYVDGVEVHNAKTKPREEQY

NSTYRVVSVLTVLHQDWLNGKEYKCKVSNKALPAPIEKTISKA

KGQPREPQVYTLPPSREEMTKNQVSLSCAVKGFYPSDIAVEWE

SNGQPENNYKTTPPVLDSDGSFFLVSKLTVDKSRWQQGNVFSC

SVMHEALHNHYTQKSLSLSPGK

>SEQ ID NO: 129
(SEQ ID NO: 129)
EVQLLESGGGLVQPGGSLRLSCAASGFSFTGYTMNWVRQAPG

KGLEWMGLINPYKGVSTYNQKVKGRFTISRDNSKNTLYLQM

NSLRAEDTAVYYCARSGYYGDSDWYFDVWGQGTLVTVSSAS

TKGPSVFPLAPSSKSTSGGTAALGCLVKDYFPEPVTVSWNSGA

LTSGVHTFPAVLQSSGLYSLSSVVTVPSSSLGTQTYICNVNHKP

SNTKVDKKVEPKSCDKTHTCPPCPAPEAAGGPSVFLFPPKPKDT

LMISRTPEVTCVVVDVSHEDPEVKFNWYVDGVEVHNAKTKPR

EEQYNSTYRVVSVLTVLHQDWLNGKEYKCKVSNKALPAPIEK

TISKAKGQPREPQVYTLPPSREEMTKNQVSLSCAVKGFYPSDIA

VEWESNGQPENNYKTTPPVLDSDGSFFLVSKLTVDKSRWQQG

NVFSCSVMHEALHNHYTQKSLSLSPGK

>SEQ ID NO: 122
(SEQ ID NO: 122)
QAVVTQEPSLTVSPGGTVTLTCGSSTGAVTTSNYANWVQQKP

GKSPRGLIGGTNKRAPGVPARFSGSLLGGKAALTISGAQPEDE

ADYYCALWYSNHWVFGGGTKLTVLGQPKAAPSVTLFPPSSEE

LQANKATLVCLISDFYPGAVTVAWKADSSPVKAGVETTTPSKQ

SNNKYAASSYLSLTPEQWKSHRSYSCQVTHEGSTVEKTVAPTE

CS

>SEQ ID NO: 124
(SEQ ID NO: 124)
EIVVTQSPATLSVSPGERATLSCRSSTGAVTTSNYANWVQEPG

QAFRGLIGGANKRAPGVPARFSGSLSGDEATLTISSLQSEDFAV

YYCALWYSNLWVFGQGTKLEIKTVAAPSVFIFPPSDEQLKSGT

ASVVCLLNNFYPREAKVQWKVDNALQSGNSQESVTEQDSKDS

TYSLSSTLTLSKADYEKHKVYACEVTHQGLSSPVTKSFNRGEC

>SEQ ID NO: 126

(SEQ ID NO: 126)
EQTVVTQEPSLTVSPGGTVTLTCGSSTGAVTSGNYPNWVQQK

PGQAPRGLIGGTKFLAPGTPARFSGSLLGGKAALTLSGVQPED

EAEYYCVLWYSNRWVFGGGTKLTVLGQPKAAPSVTLFPPSSE

ELQANKATLVCLISDFYPGAVTVAWKADSSPVKAGVETTTPSK

QSNNKYAASSYLSLTPEQWKSHRSYSCQVTHEGSTVEKTVAPT

ECS

>SEQ ID NO: 128

(SEQ ID NO: 128)
DIQMTQSPSSLSASVGDRVTITCSASSSVSYMNWYQQTPGKAP

KRWIYDTSKLASGVPSRFSGSGSGTDYTFTISSLQPEDIATYYC

QQWSSNPFTFGQGTKLQITRRTVAAPSVFIFPPSDEQLKSGTAS

VVCLLNNFYPREAKVQWKVDNALQSGNSQESVTEQDSKDSTY

SLSSTLTLSKADYEKHKVYACEVTHQGLSSPVTKSFNRGEC

>SEQ ID NO: 130

(SEQ ID NO: 130)
DIQMTQSPSSLSASVGDRVTITCRASQDIRNYLNWYQQTPGKA

PKRWIYYTSRLHSGVPSRFSGSGSGTDYTFTYSSLQPEDIATYY

CQQGNTLPWTFGQGTKLEIKTVAAPSVFIFPPSDEQLKSGTAS

VVCLLNNFYPREAKVQWKVDNALQSGNSQESVTEQDSKDSTY

SLSSTLTLSKADYEKHKVYACEVTHQGLSSPVTKSFNRGEC

>SEQ ID NO: 117

(SEQ ID NO: 117)
EVQLLESGGGLVQPGGSLRLSCAASGFTFSSYAMNWVRQAPG

KGLEWVAGISSSGRYTGYADSVKGRFTISRDNSKNTLYLQMNS

LRAEDTAVYYCAKSVGSGVSWSGYVATSLDAWGQGTLVTVS

SASTKGPSVFPLAPSSKSTSGGTAALGCLVKDYFPEPVTVSWNS

GALTSGVHTFPAVLQSSGLYSLSSVVTVPSSSLGTQTYICNVNH

KPSNTKVDKKVEPKSCDKTHTCPPCPAPEAAGGPSVFLFPPKPK

DTLMISRTPEVTCVVVDVSHEDPEVKFNWYVDGVEVHNAKTK

PREEQYNSTYRVVSVLTVLHQDWLNGKEYKCKVSNKALPAPI

EKTISKAKGQPREPQVYTLPPSREEMTKNQVSLSCAVKGFYPSD

IAVEWESNGQPENNYKTTPPVLDSDGSFFLVSKLTVDKSRWQQ

GNVFSCSVMHEALHNHYTQKSLSLSPGKGGGGSGGGGTGGGG

SEVQLVESGGGPVQAGGSLRLSCAASGRTYRGYSMGWFRQAP

GKEREFVAAIVWSGGNTYYEDSVKGRFTISRDNAKNTMYLQM

TSLKPEDSATYYCAAKIRPYIFKIAGQYDYWGQGTQVTVSS

>SEQ ID NO: 119

(SEQ ID NO: 119)
EVQLLESGGGLVQPGGSLRLSCAASGFTFSSYAMNWVRQAPG

KGLEWVAGISSSGRYTGYADSVKGRFTISRDNSKNTLYLQMNS

LRAEDTAVYYCAKSVGSGVSWSGYVATSLDVWGQGTLVTVS

SASTKGPSVFPLAPSSKSTSGGTAALGCLVKDYFPEPVTVSWNS

GALTSGVHTFPAVLQSSGLYSLSSVVTVPSSSLGTQTYICNVNH

KPSNTKVDKKVEPKSCDKTHTCPPCPAPEAAGGPSVFLFPPKPK

DTLMISRTPEVTCVVVDVSHEDPEVKFNWYVDGVEVHNAKTK

PREEQYNSTYRVVSVLTVLHQDWLNGKEYKCKVSNKALPAPI

EKTISKAKGQPREPQVYTLPPSREEMTKNQVSLSCAVKGFYPSD

IAVEWESNGQPENNYKTTPPVLDSDGSFFLVSKLTVDKSRWQQ

GNVFSCSVMHEALHNHYTQKSLSLSPGKGGGGSGGGGTGGGG

SEVQLVESGGGPVQAGGSLRLSCAASGRTYRGYSMGWFRQAP

GKEREFVAAIVWSGGNTYYEDSVKGRFTISRDNAKNTMYLQM

TSLKPEDSATYYCAAKIRPYIFKIAGQYDYWGQGTQVTVSS

>SEQ ID NO: 118

(SEQ ID NO: 118)
EVQLVESGGGPVQAGGSLRLSCAASGRTYRGYSMGWFRQAPG

KEREFVAAIVWSGGNTYYEDSVKGRFTISRDNAKNTMYLQMT

SLKPEDSATYYCAAKIRPYIFKIAGQYDYWGQGTQVTVSSGGG

GSGGGGTGGGGSEVQLLESGGGLVQPGGSLRLSCAASGFTFSS

YAMNWVRQAPGKGLEWVAGISSSGRYTGYADSVKGRFTISRD

NSKNTLYLQMNSLRAEDTAVYYCAKSVGSGVSWSGYVATSLD

AWGQGTLVTVSSASTKGPSVFPLAPSSKSTSGGTAALGCLVKD

YFPEPVTVSWNSGALTSGVHTFPAVLQSSGLYSLSSVVTVPSSS

LGTQTYICNVNHKPSNTKVDKKVEPKSCDKTHTCPPCPAPEAA

GGPSVFLFPPKPKDTLMISRTPEVTCVVVDVSHEDPEVKFNWY

VDGVEVHNAKTKPREEQYNSTYRVVSVLTVLHQDWLNGKEY

KCKVSNKALPAPIEKTISKAKGQPREPQVYTLPPSREEMTKNQV

SLSCAVKGFYPSDIAVEWESNGQPENNYKTTPPVLDSDGSFFLV

SKLTVDKSRWQQGNVFSCSVMHEALHNHYTQKSLSLSPGK

>SEQ ID NO: 120

(SEQ ID NO: 120)
EVQLVESGGGPVQAGGSLRLSCAASGRTYRGYSMGWFRQAPG

KEREFVAAIVWSGGNTYYEDSVKGRFTISRDNAKNTMYLQMT

SLKPEDSATYYCAAKIRPYIFKIAGQYDYWGQGTQVTVSSGGG

GSGGGGTGGGGSEVQLLESGGGLVQPGGSLRLSCAASGFTFSS

YAMNWVRQAPGKGLEWVAGISSSGRYTGYADSVKGRFTISRD

NSKNTLYLQMNSLRAEDTAVYYCAKSVGSGVSWSGYVATSLD

VWGQGTLVTVSSASTKGPSVFPLAPSSKSTSGGTAALGCLVKD

YFPEPVTVSWNSGALTSGVHTFPAVLQSSGLYSLSSVVTVPSSS

LGTQTYICNVNHKPSNTKVDKKVEPKSCDKTHTCPPCPAPEAA

GGPSVFLFPPKPKDTLMISRTPEVTCVVVDVSHEDPEVKFNWY

VDGVEVHNAKTKPREEQYNSTYRVVSVLTVLHQDWLNGKEY

KCKVSNKALPAPIEKTISKAKGQPREPQVYTLPPSREEMTKNQV

```
SLSCAVKGFYPSDIAVEWESNGQPENNYKTTPPVLDSDGSFFLV

SKLTVDKSRWQQGNVFSCSVMHEALHNHYTQKSLSLSPGK
```

In some embodiments, the antibody specific for claudin 6 and CD3 (e.g. a tandem scFv antibody, scFv-Fab Fc antibody, IgG-(scFV)₂ antibody, and a scFv-Fab Fc antibody), or fragment thereof, or variant thereof, is selected from one of the following amino acid sequences:

```
>CH-HAMF5-1HEP-VH (SEQ ID NO: 69)
                                        (SEQ ID NO: 69)
EVQLLESGGGLVQPGGSLRLSCAASGFTFSSYAMNWVRQAPG

KGLEWVAGISSSGRYTGYADSVKGRFTISRDNSKNTLYLQMNS

LRAEDTAVYYCAKSVGSGVSWSGYVATSLDAWGQGTLVTVS

S

>CH-HAMF5-1HEP-VL (SEQ ID NO: 68)
                                        (SEQ ID NO: 68)
SYELTQPPSVSVSPGQTARITCSAGSGLYGWYQQKPGQAPVLVI

YGTNKRPSGIPERFSGSSSGTTVTLTISGVQAEDEADYYCGSAD

SSTNAGIFGGGTKLTVL

>CD3engager (SEQ ID NO: 75)
                                        (SEQ ID NO: 75)
EVQLVESGGGPVQAGGSLRLSCAASGRTYRGYSMGWFRQAPG

KEREFVAAIVWSGGNTYYEDSVKGRFTISRDNAKNTMYLQMT

SLKPEDSATYYCAAKIRPYIFKIAGQYDYWGQGTQVTVSS
```

In some embodiments, the antibody specific for claudin 6 and CD3 (e.g. a tandem scFv antibody, scFv-Fab Fc antibody, IgG-(scFV)₂ antibody, and a scFv-Fab Fc antibody), or fragment thereof, or variant thereof, is selected from one of the following amino acid sequences:

```
>CH-HAMF5-1HEP-HC (SEQ ID NO: 76)
                                        (SEQ ID NO: 76)
EVQLLESGGGLVQPGGSLRLSCAASGFTFSSYAMNWVRQAPG

KGLEWVAGISSSGRYTGYADSVKGRFTISRDNSKNTLYLQMNS

LRAEDTAVYYCAKSVGSGVSWSGYVATSLDAWGQGTLVTVS

SASTKGPSVFPLAPSSKSTSGGTAALGCLVKDYFPEPVTVSWNS

GALTSGVHTFPAVLQSSGLYSLSSVVTVPSSSLGTQTYICNVNH

KPSNTKVDKKVEPKSCDKTHTCPPCPAPEAAGGPSVFLFPPKPK

DTLMISRTPEVTCVVVDVSHEDPEVKFNWYVDGVEVHNAKTK

PREEQYNSTYRVVSVLTVLHQDWLNGKEYKCKVSNKALPAPI

EKTISKAKGQPREPQVYTLPPSREEMTKNQVSLWCLVKGFYPS

DIAVEWESNGQPENNYKTTPPVLDSDGSFFLYSKLTVDKSRWQ

QGNVFSCSVMHEALHNHYTQKSLSLSPGK

>CH-HAMF5-1HEP-LC (SEQ ID NO: 77)
                                        (SEQ ID NO: 77)
SYELTQPPSVSVSPGQTARITCSAGSGLYGWYQQKPGQAPVLVI

YGTNKRPSGIPERFSGSSSGTTVTLTISGVQAEDEADYYCGSAD

SSTNAGIFGGGTKLTVLGQPKAAPSVTLFPPSSEELQANKATLV

CLISDFYPGAVTVAWKADSSPVKAGVETTTPSKQSNNKYAASS

YLSLTPEQWKSHRSYSCQVTHEGSTVEKTVAPTECS

>3983-HC (SEQ ID NO: 78)
                                        (SEQ ID NO: 78)
EVQLVESGGGPVQAGGSLRLSCAASGRTYRGYSMGWFRQAPG

KEREFVAAIVWSGGNTYYEDSVKGRFTISRDNAKNTMYLQMT

SLKPEDSATYYCAAKIRPYIFKIAGQYDYWGQGTQVTVSSASP

KSSDKTHTCPPCPAPEAAGGPSVFLFPPKPKDTLMISRTPEVTCV

VVDVSHEDPEVKFNWYVDGVEVHNAKTKPREEQYNSTYRVV

SVLTVLHQDWLNGKEYKCKVSNKALPAPIEKTISKAKGQPREP

QVYTLPPSREEMTKNQVSLSCAVKGFYPSDIAVEWESNGQPEN

NYKTTPPVLDSDGSFFLVSKLTVDKSRWQQGNVFSCSVMHEA

LHNHYTQKSLSLSPGK
```

In some embodiments, the antibody or antibody fragment or variant disclosed herein (e.g., a tandem scFv antibody, scFv-Fab Fc antibody, IgG-(scFV)2 antibody, and a scFv-Fab Fc antibody) comprises a CD3 engager. In some embodiments, the CD3 engager can be selected from muOKT3, huOKT3, huSP34, huUCHT1 and a CD3 nanobody (VHH).

In some embodiments, the antibody or antibody fragment or variant disclosed herein (e.g., a tandem scFv antibody, scFv-Fab Fc antibody, IgG-(scFV)2 antibody, and a scFv-Fab Fc antibody) comprise a linker having one or more glycines and serines replaced with a functionally equivalent variation thereof. In some embodiments, the linker is identified in the underlined text above. For example, in some embodiments, the linker is selected from the amino acid sequence of GGGGSGGGGSGGGGS (SEQ ID NO: 50), GGGGS (SEQ ID NO: 51), GGSGGSGGSGGSGGVD (SEQ ID NO: 52), and GKPGSGKPGSGKPGSGKPGS (SEQ ID NO: 53).

In some embodiments, the linker may be derived from naturally-occurring multi-domain proteins or are empirical linkers as described, for example, in Chichili et al., (2013), Protein Sci. 22(2): 153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et. al., (2000), Protein Eng. 13(5):309-312, the entire contents of which are hereby incorporated by reference.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid. In various embodiments, the linker is substantially comprised of glycine and serine residues (e.g. about 30%, or about 40%, or about 50%, or about 60%, or about 70%, or about 80%, or about 90%, or about 95%, or about 97% glycines and serines).

Additional illustrative linkers include, but are not limited to, linkers having the sequence LE, GGGGS (SEQ ID NO: 51), (GGGGS)$_n$ (n=1-4) (SEQ ID NO: 54), (Gly)$_8$ (SEQ ID NO: 55), (Gly)$_6$ (SEQ ID NO: 56), (EAAAK)$_n$ (n=1-3) (SEQ ID NO: 57), A(EAAAK)$_n$A (n=2-5) (SEQ ID NO: 58), AEAAAKEAAAKA (SEQ ID NO: 59), A(EAAAK)$_4$ALEA (EAAAK)$_4$A (SEQ ID NO: 60), PAPAP (SEQ ID NO: 61), KESGSVSSEQLAQFRSLD (SEQ ID NO: 62), EGKSSGSGSESKST (SEQ ID NO: 63), GSAGSAAGSGEF (SEQ ID NO: 64), and (XP)$_n$ (n=1-5) (SEQ ID NO: 131), with X designating any amino acid, e.g., Ala, Lys, or Glu.

In various embodiments, the linker may be functional. For example, without limitation, the linker may function to improve the folding and/or stability, improve the expression, improve the pharmacokinetics, and/or improve the bioactivity of the present compositions. In another example, the linker may function to target the compositions to a particular cell type or location.

In some embodiments, disclosed herein is a composition comprising a tandem single-chain variable fragment (scFv) specific for claudin 6 and CD3 comprising one or more of:

I.
(a) an amino acid sequence of SEQ ID NO. 82, or an amino acid sequence having at least about 90%, or about 93%, or about 95%, or about 97%, or about 98%, or about 99% identity thereto, or
(b)
(i) a light chain variable region (VL) comprising LCDR1, LCDR2, and LCDR3 sequences, wherein the LCDR1 comprises an amino acid sequence of SAGSGLYG (SEQ ID NO: 1), or a variant thereof, the lCDR2 sequence comprises an amino acid sequence of GTNKRPS (SEQ ID NO: 2), or a variant thereof, and the LCDR3 sequence comprises an amino acid sequence of GSADSSTNAGI (SEQ ID NO: 3), or a variant thereof,
(ii) a heavy chain variable region (VH) comprising HCDR1, HCDR2, and HCDR3 sequences, wherein the HCDR1 comprises an amino acid sequence of SYAMN (SEQ ID NO: 4) or a variant thereof, the HCDR2 comprises an amino acid sequence of GISSSGRYTGYADSVKG (SEQ ID NO: 5), or a variant thereof, and the HCDR3 comprises an amino acid sequence of SVGSGVSWSGYVATSLDA (SEQ ID NO: 6), or a variant thereof,
(iii) a VH comprising HCDR1, HCDR2, and HCDR3 sequences, wherein the HCDR1 comprises an amino acid sequence of RYTMH (SEQ ID NO: 7), or a variant thereof, the HCDR2 comprises an amino acid sequence of YINPSRGYTNYNQKFKD (SEQ ID NO: 8), or a variant thereof, and the HCDR3 comprises an amino acid sequence of YYDDHYCLDY (SEQ ID NO: 9), or a variant thereof, and
(iv) a VL comprising LCDR1, LCDR2, and LCDR3 sequences, wherein the LCDR1 comprises an amino acid sequence of RASSSVSYMN (SEQ ID NO: 10), or a variant thereof, the LCDR2 comprises an amino acid sequence of DTSKVAS (SEQ ID NO: 11), or a variant thereof, and the LCDR3 comprises an amino acid sequence of QQWSSNPLT (SEQ ID NO: 12), or a variant thereof, II.
(a) an amino acid sequence of SEQ ID NO. 83, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SGGSGSYG (SEQ ID NO: 13), or a variant thereof, the LCDR2 comprises an amino acid sequence of GTYKRPS (SEQ ID NO: 14), or a variant thereof, and the LCDR3 comprises an amino acid sequence of SEQ ID NO: 3, or a variant thereof,
(ii) a VH comprising HCDR1, HCDR2, and HCDR3 sequences, wherein the HCDR1 comprises an amino acid sequence is SEQ ID NO: 4, or a variant thereof, the HCDR2 comprises an amino acid sequence of SEQ ID NO: 5, or a variant thereof, and the HCDR3 comprises an amino acid sequence of SVGSGVSWSGYVATSLDV (SEQ ID NO: 15), or a variant thereof,
(iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of SEQ ID NO: 8, or a variant thereof, and the HCDR3 comprises an amino acid sequence of SEQ ID NO: 9, or a variant thereof, and
(iv) a VL comprising LCDR1, LCDR2, and LCDR3 sequences, wherein the LCDR1 comprises an amino acid sequence of SEQ ID NO: 10, or a variant thereof, the LCDR2 comprises an amino acid sequence of SEQ ID NO: 11, or a variant thereof, and the LCDR3 comprises an amino acid sequence of SEQ ID NO: 12, or a variant thereof, III.
(a) an amino acid sequence of SEQ ID NO. 84, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
(ii) a VH comprising HCDR1, HCDR2, and HCDR3 sequences, wherein the HCDR1 comprises an amino acid sequence of SEQ ID NO: 4, or a variant thereof, the HCDR2 sequence of SEQ ID NO: 5, or a variant thereof, and the HCDR3 sequence of SEQ ID NO: 6, or a variant thereof, and
(iii) a VH comprising HCDR1, HCDR2, and HCDR3 sequences, wherein the HCDR1 comprises an amino acid sequence of GYSMG (SEQ ID NO: 16), or a variant thereof, the HCDR2 comprises an amino acid sequence of AIVWSGGNTYYEDSVKG (SEQ ID NO: 17), or a variant thereof, and the HCDR3 comprises an amino acid sequence of KIRPYIFKIAGQYDY (SEQ ID NO: 18), or a variant thereof, IV.
(a) an amino acid sequence of SEQ ID NO: 85, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof, (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof, and (iii) a VH comprising HCDR1, HCDR2, and HCDR3 sequences, wherein the HCDR1 comprises an amino acid sequence of SEQ ID NO: 16, or a variant thereof, the HCDR2 comprises an amino acid sequence of SEQ ID NO: 17, or a variant thereof, and the HCDR3 comprises an amino acid sequence of SEQ ID NO: 18, or a variant thereof, V.
(a) an amino acid sequence of SEQ ID NO. 93, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof, (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof, (iii) a VH comprising HCDR1, HCDR2, and HCDR3 sequences, wherein the HCDR1 comprises an amino acid sequence of KYAMN (SEQ ID NO: 19), or a variant thereof, the HCDR2 comprises an amino acid sequence of RIRSKYNNYATYYADSVKD (SEQ ID NO: 20), or a variant thereof, and the HCDR3 comprises an amino acid sequence of HGNFGNSYISYWAY (SEQ ID NO: 21), or a variant thereof, and (iv) a VL comprising LCDR1, LCDR2, and LCDR3 sequences, wherein the LCDR1 comprises an amino acid sequence of GSSTGAVTSGNYPN (SEQ ID NO: 22), or a variant thereof, the LCDR2 comprises an amino acid sequence of GTKFLAP (SEQ ID NO: 23), or a variant thereof, and the LCDR3 comprises an amino acid sequence of VLWYSNRWV (SEQ ID NO: 24), or a variant thereof, VI.
(a) an amino acid sequence of SEQ ID NO. 94, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof, (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof, (iii) a VH comprising HCDR1, HCDR2, and HCDR3 sequences, wherein the HCDR1 comprises an amino acid sequence of SEQ ID NO: 19, or a variant thereof, the HCDR2 comprises an amino acid sequence of SEQ ID NO: 20, or a variant thereof, and the HCDR3 comprises an amino acid sequence of SEQ ID NO: 21, or a variant thereof, and (iv) a VL comprising LCDR1, LCDR2, and LCDR3 sequences, wherein the LCDR1 comprises an amino acid sequence of SEQ ID NO: 22, or a variant thereof, the LCDR2 comprises an amino acid sequence of SEQ ID NO: 23, or a variant thereof, and the LCDR3 comprises an amino acid sequence of SEQ ID NO: 24, or a variant thereof, VII.
(a) an amino acid sequence of SEQ ID NO. 95, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof, (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof, (iii) a VH comprising HCDR1, HCDR2, and HCDR3 sequences, wherein the HCDR1 comprises an amino acid sequence of TYAMN (SEQ ID NO: 25), or a variant thereof, the HCDR2 comprises an amino acid sequence of RIRSKYNNYATYYADSVKG (SEQ ID NO: 26), or a variant thereof, and the HCDR3 comprises an amino acid sequence of HGNFGDSYVSWFAY (SEQ ID NO: 27), or a variant thereof, and (iv) a VL comprising LCDR1, LCDR2, and LCDR3 sequences, wherein the LCDR1 comprises an amino acid sequence of GSSTGAVTTSNYAN (SEQ ID NO: 28), or a variant thereof, the LCDR2 comprises an amino acid sequence of GTNKRAP (SEQ ID NO: 29), or a variant thereof, and the LCDR3 comprises an amino acid sequence of ALWYSNHWV (SEQ ID NO: 30), or a variant thereof, VIII.
(a) an amino acid sequence of SEQ ID NO. 96, or an amino acid sequence having at least about 90%, or about 93%, or about 95%, or about 97%, or about 98%, or about 99% identity thereto, or
(b)
(i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
(ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
(iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 26, or a variant thereof, and the HCDR3 comprises an amino acid sequence of SEQ ID NO: 27, or a variant thereof, and
(iv) a VL comprising LCDR1, LCDR2, and LCDR3 sequences, wherein the LCDR1 comprises an amino acid sequence of SEQ ID NO: 28, or a variant thereof, the LCDR2 comprises an amino acid sequence of SEQ ID NO: 29, or a variant thereof, and the LCDR3 comprises an amino acid sequence of SEQ ID NO: 30, or a variant thereof, IX.
(a) an amino acid sequence of SEQ ID NO. 97, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of RIRSKYNNYATYYADSVKS (SEQ ID NO: 31), or a variant thereof, and the HCDR3 comprises an amino acid sequence of HGNFGN-SYVSWFAY (SEQ ID NO: 32), or a variant thereof, and
  (iv) a VL comprising LCDR1, LCDR2, and LCDR3 sequences, wherein the LCDR1 comprises an amino acid sequence of RSSTGAVTTSNYAN (SEQ ID NO: 33), or a variant thereof, the LCDR2 comprises an amino acid sequence of GANKRAP (SEQ ID NO: 34), or a variant thereof, and the LCDR3 comprises an amino acid sequence of ALWYSNLWV (SEQ ID NO: 35), or a variant thereof, X.
(a) an amino acid sequence of SEQ ID NO. 98, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 31, or a variant thereof, and the HCDR3 comprises an amino acid sequence of SEQ ID NO: 32, or a variant thereof, and
  (iv) a VL comprising LCDR1, LCDR2, and LCDR3 sequences, wherein the LCDR1 comprises an amino acid sequence of SEQ ID NO: 33, or a variant thereof, the LCDR2 comprises an amino acid sequence of SEQ ID NO: 34, or a variant thereof, and the LCDR3 comprises an amino acid sequence of SEQ ID NO: 35, or a variant thereof, XI.
(a) an amino acid sequence of SEQ ID NO. 99, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of YINPSRGYTNYNQKVKD (SEQ ID NO: 36), or a variant thereof, and the HCDR3 comprises an amino acid sequence of SEQ ID NO: 9, or a variant thereof, and
  (iv) a VL comprising LCDR1, LCDR2, and LCDR3 sequences, wherein the LCDR1 comprises an amino acid sequence of SASSSVSYMN (SEQ ID NO: 37), or a variant thereof, the LCDR2 comprises an amino acid sequence of DTSKLAS (SEQ ID NO: 38), or a variant thereof, and the LCDR3 comprises an amino acid sequence of QQWSSNPFT (SEQ ID NO: 39), or a variant thereof, XII.
(a) an amino acid sequence of SEQ ID NO. 100, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of SEQ ID NO: 36, or a variant thereof, and the HCDR3 comprises an amino acid sequence of SEQ ID NO: 9, or a variant thereof, and
  (iv) a VL comprising LCDR1, LCDR2, and LCDR3 sequences, wherein the LCDR1 comprises an amino acid sequence of SEQ ID NO: 37, or a variant thereof, the LCDR2 comprises an amino acid sequence of SEQ ID NO: 38, or a variant thereof, and the LCDR3 comprises an amino acid sequence of SEQ ID NO: 39, or a variant thereof, XIII.
(a) an amino acid sequence of SEQ ID NO: 109, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of GYTMN (SEQ ID NO: 40), or a variant thereof, the HCDR2 comprises an amino acid sequence of LINPYKGVSTYNQKVKG (SEQ ID NO: 41), or a variant thereof, and the HCDR3 comprises an amino acid sequence of SGYYGDSDWYFDV (SEQ ID NO: 42), or a variant thereof, and
  (iv) a VL comprising LCDR1, LCDR2, and LCDR3 sequences, wherein the LCDR1 comprises an amino acid sequence of RASQDIRNYLN (SEQ ID NO: 43), or a variant thereof, the LCDR2 comprises an amino acid sequence of YTSRLHS (SEQ ID NO: 44), or a variant thereof, and the LCDR3 comprises an amino acid sequence of QQGNTLPWT (SEQ ID NO: 45), or a variant thereof, and XIV.
(a) an amino acid sequence of SEQ ID NO: 110, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4), or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 40, or a variant thereof, the HCDR2 comprises an amino acid sequence of SEQ ID NO: 41, or a variant thereof, and the HCDR3 comprises an amino acid sequence of SEQ ID NO: 42, or a variant thereof, and
  (iv) a VL comprising LCDR1, LCDR2, and LCDR3 sequences, wherein the LCDR1 comprises an amino acid sequence of SEQ ID NO: 43, or a variant thereof, the LCDR2 comprises an amino acid sequence of SEQ ID NO: 44, or a variant thereof, and the LCDR3 comprises an amino acid sequence of SEQ ID NO: 45, or a variant thereof, or wherein:
  any of the above sequences in subsections (a) optionally can have a His6 tag (e.g., HHHHHH (SEQ ID NO: 46)) added to the N or C-terminus and
  any of the above sequences optionally have the linker comprising one or more glycines and serines replaced with another peptide linker or functionally equivalent variation thereof.

In some embodiments, the antibody, such as a tandem scFv antibody specific for claudin 6 and CD3 comprise the CDR sequences as shown in Table 1 below:

| Tandem scFv | Domain | CDR1 | CDR2 | CDR3 |
| --- | --- | --- | --- | --- |
| SEQ ID NO: 82 | First VL | SEQ ID NO: 1<br>SAGSGLYG | SEQ ID NO: 2<br>GTNKRPS | SEQ ID NO: 3<br>GSADSSTNAGI |
| | First VH | SEQ ID NO: 4<br>SYAMN | SEQ ID NO: 5<br>GISSSGRYTGYAD SVKG | SEQ ID NO: 6<br>SVGSGVSWSGYVA TSLDA |

-continued

| Tandem scFv | Domain | CDR1 | CDR2 | CDR3 |
|---|---|---|---|---|
| | Second VH | SEQ ID NO: 7 RYTMH | SEQ ID NO: 8 YINPSRGYTNYNQKFKD | SEQ ID NO: 9 YYDDHYCLDY |
| | Second VL | SEQ ID NO: 10 RASSSVSYMN | SEQ ID NO: 11 DTSKVAS | SEQ ID NO: 12 QQWSSNPLT |
| SEQ ID NO: 83 | First VL | SEQ ID NO: 13 SGGSGSYG | SEQ ID NO: 14 GTYKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 15 SVGSGVSWSGYVATSLDV |
| | Second VH | SEQ ID NO: 7 RYTMH | SEQ ID NO: 8 YINPSRGYTNYNQKFKD | SEQ ID NO: 9 YYDDHYCLDY |
| | Second VL | SEQ ID NO: 10 RASSSVSYMN | SEQ ID NO: 11 DTSKVAS | SEQ ID NO: 12 QQWSSNPLT |
| SEQ ID NO: 84 | First VL | SEQ ID NO: 1 SAGSGLYG | SEQ ID NO: 2 GTNKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 6 SVGSGVSWSGYVATSLDA |
| | Second VH | SEQ ID NO: 16 GYSMG | SEQ ID NO: 17 AIVWSGGNTYYEDSVKG | SEQ ID NO: 18 KIRPYIFKIAGQYDY |
| | Second VL | | | |
| SEQ ID NO: 85 | First VL | SEQ ID NO: 13 SGGSGSYG | SEQ ID NO: 14 GTYKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 15 SVGSGVSWSGYVATSLDV |
| | Second VH | SEQ ID NO: 16 GYSMG | SEQ ID NO: 17 AIVWSGGNTYYEDSVKG | SEQ ID NO: 18 KIRPYIFKIAGQYDY |
| | Second VL | | | |
| SEQ ID NO: 93 | First VL | SEQ ID NO: 1 SAGSGLYG | SEQ ID NO: 2 GTNKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 6 SVGSGVSWSGYVATSLDA |
| | Second VH | SEQ ID NO: 19 KYAMN | SEQ ID NO: 20 RIRSKYNNYATYYADSVKD | SEQ ID NO: 21 HGNFGNSYISYWAY |
| | Second VL | SEQ ID NO: 22 GSSTGAVTSGNYPN | SEQ ID NO: 23 GTKFLAP | SEQ ID NO: 24 VLWYSNRWV |
| SEQ ID NO: 94 | First VL | SEQ ID NO: 13 SGGSGSYG | SEQ ID NO: 14 GTYKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 15 SVGSGVSWSGYVATSLDV |
| | Second VH | SEQ ID NO: 19 KYAMN | SEQ ID NO: 20 RIRSKYNNYATYYADSVKD | SEQ ID NO: 21 HGNFGNSYISYWAY |
| | Second VL | SEQ ID NO: 22 GSSTGAVTSGNYPN | SEQ ID NO: 23 GTKFLAP | SEQ ID NO: 24 VLWYSNRWV |
| SEQ ID NO: 95 | First VL | SEQ ID NO: 1 SAGSGLYG | SEQ ID NO: 2 GTNKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 6 SVGSGVSWSGYVATSLDA |
| | Second VH | SEQ ID NO: 25 TYAMN | SEQ ID NO: 26 RIRSKYNNYATYYADSVKG | SEQ ID NO: 27 HGNFGDSYVSWFAY |
| | Second VL | SEQ ID NO: 28 GSSTGAVTTSNYAN | SEQ ID NO: 29 GTNKRAP | SEQ ID NO: 30 ALWYSNHWV |
| SEQ ID NO: 96 | First VL | SEQ ID NO: 13 SGGSGSYG | SEQ ID NO: 14 GTYKRPS | SEQ ID NO: 3 GSADSSTNAGI |
| | First VH | SEQ ID NO: 4 SYAMN | SEQ ID NO: 5 GISSSGRYTGYADSVKG | SEQ ID NO: 15 SVGSGVSWSGYVATSLDV |
| | Second VH | SEQ ID NO: 25 TYAMN | SEQ ID NO: 26 RIRSKYNNYATYYADSVKG | SEQ ID NO: 27 HGNFGDSYVSWFAY |
| | Second VL | SEQ ID NO: 28 GSSTGAVTTSNYAN | SEQ ID NO: 29 GTNKRAP | SEQ ID NO: 30 ALWYSNHWV |

| Tandem scFv | Domain | CDR1 | CDR2 | CDR3 |
|---|---|---|---|---|
| SEQ ID NO: 97 | First VL | SEQ ID NO: 1<br>SAGSGLYG | SEQ ID NO: 2<br>GTNKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 6<br>SVGSGVSWSGYVA<br>TSLDA |
| | Second VH | SEQ ID NO: 25<br>TYAMN | SEQ ID NO: 31<br>RIRSKYNNYATYY<br>ADSVKS | SEQ ID NO: 32<br>HGNFGNSYVSWFA<br>Y |
| | Second VL | SEQ ID NO: 33<br>RSSTGAVTTSNYA<br>N | SEQ ID NO: 34<br>GANKRAP | SEQ ID NO: 35<br>ALWYSNLWV |
| SEQ ID NO: 98 | First VL | SEQ ID NO: 13<br>SGGSGSYG | SEQ ID NO: 14<br>GTYKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 15<br>SVGSGVSWSGYVA<br>TSLDV |
| | Second VH | SEQ ID NO: 25<br>TYAMN | SEQ ID NO: 31<br>RIRSKYNNYATYY<br>ADSVKS | SEQ ID NO: 32<br>HGNFGNSYVSWFA<br>Y |
| | Second VL | SEQ ID NO: 33<br>RSSTGAVTTSNYA<br>N | SEQ ID NO: 34<br>GANKRAP | SEQ ID NO: 35<br>ALWYSNLWV |
| SEQ ID NO: 99 | First VL | SEQ ID NO: 1<br>SAGSGLYG | SEQ ID NO: 2<br>GTNKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 6<br>SVGSGVSWSGYVA<br>TSLDA |
| | Second VH | SEQ ID NO: 7<br>RYTMH | SEQ ID NO: 36<br>YINPSRGYTNYNQ<br>KVKD | SEQ ID NO: 9<br>YYDDHYCLDY |
| | Second VL | SEQ ID NO: 37<br>SASSSVSYMN | SEQ ID NO: 38<br>DTSKLAS | SEQ ID NO: 39<br>QQWSSNPFT |
| SEQ ID NO: 100 | First VL | SEQ ID NO: 13<br>SGGSGSYG | SEQ ID NO: 14<br>GTYKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 15<br>SVGSGVSWSGYVA<br>TSLDV |
| | Second VH | SEQ ID NO: 7<br>RYTMH | SEQ ID NO: 36<br>YINPSRGYTNYNQ<br>KVKD | SEQ ID NO: 9<br>YYDDHYCLDY |
| | Second VL | SEQ ID NO: 37<br>SASSSVSYMN | SEQ ID NO: 38<br>DTSKLAS | SEQ ID NO: 39<br>QQWSSNPFT |
| SEQ ID NO: 109 | First VL | SEQ ID NO: 1<br>SAGSGLYG | SEQ ID NO: 2<br>GTNKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 6<br>SVGSGVSWSGYVA<br>TSLDA |
| | Second VH | SEQ ID NO: 40<br>GYTMN | SEQ ID NO: 41<br>LINPYKGVSTYNQ<br>KVKG | SEQ ID NO: 42<br>SGYYGDSDWYFDV |
| | Second VL | SEQ ID NO: 43<br>RASQDIRNYLN | SEQ ID NO: 44<br>YTSRLHS | SEQ ID NO: 45<br>QQGNTLPWT |
| SEQ ID NO: 110 | First VL | SEQ ID NO: 13<br>SGGSGSYG | SEQ ID NO: 14<br>GTYKRPS | SEQ ID NO: 3<br>GSADSSTNAGI |
| | First VH | SEQ ID NO: 4<br>SYAMN | SEQ ID NO: 5<br>GISSSGRYTGYAD<br>SVKG | SEQ ID NO: 15<br>SVGSGVSWSGYVA<br>TSLDV |
| | Second VH | SEQ ID NO: 40<br>GYTMN | SEQ ID NO: 41<br>LINPYKGVSTYNQ<br>KVKG | SEQ ID NO: 42<br>SGYYGDSDWYFDV |
| | Second VL | SEQ ID NO: 43<br>RASQDIRNYLN | SEQ ID NO: 44<br>YTSRLHS | SEQ ID NO: 45<br>QQGNTLPWT |

In some embodiments, disclosed herein is a composition comprising a scFv-Fab Fc antibody specific for claudin 6 and CD3 comprising:
(a) a first heavy chain selected from:
  (i) SEQ ID NO: 79,
    an amino acid sequence having at least about 90%, or about 93%, or about 95%, or about 97%, or about 98%, or about 99% identity thereto, or
    a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or
  (ii) SEQ ID NO: 88,
    an amino acid sequence having at least about 90%, or about 93%, or about 95%, or about 97%, or about 98%, or about 99% identity thereto, or
    a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or
(iii) SEQ ID NO: 114,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SMGSGVSWSGYVATSIDV (SEQ ID NO: 47), or a variant thereof,
(b) a second heavy chain selected from:
(i.) SEQ ID NO: 80,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or
(ii.) SEQ ID NO: 89,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or
  a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, or
(iii.) SEQ ID NO: 90,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or
  a heavy chain variable region comprising heavy chain CDR1, CDR2, and CDR3 sequences, wherein the heavy chain CDR1 comprises an amino acid sequence of RSSTGAVTTSNYA (SEQ ID NO: 48), or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, or
(iv.) SEQ ID NO: 91,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or
  a heavy chain variable region comprising heavy chain CDR1, CDR2, and CDR3 sequences, wherein the heavy chain CDR1 comprises an amino acid sequence is GSSTGAVTSGNYP (SEQ ID NO: 49), or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, or
(v.) SEQ ID NO: 92,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or
  a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, or
(vi.) SEQ ID NO: 111,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or
  a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof; and
(c) a first light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

In some embodiments, the Fc is from IgG.

In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are selected from:
(a) T366Y and Y407T or T366Y/F405A and T394W/Y407T in human IgG1, or
(b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
in human IgG1.

In some embodiments, the human IgG Fc comprises one or mutations to reduce or eliminate the effector function of the Fc domains. In some embodiments, the mutations are L234A and L235A (LALA) substitutions in human IgG1.

In some embodiments, the human IgG Fc comprises one or mutations to stabilize a hinge region in the Fc domain. In some embodiments, the mutation is S228P.

In some embodiments, the scFv-Fab antibody specific for claudin 6 and CD3 comprise the CDR sequences as shown in Table 2 below:

TABLE 2

Exemplary scFv-Fab sequences

| Domain | SEQ ID NO | CDR1 | CDR2 | CDR3 |
|---|---|---|---|---|
| First Heavy Chain | SEQ ID NO: 79 | SEQ ID NO: 4<br>SYAMN | SEQ ID NO: 5<br>GISSSGRYTGYAD SVKG | SEQ ID NO: 6<br>SVGSGVSWSGYVA TSLDA |
| | SEQ ID NO: 88 | SEQ ID NO: 4<br>SYAMN | SEQ ID NO: 5<br>GISSSGRYTGYAD SVKG | SEQ ID NO: 15<br>SVGSGVSWSGYVA TSLDV |
| | SEQ ID NO: 114 | SEQ ID NO: 4<br>SYAMN | SEQ ID NO: 5<br>GISSSGRYTGYAD SVKG | SEQ ID NO: 47<br>SMGSGVSWSGYVA TSIDV |
| SCFV | SEQ ID NO: 80 | (HCDR1)<br>SEQ ID NO: 16<br>GYSMG | (HCDR2)<br>SEQ ID NO: 17<br>AIVWSGGNTYYED SVKG | (HCDR3)<br>SEQ ID NO: 18<br>KIRPYIFKIAGQY DY |
| | SEQ ID NO: 81 | (HCDR1)<br>SEQ ID NO: 16<br>GYSMG | (HCDR2)<br>SEQ ID NO: 17<br>AIVWSGGNTYYED SVKG | (HCDR3)<br>SEQ ID NO: 18<br>KIRPYIFKIAGQY DY |
| | SEQ ID NO: 89 | (HCDR1)<br>SEQ ID NO: 25<br>TYAMN | (HCDR2)<br>SEQ ID NO: 26<br>RIRSKYNNYATYY ADSVKG | (HCDR3)<br>SEQ ID NO: 27<br>HGNFGDSYVSWFA Y |
| | | (LCDR1)<br>SEQ ID NO: 28<br>GSSTGAVTTSNYA N | (LCDR2)<br>SEQ ID NO: 29<br>GTNKRAP | (LCDR3)<br>SEQ ID NO: 30<br>ALWYSNHWV |

TABLE 2-continued

Exemplary scFv-Fab sequences

| Domain | SEQ ID NO | CDR1 | CDR2 | CDR3 |
|---|---|---|---|---|
| | SEQ ID NO: 90 | (HCDR1) SEQ ID NO: 25 TYAMN | (HCDR2) SEQ ID NO: 31 RIRSKYNNYATYY ADSVKS | (HCDR3) SEQ ID NO: 32 HGNFGNSYVSWFA Y |
| | | (LCDR1) SEQ ID NO: 48 RSSTGAVTTSNYA | (LCDR2) SEQ ID NO: 34 GANKRAP | (LCDR3) SEQ ID NO: 35 ALWYSNLWV |
| | SEQ ID NO: 91 | (HCDR1) SEQ ID NO: 19 KYAMN | (HCDR2) SEQ ID NO: 20 RIRSKYNNYATYY ADSVKD | (HCDR3) SEQ ID NO: 21 HGNFGNSYISYWA Y |
| | | (LCDR1) SEQ ID NO: 49 GSSTGAVTSGNYP | (LCDR2) SEQ ID NO: 23 GTKFLAP | (LCDR3) SEQ ID NO: 24 VLWYSNRWV |
| | SEQ ID NO: 92 | (HCDR1) SEQ ID NO: 7 RYTMH | (HCDR2) SEQ ID NO: 36 YINPSRGYTNYNQ KVKD | (HCDR3) SEQ ID NO: 9 YYDDHYCLDY |
| | | (LCDR1) SEQ ID NO: 37 SASSSVSYMN | (LCDR2) SEQ ID NO: 38 DTSKLAS | (LCDR3) SEQ ID NO: 39 QQWSSNPFT |
| | SEQ ID NO: 111 | (HCDR1) SEQ ID NO: 40 GYTMN | (HCDR2) SEQ ID NO: 41 LINPYKGVSTYNQ KVKG | (HCDR3) SEQ ID NO: 42 SGYYGDSDWYFDV |
| | | (LCDR1) SEQ ID NO: 43 RASQDIRNYLN | (LCDR2) SEQ ID NO: 44 YTSRLHS | (LCDR3) SEQ ID NO: 45 QQGNTLPWT |
| First Light Chain | SEQ ID NO: 65 | SEQ ID NO: 1 SAGSGLYG | SEQ ID NO: 2 GTNKRPS | SEQ ID NO: 3 GSADSSTNAGI |
| | SEQ ID NO: 66 | SEQ ID NO: 13 SGGSGSYG | SEQ ID NO: 14 GTYKRPS | SEQ ID NO: 3 GSADSSTNAGI |
| | SEQ ID NO: 67 | SEQ ID NO: 1 SAGSGLYG | SEQ ID NO: 2 GTNKRPS | SEQ ID NO: 3 GSADSSTNAGI |

In some embodiments, the scFv-Fab antibody specific for claudin 6 and CD3 comprise the CDR sequences as shown in Table 3 below:

TABLE 3

Exemplary scFv-Fab sequences

| Domain | SEQ ID NO | CDR1 | CDR2 | CDR3 |
|---|---|---|---|---|
| First Heavy Chain | SEQ ID NO: 79 | SEQ ID NO: 4 SYAMN | SEQ ID NO: 5 GISSSGRYTGYAD SVKG | SEQ ID NO: 6 SVGSGVSWSGYVA TSLDA |
| | SEQ ID NO: 88 | SEQ ID NO: 4 SYAMN | SEQ ID NO: 5 GISSSGRYTGYAD SVKG | SEQ ID NO: 15 SVGSGVSWSGYVA TSLDV |
| | SEQ ID NO: 114 | SEQ ID NO: 4 SYAMN | SEQ ID NO: 5 GISSSGRYTGYAD SVKG | SEQ ID NO: 47 SMGSGVSWSGYVA TSIDV |
| Second Heavy Chain | SEQ ID NO: 117 | (VH1HCDR1) SEQ ID NO: 4 SYAMN | (VH1HCDR2) SEQ ID NO: 5 GISSSGRYTGYAD SVKG | (VH1HCDR3) SEQ ID NO: 6 SVGSGVSWSGYVA TSLDA |
| | | (VH2HCDR1) SEQ ID NO: 16 GYSMG | (VH2HCDR2) SEQ ID NO: 17 AIVWSGGNTYYED SVKG | (VH2HCDR3) SEQ ID NO: 18 KIRPYIFKIAGQY DY |
| | SEQ ID NO: 118 | (VH1HCDR1) SEQ ID NO: 16 GYSMG | (VH1HCDR2) SEQ ID NO: 17 AIVWSGGNTYYED SVKG | (VH1HCDR3) SEQ ID NO: 18 KIRPYIFKIAGQY DY |
| | | (VH2HCDR1) SEQ ID NO: 4 SYAMN | (VH2HCDR2) SEQ ID NO: 5 GISSSGRYTGYAD SVKG | (VH2HCDR3) SEQ ID NO: 6 SVGSGVSWSGYVA TSLDA |
| | SEQ ID NO: 119 | (VH1HCDR1) SEQ ID NO: 4 | (VH1HCDR2) SEQ ID NO: 5 | (VH1HCDR3) SEQ ID NO: 15 |

TABLE 3-continued

Exemplary scFv-Fab sequences

| Domain | SEQ ID NO | CDR1 | CDR2 | CDR3 |
|---|---|---|---|---|
| | | SYAMN (VH2HCDR1) | GISSSGRYTGYAD SVKG (VH2HCDR2) | SVGSGVSWSGYVA TSLDV (VH2HCDR3) |
| | | SEQ ID NO: 16 GYSMG | SEQ ID NO: 17 AIVWSGGNTYYED SVKG | SEQ ID NO: 18 KIRPYIFKIAGQY DY |
| | SEQ ID NO: 120 | (VH1HCDR1) SEQ ID NO: 16 GYSMG | (VH1HCDR2) SEQ ID NO: 17 AIVWSGGNTYYED SVKG | (VH1HCDR3) SEQ ID NO: 18 KIRPYIFKIAGQY DY |
| | | (VH2HCDR1) SEQ ID NO: 4 SYAMN | (VH2HCDR2) SEQ ID NO: 5 GISSSGRYTGYAD SVKG | (VH2HCDR3) SEQ ID NO: 15 SVGSGVSWSGYVA TSLDV |
| | SEQ ID NO: 121 | SEQ ID NO: 25 TYAMN | SEQ ID NO: 26 RIRSKYNNYATYY ADSVKG | SEQ ID NO: 27 HGNFGDSYVSWFA Y |
| | SEQ ID NO: 123 | SEQ ID NO: 25 TYAMN | SEQ ID NO: 31 RIRSKYNNYATYY ADSVKS | SEQ ID NO: 32 HGNFGNSYVSWFA Y |
| | SEQ ID NO: 125 | SEQ ID NO: 19 KYAMN | SEQ ID NO: 20 RIRSKYNNYATYY ADSVKD | SEQ ID NO: 21 HGNFGNSYISYWA Y |
| | SEQ ID NO: 127 | SEQ ID NO: 7 RYTMH | SEQ ID NO: 36 YINPSRGYTNYNQ KVKD | SEQ ID NO: 9 YYDDHYCLDY |
| First Light Chain | SEQ ID NO: 65 | SEQ ID NO: 1 SAGSGLYG | SEQ ID NO: 2 GTNKRPS | SEQ ID NO: 3 GSADSSTNAGI |
| | SEQ ID NO: 66 | SEQ ID NO: 13 SGGSGSYG | SEQ ID NO: 14 GTYKRPS | SEQ ID NO: 3 GSADSSTNAGI |
| | SEQ ID NO: 67 | SEQ ID NO: 1 SAGSGLYG | SEQ ID NO: 2 GTNKRPS | SEQ ID NO: 3 GSADSSTNAGI |
| Second Light Chain | SEQ ID NO: 122 | SEQ ID NO: 28 GSSTGAVTTSNYA N | SEQ ID NO: 29 GTNKRAP | SEQ ID NO: 30 ALWYSNHWV |
| | SEQ ID NO: 124 | SEQ ID NO: 33 RSSTGAVTTSNYA N | SEQ ID NO: 34 GANKRAP | SEQ ID NO: 35 ALWYSNLWV |
| | SEQ ID NO: 126 | SEQ ID NO: 22 GSSTGAVTSGNYP N | SEQ ID NO: 23 GTKFLAP | SEQ ID NO: 24 VLWYSNRWV |
| | SEQ ID NO: 128 | SEQ ID NO: 37 SASSSVSYMN | SEQ ID NO: 38 DTSKLAS | SEQ ID NO: 39 QQWSSNPFT |
| | SEQ ID NO: 130 | SEQ ID NO: 43 RASQDIRNYLN | SEQ ID NO: 44 YTSRLHS | SEQ ID NO: 45 QQGNTLPWT |

In some embodiments, the scFv-Fab antibody specific for claudin 6 and CD3 comprise the CDR sequences as shown in Table 4 below:

TABLE 4

Exemplary scFv-Fab antibodies

| Antibody | Domain | CDR1 | CDR2 | CDR3 |
|---|---|---|---|---|
| IMC-16-3 | First Heavy Chain-SEQ ID NO: 79 SCFV-SEQ ID NO: 89 | SEQ ID NO: 4 SYAMN (HCDR1) SEQ ID NO: 25 TYAMN (LCDR1) SEQ ID NO: 28 GSSTGAVTTSNYA N | SEQ ID NO: 5 GISSSGRYTGYAD SVKG (HCDR2) SEQ ID NO: 26 RIRSKYNNYATYY ADSVKG (LCDR2) SEQ ID NO: 29 GTNKRAP | SEQ ID NO: 6 SVGSGVSWSGYVA TSLDA (HCDR3) SEQ ID NO: 27 HGNFGDSYVSWFA Y (LCDR3) SEQ ID NO: 30 ALWYSNHWV |
| | First Light Chain-SEQ ID NO: 67 | SEQ ID NO: 1 SAGSGLYG | SEQ ID NO: 2 GTNKRPS | SEQ ID NO: 3 GSADSSTNAGI |
| IMC-16-7 | First Heavy Chain-SEQ ID NO: 79 | SEQ ID NO: 4 SYAMN | SEQ ID NO: 5 GISSSGRYTGYAD SVKG | SEQ ID NO: 6 SVGSGVSWSGYVA TSLDA |

TABLE 4-continued

Exemplary scFv-Fab antibodies

| Antibody | Domain | CDR1 | CDR2 | CDR3 |
|---|---|---|---|---|
| | SCFV-SEQ ID NO: 91 | (HCDR1) SEQ ID NO: 19 KYAMN | (HCDR2) SEQ ID NO: 20 RIRSKYNNYATYY ADSVKD | (HCDR3) SEQ ID NO: 21 HGNFGNSYISYWA Y |
| | | (LCDR1) SEQ ID NO: 49 GSSTGAVTSGNYP | (LCDR2) SEQ ID NO: 23 GTKFLAP | (LCDR3) SEQ ID NO: 24 VLWYSNRWV |
| | First Light Chain-SEQ ID NO: 67 | SEQ ID NO: 1 SAGSGLYG | SEQ ID NO: 2 GTNKRPS | SEQ ID NO: 3 GSADSSTNAGI |
| IMC-16-13 | First Heavy Chain-SEQ ID NO: 114 | SEQ ID NO: 4 SYAMN | SEQ ID NO: 5 GISSSGRYTGYAD SVKG | SEQ ID NO: 47 SMGSGVSWSGYVA TSIDV |
| | SCFV-SEQ ID NO: 80 | (HCDR1) SEQ ID NO: 16 GYSMG | (HCDR2) SEQ ID NO: 17 AIVWSGGNTYYED SVKG | (HCDR3) SEQ ID NO: 18 KIRPYIFKIAGQY DY |
| | First Light Chain SEQ ID NO: 65 | SEQ ID NO: 1 SAGSGLYG | SEQ ID NO: 2 GTNKRPS | SEQ ID NO: 3 GSADSSTNAGI |
| IMC-16-15 | First Heavy Chain-SEQ ID NO: 114 | SEQ ID NO: 4 SYAMN | SEQ ID NO: 5 GISSSGRYTGYAD SVKG | SEQ ID NO: 47 SMGSGVSWSGYVA TSIDV |
| | SCFV-SEQ ID NO: 89 | (HCDR1) SEQ ID NO: 25 TYAMN | (HCDR2) SEQ ID NO: 26 RIRSKYNNYATYY ADSVKG | (HCDR3) SEQ ID NO: 27 HGNFGDSYVSWFA Y |
| | | (LCDR1) SEQ ID NO: 28 GSSTGAVTTSNYAN | (LCDR2) SEQ ID NO: 29 GTNKRAP | (LCDR3) SEQ ID NO: 30 ALWYSNHWV |
| | First Light Chain SEQ ID NO: 65 | SEQ ID NO: 1 SAGSGLYG | SEQ ID NO: 2 GTNKRPS | SEQ ID NO: 3 GSADSSTNAGI |

In some embodiments, disclosed herein is a composition comprising an IgG-(scFV)$_2$ antibody specific for claudin 6 and CD3 comprising:
(a) a heavy chain selected from:
  (i.) SEQ ID NO: 86,
    an amino acid sequence having at least about 90%, or about 93%, or about 95%, or about 97%, or about 98%, or about 99% identity thereto, or
    a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or
    a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
  (ii.) SEQ ID NO: 87,
    an amino acid sequence having at least about 90%, or about 93%, or about 95%, or about 97%, or about 98%, or about 99% identity thereto, or
    a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or
    a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
  (iii.) SEQ ID NO: 101,
    an amino acid sequence having at least about 90%, or about 93%, or about 95%, or about 97%, or about 98%, or about 99% identity thereto, or
    a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or
    a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, (iv.) SEQ ID NO: 102, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, (v.) SEQ ID NO: 103, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, (vi.) SEQ ID NO: 104, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence is of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, (vii.) SEQ ID NO: 105, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or a heavy chain variable region comprising heavy chain CDR1, CDR2, and CDR3 sequences, wherein the heavy chain CDR1 comprises an amino acid sequence of SEQ ID NO: 33, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, (viii.) SEQ ID NO: 106, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or a heavy chain variable region comprising heavy chain CDR1, CDR2, and CDR3 sequences, wherein the heavy chain CDR1 comprises an amino acid sequence of SEQ ID NO: 33, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, (ix.) SEQ ID NO: 107, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or a heavy chain variable region comprising heavy chain CDR1, CDR2, and CDR3 sequences, wherein the heavy chain CDR1 comprises an amino acid sequence of SEQ ID NO: 22, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, (x.) SEQ ID NO: 108, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or a heavy chain variable region comprising heavy chain CDR1, CDR2, and CDR3 sequences, wherein the heavy chain CDR1 comprises an amino acid sequence of SEQ ID NO: 22, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, (xi.) SEQ ID NO: 112, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof, (xii.) SEQ ID NO: 113, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof;

and (b) a light chain selected from:

(i) SEQ ID NO: 67, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:
  any of the above sequences in subsections (a) optionally can have a His6 tag (e.g., HHHHHH (SEQ ID NO: 46)) added to the N or C-terminus and
  any of the above sequences optionally have the linker comprising one or more glycines and serines replaced with another peptide linker or functionally equivalent variation thereof.

In some embodiments, the Fc is from IgG. In some embodiments, the IgG is human IgG. In some embodiments, the human IgG is selected from IgG1, IgG2, IgG3, and IgG4.

In some embodiments, the human IgG Fc comprises one or mutations to reduce or eliminate the effector function of the Fc domains. In some embodiments, the mutations are L234A and L235A (LALA) substitutions in human IgG1.

In some embodiments, the human IgG Fc comprises one or mutations to stabilize a hinge region in the Fc domain. In some embodiments, the mutation is S228P.

In some embodiments, the IgG-(scFv)$_2$ antibody specific for claudin 6 and CD3 comprise the CDR sequences as shown in Table 5 below:

| Domain | SEQ ID NO | CDR1 | CDR2 | CDR3 |
|---|---|---|---|---|
| Heavy Chain and scFv | SEQ ID NO: 86 | (VH1 HCDR1) SEQ ID NO: 4 SYAMN | (VH1 HCDR2) SEQ ID NO: 5 GISSSGRYTGYADSVKG | (VH1 HCDR3) SEQ ID NO: 6 SVGSGVSWSGYVATSLDA |
| | | (scFv HCDR1) SEQ ID NO: 16 GYSMG | (scFv HCDR2) SEQ ID NO: 17 AIVWSGGNTYYEDSVKG | (scFv HCDR3) SEQ ID NO: 18 KIRPYIFKIAGQYDY |
| | | (scFv LCDR1) | (scFv LCDR2) | (scFv LCDR3) |
| | SEQ ID NO: 87 | (VH1 HCDR1) SEQ ID NO: 4 SYAMN | (VH1 HCDR2) SEQ ID NO: 5 GISSSGRYTGYADSVKG | (VH1 HCDR3) SEQ ID NO: 15 SVGSGVSWSGYVATSLDV |
| | | (scFv HCDR1) SEQ ID NO: 16 GYSMG | (scFv HCDR2) SEQ ID NO: 17 AIVWSGGNTYYEDSVKG | (scFv HCDR3) SEQ ID NO: 18 KIRPYIFKIAGQYDY |
| | | (scFv LCDR1) | (scFv LCDR2) | (scFv LCDR3) |
| | SEQ ID NO: 101 | (VH1 HCDR1) SEQ ID NO: 4 SYAMN | (VH1 HCDR2) SEQ ID NO: 5 GISSSGRYTGYADSVKG | (VH1 HCDR3) SEQ ID NO: 6 SVGSGVSWSGYVATSLDA |
| | | (scFv HCDR1) SEQ ID NO: 7 RYTMH | (scFv HCDR2) SEQ ID NO: 36 YINPSRGYTNYNQKVKD | (scFv HCDR3) SEQ ID NO: 9 YYDDHYCLDY |
| | | (scFv LCDR1) SEQ ID NO: 37 SASSSVSYMN | (scFv LCDR2) SEQ ID NO: 38 DTSKLAS | (scFv LCDR3) SEQ ID NO: 39 QQWSSNPFT |
| | SEQ ID NO: 102 | (VH1 HCDR1) SEQ ID NO: 4 SYAMN | (VH1 HCDR2) SEQ ID NO: 5 GISSSGRYTGYADSVKG | (VH1 HCDR3) SEQ ID NO: 15 SVGSGVSWSGYVATSLDV |
| | | (SCFv HCDR1) SEQ ID NO: 7 RYTMH | (scFv HCDR2) SEQ ID NO: 36 YINPSRGYTNYNQKVKD | (scFv HCDR3) SEQ ID NO: 9 YYDDHYCLDY |
| | | (scFv LCDR1) SEQ ID NO: 37 SASSSVSYMN | (scFv LCDR2) SEQ ID NO: 38 DTSKLAS | (scFv LCDR3) SEQ ID NO: 39 QQWSSNPFT |
| | SEQ ID NO: 103 | (VH1 HCDR1) SEQ ID NO: 4 SYAMN | (VH1 HCDR2) SEQ ID NO: 5 GISSSGRYTGYADSVKG | (VH1 HCDR3) SEQ ID NO: 6 SVGSGVSWSGYVATSLDA |

| Domain | SEQ ID NO | CDR1 | CDR2 | CDR3 |
|---|---|---|---|---|
| | | (scFv HCDR1) SEQ ID NO: 25 TYAMN | (scFv HCDR2) SEQ ID NO: 26 RIRSKYNNYATYY ADSVKG | (scFv HCDR3) SEQ ID NO: 27 HGNFGDSYVSWFA Y |
| | | (scFv LCDR1) SEQ ID NO: 28 GSSTGAVTTSNYA N | (scFv LCDR2) SEQ ID NO: 29 GTNKRAP | (scFv LCDR3) SEQ ID NO: 30 ALWYSNHWV |
| | SEQ ID NO: 104 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 15 SVGSGVSWSGYVA TSLDV |
| | | (scFv HCDR1) SEQ ID NO: 25 TYAMN | (scFv HCDR2) SEQ ID NO: 26 RIRSKYNNYATYY ADSVKG | (scFv HCDR3) SEQ ID NO: 27 HGNFGDSYVSWFA Y |
| | | (scFv LCDR1) SEQ ID NO: 28 GSSTGAVTTSNYA N | (scFv LCDR2) SEQ ID NO: 29 GTNKRAP | (scFv LCDR3) SEQ ID NO: 30 ALWYSNHWV |
| | SEQ ID NO: 105 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 6 SVGSGVSWSGYVA TSLDA |
| | | (scFv HCDR1) SEQ ID NO: 25 TYAMN | (scFv HCDR2) SEQ ID NO: 31 RIRSKYNNYATYY ADSVKS | (scFv HCDR3) SEQ ID NO: 32 HGNFGNSYVSWFA Y |
| | | (scFv LCDR1) SEQ ID NO: 33 RSSTGAVTTSNYA N | (scFv LCDR2) SEQ ID NO: 34 GANKRAP | (scFv LCDR3) SEQ ID NO: 35 ALWYSNLWV |
| | SEQ ID NO: 106 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 15 SVGSGVSWSGYVA TSLDV |
| | | (scFv HCDR1) SEQ ID NO: 25 TYAMN | (scFv HCDR2) SEQ ID NO: 31 RIRSKYNNYATYY ADSVKS | (scFv HCDR3) SEQ ID NO: 32 HGNFGNSYVSWFA Y |
| | | (scFv LCDR1) SEQ ID NO: 33 RSSTGAVTTSNYA N | (scFv LCDR2) SEQ ID NO: 34 GANKRAP | (scFv LCDR3) SEQ ID NO: 35 ALWYSNLWV |
| | SEQ ID NO: 107 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 6 SVGSGVSWSGYVA TSLDA |
| | | (scFv HCDR1) SEQ ID NO: 19 KYAMN | (scFv HCDR2) SEQ ID NO: 20 RIRSKYNNYATYY ADSVKD | (scFv HCDR3) SEQ ID NO: 21 HGNFGNSYISYWA Y |
| | | (SCFV LCDR1) SEQ ID NO: 22 GSSTGAVTSGNYP N | (scFv LCDR2) SEQ ID NO: 23 GTKFLAP | (scFv LCDR3) SEQ ID NO: 24 VLWYSNRWV |
| | SEQ ID NO:108 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 15 SVGSGVSWSGYVA TSLDV |
| | | (scFv HCDR1) SEQ ID NO: 19 KYAMN | (scFv HCDR2) SEQ ID NO: 20 RIRSKYNNYATYY ADSVKD | (scFv HCDR3) SEQ ID NO: 21 HGNFGNSYISYWA Y |
| | | (scFv LCDR1) SEQ ID NO: 22 GSSTGAVTSGNYP N | (scFv LCDR2) SEQ ID NO: 23 GTKFLAP | (scFv LCDR3) SEQ ID NO: 24 VLWYSNRWV |
| | SEQ ID NO: 112 | (VH1 HCDR1) SEQ ID NO: 4 SYAMN | (VH1 HCDR2) SEQ ID NO: 5 GISSSGRYTGYAD SVKG | (VH1 HCDR3) SEQ ID NO: 6 SVGSGVSWSGYVA TSLDA |
| | | (scFv HCDR1) SEQ ID NO: 40 GYTMN | (scFv HCDR2) SEQ ID NO: 41 LINPYKGVSTYNQ KVKG | (scFv HCDR3) SEQ ID NO: 42 SGYYGDSDWYFDV |

-continued

| Domain | SEQ ID NO | CDR1 | CDR2 | CDR3 |
|---|---|---|---|---|
| | SEQ ID NO: 113 | (scFv LCDR1)<br>SEQ ID NO: 43<br>RASQDIRNYLN<br>(VH1 HCDR1)<br>SEQ ID NO: 4<br>SYAMN<br>(scFv HCDR1)<br>SEQ ID NO: 40<br>GYTMN<br>(scFv LCDR1)<br>SEQ ID NO: 43<br>RASQDIRNYLN | (scFv LCDR2)<br>SEQ ID NO: 44<br>YTSRLHS<br>(VH1 HCDR2)<br>SEQ ID NO: 5<br>GISSSGRYTGYAD<br>SVKG<br>(scFv HCDR2)<br>SEQ ID NO: 41<br>LINPYKGVSTYNQ<br>KVKG<br>(scFv LCDR2)<br>SEQ ID NO: 44<br>YTSRLHS | (scFv LCDR3)<br>SEQ ID NO: 45<br>QQGNTLPWT<br>(VH1 HCDR3)<br>SEQ ID NO: 15<br>SVGSGVSWSGYVA<br>TSLDV<br>(scFv HCDR3)<br>SEQ ID NO: 42<br>SGYYGDSDWYFDV<br>(scFv LCDR3)<br>SEQ ID NO: 45<br>QQGNTLPWT |
| Light Chain | SEQ ID NO: 65 | SEQ ID NO: 1<br>SAGSGLYG | SEQ ID NO: 2<br>GTNKRPS | SEQ ID NO: 3<br>GSADSSTNAGI |
| | SEQ ID NO: 66 | SEQ ID NO: 13<br>SGGSGSYG | SEQ ID NO: 14<br>GTYKRPS | SEQ ID NO: 3<br>GSADSSTNAGI |
| | SEQ ID NO: 67 | SEQ ID NO: 1<br>SAGSGLYG | SEQ ID NO: 2<br>GTNKRPS | SEQ ID NO: 3<br>GSADSSTNAGI |

In some embodiments, disclosed herein is a composition comprising a scFv-Fab Fc antibody specific for claudin 6 and CD3 comprising:

(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, (ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof, (b) a second heavy chain selected from:
SEQ ID NO: 81,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
and
(c) a light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or
(iii) SEQ ID NO: 65,
an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:
  any of the above sequences in subsections (a) optionally can have a His6 tag (e.g., HHHHHH (SEQ ID NO: 46)) added to the N or C-terminus and
  any of the above sequences optionally have the linker comprising one or more glycines and serines replaced with another peptide linker or functionally equivalent variation thereof.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, mutations are:
  (a) T366Y and Y407T or T366Y/F405A and T394W/Y407T in human IgG1 or
  (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
  in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, mutation is S228P.

In some embodiments, disclosed herein is a composition comprising a scFv-Fab Fc antibody specific for claudin 6 and CD3 comprising:
  (a) a first heavy chain selected from:
  (i) SEQ ID NO: 79,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
  (ii) SEQ ID NO: 88,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
  or
  (iii) SEQ ID NO: 114,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof
  (b) a second heavy chain selected from:
  (i.) SEQ ID NO: 117,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
  or
  a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
  (ii.) SEQ ID NO: 119,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
  or
  a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
  (iii.) SEQ ID NO: 118,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, (iv.) SEQ ID NO: 120, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, and (c) a light chain selected from:

(i) SEQ ID NO: 67, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66 an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:

any of the above sequences in subsections (a) optionally can have a His6 tag (e.g., HHHHHH (SEQ ID NO: 46)) added to the N or C-terminus and any of the above sequences optionally have the linker comprising one or more glycines and serines replaced with another peptide linker or functionally equivalent variation thereof.

For example, the linker of GGGGSGGGGSGGGGS(SEQ ID NO: 50) that is illustrated in various embodiments herein (above and below), can be replaced with a linker of LE, SEQ ID NO: 51, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, or SEQ ID NO: 131.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are:

(a) T366Y and Y407T or T366Y/F405A and T394W/Y407T in human IgG1 or (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V, in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, the mutation is S228P.

In some embodiments, disclosed herein is a composition comprising a scFv-Fab Fc antibody specific for claudin 6 and CD3 comprising:

(a) a first heavy chain selected from:

(i) SEQ ID NO: 79, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, (ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof,
(b) a second heavy chain selected from:
(i) SEQ ID NO: 121,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof,
(ii) SEQ ID NO: 123,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof,
(iii) SEQ ID NO: 125,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof,
(iv) SEQ ID NO: 127,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof,
(v) SEQ ID NO: 129,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof,
and
(c) a first light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
and
(d) a second light chain selected from:
(i) SEQ ID NO: 122,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 28, or a variant thereof, the light chain CDR2 comprises an amino acid sequence of SEQ ID NO: 29, or a variant thereof, and the light chain CDR3 comprises an amino acid sequence of SEQ ID NO: 30, or a variant thereof, or (ii) SEQ ID NO: 124,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 33, or a variant thereof, the light chain CDR2 comprises an amino acid sequence of SEQ ID NO: 34, or a variant thereof, and the light chain CDR3 comprises an amino acid sequence of SEQ ID NO: 35, or a variant thereof, or (iii) SEQ ID NO: 126,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 22, or a variant thereof, the light chain CDR2 comprises an amino acid sequence of SEQ ID NO: 23, or a variant thereof, and the light chain CDR3 comprises an amino acid sequence of SEQ ID NO: 24, or a variant thereof, or (iv) SEQ ID NO: 128,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 37, or a variant thereof, the light chain CDR2 comprises an amino acid sequence of SEQ ID NO: 38, or a variant thereof, and the light chain CDR3 comprises an amino acid sequence of SEQ ID NO: 39, or a variant thereof: or (v) SEQ ID NO: 130
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 43, or a variant thereof, the light chain CDR2 comprises an amino acid sequence of SEQ ID NO: 44, or a variant thereof, and the light chain CDR3 comprises an amino acid sequence of SEQ ID NO: 45, or a variant thereof, or wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

In some embodiments, disclosed herein is a bispecific antibody, wherein the bispecific antibody comprises three polypeptides (e.g., a first polypeptide, a second polypeptide, and a third polypeptide) that form a first antigen binding domain that binds to CLDN6, and a second antigen binding domain that binds to CD3. In some embodiments, the first polypeptide comprises a first light chain comprising a first variable light chain region (first $V_L$), wherein the first variable light chain region comprises a CDR1 sequence comprising the amino acid sequence of SEQ ID NO: 1, a CDR2 sequence comprising the amino acid sequence of SEQ ID NO: 2, and a CDR3 sequence comprising the amino acid sequence of SEQ ID NO: 3. In some embodiments, the second polypeptide comprises a first heavy chain comprising a first variable region heavy chain region (first $V_H$), wherein the first variable heavy chain region comprises a CDR1 sequence comprising the amino acid sequence of SEQ ID NO: 4, a CDR2 sequence comprising the amino acid sequence of SEQ ID NO: 5, and a CDR3 sequence comprising the amino acid sequence of SEQ ID NO: 6. In some embodiments, the third polypeptide comprises a second heavy chain and a second a light chain, wherein the second heavy chain comprises a second variable heavy chain region (second $V_H$) comprising a CDR1 sequence comprising the amino acid sequence of SEQ ID NO: 25, a CDR2 sequence comprising the amino acid sequence of SEQ ID NO: 26, and a CDR3 sequence comprising the amino acid sequence of SEQ ID NO: 27; wherein the second light chain comprises a second variable light chain region (second $V_L$) comprising a CDR1 sequence comprising the amino sequence of SEQ ID NO: 28, a CDR2 sequence comprising the amino acid sequence of SEQ ID NO: 29, and a CDR3 sequence comprising the amino acid sequence of SEQ ID NO: 30. In some embodiments, the second heavy chain and the second light chain are linked by a peptide linker. In some embodiments, the peptide linker is as described herein. In some embodiments, the peptide linker comprises the amino acid sequence of SEQ ID NO: 53. In some embodiments, the peptide linker comprising one or more glycines and serines is replaced with another peptide linker or functionally equivalent variation thereof. In some embodiments, the first $V_L$ and the first $V_H$ interact to form the antigen binding domain that binds to CLDN6. In some embodiments, the second $V_L$ and the second $V_H$ interact to form the antigen binding domain that binds to CD3. In some embodiments, the second $V_L$ and the second $V_H$ are in a scFv format. In some embodiments, the first VI, and the first Vu are in a Fab format, or a fragment thereof.

In some embodiments, the first variable light chain region of the first polypeptide comprises the amino acid sequence of SEQ ID NO: 68, or an amino acid sequence having at least about 90%, or about 93%, or about 95%, or about 97%, or about 98%, or about 99% identity thereto.

In some embodiments, the first variable heavy chain region of the second polypeptide comprises the amino acid sequence of SEQ ID NO: 69, or an amino acid sequence having at least about 90%, or about 93%, or about 95%, or about 97%, or about 98%, or about 99% identity thereto.

In some embodiments, the second variable heavy chain region of the third polypeptide comprises the amino acid sequence of:

(SEQ ID NO: 70)
EVQLVESGGGLVQPGGSLRLSCAASGFTFSTYAMNWVR

QAPGKGLEWVGRIRSKYNNYATYYADSVKGRFTISRDD

SKNTLYLQMNSLRAEDTAVYYCVRHGNFGDSYVSWFA

YWGQGTLVTVSS, or an amino acid sequence having at least about 90%, or about 93%, or about 95%, or about 97%, or about 98%, or about 99% identity thereto.

In some embodiments, the second variable light chain region of the third polypeptide comprises the amino acid sequence of:

```
                                            (SEQ ID NO: 71)
QAVVTQEPSLTVSPGGTVTLTCGSSTGAVTTSNYANWV

QQKPGKSPRGLIGGTNKRAPGVPARFSGSLLGGKAALTI

SGAQPEDEADYYCALWYSNHWVFGGGTKLTVL,
``` or an amino acid sequence having at least about 90%, or about 93%, or about 95%, or about 97%, or about 98%, or about 99% identity thereto.

In some embodiments, the first polypeptide compromising the light chain comprises the first variable light chain region and a light chain constant domain, which can be referred to as the first light chain constant domain. In some embodiments, the first light chain constant domain comprises the amino acid sequence of:

```
                                            (SEQ ID NO: 72)
GQPKAAPSVTLFPPSSEELQANKATLVCLISDFYPGAVT

VAWKADSSPVKAGVETTTPSKQSNNKYAASSYLSLTPE

QWKSHRSYSCQVTHEGSTVEKTVAPTECS,
``` or an amino acid sequence having at least about 90%, or about 93%, or about 95%, or about 97%, or about 98%, or about 99% identity thereto.

In some embodiments, the first polypeptide comprises the amino acid sequence of SEQ ID NO: 67, or an amino acid sequence having at least about 90%, or about 93%, or about 95%, or about 97%, or about 98%, or about 99% identity thereto.

In some embodiments, the second polypeptide compromising the first heavy chain comprises the first variable heavy chain region and a heavy chain constant domain, which can be referred to as the first heavy chain constant domain. In some embodiments, the first heavy chain constant domain comprises the amino acid sequence of:

```
                                            (SEQ ID NO: 73)
ASTKGPSVFPLAPSSKSTSGGTAALGCLVKDYFPEPVTV

SWNSGALTSGVHTFPAVLQSSGLYSLSSVVTVPSSSLGT

QTYICNVNHKPSNTKVDKKVEPKSCDKTHTCPPCPAPEA

AGGPSVFLFPPKPKDTLMISRTPEVTCVVVDVSHEDPEV

KFNWYVDGVEVHNAKTKPREEQYNSTYRVVSVLTVLH

QDWLNGKEYKCKVSNKALPAPIEKTISKAKGQPREPQV

YTLPPSREEMTKNQVSLWCLVKGFYPSDIAVEWESNGQ

PENNYKTTPPVLDSDGSFFLYSKLTVDKSRWQQGNVFS

CSVMHEALHNHYTQKSLSLSPGK,
``` or an amino acid sequence having at least about 90%, or about 93%, or about 95%, or about 97%, or about 98%, or about 99% identity thereto.

In some embodiments, the second polypeptide comprises the amino acid sequence of SEQ ID NO: 79, or an amino acid sequence having at least about 90%, or about 93%, or about 95%, or about 97%, or about 98%, or about 99% identity thereto.

In some embodiments, the third polypeptide comprises a constant domain. In some embodiments, the constant domain is linked to the C-terminus of the second variable light chain region. In some embodiments, there is no peptide linker between the C-terminus of the second variable light chain region and the constant domain. In some embodiments, the constant domain present in the third polypeptide comprises the amino acid sequence of:

```
                                            (SEQ ID NO: 74)
ASPKSSDKTHTCPPCPAPEAAGGPSVFLFPPKPKDTLMIS

RTPEVTCVVVDVSHEDPEVKFNWYVDGVEVHNAKTKP

REEQYNSTYRVVSVLTVLHQDWLNGKEYKCKVSNKAL

PAPIEKTISKAKGQPREPQVYTLPPSREEMTKNQVSLSCA

VKGFYPSDIAVEWESNGQPENNYKTTPPVLDSDGSFFLV

SKLTVDKSRWQQGNVFSCSVMHEALHNHYTQKSLSLSP

GK,
``` or an amino acid sequence having at least about 90%, or about 93%, or about 95%, or about 97%, or about 98%, or about 99% identity thereto.

In some embodiments, the third polypeptide comprises the amino acid sequence of SEQ ID NO: 89, or an amino acid sequence having at least about 90%, or about 93%, or about 95%, or about 97%, or about 98%, or about 99% identity thereto.

In some embodiments, the first polypeptide comprises the amino acid sequence of SEQ ID NO: 67; the second polypeptide comprises the amino acid sequence of SEQ ID NO: 79; and the third polypeptide comprises the amino acid sequence of SEQ ID NO: 89.

As used herein, the term constant domain refers to the Fc domain. The constant domains exemplified above are optional embodiments and other constant domains can be substituted for the constant domains described herein.

In some embodiments, the Fc is from IgG. In some embodiments, the IgG is human IgG. In some embodiments, the human IgG is selected from IgG1, IgG2, IgG3, and IgG4.

In some embodiments, the antibody is formed through a knob-in-hole interaction in the Fc region. In some embodiments, the human IgG Fc comprises one or mutations to promote knob-in-hole interaction. In some embodiments, the mutations are selected from (i) T366Y or T366W, and (ii) Y407T, Y407A, or Y407V. In some embodiments, the mutations are:
  (a) T366Y and Y407T or T366Y/F405A and T394W/Y407T in human IgG1 or
  (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
  in human IgG1.

In some embodiments, the human IgG Fc comprises one or mutations to reduce or eliminate the effector function of the Fc domains. In some embodiments, the mutations are L234A and L235A (LALA) substitutions in human IgG1. In some embodiments, the human IgG Fc comprises one or mutations to stabilize a hinge region in the Fc domain. In some embodiments, the mutation is S228P.

In some embodiments, the composition binds claudin 6 and CD3 contemporaneously.

In some embodiments, the composition binds claudin 6 with an affinity of less than 10 nM and with at least 100 fold greater affinity than claudin 9, claudin 3, and/or claudin 4.

In any of the embodiments disclosed herein, the composition induces cellular cytotoxicity.

In any of the embodiments disclosed herein, the composition induces T cell cytotoxicity.

In any of the embodiments disclosed herein, the composition induces T cell dependent cytotoxicity.

In any of the embodiments disclosed herein, the composition increases the expression and/or the release of one or more cytokines. In any of the embodiments disclosed herein, the composition increases the expression and/or the release of one or more cytokines selected from IL-2, IL-6, IL-10, IFN-$\gamma$, and TNF-$\alpha$.

As provided for herein, an antibody can be formed by the heterodimerization of two Fc domains that are linked to antibody variable domains, which can be either be a VH or can be linked to a scFv format antibody. In some embodiments, the antibody polypeptides comprise a first constant domain and a second constant domain. The constant domain can be based on IgG1, IgG2, IgG3, or IgG4. In some embodiments, the constant domain is a human constant domain. As provided for herein, the constant domain is based on human IgG1 constant domain, which is provided for herein. These constant domains can be incorporated into any of the formats of the antibodies provided for herein.

In some embodiments, the first constant domain comprises a T366W mutation and second constant domain comprises T366S, L368A and Y407V mutations. In some embodiments, the first constant domain comprises T366Y and Y407T mutations or T366Y and F405A mutations and the second constant domain comprises T394W and Y407T mutations. In some embodiments, the first constant domain comprises T366W and D399C mutations and the second constant domain comprises T366S, L368A, K392C, and Y407V mutations. In some embodiments, the first constant domain comprises T366W and K392C mutations and the second constant domain comprises T366S, L368A, D399C and Y407V mutations. In some embodiments, the first constant domain comprises S354C and T366W mutations and the second constant domain comprises Y349C, T366S, L368A and Y407V mutations. In some embodiments, the first constant domain comprises Y349C and T366W mutations and the second constant domain comprises S354C, T366S, L368A and Y407V mutations. In some embodiments, the first constant domain comprises E356C and T366W mutations and the second constant domain comprises Y349C, T366S, L368A and Y407V mutations. In some embodiments, the first constant domain comprises Y349C and T366W mutations and the second constant domain comprises E356C, T366S, L368A and Y407V mutations. In some embodiments, the first constant domain comprises E357C and T366W mutations and the second constant domain comprises Y349C, T366S, L368A and Y407V mutations. In some embodiments, the first constant domain comprises Y349C and T366W mutations and the second constant domain comprises E357C, T366S, L368A and Y407V mutations.

In some embodiments, first and second constant domains each, independently, comprise L234A and L235A (LALA) substitutions, wherein the numbering is according to the EU numbering in human IgG1. In some embodiments, the first and second constant domains each comprise the L234A and L235A (LALA) substitutions.

The constant domains (Fc), such as the first and second constant domains can also comprise other mutations as provided for herein. These mutations can confer increased specificity for Fc receptor types, such as Fc$\gamma$RIIA.

Pharmaceutical Compositions

In some embodiments, disclosed herein is a pharmaceutical composition comprising an isolated antibody of any one of the preceding embodiments, or a nucleic acid molecule encoding the same. In some embodiments, the composition is an injectable pharmaceutical composition. In some embodiments, the composition is sterile. In some embodiments, the composition is pyrogen free.

In addition, this document also provides pharmaceutical compositions that composition as described herein, in combination with a pharmaceutically acceptable carrier. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a mammal, such as a human, non-human primate, dog, cat, sheep, pig, horse, cow, mouse, rat, or rabbit), which is nontoxic to the cell or subject being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed. Mack Publishing Company, Easton, PA (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™). DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al. *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can contain sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing a composition as provided herein can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Any appropriate method can be used to administer a composition as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing a composition as described herein can be administered prior to, after, or in lieu of surgical resection of a tumor.

The antibodies, compositions, or pharmaceutical compositions provided for herein may be administered at any appropriate interval to achieve the desired effect in a subject. In some embodiments, the antibodies, compositions, or pharmaceutical compositions, are administered daily, every other day, weekly, biweekly, once every three weeks, or monthly (i.e. once every four weeks). In some embodiments, a method as provided for herein comprises administering an antibody, composition, or pharmaceutical composition to a cell or to a subject in need thereof at an interval of daily, every other day, weekly, biweekly, once every three weeks, or monthly (i.e. once every four weeks).

In some embodiments, disclosed herein is a nucleic acid molecule encoding an antibody or an amino acid sequence of any of the preceding embodiments.

In some embodiments, disclosed herein is a vector comprising the nucleic acid molecule of any of the preceding embodiments.

In some embodiments, disclosed herein is a cell comprising the nucleic acid molecule of any of the preceding embodiments, or the vector of any of the preceding embodiments.

In some embodiments, disclosed herein is a method for modulating and/or targeting claudin 6 and CD3 in a biological cell, comprising contacting the cell with a composition of any of the preceding embodiments.

In some embodiments, disclosed herein is a method for modulating claudin 6 activity in a biological cell comprising contacting a cell expressing claudin 6 with a composition of any of the preceding embodiments.

In some embodiments, disclosed herein is a method for inhibiting the function of claudin 6 in a biological cell comprising contacting a cell expressing claudin 6 with a composition of any of the preceding embodiments.

Methods of Treatment

In some embodiments, disclosed herein is a method for treating or preventing cancer comprising administering an effective amount of the composition of any of the preceding embodiments to a subject in need thereof.

In some embodiments, disclosed herein is a use of the composition of any of the preceding embodiments for the preparation of a medicament for the treatment of prevention of cancer.

In some embodiments, disclosed herein is a method or use of any one of the preceding embodiments, wherein the cancer is selected form one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; glioma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; malignant rhabdoid tumor; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses; edema (e.g. that associated with brain tumors); and Meigs' syndrome.

As a non-limiting example, the prevention of an onset, the presence, and/or the evaluation of the progression of a cancer in a subject can be assessed according to the Tumor/Nodes/Metastases (TNM) system of classification (International Union Against Cancer, 6th edition, 2002), or the Whitmore-Jewett staging system (American Urological Association). Typically, cancers are staged using a combination of physical examination, blood tests, and medical imaging. If tumor tissue is obtained via biopsy or surgery, examination of the tissue under a microscope can also provide pathologic staging. In some embodiments, the stage or grade of a cancer assists a practitioner in determining the prognosis for the cancer and in selecting the appropriate modulating therapy.

In some embodiments, the prevention of an onset, or progression, of cancer is assessed using the overall stage grouping as a non-limiting example: Stage I cancers are localized to one part of the body, typically in a small area: Stage II cancers are locally advanced and have grown into nearby tissues or lymph nodes, as are Stage III cancers. Whether a cancer is designated as Stage II or Stage III can depend on the specific type of cancer. The specific criteria for Stages II and III can differ according to diagnosis. Stage IV cancers have often metastasized or spread to other organs or throughout the body. The onset or progression of cancer can be assessed using conventional methods available to one of skill in the art, such as a physical exam, blood tests, and imaging scans (e.g., X-rays, MRI, CT scans, ultrasound etc.).

As disclosed herein, administering, or administering a treatment/therapy, refers to a treatment/therapy from which a subject receives a beneficial effect, such as the reduction, decrease, attenuation, diminishment, stabilization, remission, suppression, inhibition or arrest of the development or progression of cancer, or a symptom thereof.

In some embodiments, the treatment/therapy that a subject receives, or the prevention in the onset of cancer results in at least one or more of the following effects: (1) the reduction or amelioration of the severity of cancer and/or a genetic disease or disorder, and/or a symptom associated therewith; (2) the reduction in the duration of a symptom associated with cancer and/or a genetic disease or disorder; (3) the prevention in the recurrence of a symptom associated with cancer and/or a genetic disease or disorder; (4) the regression of cancer and/or a genetic disease or disorder, and/or a symptom associated therewith; (5) the reduction in hospitalization of a subject; (6) the reduction in hospitalization length; (7) the increase in the survival of a subject; (8) the inhibition of the progression of cancer and/or a genetic disease or disorder and/or a symptom associated therewith; (9) the enhancement or improvement the therapeutic effect of another therapy; (10) a reduction or elimination in the cancer cell population, and/or a cell population associated with a genetic disease or disorder; (11) a reduction in the growth of a tumor or neoplasm; (12) a decrease in tumor size; (13) a reduction in the formation of a tumor; (14) eradication, removal, or control of primary, regional and/or metastatic cancer; (15) a decrease in the number or size of metastases; (16) a reduction in mortality; (17) an increase in cancer-free survival rate of a subject; (18) an increase in relapse-free survival; (19) an increase in the number of subjects in remission; (20) a decrease in hospitalization rate; (21) the size of the tumor is maintained and does not increase in size or increases the size of the tumor by less 5% or 10% after administration of a therapy as measured by conventional methods available to one of skill in the art, e.g., X-rays, MRI, CAT scan, ultrasound etc.; (22) the prevention of the development or onset of cancer and/or a genetic disease or disorder, and/or a symptom associated therewith; (23) an increase in the length of remission for a subject; (24) the reduction in the number of symptoms associated with cancer and/or a genetic disease or disorder; (25) an increase in symptom-free survival of a cancer subject and/or a subject associated with a genetic disease or disorder: and/or (26) limitation of or reduction in metastasis. In some embodiments, the treatment/therapy that a subject receives does not cure cancer, but prevents the progression or worsening of the disease. In certain embodiments, the treatment/therapy that a subject receives does not prevent the onset/development of cancer, but may prevent the onset of cancer symptoms.

In some embodiments, the subject that is treated does not develop cytokine release syndrome (CRS), or does not develop significant CRS-associated clinical symptoms or toxicity. These symptoms include, but are not limited to fever, chills, fatigue, weakness, loss of appetite, nausea, vomiting, diarrhea, headache, joint or muscle aches, skin rash, low blood pressure, increased heart rate, irregular heartbeat, tachycardia, decreased heart function, swelling, buildup of fluids (edema), confusion, dizziness, seizures, hallucinations, decreased coordination, problems talking or swallowing, shaking, problems controlling movements, cough, shortness of breath, tachypnoea, decreased lung function, reduced oxygen levels, decreased kidney or liver function, increased cytokine levels in the blood, change in electrolytes, change in blood clotting. In some embodiments, there is no increase or no significant increase in the blood levels of interleukin-6 (IL-6), interleukin-10 (IL-10), interferon (IFN)-γ, monocyte chemoattractant protein 1 (MCP-1) granulocyte-macrophage colony-stimulating factor (GM-CSF), tumor necrosis factor (TNF), IL-1, IL-2, IL-2-receptor-α, or IL-8 after administration of an antibody as provided for herein.

In some embodiments, "preventing" an onset or progression of cancer in a subject in need thereof, is inhibiting or blocking the cancer or disorder. In some embodiments, the methods disclosed herein prevent, or inhibit, the cancer or disorder at any amount or level. In some embodiments, the methods disclosed herein prevent or inhibit the cancer or genetic disease or disorder by at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition, or at least or about a 100% inhibition).

In some embodiments, disclosed herein is an isolated antibody comprising one or more of the sequences disclosed herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

ENUMERATED EMBODIMENTS

In some embodiments, the following embodiments are provided:
1. A composition comprising a tandem single-chain variable fragment (scFv) specific for claudin 6 and CD3 comprising one or more or:
   I.
   (a) an amino acid sequence of SEQ ID NO. 82, or an amino acid sequence having at least about 90%, or about 93%, or about 95%, or about 97%, or about 98%, or about 99% identity thereto, or
   (b)
      (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
      (ii) a VH comprising HCDR1, HCDR2, and HCDR3 sequences, wherein the HCDR1 comprises an amino acid sequence of SEQ ID NO: 4 or a variant thereof, the HCDR2 comprises an amino acid sequence of SEQ ID NO: 5, or a variant thereof, and the HCDR3 comprises an amino acid sequence of SEQ ID NO: 6, or a variant thereof,
      (iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of SEQ ID NO: 8, or a variant thereof, and the HCDR3 comprises an amino acid sequence of SEQ ID NO: 9, or a variant thereof, and
      (iv) a VL comprising LCDR1, LCDR2, and LCDR3 sequences, wherein the LCDR1 comprises an amino acid sequence of SEQ ID NO: 10, or a variant thereof, the LCDR2 comprises an amino acid sequence of SEQ ID NO: 11, or a variant thereof, and the LCDR3 comprises an amino acid sequence of SEQ ID NO: 12, or a variant thereof,
   II.
   (a) an amino acid sequence of SEQ ID NO. 83, or an amino acid sequence having at least about 90%, or about 93%, or about 95%, or about 97%, or about 98%, or about 99% identity thereto, or
   (b)
      (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
      (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
      (iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of SEQ ID NO: 8, or a variant thereof, and the HCDR3 comprises an amino acid sequence of SEQ ID NO: 9, or a variant thereof, and
      (iv) a VL comprising LCDR1, LCDR2, and LCDR3 sequences, wherein the LCDR1 comprises an amino acid sequence of SEQ ID NO: 10, or a variant thereof, the LCDR2 comprises an amino acid sequence of SEQ ID NO: 11, or a variant thereof, and the LCDR3 comprises an amino acid sequence of SEQ ID NO: 12, or a variant thereof,
   III.
   (a) an amino acid sequence of SEQ ID NO. 84, or an amino acid sequence having at least about 90%, or about 93%, or about 95%, or about 97%, or about 98%, or about 99% identity thereto, or
   (b)
      (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
      (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof, and (iii) a VH comprising HCDR1, HCDR2, and HCDR3 sequences, wherein the HCDR1 comprises an amino acid sequence of SEQ ID NO: 16, or a variant thereof, the HCDR2 comprises an amino acid sequence of SEQ ID NO: 17, or a variant thereof, and the HCDR3 comprises an amino acid sequence of SEQ ID NO: 18, or a variant thereof, IV.
(a) an amino acid sequence of SEQ ID NO: 85, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof, and
  (iii) a VH comprising HCDR1, HCDR2, and HCDR3 sequences, wherein the HCDR1 comprises an amino acid sequence of SEQ ID NO: 16, or a variant thereof, the HCDR2 comprises an amino acid sequence of SEQ ID NO: 17, or a variant thereof, and the HCDR3 comprises an amino acid sequence of SEQ ID NO: 18, or a variant thereof, V.
(a) an amino acid sequence of SEQ ID NO. 93, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 19, or a variant thereof, the HCDR2 comprises an amino acid sequence of SEQ ID NO: 20, or a variant thereof, and the HCDR3 comprises an amino acid sequence of SEQ ID NO: 21, or a variant thereof, and
  (iv) a VL comprising LCDR1, LCDR2, and LCDR3 sequences, wherein the LCDR1 comprises an amino acid sequence of SEQ ID NO: 22, or a variant thereof, the LCDR2 comprises an amino acid sequence of SEQ ID NO: 23, or a variant thereof, and the LCDR3 comprises an amino acid sequence of SEQ ID NO: 24, or a variant thereof, VI.
(a) an amino acid sequence of SEQ ID NO. 94, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 19, or a variant thereof, the HCDR2 comprises an amino acid sequence of SEQ ID NO: 20, or a variant thereof, and the HCDR3 comprises an amino acid sequence of SEQ ID NO: 21, or a variant thereof, and
  (iv) a VL comprising LCDR1, LCDR2, and LCDR3 sequences, wherein the LCDR1 comprises an amino acid sequence of SEQ ID NO: 22, or a variant thereof, the LCDR2 comprises an amino acid sequence of SEQ ID NO: 23, or a variant thereof, and the LCDR3 comprises an amino acid sequence of SEQ ID NO: 24, or a variant thereof, VII.
(a) an amino acid sequence of SEQ ID NO. 95, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence is of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 26, or a variant thereof, and the HCDR3 comprises an amino acid sequence of SEQ ID NO: 27, or a variant thereof, and
(iv) a VL comprising LCDR1, LCDR2, and LCDR3 sequences, wherein the LCDR1 comprises an amino acid sequence of SEQ ID NO: 28, or a variant thereof, the LCDR2 comprises an amino acid sequence of SEQ ID NO: 29, or a variant thereof, and the LCDR3 comprises an amino acid sequence of SEQ ID NO: 30, or a variant thereof, VIII.
(a) an amino acid sequence of SEQ ID NO. 96, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 26, or a variant thereof, and the HCDR3 comprises an amino acid sequence of SEQ ID NO: 27, or a variant thereof, and
  (iv) a VL comprising LCDR1, LCDR2, and LCDR3 sequences, wherein the LCDR1 comprises an amino acid sequence of SEQ ID NO: 28, or a variant thereof, the LCDR2 comprises an amino acid sequence of SEQ ID NO: 29, or a variant thereof, and the LCDR3 comprises an amino acid sequence of SEQ ID NO: 30, or a variant thereof, IX.
(a) an amino acid sequence of SEQ ID NO. 97, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 31, or a variant thereof, and the HCDR3 comprises an amino acid sequence of SEQ ID NO: 32, or a variant thereof, and
  (iv) a VL comprising LCDR1, LCDR2, and LCDR3 sequences, wherein the LCDR1 comprises an amino acid sequence of SEQ ID NO: 33, or a variant thereof, the LCDR2 comprises an amino acid sequence of SEQ ID NO: 34, or a variant thereof, and the LCDR3 comprises an amino acid sequence of SEQ ID NO: 35, or a variant thereof, X.
(a) an amino acid sequence of SEQ ID NO. 98, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 25, or a variant thereof, the HCDR2 comprises an amino acid sequence of SEQ ID NO: 31, or a variant thereof, and the HCDR3 comprises an amino acid sequence of SEQ ID NO: 32, or a variant thereof, and
  (iv) a VL comprising LCDR1, LCDR2, and LCDR3 sequences, wherein the LCDR1 comprises an amino acid sequence of SEQ ID NO: 33, or a variant thereof, the LCDR2 comprises an amino acid sequence of SEQ ID NO: 34, or a variant thereof, and the LCDR3 comprises an amino acid sequence of SEQ ID NO: 35, or a variant thereof, XI.
(a) an amino acid sequence of SEQ ID NO. 99, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
(iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of SEQ ID NO: 36, or a variant thereof, and the HCDR3 comprises an amino acid sequence of SEQ ID NO: 9, or a variant thereof, and
(iv) a VL comprising LCDR1, LCDR2, and LCDR3 sequences, wherein the LCDR1 comprises an amino acid sequence of SEQ ID NO: 37, or a variant thereof, the LCDR2 comprises an amino acid sequence of SEQ ID NO: 38, or a variant thereof, and the LCDR3 comprises an amino acid sequence of SEQ ID NO: 39, or a variant thereof, XII.
(a) an amino acid sequence of SEQ ID NO. 100, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 7, or a variant thereof, the HCDR2 comprises an amino acid sequence of ID NO: 36, or a variant thereof, and the HCDR3 comprises an amino acid sequence of SEQ ID NO: 9, or a variant thereof, and
  (iv) a VL comprising LCDR1, LCDR2, and LCDR3 sequences, wherein the LCDR1 comprises an amino acid sequence of SEQ ID NO: 37, or a variant thereof, the LCDR2 comprises an amino acid sequence of SEQ ID NO: 38, or a variant thereof, and the LCDR3 comprises an amino acid sequence of SEQ ID NO: 39, or a variant thereof, XIII.
(a) an amino acid sequence of SEQ ID NO: 109, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 1, or a variant thereof, the LCDR2 comprises an amino acid sequence of SEQ ID NO: 2, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 6, or a variant thereof,
  (iii) a VH comprising HCDR1, HCDR2, and HCDR3 sequences, wherein the HCDR1 comprises an amino acid sequence of SEQ ID NO: 40, or a variant thereof, the HCDR2 comprises an amino acid sequence of SEQ ID NO: 41, or a variant thereof, and the HCDR3 comprises an amino acid sequence of SEQ ID NO: 42, or a variant thereof, and
  (iv) a VL comprising LCDR1, LCDR2, and LCDR3 sequences, wherein the LCDR1 comprises an amino acid sequence of SEQ ID NO: 43, or a variant thereof, the LCDR2 comprises an amino acid sequence of SEQ ID NO: 44, or a variant thereof, and the LCDR3 comprises an amino acid sequence of SEQ ID NO: 45, or a variant thereof, and XIV.
(a) an amino acid sequence of SEQ ID NO: 110, or an amino acid sequence having at least about 90%, or about 93%, or about 95%, or about 97%, or about 98%, or about 99% identity thereto, or
(b)
  (i) a VL comprising LCDR1, LCDR2, and LCDR3 sequences, wherein the LCDR1 comprises an amino acid sequence of SEQ ID NO: 13, or a variant thereof, the LCDR2 comprises an amino acid sequence of SEQ ID NO: 14, or a variant thereof, and the LCDR3 comprises an amino acid sequence of SEQ ID NO: 3, or a variant thereof,
  (ii) a VH comprising HCDR1, HCDR2, and HCDR3 sequences, wherein the HCDR1 comprises an amino acid sequence of SEQ ID NO: 4, or a variant thereof, the HCDR2 comprises an amino acid sequence of SEQ ID NO: 5, or a variant thereof, and the HCDR3 comprises an amino acid sequence of SEQ ID NO: 15, or a variant thereof,
  (iii) a VH comprising HCDR1, HCDR2, and HCDR3 sequences, wherein the HCDR1 comprises an amino acid sequence of SEQ ID NO: 40, or a variant thereof, the HCDR2 comprises an amino acid sequence of SEQ ID NO: 41, or a variant thereof, and the HCDR3 comprises an amino acid sequence of SEQ ID NO: 42, or a variant thereof, and
  (iv) a VL comprising LCDR1, LCDR2, and LCDR3 sequences, wherein the LCDR1 comprises an amino acid sequence of SEQ ID NO: 43, or a variant thereof, the LCDR2 comprises an amino acid sequence of SEQ ID NO: 44, or a variant thereof, and the LCDR3 comprises an amino acid sequence of SEQ ID NO: 45, or a variant thereof, or wherein:
  any of the above sequences in subsections (a) optionally can have a His6 tag (e.g., HHHHHH (SEQ ID NO: 46)) added to the N or C-terminus and
  any of the above sequences optionally have the linker comprising one or more glycines and serines replaced with another peptide linker or functionally equivalent variation thereof.

2. A composition comprising a scFv-Fab Fc antibody specific for claudin 6 and CD3 comprising:

(a) a first heavy chain selected from:
(i) SEQ ID NO: 79,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(ii) SEQ ID NO: 88,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof,
(b) a second heavy chain selected from:
(i.) SEQ ID NO: 80,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, or
(ii.) SEQ ID NO: 89,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or
   a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, or
(iii.) SEQ ID NO: 90,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or
   a heavy chain variable region comprising heavy chain CDR1, CDR2, and CDR3 sequences, wherein the heavy chain CDR1 comprises an amino acid sequence of SEQ ID NO: 48, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, or
(iv.) SEQ ID NO: 91,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or
   a heavy chain variable region comprising heavy chain CDR1, CDR2, and CDR3 sequences, wherein the heavy chain CDR1 comprises an amino acid sequence of SEQ ID NO: 49, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, or
(v.) SEQ ID NO: 92,
   an amino acid sequence having at least about 90%, or about 93%, or about 95%, or about 97%, or about 98%, or about 99% identity thereto, or
   a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or
a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, or
(vi.) SEQ ID NO: 111,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or
a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof,
and
(c) a first light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

3. The composition of embodiment 2, wherein the Fc is from IgG.
4. The composition of embodiment 3, wherein the IgG is human IgG.
5. The composition of embodiment 4, wherein the human IgG is selected from IgG1, IgG2, IgG3, and IgG4.
6. The composition of any one of embodiments 2 to 5, wherein the antibody is formed through a knob-in-hole interaction in the Fc region.
7. The composition of embodiment 4 or embodiment 5, wherein the human IgG Fc comprises one or mutations to promote knob-in-hole interaction.
8. The composition of embodiment 7, wherein the mutations are selected from (i) T366Y or T366W, and (ii) Y407T, Y407A, or Y407V.
9. The composition of embodiment 7, wherein the mutations are selected from:
(a) T366Y and Y407T or T366Y/F405A and T394W/Y407T in human IgG1, or
(b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
in human IgG1.
10. The composition of embodiment 4, wherein the human IgG Fc comprises one or mutations to reduce or eliminate the effector function of the Fc domains.
11. The composition of embodiment 10, wherein the mutations are L234A and L235A (LALA) substitutions in human IgG1.
12. The composition of embodiment 4, wherein the human IgG Fc comprises one or mutations to stabilize a hinge region in the Fc domain.
13. The composition of embodiment 12, wherein the mutation is S228P.
14. A composition comprising an IgG-(scFV)$_2$ antibody specific for claudin 6 and CD3 comprising:
(a) a heavy chain selected from:
(i.) SEQ ID NO: 86,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, (ii.) SEQ ID NO: 87, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, (iii.) SEQ ID NO: 101, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, (iv.) SEQ ID NO: 102, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof, or a heavy chain variable region comprising heavy chain CDR1, CDR2, and CDR3 sequences, wherein the heavy chain CDR1 comprises an amino acid sequence of SEQ ID NO: 37, or a variant thereof, the heavy chain CDR2 comprises an amino acid sequence of SEQ ID NO: 38, or a variant thereof, and the heavy chain CDR3 comprises an amino acid sequence of SEQ ID NO: 39, or a variant thereof, (v.) SEQ ID NO: 103, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, (vi.) SEQ ID NO: 104, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof, or
a heavy chain variable region comprising heavy chain CDR1, CDR2, and CDR3 sequences, wherein the heavy chain CDR1 comprises an amino acid sequence of SEQ ID NO: 28, or a variant thereof, the heavy chain CDR2 comprises an amino acid sequence of SEQ ID NO: 29, or a variant thereof, and the heavy chain CDR3 comprises an amino acid sequence of SEQ ID NO: 30, or a variant thereof, (vii.) SEQ ID NO: 105, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or a heavy chain variable region comprising heavy chain CDR1, CDR2, and CDR3 sequences, wherein the heavy chain CDR1 comprises an amino acid sequence of SEQ ID NO: 33, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, (viii.) SEQ ID NO: 106, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof, or a heavy chain variable region comprising heavy chain CDR1, CDR2, and CDR3 sequences, wherein the heavy chain CDR1 comprises an amino acid sequence of SEQ ID NO: 33, or a variant thereof, the heavy chain CDR2 comprises an amino acid sequence of SEQ ID NO: 34, or a variant thereof, and the heavy chain CDR3 comprises an amino acid sequence of SEQ ID NO: 35, or a variant thereof, (ix.) SEQ ID NO: 107, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or a heavy chain variable region comprising heavy chain CDR1, CDR2, and CDR3 sequences, wherein the heavy chain CDR1 comprises an amino acid sequence of SEQ ID NO: 22, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, (x.) SEQ ID NO: 108, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof, or a heavy chain variable region comprising heavy chain CDR1, CDR2, and CDR3 sequences, wherein the heavy chain CDR1 comprises an amino acid sequence of SEQ ID NO: 22, or a variant thereof, the heavy chain CDR2 comprises an amino acid sequence of SEQ ID NO: 23, or a variant thereof, and the heavy chain CDR3 comprises an amino acid sequence of SEQ ID NO: 24, or a variant thereof, (xi.) SEQ ID NO: 112, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof, (xii.) SEQ ID NO: 113, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence is of SEQ ID NO: 5, or a variant thereof, and the heavy chain CDR3 comprises an amino acid sequence of SEQ ID NO: 15, or a variant thereof, or a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof, or a heavy chain variable region comprising heavy chain CDR1, CDR2, and CDR3 sequences, wherein the heavy chain CDR1 comprises an amino acid sequence of SEQ ID NO: 43, or a variant thereof, the heavy chain CDR2 comprises an amino acid sequence of SEQ ID NO: 44, or a variant thereof, and the heavy chain CDR3 comprises an amino acid sequence of SEQ ID NO: 45, or a variant thereof, and (b) a light chain selected from:

(i) SEQ ID NO: 67, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:

any of the above sequences in subsections (a) optionally can have a His6 tag (e.g., HHHHHH (SEQ ID NO: 46)) added to the N or C-terminus and any of the above sequences optionally have the linker comprising one or more glycines and serines replaced with another peptide linker or functionally equivalent variation thereof.

15. The composition of embodiment 14, wherein the Fc is from IgG.

16. The composition of embodiment 15, wherein the IgG is human IgG.

17. The composition of embodiment 16, wherein the human IgG is selected from IgG1, IgG2, IgG3, and IgG4.

18. The composition of embodiment 16, wherein the human IgG Fc comprises one or mutations to reduce or eliminate the effector function of the Fc domains.

19. The composition of embodiment 18, wherein the mutations are L234A and L235A (LALA) substitutions in human IgG1.

20. The composition of embodiment 16, wherein the human IgG Fc comprises one or mutations to stabilize a hinge region in the Fc domain.

21. The composition of embodiment 20, wherein the mutation is S228P.

22. A composition comprising a scFv-Fab Fc antibody specific for claudin 6 and CD3 comprising:

(a) a first heavy chain selected from:

(i) SEQ ID NO: 79, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, (ii) SEQ ID NO: 88, an amino acid sequence having at least about 90%, or about 93%, or about 95%, or about 97%, or about 98%, or about 99% identity thereto, or a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or (iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof, (b) a second heavy chain selected from:
SEQ ID NO: 81,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof, and (c) a light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, (ii) SEQ ID NO: 66
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or (iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

23. The composition of embodiment 22, wherein the Fc is from IgG.

24. The composition of embodiment 23, wherein the IgG is human IgG.

25. The composition of embodiment 24, wherein the human IgG is selected from IgG1, IgG2, IgG3, and IgG4.

26. The composition of any one of embodiments 22 to 25, wherein the antibody is formed through a knob-in-hole interaction in the Fc region.

27. The composition of embodiment 24, wherein the human IgG Fc comprises one or mutations to promote knob-in-hole interaction.

28. The composition of embodiment 27, wherein the mutations are selected from (i) T366Y or T366W, and (ii) Y407T, Y407A, or Y407V.

29. The composition of embodiment 24, wherein the mutations are:
(a) T366Y and Y407T or T366Y/F405A and T394W/Y407T in human IgG1 or
(b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
in human IgG1.

30. The composition of embodiment 24, wherein the human IgG Fc comprises one or mutations to reduce or eliminate the effector function of the Fc domains.

31. The composition of embodiment 30, wherein the mutations are L234A and L235A (LALA) substitutions in human IgG1.

32. The composition of embodiment 24, wherein the human IgG Fc comprises one or mutations to stabilize a hinge region in the Fc domain.

33. The composition of embodiment 32, wherein the mutation is S228P.

34. A composition comprising a scFv-Fab Fc antibody specific for claudin 6 and CD3 comprising:
(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof, (ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof, or
(iii) SEQ ID NO: 114,
  an amino acid sequence having at least about 90%, or about 93%, or about 95%, or about 97%, or about 98%, or about 99% identity thereto, or
  a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof,
(b) a second heavy chain selected from:
(i.) SEQ ID NO: 117,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
(ii.) SEQ ID NO: 119,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
(iii.) SEQ ID NO: 118,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(iv.) SEQ ID NO: 120,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 16, or a variant thereof, the heavy chain CDR2 comprises an amino acid sequence of SEQ ID NO: 17, or a variant thereof, and the heavy chain CDR3 comprises an amino acid sequence of SEQ ID NO: 18, or a variant thereof,
or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
and
(c) a light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof, or (iii) SEQ ID NO: 65, an amino acid sequence having at least about 90%, or about 93%, or about 95%, or about 97%, or about 98%, or about 99% identity thereto, or a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof, or wherein:
any of the above sequences in subsections (a) optionally can have a His6 tag (e.g., HHHHHH (SEQ ID NO: 46)) added to the N or C-terminus and
any of the above sequences optionally have the linker comprising one or more glycines and serines replaced with another peptide linker or functionally equivalent variation thereof.

35. The composition of embodiment 34, wherein the Fc is from IgG.
36. The composition of embodiment 35, wherein the IgG is human IgG.
37. The composition of embodiment 36, wherein the human IgG is selected from IgG1, IgG2, IgG3, and IgG4.
38. The composition of any one of embodiments 34 to 37, wherein the antibody is formed through a knob-in-hole interaction in the Fc region.
39. The composition of embodiment 36, wherein the human IgG Fc comprises one or mutations to promote knob-in-hole interaction.
40. The composition of embodiment 39, wherein the mutations are selected from (i) T366Y or T366W, and (ii) Y407T, Y407A, or Y407V.
41. The composition of embodiment 36, wherein the mutations are:
   (a) T366Y and Y407T or T366Y/F405A and T394W/Y407T in human IgG1 or
   (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
   in human IgG1.
42. The composition of embodiment 36, wherein the human IgG Fc comprises one or mutations to reduce or eliminate the effector function of the Fc domains.
43. The composition of embodiment 42, wherein the mutations are L234A and L235A (LALA) substitutions in human IgG1.
44. The composition of embodiment 36, wherein the human IgG Fc comprises one or mutations to stabilize a hinge region in the Fc domain.
45. The composition of embodiment 44, wherein the mutation is S228P.
46. A composition comprising a scFv-Fab Fc antibody specific for claudin 6 and CD3 comprising:

(a) a first heavy chain selected from:
(i) SEQ ID NO: 79,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 6, or a variant thereof,
(ii) SEQ ID NO: 88,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 15, or a variant thereof,
or
(iii) SEQ ID NO: 114,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 4, or a variant thereof, the heavy chain CDR2 comprises an amino acid sequence of SEQ ID NO: 5, or a variant thereof, and the heavy chain CDR3 comprises an amino acid sequence of SEQ ID NO: 47, or a variant thereof,
(b) a second heavy chain selected from:
(i) SEQ ID NO: 121,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 26, or a variant thereof, and the heavy chain CDR3 comprises an amino acid sequence of SEQ ID NO: 27, or a variant thereof,
(ii) SEQ ID NO: 123,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 25, or a variant thereof, the heavy chain CDR2 comprises an amino acid sequence of SEQ ID NO: 31, or a variant thereof, and the heavy chain CDR3 comprises an amino acid sequence of SEQ ID NO: 32, or a variant thereof,
(iii) SEQ ID NO: 125, an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 19, or a variant thereof, the heavy chain CDR2 comprises an amino acid sequence of SEQ ID NO: 20, or a variant thereof, and the heavy chain CDR3 comprises an amino acid sequence of SEQ ID NO: 21, or a variant thereof,
(iv) SEQ ID NO: 127,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 7, or a variant thereof, the heavy chain CDR2 comprises an amino acid sequence of SEQ ID NO: 36, or a variant thereof, and the heavy chain CDR3 comprises an amino acid sequence of SEQ ID NO: 9, or a variant thereof,
(v) SEQ ID NO: 129,
an amino acid sequence having at least about 90%, or about 93%, or about 95%, or about 97%, or about 98%, or about 99% identity thereto, or
a heavy chain variable region comprising heavy chain CDR1, CDR2, and CDR3 sequences, wherein the heavy chain CDR1 comprises an amino acid sequence of SEQ ID NO: 40, or a variant thereof, the heavy chain CDR2 comprises an amino acid sequence of SEQ ID NO: 41, or a variant thereof, and the heavy chain CDR3 comprises an amino acid sequence of SEQ ID NO: 42, or a variant thereof,
and
(c) a first light chain selected from:
(i) SEQ ID NO: 67,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof,
(ii) SEQ ID NO: 66,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 13, or a variant thereof, the light chain CDR2 comprises an amino acid sequence of SEQ ID NO: 14, or a variant thereof, and the light chain CDR3 comprises an amino acid sequence of SEQ ID NO: 3, or a variant thereof,
or
(iii) SEQ ID NO: 65,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 1, or a variant thereof, the light chain CDR2 comprises an amino acid sequence of SEQ ID NO: 2, or a variant thereof, and the light chain CDR3 comprises an amino acid sequence of SEQ ID NO: 3, or a variant thereof
and
(d) a second light chain selected from:
(i) SEQ ID NO: 122,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 28, or a variant thereof, the light chain CDR2 comprises an amino acid sequence of SEQ ID NO: 29, or a variant thereof, and the light chain CDR3 comprises an amino acid sequence of SEQ ID NO: 30, or a variant thereof, or
(ii) SEQ ID NO: 124,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 33, or a variant thereof, the light chain CDR2 comprises an amino acid sequence of SEQ ID NO: 34, or a variant thereof, and the light chain CDR3 comprises an amino acid sequence of SEQ ID NO: 35, or a variant thereof, or
(iii) SEQ ID NO: 126,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 22, or a variant thereof, the light chain CDR2 comprises an amino acid sequence of SEQ ID NO: 23, or a variant thereof, and the light chain CDR3 comprises an amino acid sequence of SEQ ID NO: 24, or a variant thereof, or
(iv) SEQ ID NO: 128,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 37, or a variant thereof, the light chain CDR2 comprises an amino acid sequence of SEQ ID NO: 38, or a variant thereof, and the light chain CDR3 comprises an amino acid sequence of SEQ ID NO: 39, or a variant thereof, or
(v) SEQ ID NO: 130,
an amino acid sequence having at least about 90%, or about 93%, or about 95%, or about 97%, or about 98%, or about 99% identity thereto, or
a light chain variable region comprising light chain CDR1, CDR2, and CDR3 sequences, wherein the light chain CDR1 comprises an amino acid sequence of SEQ ID NO: 43, or a variant thereof, the light chain CDR2 comprises an amino acid sequence of SEQ ID NO: 44, or a variant thereof, and the light chain CDR3 comprises an amino acid sequence of SEQ ID NO: 45, or a variant thereof, or wherein:
 any of the above sequences in subsections (a) optionally can have a His6 tag (e.g., HHHHHH (SEQ ID NO: 46)) added to the N or C-terminus and
 any of the above sequences optionally have the linker comprising one or more glycines and serines replaced with another peptide linker or functionally equivalent variation thereof.

47. The composition of embodiment 46, wherein the Fc is from IgG.
48. The composition of embodiment 47, wherein the IgG is human IgG.
49. The composition of embodiment 48, wherein the human IgG is selected from IgG1, IgG2, IgG3, and IgG4.
50. The composition of any one of embodiments 46 to 49, wherein the antibody is formed through a knob-in-hole interaction in the Fc region.
51. The composition of embodiment 46, wherein the human IgG Fc comprises one or mutations to promote knob-in-hole interaction.
52. The composition of embodiment 51, wherein the mutations are selected from (i) T366Y or T366W, and (ii) Y407T, Y407A, or Y407V.
53. The composition of embodiment 51, wherein the mutations are:
 (a) T366Y and Y407T or T366Y/F405A and T394W/Y407T in human IgG1 or
 (b) T366W/D399C and T366S/L368A/K392C/Y407V; T366W/K392C and T366S/L368A/D399C/Y407V; S354C/T366W and Y349C/T366S/L368A/Y407V; Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V,
 in human IgG1.
54. The composition of embodiment 46, wherein the human IgG Fc comprises one or mutations to reduce or eliminate the effector function of the Fc domains.
55. The composition of embodiment 54, wherein the mutations are L234A and L235A (LALA) substitutions in human IgG1.
56. The composition of embodiment 46, wherein the human IgG Fc comprises one or mutations to stabilize a hinge region in the Fc domain.
57. The composition of embodiment 56, wherein the mutation is S228P.
58. The composition of any one of embodiments 1 to 57, wherein the composition binds claudin 6 and CD3 contemporaneously.
59. The composition of any one of embodiments 1 to 58, wherein the composition binds claudin 6 with an affinity of less than 10 nM and with at least 100 fold greater affinity than claudin 9, claudin 3, and/or claudin 4.
60. A pharmaceutical composition comprising an isolated antibody of any one of embodiments 1 to 59, or a nucleic acid molecule encoding the same.
61. The pharmaceutical composition of embodiment 60, wherein the composition is an injectable pharmaceutical composition.
62. The pharmaceutical compositions of embodiments 60 or 61, wherein the composition is sterile.
63. The pharmaceutical compositions of any one of embodiments 60 to 62, wherein the composition is pyrogen free.
64. A nucleic acid molecule encoding an antibody or an amino acid sequence of any of the preceding embodiments.
65. A vector comprising the nucleic acid molecule of embodiment 64.
66. A cell comprising the nucleic acid molecule of embodiment 64, or the vector of embodiment 65.
67. A method for modulating and/or targeting claudin 6 and CD3 in a biological cell, comprising contacting the cell with a composition of any one of embodiments 1 to 59.
68. A method for modulating claudin 6 activity in a biological cell comprising contacting a cell expressing claudin 6 with a composition of any one of embodiments 1 to 59.
69. A method for inhibiting the function of claudin 6 in a biological cell comprising contacting a cell expressing claudin 6 with a composition of any one of embodiments 1 to 59.
70. A method for treating or preventing cancer comprising administering an effective amount of the composition of any one of embodiments 1 to 59 to a subject in need thereof.
71. A use of the composition of any one of embodiments 1 to 59 for the preparation of a medicament for the treatment of prevention of cancer.
72. The method or use of any one of embodiments 1 to 71, wherein the cancer is selected form one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; glioma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; malignant rhabdoid tumor; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses; edema (e.g. that associated with brain tumors); and Meigs' syndrome.

73. An isolated antibody comprising one or more of the sequences disclosed herein.

74. A bispecific antibody comprising three polypeptides, the bispecific antibody comprising:
a first polypeptide comprising a first light chain comprising a first variable light chain region, wherein the first variable light chain region comprises:
(1) a CDR1 sequence comprising the amino acid sequence of SEQ ID NO: 1, or a variant thereof:
(2) a CDR2 sequence comprising the amino acid sequence of SEQ ID NO: 2, or a variant thereof; and
(3) a CDR3 sequence comprising the amino acid sequence of SEQ ID NO: 3 or a variant thereof:
a second polypeptide comprising a first heavy chain comprising a first variable region heavy chain region, wherein the first variable heavy chain region comprises:
(1) a CDR1 comprising the amino acid sequence of SEQ ID NO: 4, or a variant thereof:
(2) a CDR2 comprising the amino acid sequence of SEQ ID NO: 5, or a variant thereof, and
(3) a CDR3 comprising the amino acid sequence of SEQ ID NO: 6, or a variant thereof; and
a third polypeptide comprising a second light chain and a second a heavy chain, wherein the second heavy chain comprises a second variable heavy chain region comprising:
(1) a CDR1 comprising the amino acid sequence of SEQ ID NO: 25, or a variant thereof:
(2) a CDR2 comprising the amino acid sequence of SEQ ID NO: 26, or a variant thereof: and
(3) a CDR3 comprising the amino acid sequence of SEQ ID NO: 27, or a variant thereof; and
the second light chain comprises a second variable light chain region comprising:
(1) a CDR1 comprising the amino sequence of SEQ ID NO: 28, or a variant thereof:
(2) a CDR2 comprising the amino acid sequence of SEQ ID NO: 29, or a variant thereof: and
(3) a CDR3 comprising the amino acid sequence of SEQ ID NO: 30, or a variant thereof.

75. The bispecific antibody of embodiment 74, wherein the first variable light chain region comprises the amino acid sequence of SEQ ID NO: 68, or an amino acid sequence having at least about 90%, or about 93%, or about 95%, or about 97%, or about 98%, or about 99% identity thereto.

76. The bispecific antibody of embodiments 74 or 75, wherein the first light chain comprises the first variable light chain region and a light chain constant domain.

77. The bispecific antibody of embodiment 76, wherein the first light chain constant domain comprises the amino acid sequence of SEQ ID NO: 72, or an amino acid sequence having at least about 90%, or about 93%, or about 95%, or about 97%, or about 98%, or about 99% identity thereto.

78. The bispecific antibody of any one of embodiments 74-77, wherein the first polypeptide comprises the amino acid sequence of SEQ ID NO: 67, or an amino acid sequence having at least about 90%, or about 93%, or about 95%, or about 97%, or about 98%, or about 99% identity thereto.

79. The bispecific antibody of any one of embodiments 74-78, wherein the first variable heavy chain region comprises the amino acid sequence of SEQ ID NO: 69, or an amino acid sequence having at least about 90%, or about 93%, or about 95%, or about 97%, or about 98%, or about 99% identity thereto.

80. The bispecific antibody of any one of embodiments 74-79, wherein the first heavy chain comprises the first heavy chain variable region and a first heavy chain constant domain.

81. The bispecific antibody of embodiment 80, wherein the first heavy chain constant domain comprises the amino acid sequence of SEQ ID NO: 73, or an amino acid sequence having at least about 90%, or about 93%, or about 95%, or about 97%, or about 98%, or about 99% identity thereto.

82. The bispecific antibody of any one of embodiments 74-81, wherein the second polypeptide comprises the amino acid sequence of SEQ ID NO: 79, or an amino acid sequence having at least about 90%, or about 93%, or about 95%, or about 97%, or about 98%, or about 99% identity thereto.

83. The bispecific antibody of any one of embodiments 74-82, wherein the second variable heavy chain region comprises the amino acid sequence of SEQ ID NO: 70, or an amino acid sequence having at least about 90%, or about 93%, or about 95%, or about 97%, or about 98%, or about 99% identity thereto.

84. The bispecific antibody of any one of embodiments 74-83, wherein the second variable light chain region comprises the amino acid sequence of SEQ ID NO: 71, or an amino acid sequence having at least about 90%, or about 93%, or about 95%, or about 97%, or about 98%, or about 99% identity thereto.

85. The bispecific antibody of any one of embodiments 74-84, wherein the second variable heavy chain region and the second variable light chain region are linked by a peptide linker, or optionally the linker comprising one or more glycines and serines is replaced with another peptide linker, or a functionally equivalent variation thereof.

86. The bispecific antibody of embodiment 85, wherein the linker comprises the amino sequence of SEQ ID NO: 53, or a variant thereof.

87. The bispecific antibody of any one of embodiments 74-86, wherein the third polypeptide comprises a constant domain.

88. The bispecific antibody of embodiment 87, wherein the constant domain is linked to the C-terminus of the second variable light chain region.

89. The bispecific antibody of embodiment 87 or 88, wherein there is no peptide linker between the C-terminus of the second variable light chain region and the constant domain.

90. The bispecific antibody of any one of embodiments 87-89, wherein the constant domain comprises the amino acid sequence of SEQ ID NO: 74, or an amino acid sequence having at least about 90%, or about 93%, or about 95%, or about 97%, or about 98%, or about 99% identity thereto.

91. The bispecific antibody of any one of embodiments 74-90, wherein the third polypeptide comprises the amino acid sequence of SEQ ID NO: 89, or an amino acid sequence having at least about 90%, or about 93%, or about 95%, or about 97%, or about 98%, or about 99% identity thereto.

92. The bispecific antibody of any one of embodiments 74-91, wherein:
the first polypeptide comprises the amino acid sequence of SEQ ID NO: 67, or an amino acid sequence having at least about 90%, or about 93%, or about 95%, or about 97%, or about 98%, or about 99% identity thereto:
the second polypeptide comprises the amino acid sequence of SEQ ID NO: 79, or an amino acid sequence having at least about 90%, or about 93%, or about 95%, or about 97%, or about 98%, or about 99% identity thereto; and
the third polypeptide comprises the amino acid sequence of SEQ ID NO: 89, or an amino acid sequence having at least about 90%, or about 93%, or about 95%, or about 97%, or about 98%, or about 99% identity thereto.

93. The bispecific antibody of any one of embodiments 80, 87, 88, or 89, wherein the constant domain comprises a human IgG Fc comprises a knob-in-hole interaction mutation.

94. The bispecific antibody of embodiment 93, wherein the mutations are selected from (i) T366Y or T366W, and (ii) Y407T, Y407A, or Y407V.

95. The bispecific antibody of embodiment 93, wherein the mutations are:
T366Y and Y407T or T366Y/F405A and T394W/Y407T; T366W/D399C and T366S/L368A/K392C/Y407V; T366W/K392C and T366S/L368A/D399C/Y407V; S354C/T366W and Y349C/T366S/L368A/Y407V;
Y349C/T366W and S354C/T366S/L368A/Y407V; E356C/T366W and Y349C/T366S/L368A/Y407V; Y349C/T366W and E356C/T366S/L368A/Y407V; E357C/T366W and Y349C/T366S/L368A/Y407V; or Y349C/T366W and E357C/T366S/L368A/Y407V; and
wherein the numbering is according to the EU numbering in human IgG1.

96. The bispecific antibody of any one of embodiments 80, 87, 88, or 89, wherein the constant domain comprises one or more mutations to reduce or eliminate the effector function of the constant domain.

97. The bispecific antibody of embodiment 96, wherein the mutations are L234A and L235A (LALA) substitutions, wherein the numbering is according to the EU numbering in human IgG1 in human IgG1.

98. The bispecific antibody any one of embodiments 80, 87, 88, or 89, wherein the constant comprises one or more mutations to stabilize a hinge region in the constant domain.

99. The bispecific antibody of embodiment 98, wherein the mutation is S228P.

100. The bispecific antibody of any of embodiments 74-99, wherein the bispecific antibody binds claudin 6 and CD3 contemporaneously.

101. The bispecific antibody of any one of embodiments 74-100, wherein the bispecific antibody binds claudin 6 with an affinity of less than about 10 nM and/or with at least about 100 fold greater affinity than claudin 9, claudin 3, and/or claudin 4.

102. A pharmaceutical composition comprising the bispecific antibody of any one of embodiments 74-101, or a nucleic acid molecule encoding the same.

103. The pharmaceutical composition of embodiment 102, wherein the composition is an injectable pharmaceutical composition, optionally a composition suitable for intravenous injection (administration) or subcutaneous injection (administration).

104. A nucleic acid molecule encoding the polypeptides of the bispecific antibody of any one of embodiments 74-101.

105. A plurality of nucleic acid molecules encoding the polypeptides of the bispecific antibody of any one of embodiments 74-101.

106. A vector comprising the nucleic acid molecule or molecules of embodiments 104 or 105.

107. A cell comprising the nucleic acid molecule of embodiments 104 or 105, or the vector of embodiment 106.

108. A method for modulating and/or targeting claudin 6 and CD3 in a biological cell, comprising contacting the cell with a bispecific antibody of any one of embodiments 74-101 or the pharmaceutical composition of embodiments 102 or 103.

109. A method for modulating claudin 6 activity in a biological cell comprising contacting a cell expressing claudin 6 with a bispecific of any one of embodiments 74-101 or the pharmaceutical composition of embodiments 102 or 103.

110. A method for inhibiting the function of claudin 6 in a biological cell comprising contacting a cell expressing claudin 6 with a bispecific antibody of any one of embodiments 74-101 or the pharmaceutical composition of embodiments 102 or 103.

111. A method for treating or preventing cancer comprising administering an effective amount of the bispecific antibody of any one of embodiments of any one of embodiments 74-101 or the pharmaceutical composition of embodiments 102 or 103.

112. A use of the bispecific antibody of any one of embodiments 74-101 or the pharmaceutical composition of embodiments 102 or 103 in the preparation of a medicament for the treatment or prevention of cancer.

113. A pharmaceutical composition for use in treating cancer, wherein the pharmaceutical composition comprises a bispecific antibody of any one of embodiments 74-101.

114. The method, use, or pharmaceutical composition of any one of embodiments 111-113, wherein the cancer is selected form one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses; edema (e.g. that associated with brain tumors); and Meigs' syndrome.

115. The method or use of embodiment 114, wherein the cancer is non-small cell lung (NSCLC), ovarian, gastric, breast, endometrial, or testicular cancer.

This disclosure is further illustrated by the following non-limiting examples.

EXAMPLES

Example 1 Overview and Development of Antibodies Specific for Claudin 6 and CD3

The experiments of this example demonstrate, inter alia, an antibody specific for claudin 6 and CD3. In this example, antibodies, antibody fragments, and antibody variants specific for claudin 6 and CD3 were isolated and characterized. This example identifies a tandem single-chain variable fragment (scFv) antibody, a scFv-Fab Fc antibody, an IgG-(scFV)$_2$ antibody, and a IgG-scFv Fc specific for claudin 6 and CD3 (FIG. 1).

Figure 2:
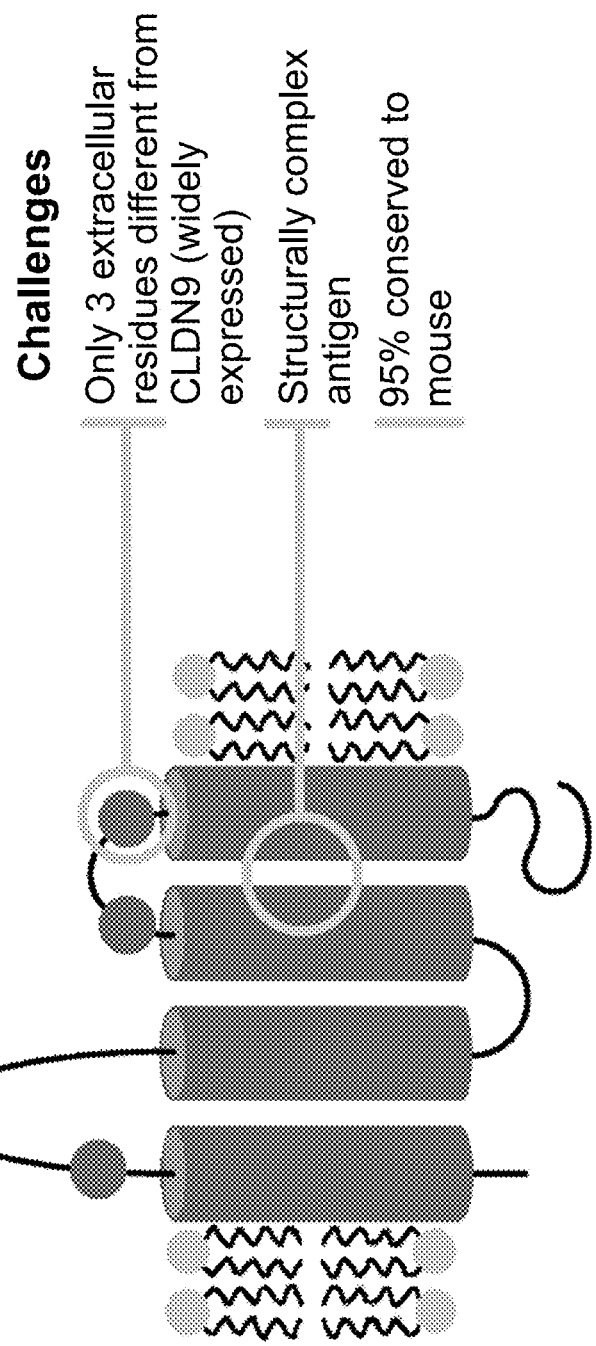
FIG. 2 is an image showing a schematic of the structure of CLDN6 and illustrating some of the challenges in developing an antibody specific for CLDN6.
Figure 3:
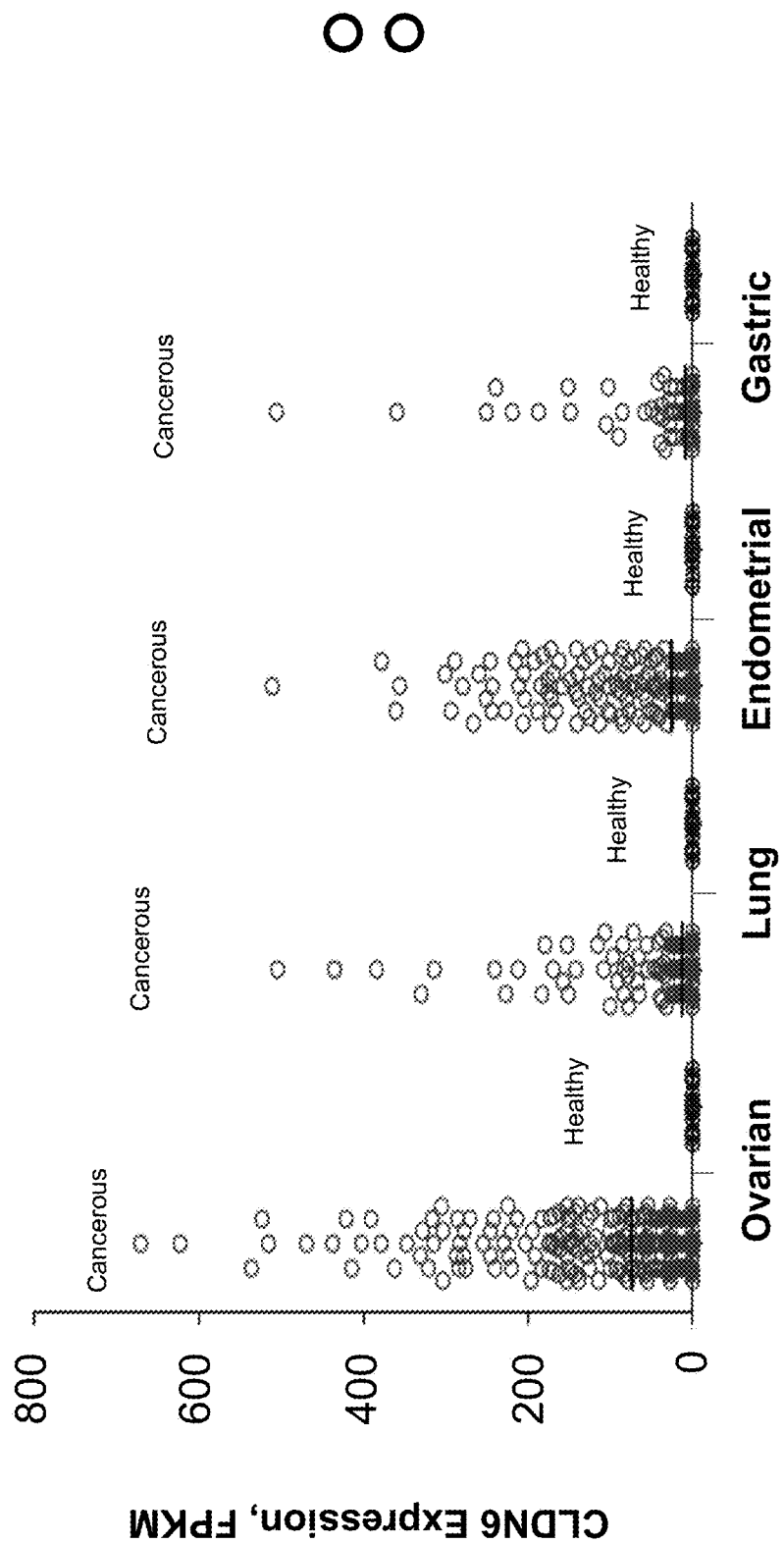
FIG. 3 is a graph of RNA sequencing data showing how claudin 6 is overexpressed in multiple cancers, including ovarian cancer, lung cancer, endometrial cancer, and gastric cancer.
Figure 4:
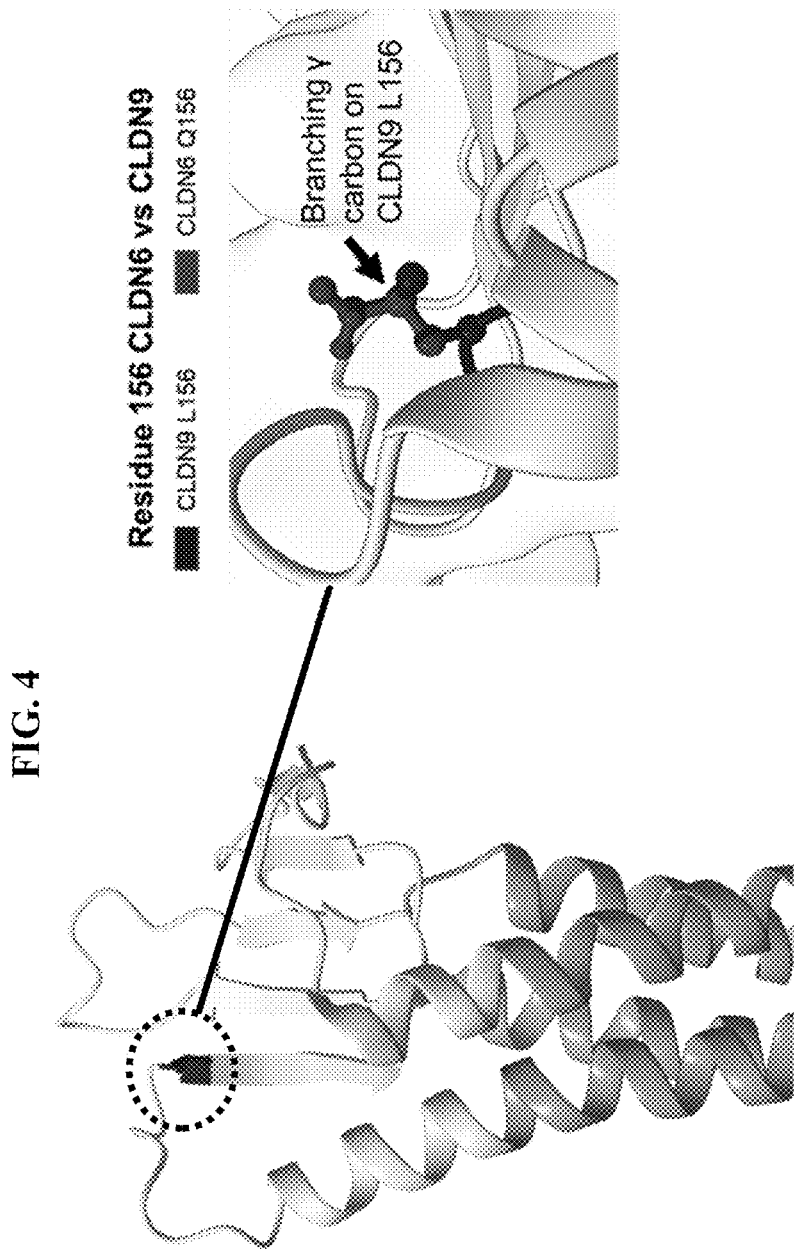
FIG. 4 is an image showing a non-limiting monospecificity challenge in developing antibodies specific to claudin 6, as the antibody needs to discriminate between a single amino acid side chain at residue 156 on CLDN6 and CLDN9.
Figure 6:
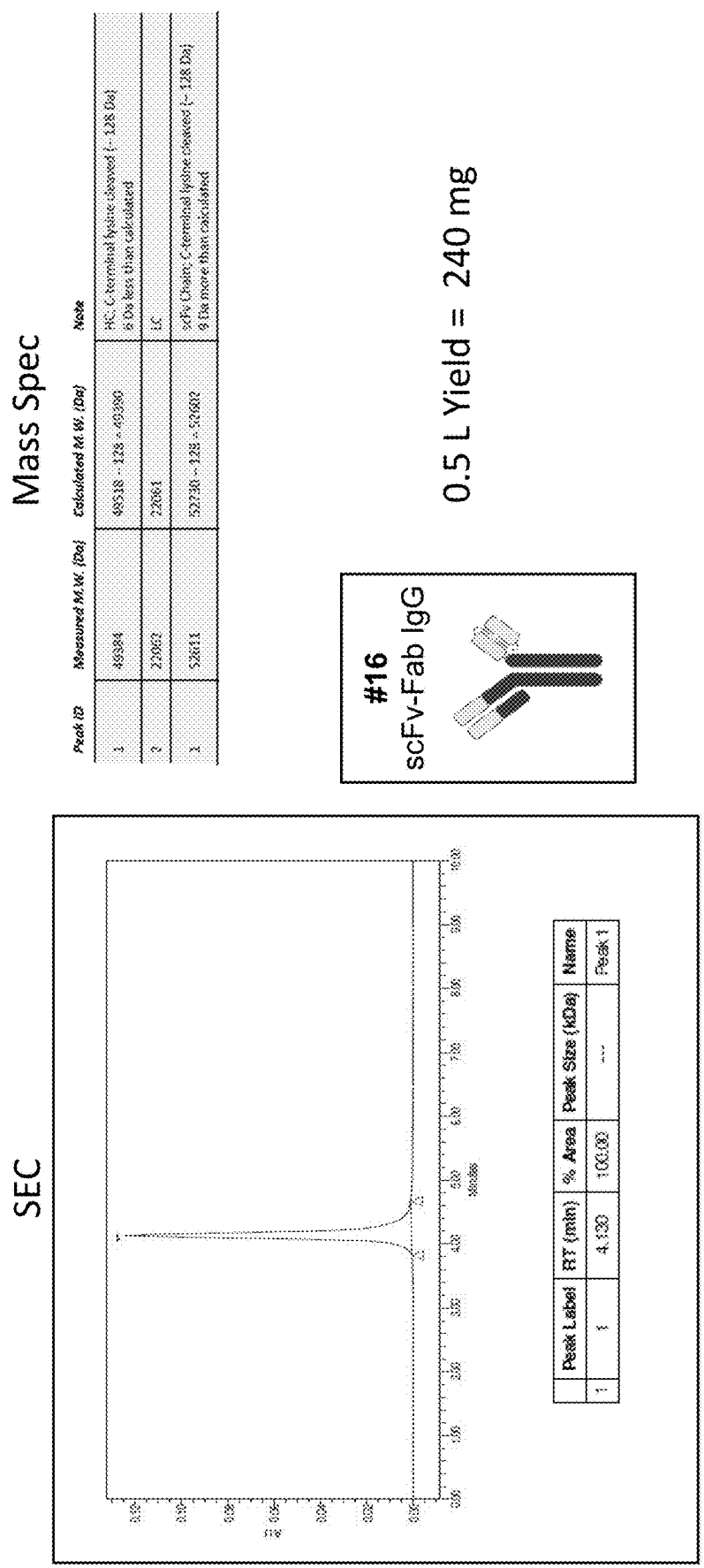
FIG. 6 shows graphs and images of quality control data from the IMC-16-3 scFv-Fab IgG antibody (SEQ ID NOs: 79, 67, and 89).
Figure 7:
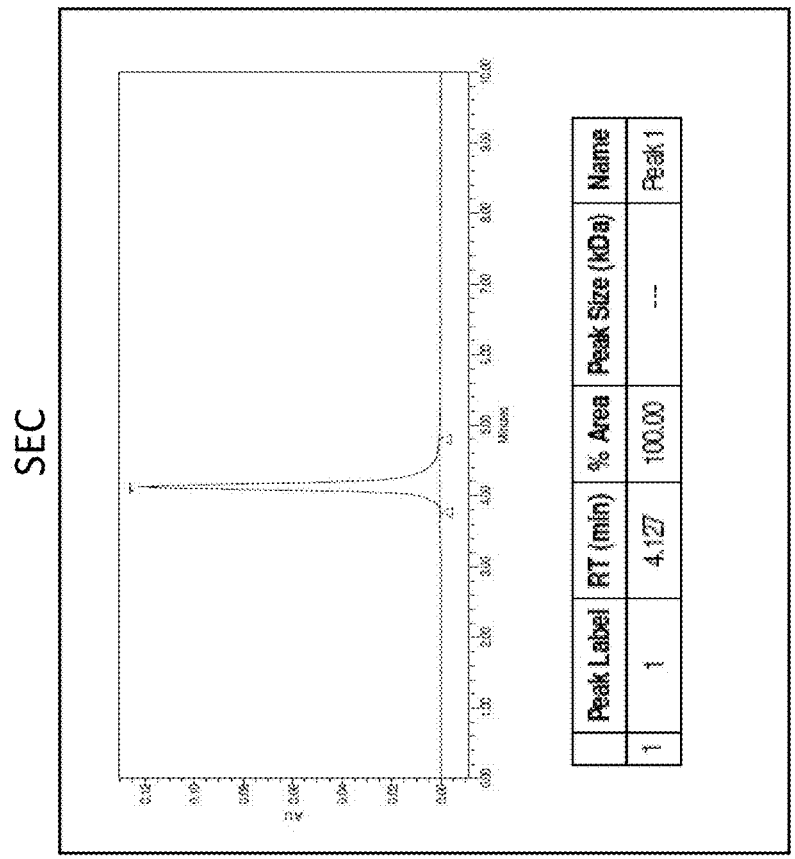
FIG. 7 shows graphs and images of quality control data from the IMC-16-15 scFv-Fab IgG antibody (SEQ ID NOs: 114, 65, and 89).
Figure 8:
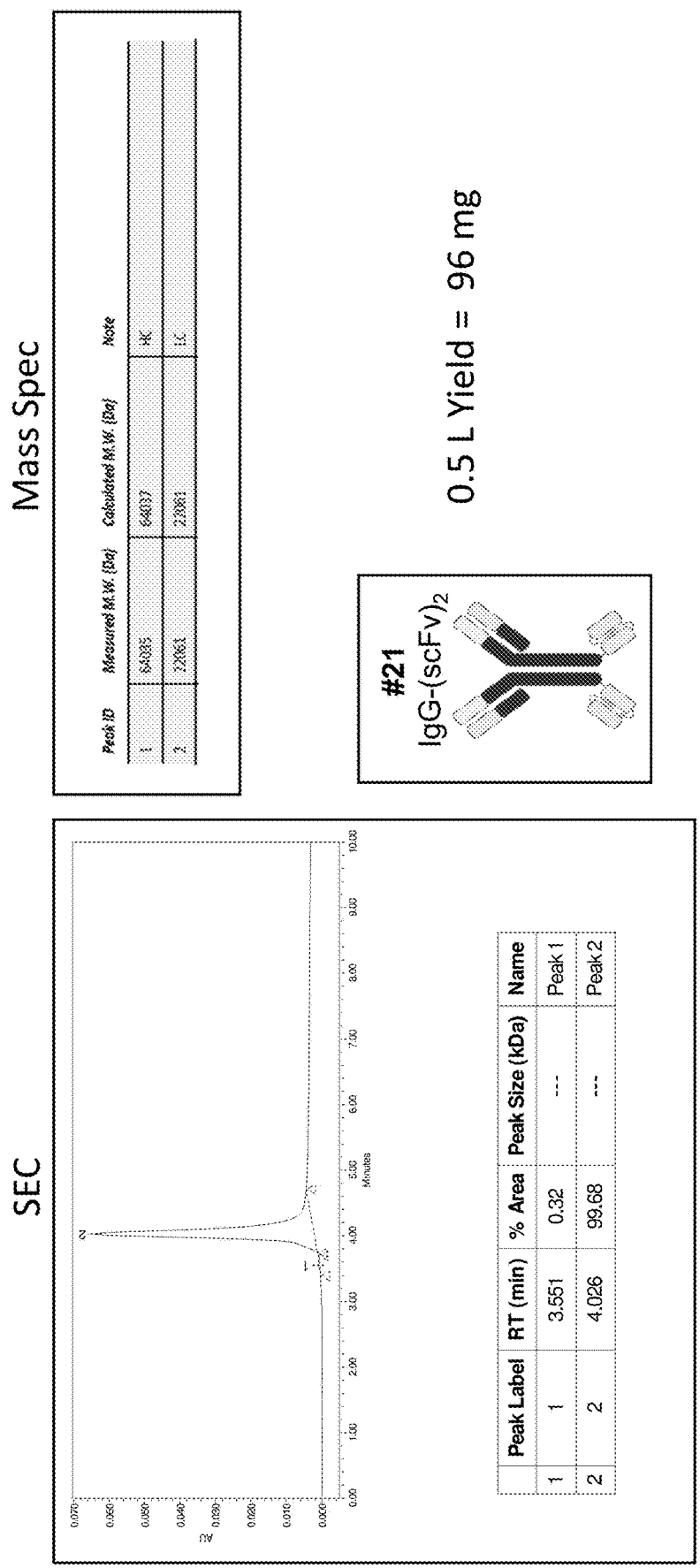
FIG. 8 shows graphs and images of quality control data from the IMC-21-1 IgG-(scFv)$_2$ antibody (SEQ ID NOs: 86, and 67).
Figure 9:
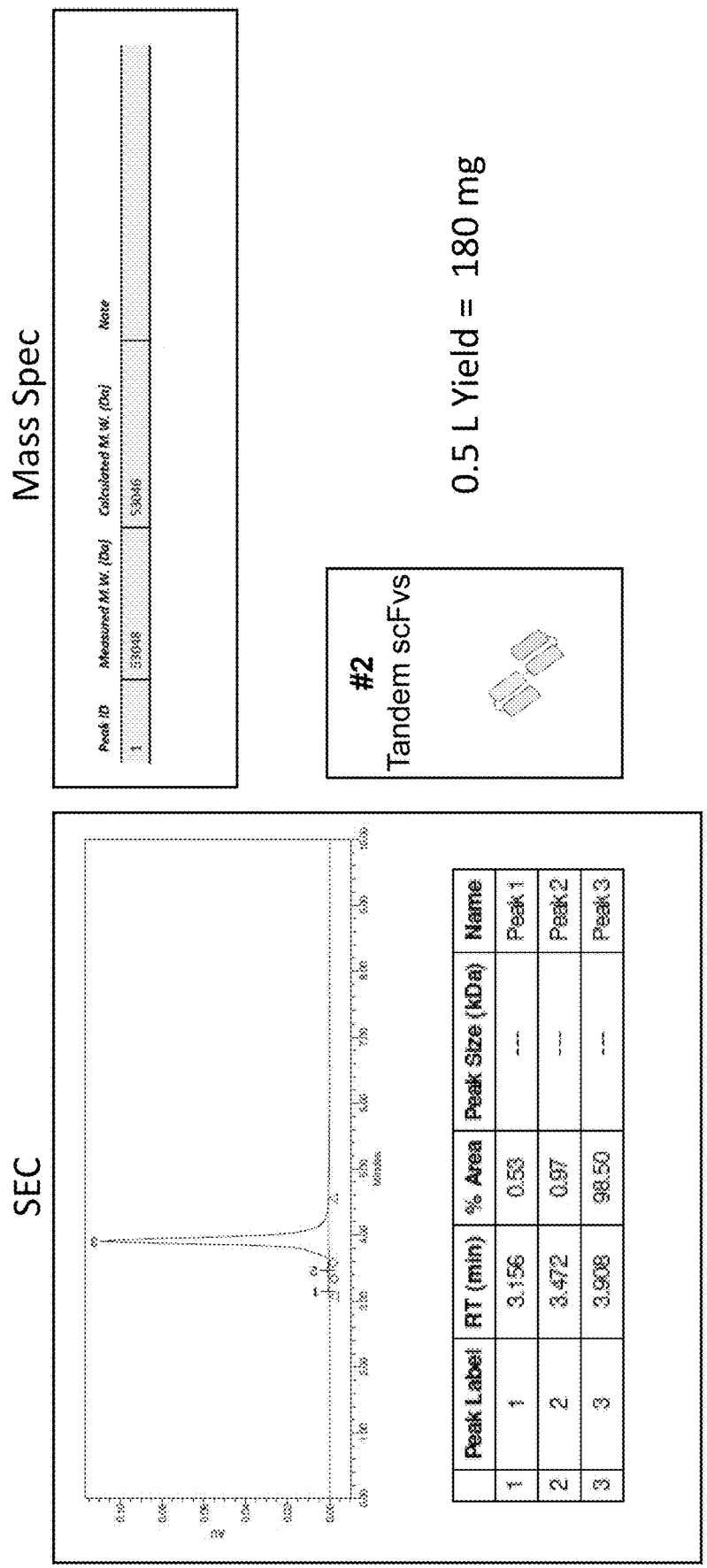
FIG. 9 shows graphs and images of quality control data from the IMC-2-7 tandem scFv antibody (SEQ ID NO: 95).

FIG. 2 is an image showing a schematic of the structure of CLDN6. Claudin 6 is expressed in ovarian, endometrial, and many other solid tumors, and based on the present disclosure, can be engaged by a bispecific antibody. Claudin 6 is not expressed in normal adult (mature) tissues. However, Claudin 6 is overexpressed in multiple cancers, including ovarian cancer, lung cancer, endometrial cancer, and gastric cancer (FIG. 3). In addition, FIG. 2 shows several of the illustrative challenges in developing an antibody specific for claudin 6. For example, Claudin 6 has only three extracellular residues that are different from CLDN9, which is widely expressed. Claudin 6 also is a structurally complex antigen, and is 95% conserved in mice. Further challenges in developing an antibody specific for claudin 6 include the "selectivity" challenge, as shown in FIG. 4. A selective CLDN6 antibody needs to discriminate between a single amino acid side chain at residue 156 on CLDN6 (Q156) and CLDN9 (L266). These challenges in the development of a selective CLDN6 antibody also hold true for the development of any bispecific construct that targets CLDN6, such as the CLDN6: CD3 bispecific constructs provided for herein.

Figure 32:
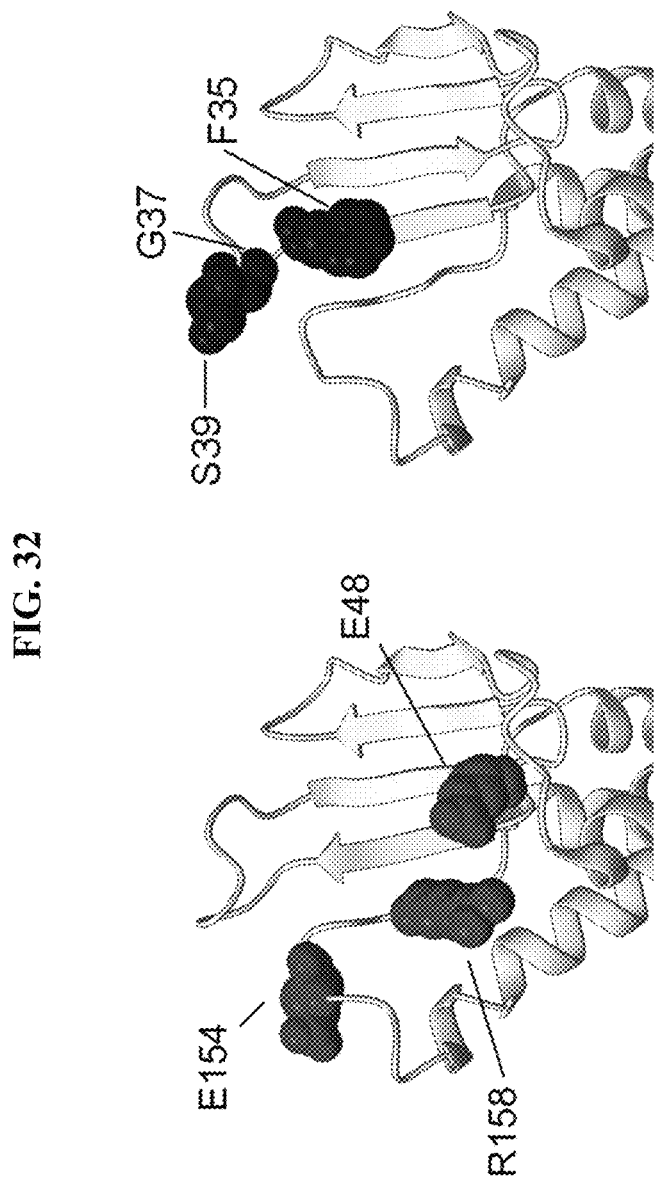
FIG. 32 is a non-limiting image showing the critical residues for monoclonal antibody binding that were identified using a CLDN6 alanine-scanning library expressed in HEK-293 T cells. CLDN6 specificity was determined by recognition of the Q156 γ carbon (FIG. 4). In CLDN9, the native L156 residue leads to steric inhibition of monoclonal antibody binding.

FIG. 32 shows the epitope of the IM271-1HEP antibody, the CLDN6 binding arm of the IMC-16-3 scFv-Fab IgG antibody, as compared to the epitope of the benchmark IMAB027 antibody. Energetically critical epitope residues were determined by alanine scanning mutagenesis and flow cytometry. The left image in FIG. 32 shows the epitope of IM271-1HEP antibody while the right image in FIG. 32 shows the IMAB027 epitope.

To develop and select a bispecific antibody to claudin 6 and CD3, a large panel of constructs were generated using the following antibody formats: tandem scFvs, scFv-Fab IgG, IgG-(scFv)$_2$, or IgG-scFv. Potential CLDN6 specific arms included those from HEP, HHP, HFJ, and 271 antibodies, and specific CD3 arms included those from muOKT3, huSP31-1, and huSP34-3 antibodies, as well as a nanobody. Based on selective binding to CLDN6 vs CLDN9, CLDN4, and CLDN3, experimental in vitro potency (including CLDN6+ cell killing and cytokine production), developability (including, without limitation, large-scale yield), and format/arm diversity, four molecules were selected for in vivo testing: an scFv-Fab IgG antibody (referred to as IMC-16-3; SEQ ID NOs: 79, 67, and 89), an scFv-Fab IgG antibody (referred to as IMC-16-15; SEQ ID NOs: 114, 65, and 89), an IgG-(scFv)$_2$ antibody (referred to as IMC-21-1; SEQ ID NOs: 86, and 67), and a tandem scFv antibody (referred to as IMC-2-7; SEQ ID NO: 95). FIG. 5, FIG. 6, FIG. 7, FIG. 8, and FIG. 9 show quality control data for the IMC-16-3 scFv-Fab IgG antibody (FIG. 6), IMC-16-15 scFv-Fab IgG antibody (FIG. 7), IMC-21-1 IgG-(scFv)$_2$ antibody (FIG. 8), and the IMC-2-7 tandem scFv antibody (FIG. 9) specific to human CLDN6 and CD3.

The experiments in FIG. 26A and FIG. 26B show TNF-α levels produced by human T cells in the presence of claudin 6 expressing HEK cells and OV-90 cells and a set of antibody constructs (i.e., IMC-16-13 scFv-Fab IgG antibody (SEQ ID NOs: 114, 65, and 80), IMC-16-15 scFv-Fab IgG antibody, IMC-16-3 scFv-Fab IgG antibody, IMC-2-7 tandem scFv antibody, IMC-2-13 tandem scFv antibody (SEQ ID NO: 115), IMC-20-13 IgG-scFv antibody (SEQ ID NOs: 114, 65, and 116), IMC-21-1 IgG-(scFv)2 antibody, IMC-21-6 IgG-(scFv)2 antibody (SEQ ID NOs: 104 and 66), and the IMC-2-3 tandem scFv antibody (SEQ ID NO: 84).

The experiments in FIG. 27A and FIG. 27B are graphs showing IFN-γ produced by human T cells in the presence of claudin 6 expressing HEK cells and OV-90 cells for a set of antibody constructs (i.e., IMC-16-13 scFv-Fab IgG antibody, IMC-16-15 scFv-Fab IgG antibody, IMC-16-3 scFv-Fab IgG antibody, IMC-2-7 tandem scFv antibody, IMC-2-13 tandem scFv antibody, IMC-20-13 IgG-scFv antibody, IMC-21-1 IgG-(scFv)2 antibody, IMC-21-6 IgG-(scFv)$_2$ antibody, and the IMC-2-3 tandem scFv antibody).

The experiments in FIG. 28A and FIG. 28B show IL-2 levels (FIG. 28A) and IL-6 levels (FIG. 28B) produced by human T cells in the presence of claudin 6 expressing OV-90 cells for a set of antibody constructs (i.e., IMC-16-13 scFv-Fab IgG antibody, IMC-16-15 scFv-Fab IgG antibody, IMC-16-3 scFv-Fab IgG antibody, IMC-2-7 tandem scFv antibody, IMC-2-13 tandem scFv antibody, IMC-20-13 IgG-scFv antibody, IMC-21-1 IgG-(scFv)2 antibody, IMC-21-6 IgG-(scFv)2 antibody, and the IMC-2-3 tandem scFv antibody). IL-6 and Il-2 levels were both marginal on the HEK-CLDN6 (<10 pg/ml).

The experiments of this example demonstrated that each selected antibody produced high yields. The IMC-16-3 scFv-Fab IgG antibody had the highest yield at 240 mg from a 0.5 L run. These experiments also demonstrated that minimal or no aggregates were observed for any of the molecules. The IMC-2-7 tandem scFv antibody had moderate levels of aggregation prior to post-polish using size-exclusion chromatography. The isoelectric points were also sufficiently high to allow wider range of pH for final buffer formulations.

Example 2: Target Binding to Human CLDN6 and Human CD3

Figure 10:
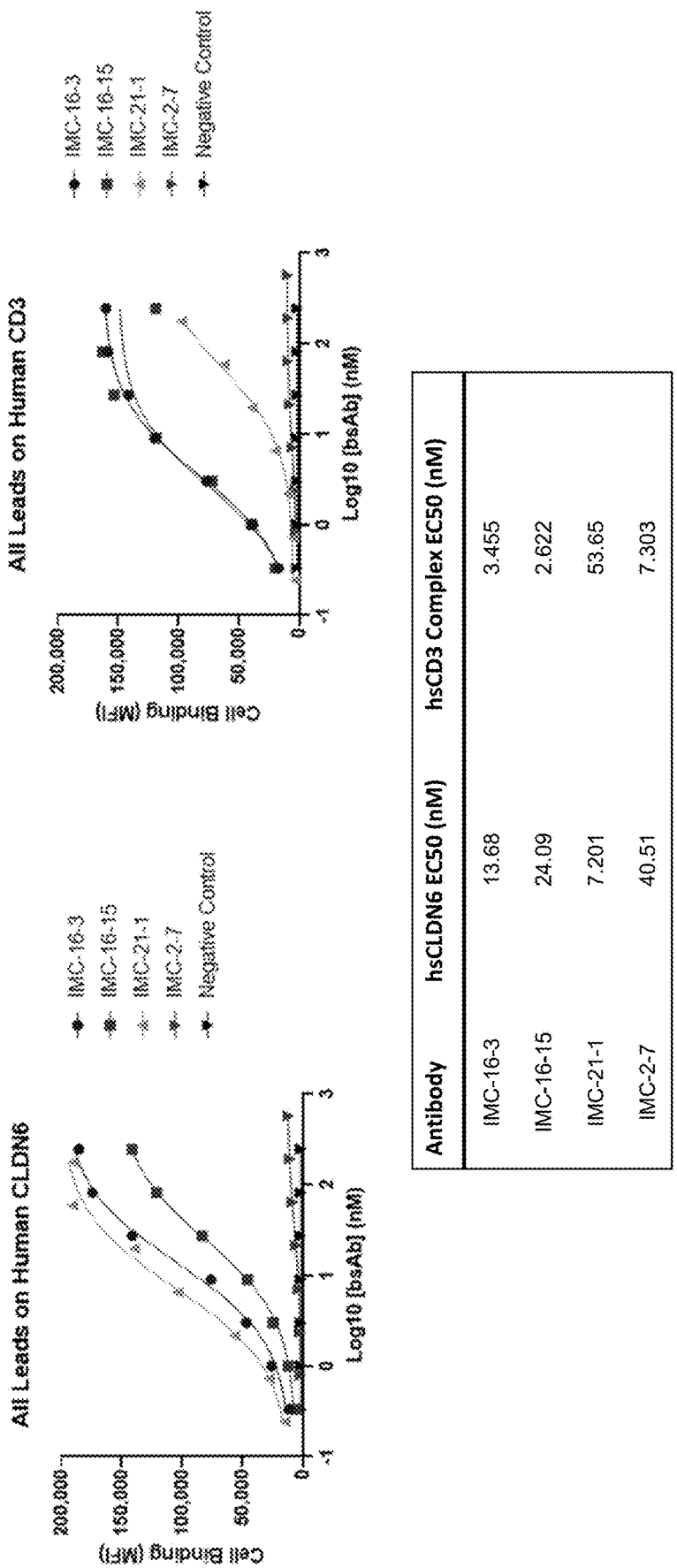
FIG. 10 shows two graphs of target binding data from flow cytometry experiments. The left panel in FIG. 10 shows target binding data of the IMC-16-3 scFv-Fab IgG antibody (circles), IMC-16-15 scFv-Fab IgG antibody (squares), IMC-21-1 IgG-(scFv)$_2$ antibody (triangles), and the IMC-2-7 tandem scFv antibody (inverted triangles) to human CLDN6. The right panel in FIG. 10 shows target binding data of the IMC-16-3 scFv-Fab IgG antibody (circles), IMC-16-15 scFv-Fab IgG antibody (squares), IMC-21-1 IgG-(scFv)$_2$ antibody (triangles), and the IMC-2-7 tandem scFv antibody (inverted triangles) to human CD3. The table at the bottom of FIG. 10 shows binding EC50 data for molecules against CLDN6 and CD3.

The experiments of this example demonstrated the antibodies disclosed herein bind to both human CLDN6 and human CD3. The experiments in FIG. 10 show two graphs of target binding data from flow cytometry experiments. The left panel in FIG. 10 shows target binding data of the IMC-16-3 scFv-Fab IgG antibody, IMC-16-15 scFv-Fab IgG antibody, IMC-21-1 IgG-(scFv)$_2$ antibody, and the IMC-2-7 tandem scFv antibody to human CLDN6-expressing cells. The right panel in FIG. 10 shows target binding data of the IMC-16-3 scFv-Fab IgG antibody, IMC-16-15 scFv-Fab IgG antibody, IMC-21-1 IgG-(scFv)$_2$ antibody, and the IMC-2-7 tandem scFv antibody to human CD3-expressing cells. These experiments show; inter alia, how the antibodies disclosed herein bind to both human CLDN6 and human CD3.

The experiments in FIG. 11A, FIG. 11B, FIG. 11C, and FIG. 11D show parental and benchmark antibody binding data from flow cytometry experiments. For each experiment, a CLDN negative parental cell line was either mock transfected or transfected with CLDN6. CLDN4, CLDN3, or CLDN9. FIG. 11A is a graph showing binding of IM271-1HEP antibody to human CLDN6 (circle shapes), human CLDN4 (square shapes), human CLDN3 (triangle shapes), human CLDN9 (inverted triangle shapes), and a negative control (diamond shapes). This experiment shows the IM271-1HEP antibody specifically binds to human CLDN6. FIG. 11B is a graph showing binding of IM271-1HHP antibody to human CLDN6 (circle shapes), human CLDN4 (square shapes), human CLDN3 (triangle shapes), human CLDN9 (inverted triangle shapes), and a negative control (diamond shapes). This experiment shows the IM271-1HHP antibody specifically binds to human CLDN6. FIG. 11C is a graph showing binding of IM271-1HFJ antibody to human CLDN6 (circle shapes), human CLDN4 (square shapes), human CLDN3 (triangle shapes), human CLDN9 (inverted triangle shapes), and a negative control (diamond shapes). This experiment shows the IM271-1HFJ antibody specifically binds to human CLDN6. FIG. 11D is a graph showing binding of an antibody to human CLDN6 (circle shapes), human CLDN4 (square shapes), human CLDN3 (triangle shapes), human CLDN9 (inverted triangle shapes), and a negative control (diamond shapes). This experiment shows how antibody in FIG. 11D does not specifically bind to human CLDN6, but binds to CLDN6 and CLDN9 equally. Collectively, these experiments show, inter alia, how CLDN6 specific arms from HEP, HHP, HFJ, and 271 antibodies bind specifically to human CLDN6.

Figure 12A:
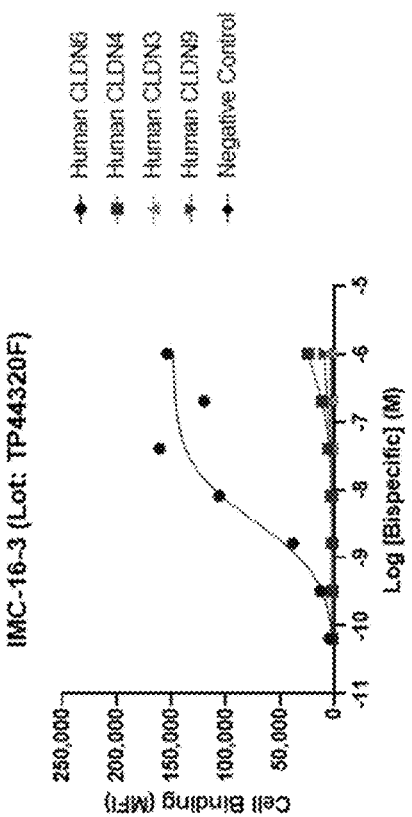
FIG. 12A, FIG. 12B, FIG. 12C, and FIG. 12D are graphs showing target binding data from flow cytometry experiments.
Figure 12C:
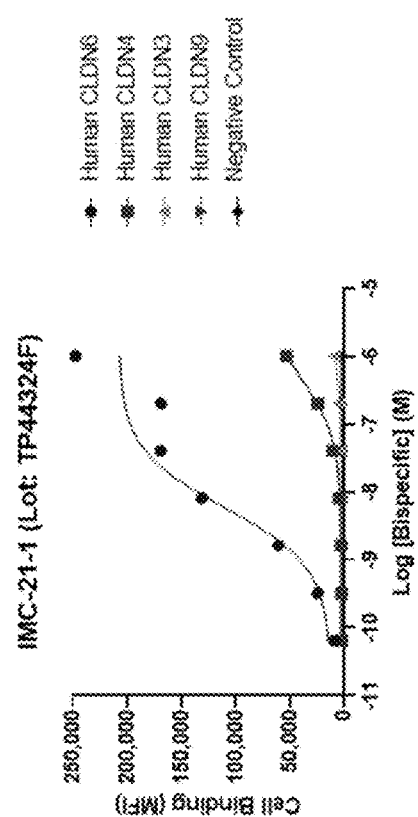
Figure 12B:
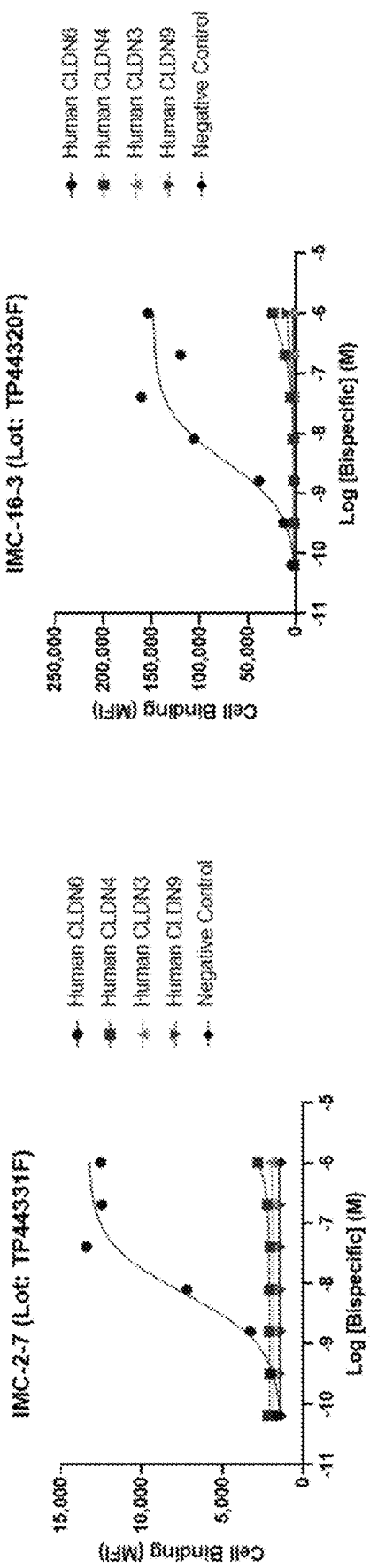
Figure 12D:
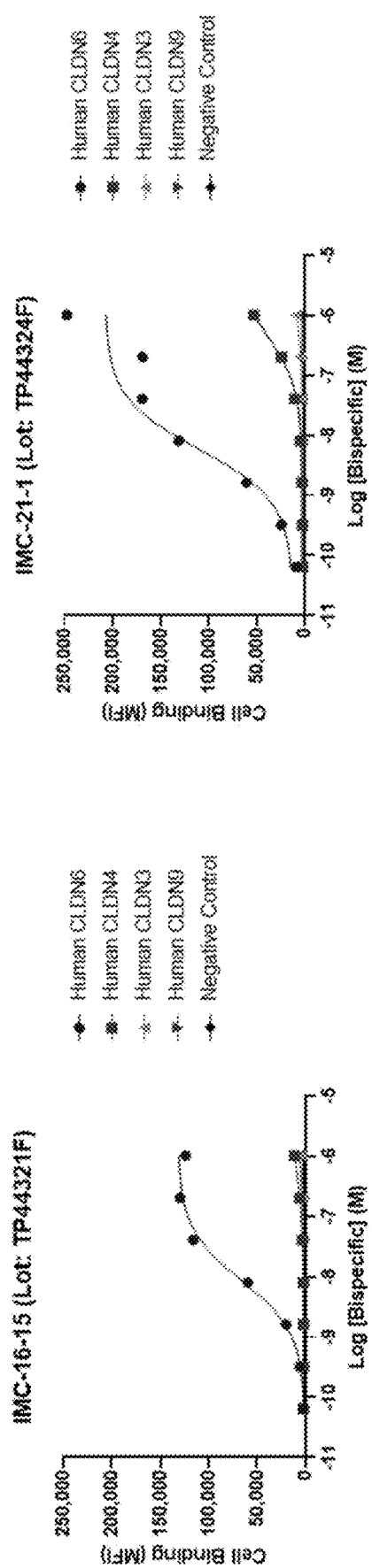

The experiments in FIG. 12A, FIG. 12B, FIG. 12C, and FIG. 12D are graphs showing target binding data from flow cytometry experiments. For each experiment, a CLDN negative parental cell line was either mock transfected or transfected with CLDN6, CLDN4, CLDN3, or CLDN9. Each experiment demonstrates that selected antibodies have one arm that specifically binds to human CLDN6. FIG. 12A is a graph showing binding of the IMC-2-7 tandem scFv antibody to human CLDN6 (circle shapes), human CLDN4 (square shapes), human CLDN3 (triangle shapes), human CLDN9 (inverted triangle shapes), and a negative control (diamond shapes). This experiment shows that the IMC-2-7 tandem scFv antibody specifically binds to human CLDN6. FIG. 12B is a graph showing binding of the IMC-16-3 scFv-Fab IgG antibody to human CLDN6 (circle shapes), human CLDN4 (square shapes), human CLDN3 (triangle shapes), human CLDN9 (inverted triangle shapes), and a negative control (diamond shapes). This experiment shows that the IMC-16-3 scFv-Fab IgG antibody specifically binds to human CLDN6. FIG. 12C is a graph showing binding of the IMC-16-15 scFv-Fab IgG antibody to human CLDN6 (circle shapes), human CLDN4 (square shapes), human CLDN3 (triangle shapes), human CLDN9 (inverted triangle shapes), and a negative control (diamond shapes). This experiment shows that the IMC-16-15 scFv-Fab IgG antibody specifically binds to human CLDN6. FIG. 12D is a graph showing binding of the IMC-21-1 IgG-(scFv)$_2$ antibody to human CLDN6 (circle shapes), human CLDN4 (square shapes), human CLDN3 (triangle shapes), human CLDN9 (inverted triangle shapes), and a negative control (diamond shapes). This experiment shows, inter alia, that the IMC-21-1 IgG-(scFv)$_2$ antibody specifically binds to human CLDN6.

Figures 37A, 37B:
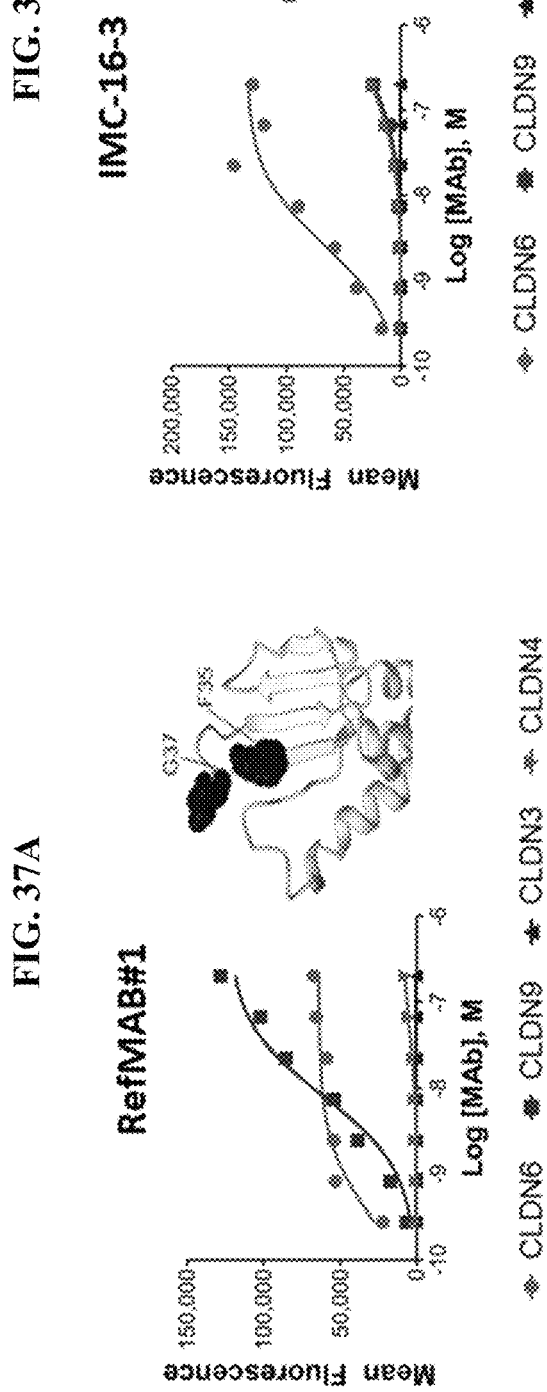
FIG. 37A and FIG. 37B illustrate the selectivity of a reference antibody (RefMAB #1, FIG. 37A) and IMC-16-3 (FIG. 37B) for various claudin proteins.

The experiment in FIG. 37 shows target binding data from flow cytometry experiments utilizing a reference antibody (RefMAB #1) and IMC-16-3. For this experiment, a CLDN negative parental cell line was transfected with CLDN6, CLDN4, CLDN3, or CLDN9. The data show binding of the antibodies to human CLDN6 (circle shapes), human CLDN4 (square shapes), human CLDN3 (triangle shapes), human CLDN9 (inverted triangle shapes), and a negative control (diamond shapes). Epitope binding data are also shown for each antibody. These data highlight that the RefMAB #1, which binds to a different epitope than IMC-16-3, shows significant binding to CLDN9, while IMC-16-3 is highly selective for CLDN6.

The experiment in FIG. 41 shows comparative target binding data between an anti-CLDN6 antibody-drug conjugate (ACD) (RefMAB #2; FIG. 41A), an anti-CLDN6×anti-CD3 BiTE molecule (RefMAB #3; FIG. 41B) and IMC-16-3 (FIG. 41C). The ADC comprises an anti-CLDN6 antibody conjugated to monomethyl auristatin E (MMAE). Binding assessment was performed after HEK293F cells were transfected with nucleic acid molecules to express various claudin proteins. These comparative data show binding of the antibodies to human CLDN3 (circle shapes), human CLDN4 (square shapes), human CLDN6 (triangle shapes), human CLDN9 (inverted triangle shapes), and a negative control (diamond shapes). Each of RefMAB #2, RefMAB #3, and IMC-16-3 were highly selective for CLDN6 over the other claudin molecules assayed, in contrast to molecules typified by RefMAB #1 (FIG. 37) which was not selective for CLDN6.

The experiments of this example demonstrate, inter alia, that the antibodies disclosed herein bind to both human CLDN6 and human CD3. The antibodies disclosed herein show a high degree of specificity in binding to CLDN6 over CLDNs 3, 4, or 9.

Example 3: T-Cell Mediated Cytotoxicity Assays

The experiments of this example demonstrated, inter alia, that the antibodies disclosed herein have high levels of T cell mediated killing specific in both endogenous and exogenous models of CLDN6 expression (OV-90 cells and CLDN6-K562 cells, respectively).

Figure 38B:
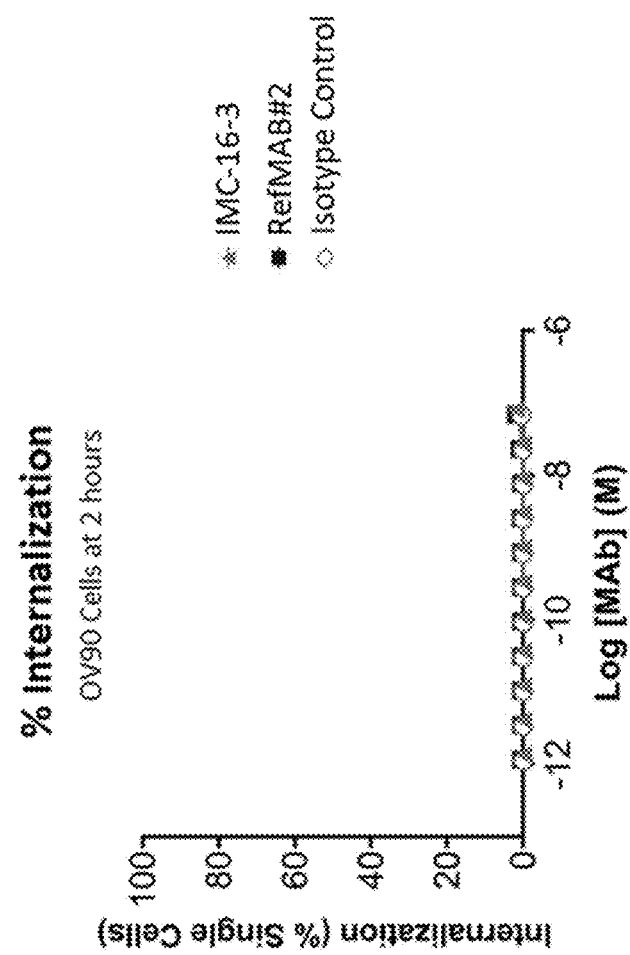
FIG. 38A and FIG. 38B illustrate the result of an internalization assessment of IMC-16-3 and RefMAB #2.
Figure 38A:
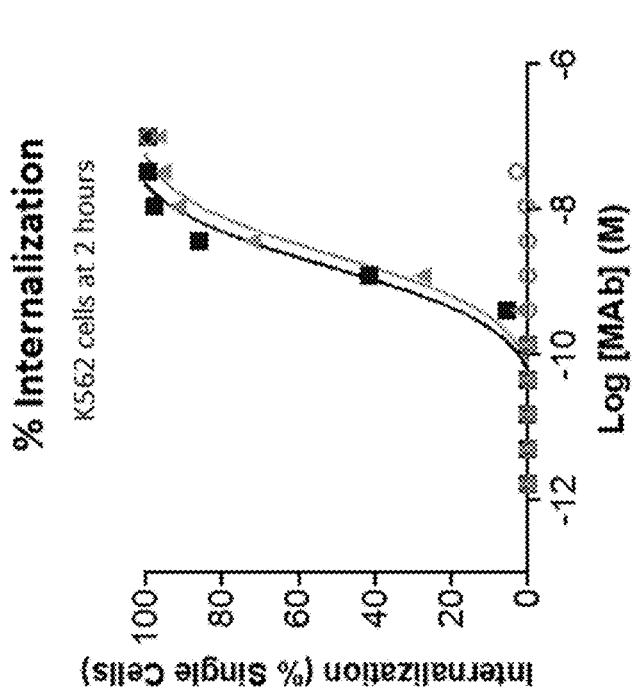

The experiments in FIG. 38 illustrate the results of an internalization study to determine whether IMC-16-3 or a reference antibody (RefMAB #2) become internalized after CLDN6 binding. IMC-16-3 and the reference antibody were labeled with the pH-sensitive dye pHrodo and incubated with either K562 cells, which stably overexpress high levels of CLDN6, or OV-90 ovarian cancer cells, which express moderate levels of CLDN6, for 2 hours. As shown in FIG. 38, both antibodies are only internalized in cells which express high levels of CLDN6. These data indicate that antibodies targeting CLDN6 are slowly internalized in moderate to low CLDN6 expressing cells, which makes CLDN6 an ideal target for a T cell engaging bispecific antibody.

Figure 13:
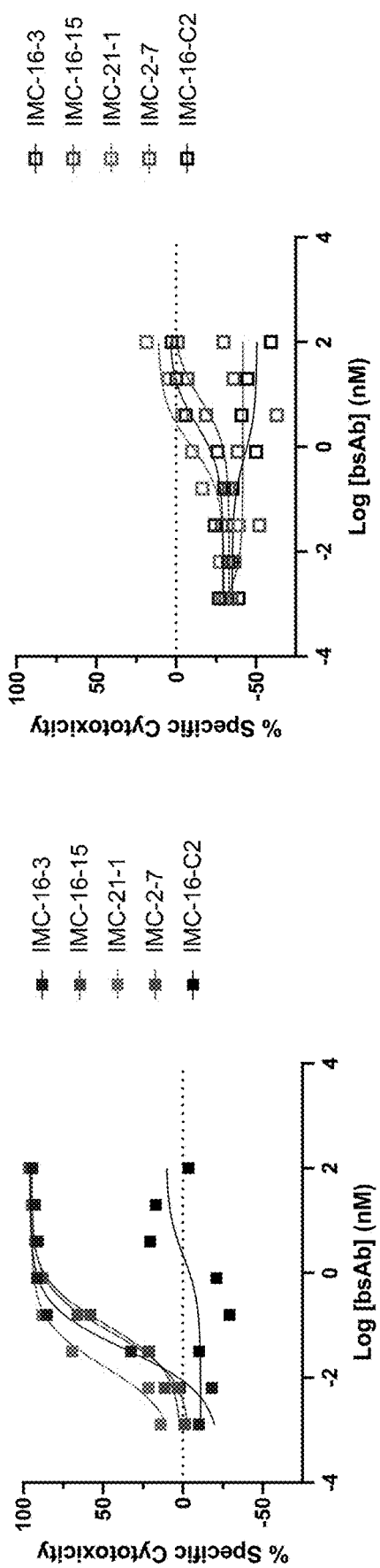
FIG. 13 shows two graphs of cellular toxicity data from T-cell dependent cellular cytotoxicity experiments. The left panel in FIG. 13 shows cytotoxicity data of the IMC-16-3 scFv-Fab IgG antibody, IMC-16-15 scFv-Fab IgG antibody, IMC-21-1 IgG-(scFv)$_2$ antibody. IMC-2-7 tandem scFv antibody, and the IMC-16-C2 antibody (negative control) in ovarian cancer OV-90 cells. The right panel in FIG. 13 shows target binding data of the IMC-16-3 scFv-Fab IgG antibody, IMC-16-15 scFv-Fab IgG antibody, IMC-21-1 IgG-(scFv)$_2$ antibody, IMC-2-7 tandem scFv antibody, and the IMC-16-C2 antibody in HEK cells.

The experiments in FIG. 13 show two graphs of cellular toxicity data from T-cell dependent cellular cytotoxicity experiments. The left panel in FIG. 13 shows cytotoxicity data of human T cells co-cultured with the IMC-16-3 scFv-Fab IgG antibody, IMC-16-15 scFv-Fab IgG antibody, IMC-21-1 IgG-(scFv)$_2$ antibody, IMC-2-7 tandem scFv antibody, and the IMC-16-C2 antibody (negative control) and ovarian cancer OV-90 cells, which express CLDN6. The right panel in FIG. 13 shows cytotoxicity data of human T cells co-cultured with the IMC-16-3 scFv-Fab IgG antibody, IMC-16-15 scFv-Fab IgG antibody, IMC-21-1 IgG-(scFv)$_2$ antibody, IMC-2-7 tandem scFv antibody, and the IMC-16-C2 antibody and HEK cells. These experiments show; inter alia, that killing was only potently induced versus CLDN6 expressing OV-90 cells.

The experiments in FIG. 14A, FIG. 14B, FIG. 14C, FIG. 14D, and FIG. 14E are graphs showing cytokines produced by human PBMC cultured with the IMC-16-3 scFv-Fab IgG antibody and OV-90 cells as compared to cellular toxicity data. FIG. 14A shows the levels of IL-2. FIG. 14B shows the levels of IL-6, FIG. 14C shows the levels of IL-10, FIG. 14D shows the levels of IFN-γ, and FIG. 14E shows the levels of TNF-α produced by human PBMC in the presence of OV-90 cells and IMC-16-3. These experiments show, inter alia, that IL-2, IL-6, IL-10, IFN-γ, and TNF-α were all induced in human PBMC by the IMC-16-3 scFv-Fab IgG antibody in the presence of CLDN6-expressing OV-90 cells.

The experiments in FIG. 15A, FIG. 15B, FIG. 15C, FIG. 15D, and FIG. 15E are graphs showing cytokines produced by human PBMC cultured with the IMC-16-15 scFv-Fab IgG antibody and OV-90 cells. FIG. 15A shows the levels of IL-2, FIG. 15B shows the levels of IL-6, FIG. 15C shows the levels of IL-10, FIG. 15D shows the levels of IFN-γ, and FIG. 15E shows the levels of TNF-α produced by human PBMC in the presence of OV-90 cells and IMC-16-15. These experiments show, inter alia, that IL-2, IL-6, IL-10, IFN-γ, and TNF-α were all induced in human PBMC by the IMC-16-15 scFv-Fab IgG antibody in the presence of CLDN6-expressing OV-90 cells.

Figure 16A:
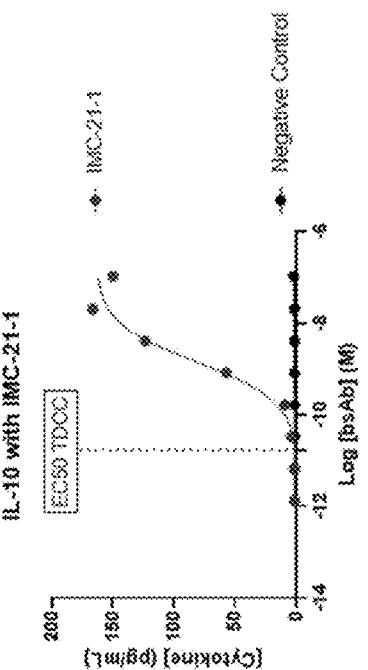
FIG. 16A, FIG. 16B, FIG. 16C, FIG. 16D, and FIG. 16E are graphs showing the production of cytokines by human PBMCs co-cultured with CLDN6 positive OV-90 cells in the presence or absence of the IMC-21-1 IgG-(scFv)$_2$ antibody.
Figure 16B:
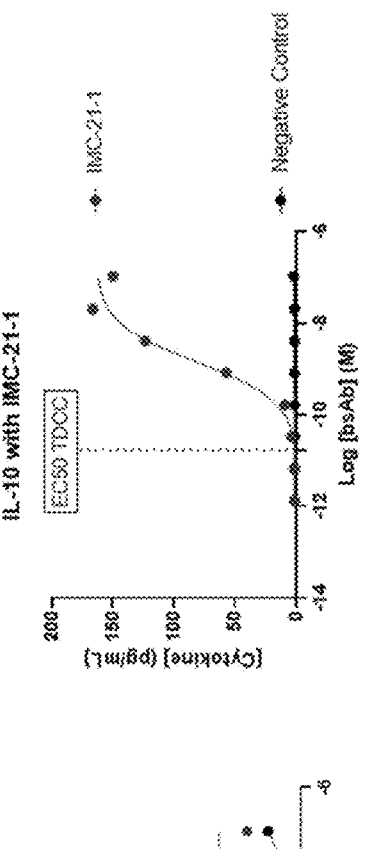
Figure 16C:
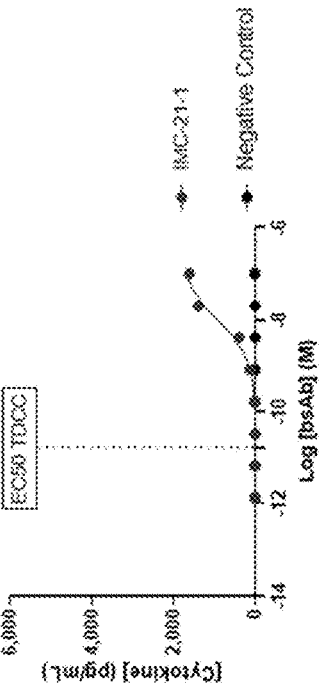
Figure 16D:
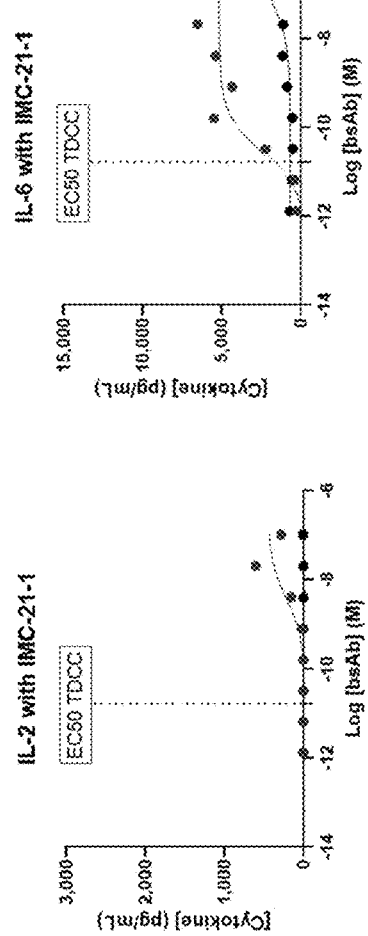
Figure 16E:
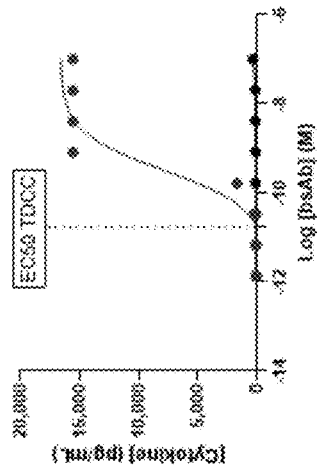

The experiments in FIG. 16A, FIG. 16B, FIG. 16C, FIG. 16D, and FIG. 16E are graphs showing cytokines produced by human PBMC cultured with the IMC-21-1 IgG-(scFv)$_2$ antibody in the presence of OV-90 cells. FIG. 16A shows the levels of IL-2, FIG. 16B shows the levels of IL-6, FIG. 16C shows the levels of IL-10, FIG. 16D shows the levels of IFN-γ, and FIG. 16E shows the levels of TNF-α produced by human PBMC in the presence of OV-90 cells and IMC-21-1. These experiments show, inter alia, that IL-2, IL-6, IL-10, IFN-γ, and TNF-α were all induced in human PBMC by the IMC-21-1 IgG-(scFv)$_2$ antibody in the presence of CLDN6-expressing OV-90 cells.

The experiments in FIG. 17A, FIG. 17B, FIG. 17C, FIG. 17D, and FIG. 17E are graphs showing cytokines produced by human PBMC cultured with the IMC-2-7 tandem scFv antibody in the presence of OV-90 cells. FIG. 17A shows the levels of IL-2, FIG. 17B shows the levels of IL-6, FIG. 17C shows the levels of IL-10, FIG. 17D shows the levels of IFN-γ, and FIG. 17E shows the levels of TNF-α produced by human PBMC in the presence of OV-90 cells and IMC-2-7. These experiments show; inter alia, that IL-2, IL-6, IL-10, IFN-γ, and TNF-α were all induced in human PBMC by the IMC-2-7 tandem scFv antibody in the presence of CLDN-6 expressing OV-90 cells.

Figure 18:
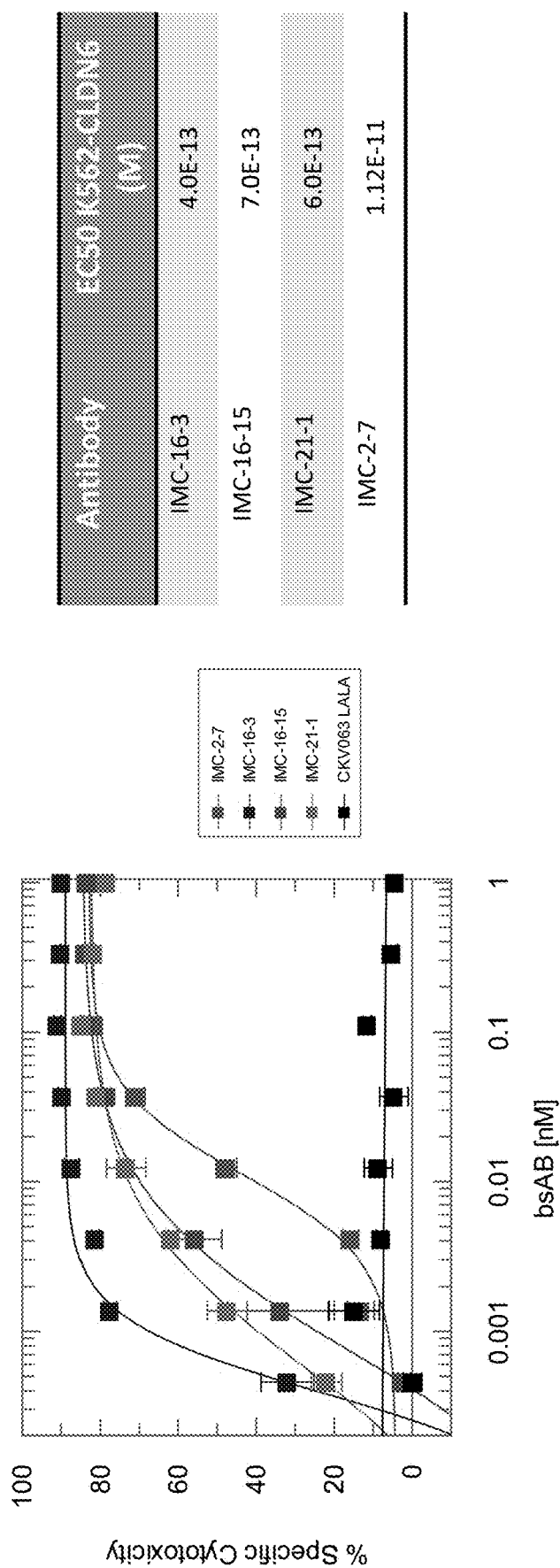
FIG. 18 shows a graph of cellular toxicity data from T-cell dependent cellular cytotoxicity experiments.

The experiments in FIG. 18 show a graph of cytotoxicity data from T-cell dependent cellular cytotoxicity experiments. FIG. 18 shows cytotoxicity data of human T cells cultured with the IMC-2-7 tandem scFv antibody, IMC-16-3 scFv-Fab IgG antibody, IMC-16-15 scFv-Fab IgG antibody, IMC-21-1 IgG-(scFv)$_2$ antibody, and a negative control (CKV063 LALA) versus CLDN6-expressing K562 cells. These experiments show; inter alia, that killing was potently induced in CLDN6 expressing K562 cells.

Figure 19B:
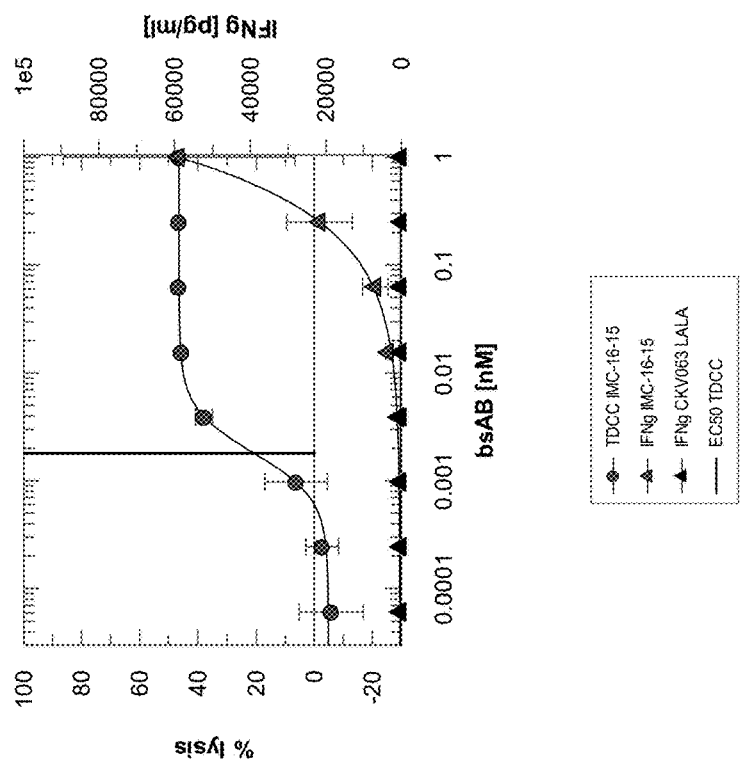
FIG. 19A, FIG. 19B, FIG. 19C, FIG. 19D, FIG. 19E, FIG. 19F, FIG. 19G, and FIG. 19H are graphs showing cellular toxicity and IFN-γ release potency data at 24 hours and 48 hours from cellular cytotoxicity experiments.
Figure 19A:
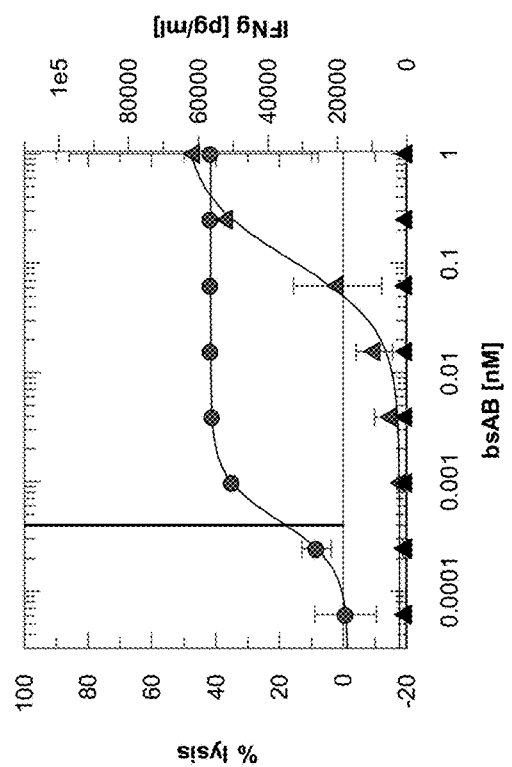
Figure 19D:
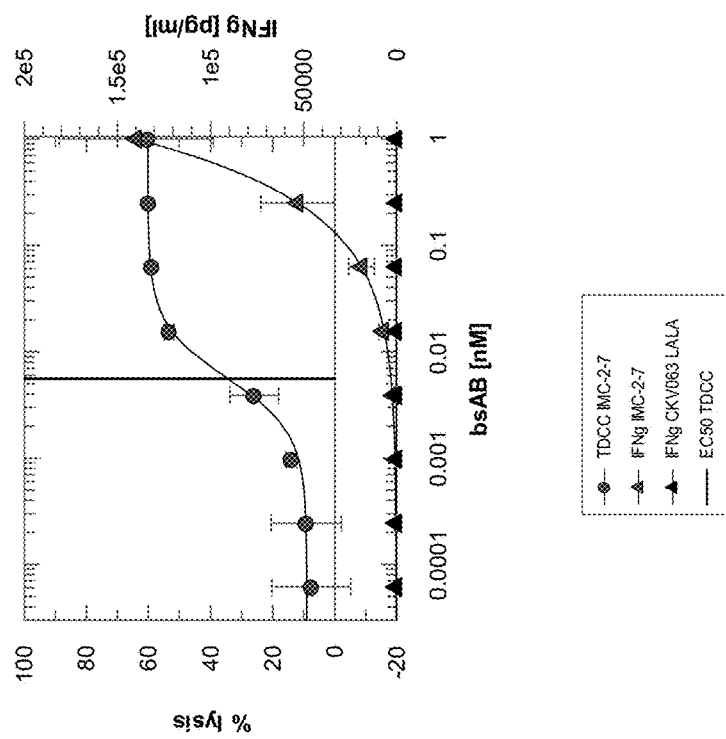
Figure 19C:
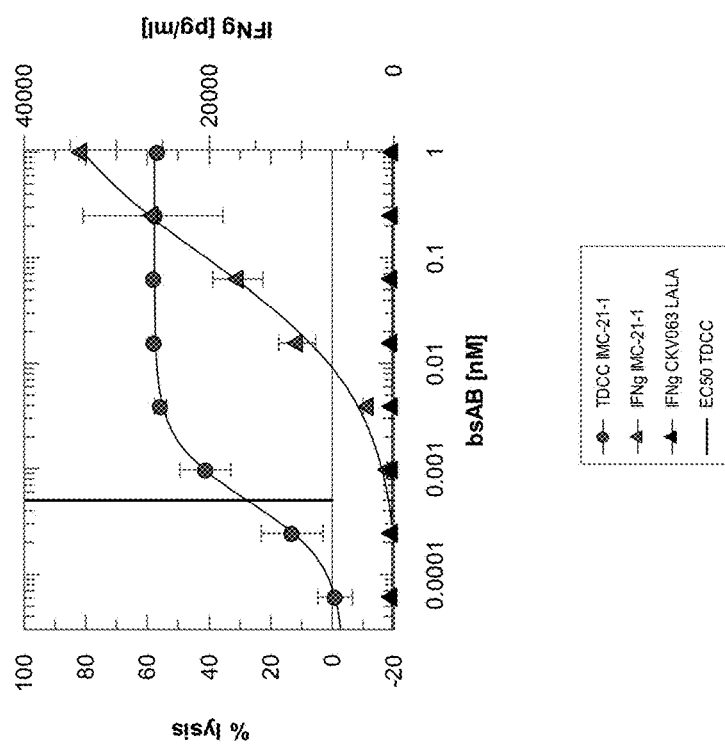
Figure 19F:
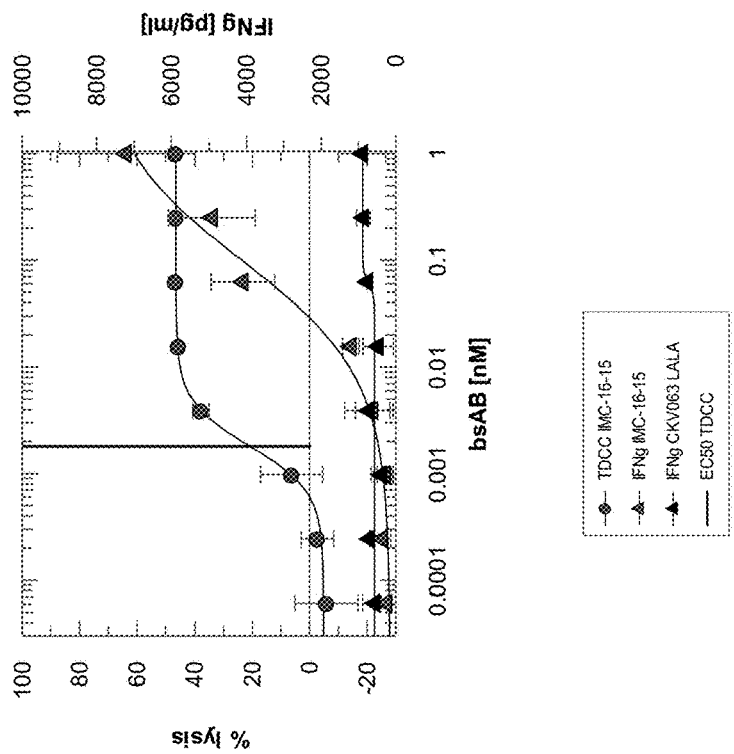
Figure 19E:
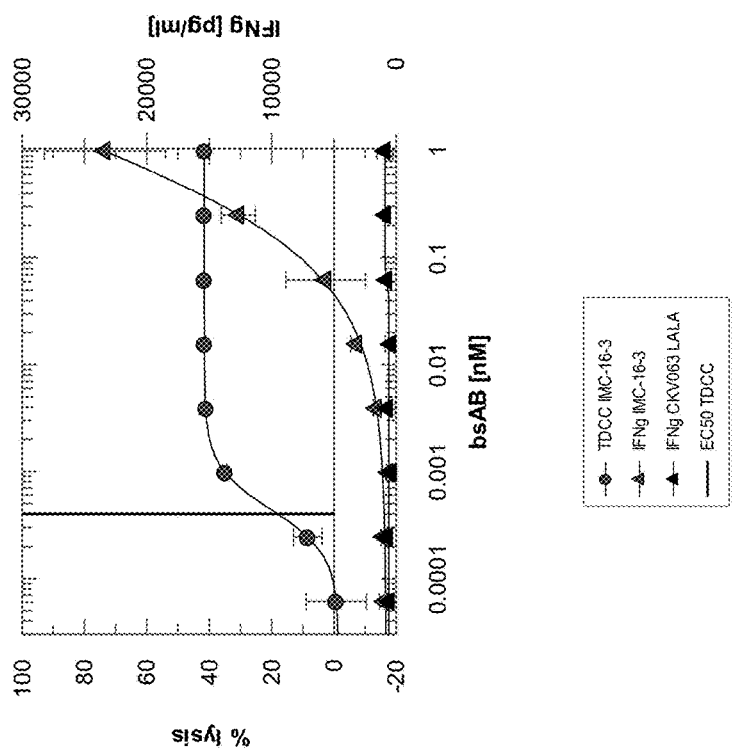
Figure 19H:
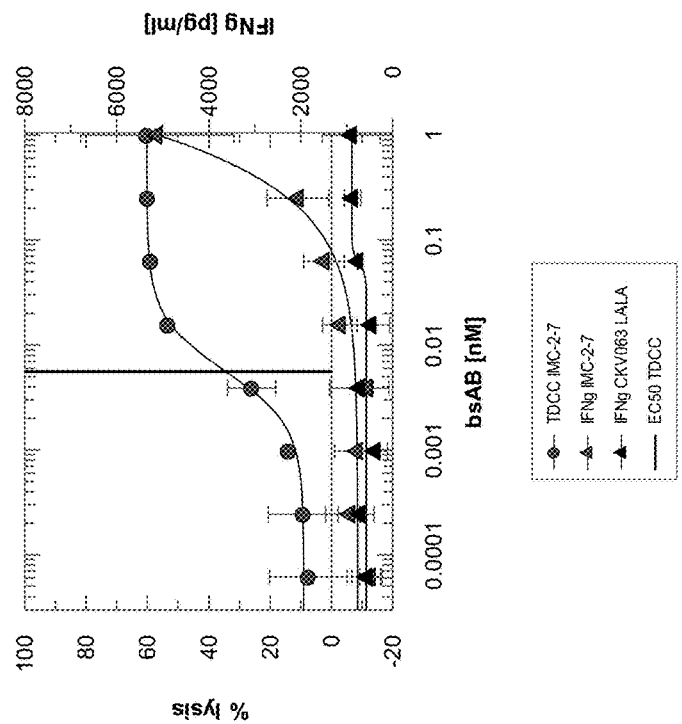
Figure 19G:
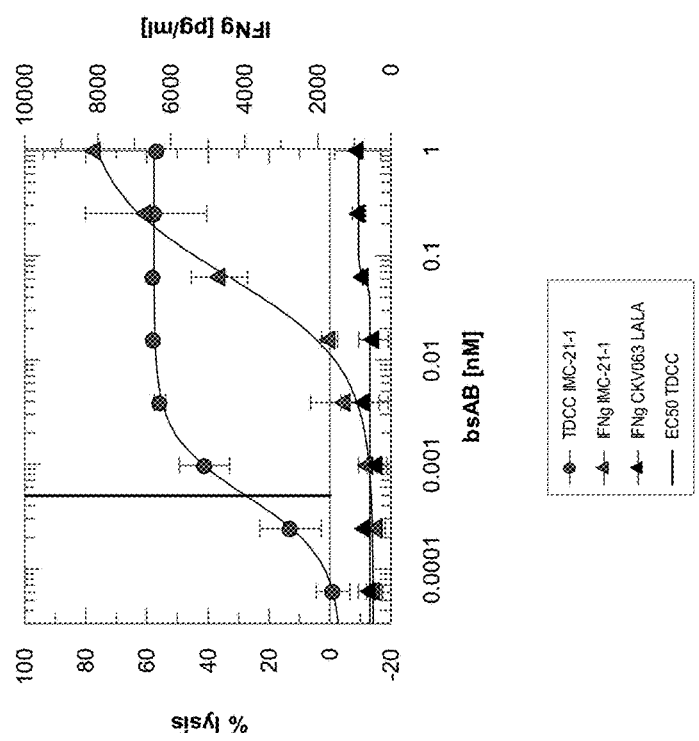

The experiments in FIG. 19A, FIG. 19B, FIG. 19C, FIG. 19D, FIG. 19E, FIG. 19F, FIG. 19G, and FIG. 19H demonstrate cellular toxicity and IFN-γ release potency data for human T cells cultured with CLDN6-expressing target cells at 24 hours and 48 hours from cellular cytotoxicity experiments. FIG. 19A shows cellular toxicity and IFN-γ release data of the IMC-16-3 scFv-Fab IgG antibody at 24 hours. FIG. 19B shows cellular toxicity and IFN-γ release data of the IMC-16-15 scFv-Fab IgG antibody at 24 hours. FIG. 19C shows cellular toxicity and IFN-γ release data of the IMC-21-1 IgG-(scFv)$_2$ antibody at 24 hours. FIG. 19D shows cellular toxicity and IFN-γ release data of the IMC-2-7 tandem scFv antibody at 24 hours. FIG. 19E shows cellular toxicity and IFN-γ release data of the IMC-16-3 scFv-Fab IgG antibody at 48 hours. FIG. 19F shows cellular toxicity and IFN-γ release data of the IMC-16-15 scFv-Fab IgG antibody at 48 hours. FIG. 19G shows cellular toxicity and IFN-γ release data of the IMC-21-1 IgG-(scFv)$_2$ antibody at 48 hours. FIG. 19H shows cellular toxicity and IFN-γ release data of the IMC-2-7 tandem scFv antibody at 48 hours. The CKV063 LALA antibody is a negative control antibody in each experiment. These experiments show, inter alia. T cell dependent cellular cytotoxicity and IFN-γ release potency at 24 hours and 48 hours for the antibodies described in this experiment.

Figure 20B:
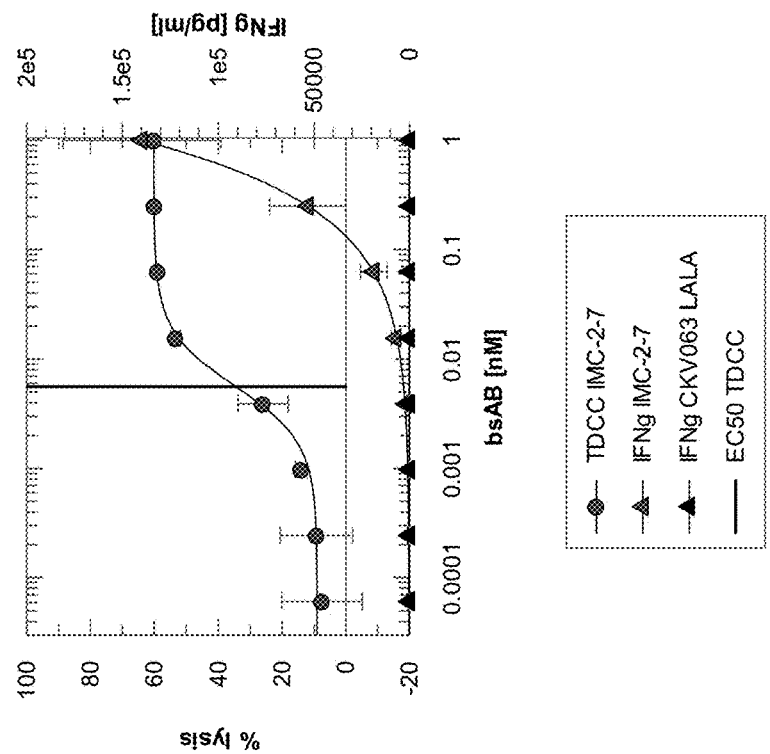
Figure 20A:
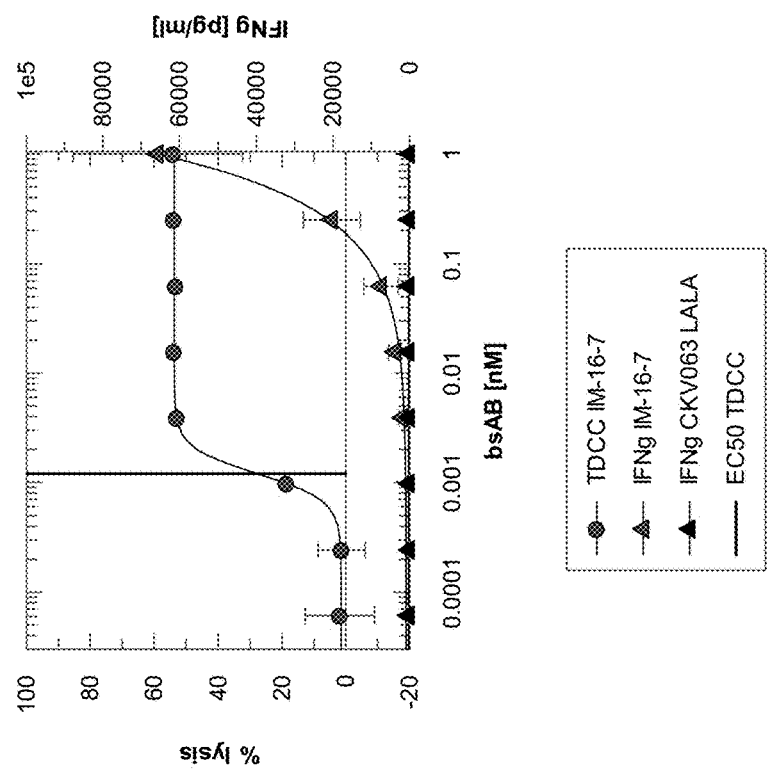
Figure 20G:
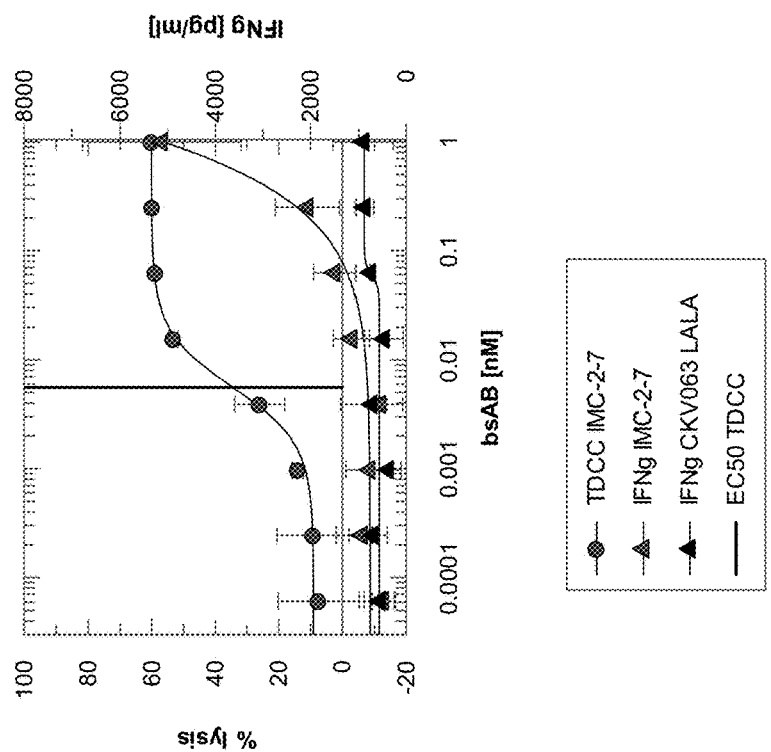
Figure 20F:
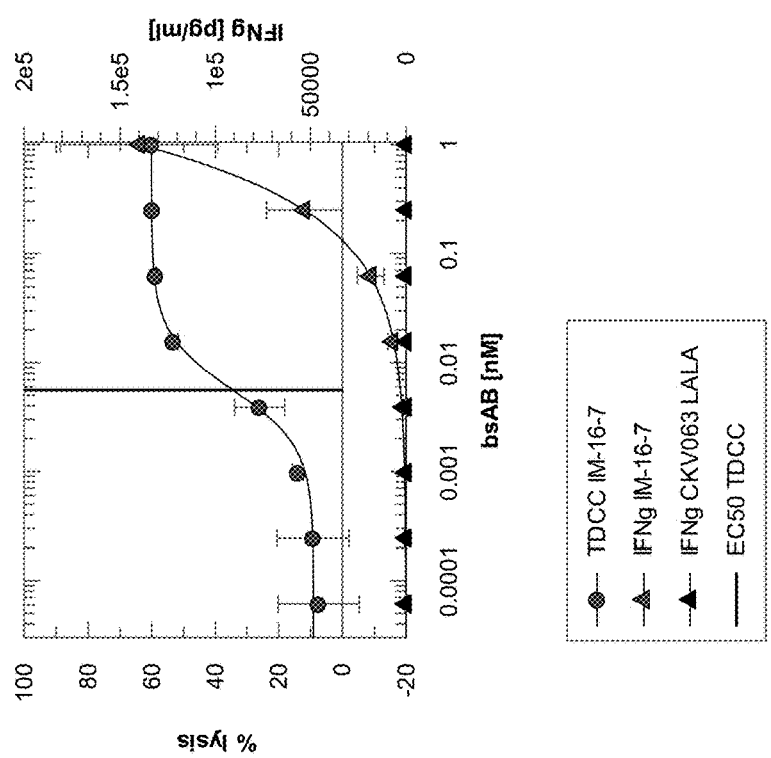

The experiments FIG. 20A, FIG. 20B, FIG. 20C, FIG. 20D, FIG. 20E, FIG. 20F, FIG. 20G, FIG. 20H, FIG. 20I, and FIG. 20J demonstrate cellular toxicity and IFN-γ release potency data for human T cells cultured with CLDN6-expressing target cells at 24 hours and 48 hours from cellular cytotoxicity experiments. FIG. 20A shows cellular toxicity and IFN-γ release data of the IMC-16-7 antibody (SEQ ID NOs: 79, 67, and 91) at 24 hours. FIG. 20B shows cellular toxicity and IFN-γ release data of the IMC-2-7 tandem scFv antibody at 24 hours. FIG. 20C shows cellular toxicity and IFN-γ release data of the IMC-16-3 scFv-Fab IgG antibody at 24 hours. FIG. 20D shows cellular toxicity and IFN-γ release data of the IMC-16-15 scFv-Fab IgG antibody at 24 hours. FIG. 20E shows cellular toxicity and IFN-γ release data of the IMC-21-1 IgG-(scFv)$_2$ antibody at 24 hours. FIG. 20F shows cellular toxicity and IFN-γ release data of the IMC-16-7 antibody at 48 hours. FIG. 20G shows cellular toxicity and IFN-γ release data of the IMC-2-7 tandem scFv antibody at 48 hours. FIG. 20H shows cellular toxicity and IFN-γ release data of the IMC-16-3 scFv-Fab IgG antibody at 48 hours. FIG. 20I shows cellular toxicity and IFN-γ release data of the IMC-16-15 scFv-Fab IgG antibody at 48 hours. FIG. 20J shows cellular toxicity and IFN-γ release data of the IMC-21-1 IgG-(scFv)$_2$ antibody at 48 hours. The CKV063 LALA antibody is a negative control antibody in each experiment. These experiments show, inter alia, T cell dependent cellular cytotoxicity and IFN-γ release potency at 24 hours and 48 hours for the antibodies described in this experiment.

Figure 21A:
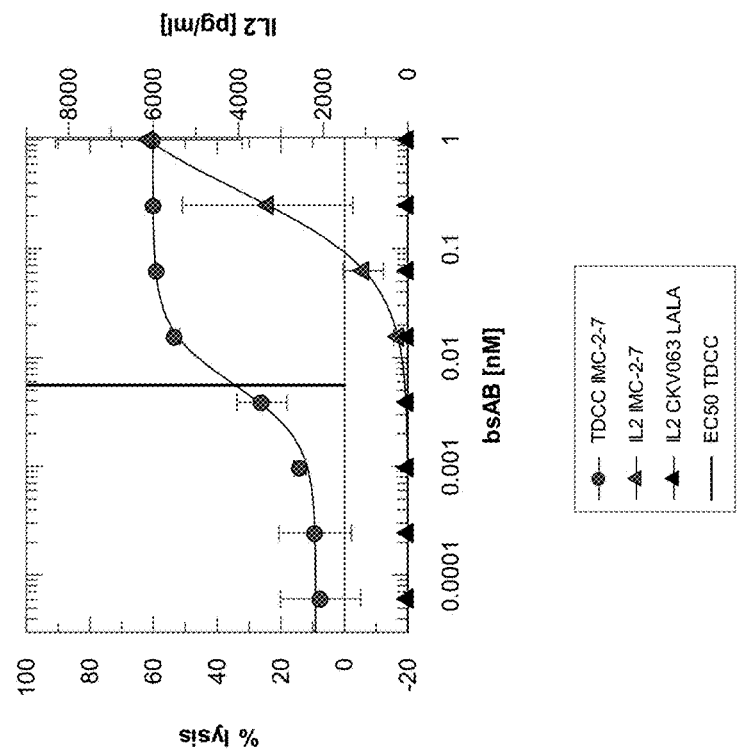
Figure 21B:
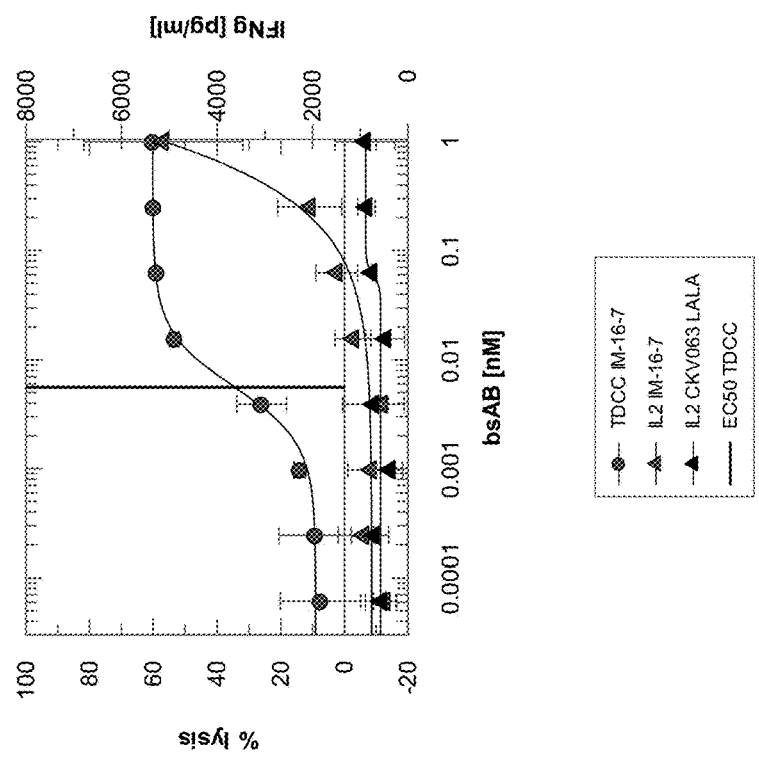
Figure 21G:
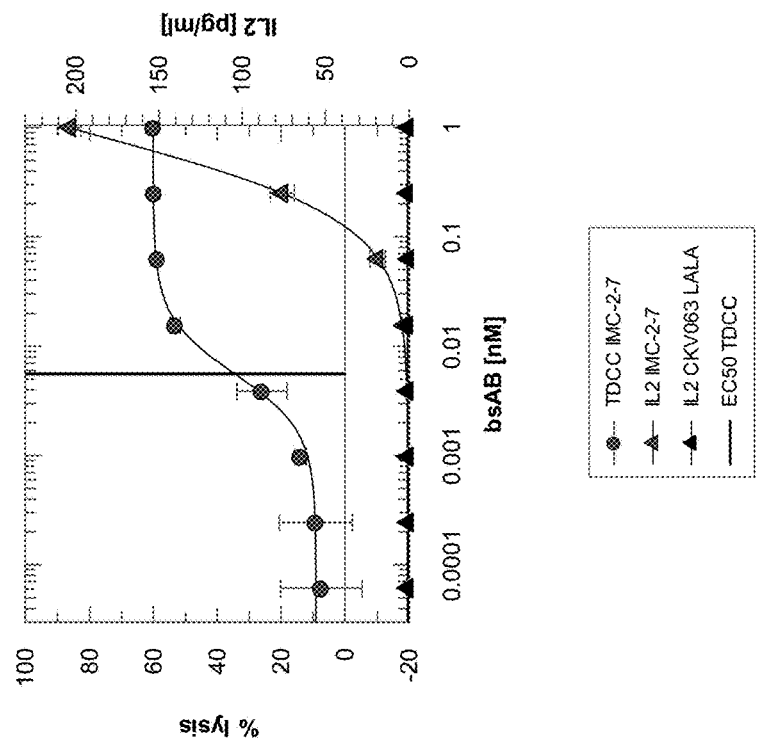
Figure 21F:
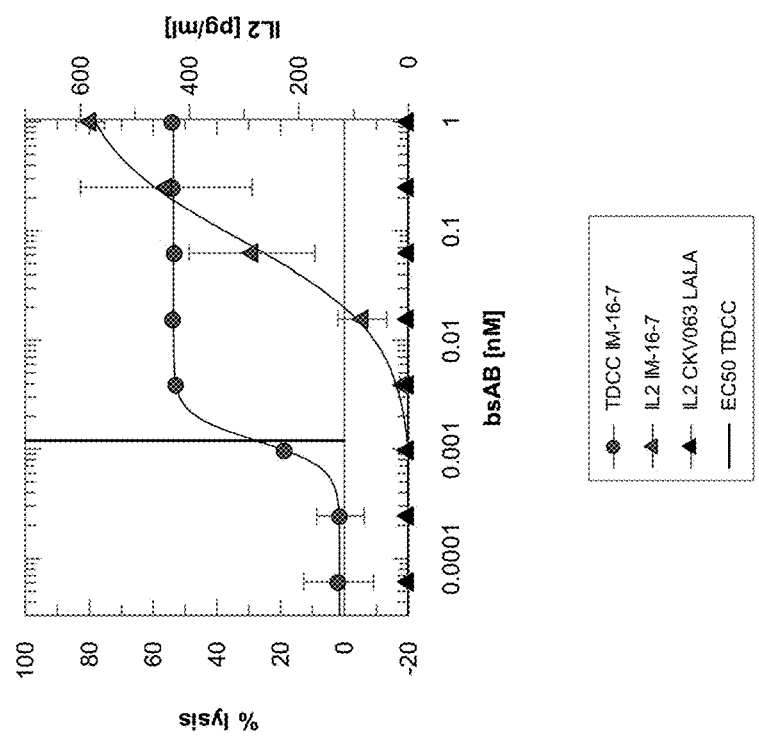
Figure 21J:
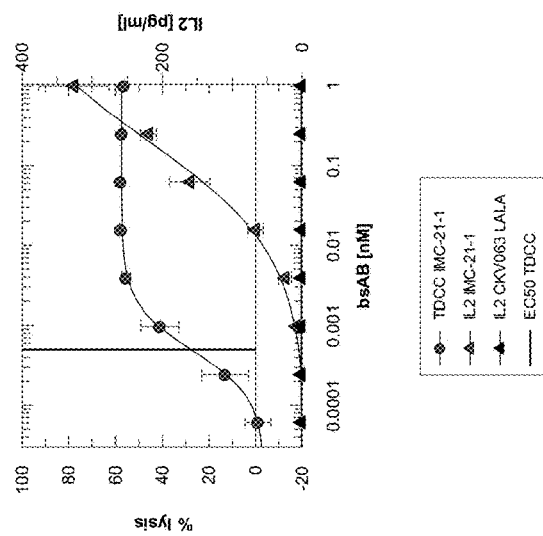
Figure 21I:
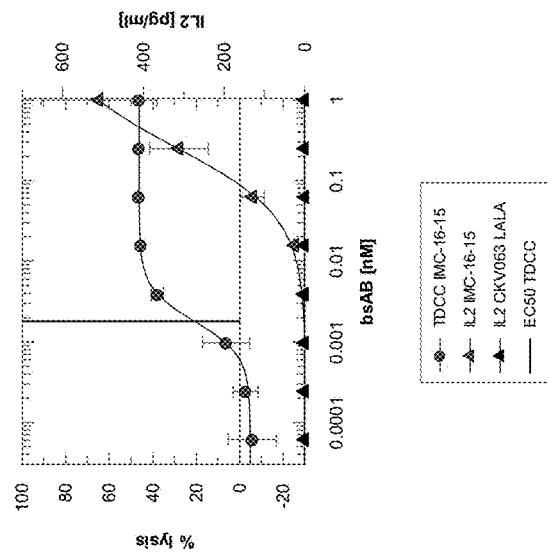
Figure 21H:
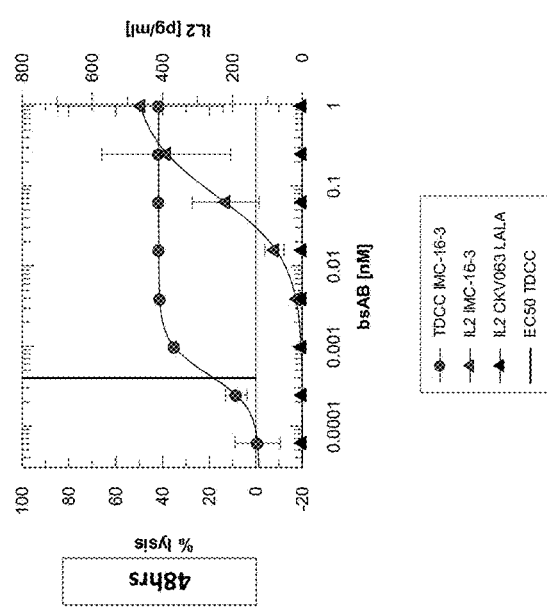

The experiments in FIG. 21A, FIG. 21B, FIG. 21C, FIG. 21D, FIG. 21E, FIG. 21F, FIG. 21G, FIG. 21H, FIG. 21I, and FIG. 21J demonstrate cellular toxicity and IL-2 release potency data at 24 hours and 48 hours from cellular cytotoxicity experiments. FIG. 21A shows cellular toxicity and IL-2 release data of the IMC-16-7 antibody at 24 hours. FIG. 21B shows cellular toxicity and IL-2 release data of the IMC-2-7 tandem scFv antibody at 24 hours. FIG. 21C shows cellular toxicity and IL-2 release data of the IMC-16-3 scFv-Fab IgG antibody at 24 hours. FIG. 21D shows cellular toxicity and IL-2 release data of the IMC-16-15 scFv-Fab IgG antibody at 24 hours. FIG. 21E shows cellular toxicity and IL-2 release data of the IMC-21-1 antibody at 24 hours. FIG. 21F shows cellular toxicity and IL-2 release data of the IMC-16-7 antibody at 48 hours. FIG. 21G shows cellular toxicity and IL-2 release data of the IMC-2-7 tandem scFv antibody at 48 hours. FIG. 21H shows cellular toxicity and IL-2 release data of the IMC-16-3 scFv-Fab IgG antibody at 48 hours. FIG. 21I shows cellular toxicity and IL-2 release data of the IMC-16-15 scFv-Fab IgG antibody at 48 hours. FIG. 21J shows cellular toxicity and IL-2 release data of the IMC-21-1 IgG-(scFv)$_2$ antibody at 48 hours. The CKV063 LALA antibody is a negative control antibody in each experiment. These experiments show, inter alia, T cell dependent cellular cytotoxicity and IL-12 release potency at 24 hours and 48 hours for the antibodies described in this experiment.

Figure 22A:
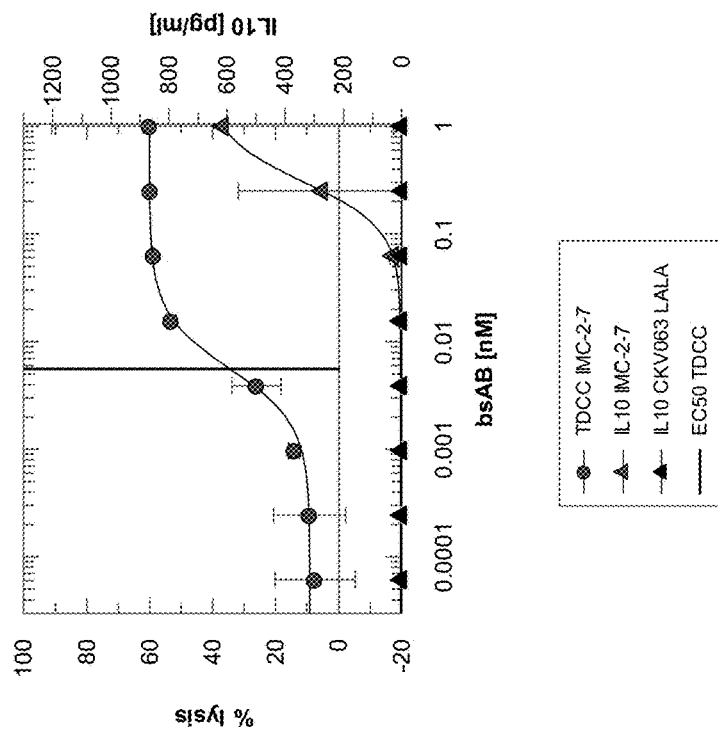
Figure 22B:
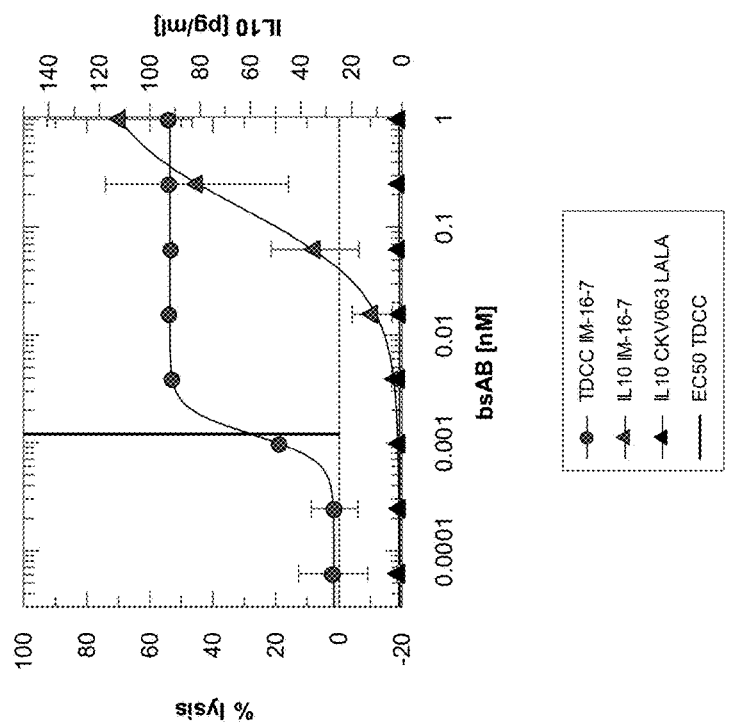
Figure 22G:
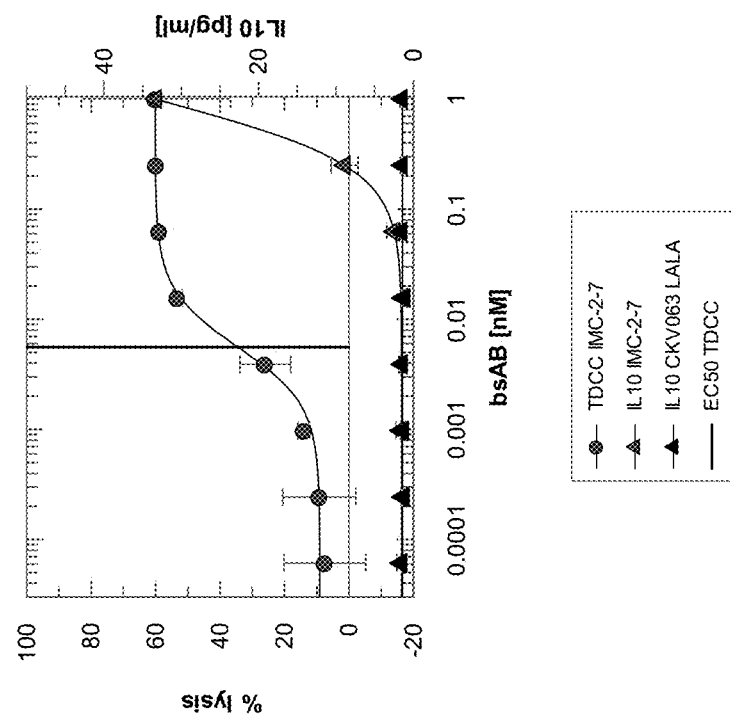
Figure 22F:
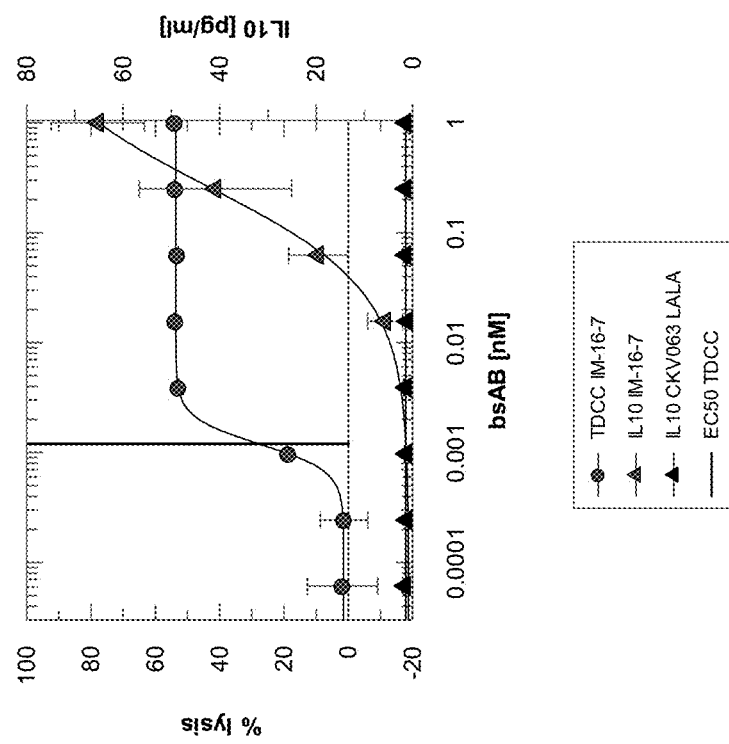
Figure 22H:
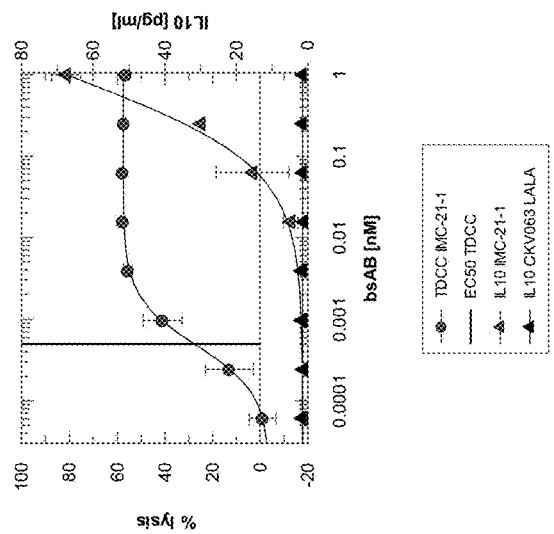
Figure 22I:
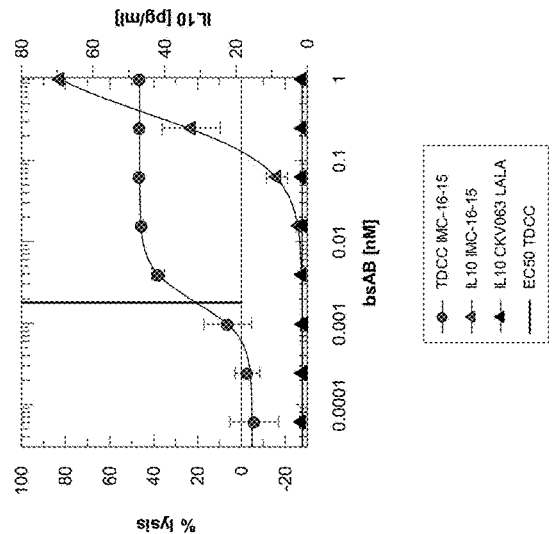
Figure 22J:
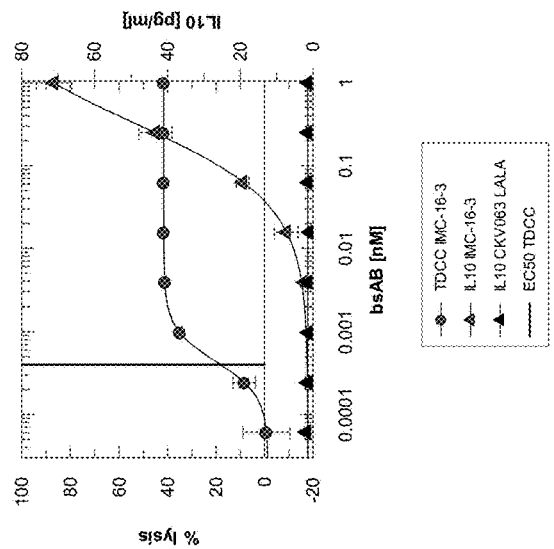

The experiments in FIG. 22A, FIG. 22B, FIG. 22C, FIG. 22D, FIG. 22E, FIG. 22F, FIG. 22G, FIG. 22H, FIG. 22I, and FIG. 22J demonstrate cellular toxicity and IL-10 release potency data at 24 hours and 48 hours from cytotoxicity experiments. FIG. 22A shows cellular toxicity and IL-10 release data of the IMC-16-7 antibody at 24 hours. FIG. 22B shows cellular toxicity and IL-10 release data of the IMC-2-7 tandem scFv antibody at 24 hours. FIG. 22C shows cellular toxicity and IL-10 release data of the IMC-16-3 scFv-Fab IgG antibody at 24 hours. FIG. 22D shows cellular toxicity and IL-10 release data of the IMC-16-15 scFv-Fab IgG antibody at 24 hours. FIG. 22E shows cellular toxicity and IL-10 release data of the IMC-21-1 IgG-(scFv)$_2$ antibody at 24 hours. FIG. 22F shows cellular toxicity and IL-10 release data of the IMC-16-7 antibody at 48 hours. FIG. 22G shows cellular toxicity and IL-10 release data of the IMC-2-7 tandem scFv antibody at 48 hours. FIG. 22H shows cellular toxicity and IL-10 release data of the IMC-16-3 scFv-Fab IgG antibody at 48 hours. FIG. 22I shows cellular toxicity and IL-10 release data of the IMC-16-15 scFv-Fab IgG antibody at 48 hours. FIG. 22J shows cellular toxicity and IL-10 release data of the IMC-21-1 IgG-(scFv)$_2$ antibody at 48 hours. The CKV063 LALA antibody is a negative control antibody in each experiment. These experiments show, inter alia, T cell dependent cellular cytotoxicity and IL-10 release potency at 24 hours and 48 hours for the antibodies described in this experiment.

Figure 23A:
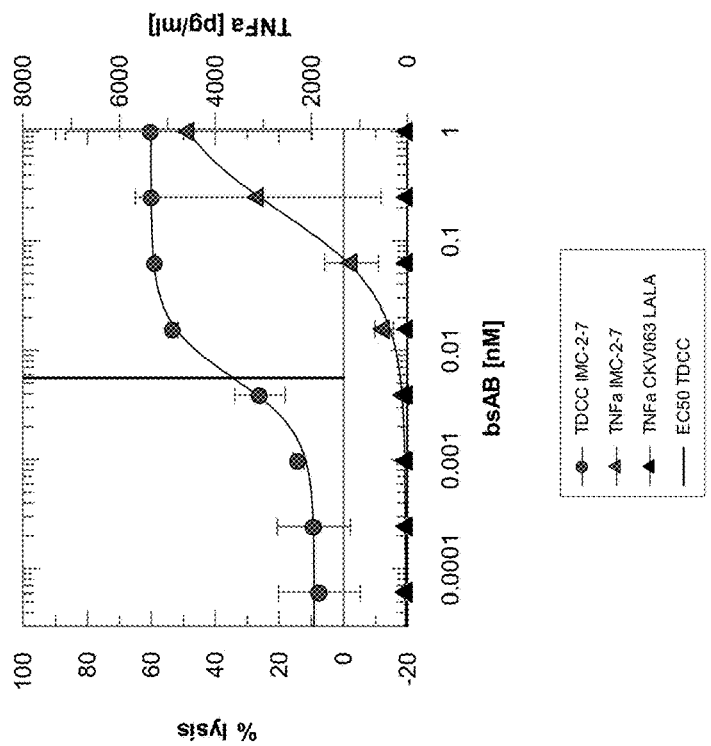
Figure 23B:
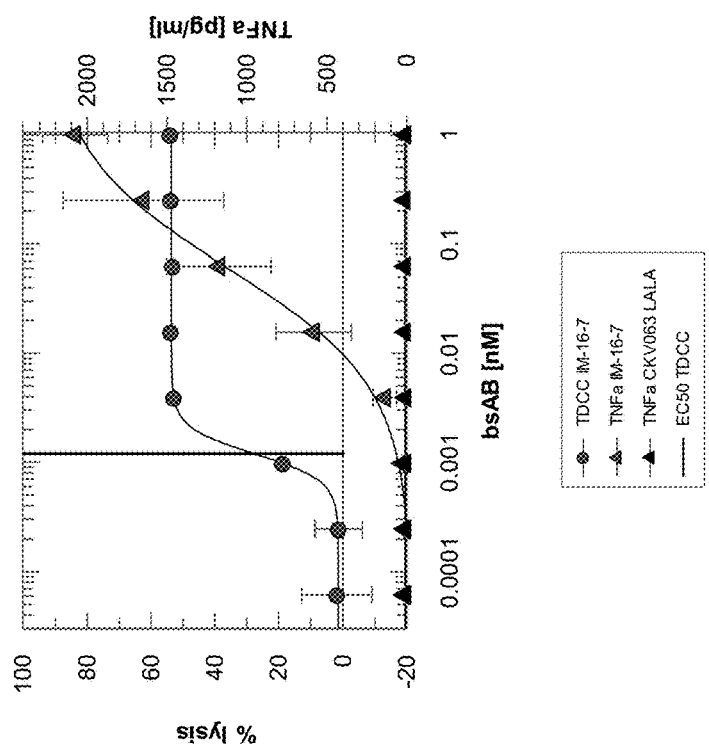
Figure 23G:
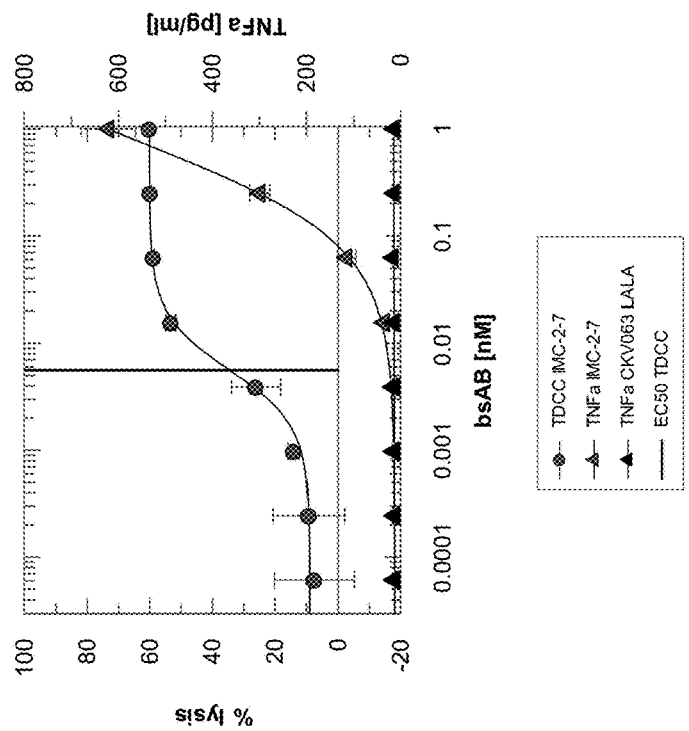
Figure 23F:
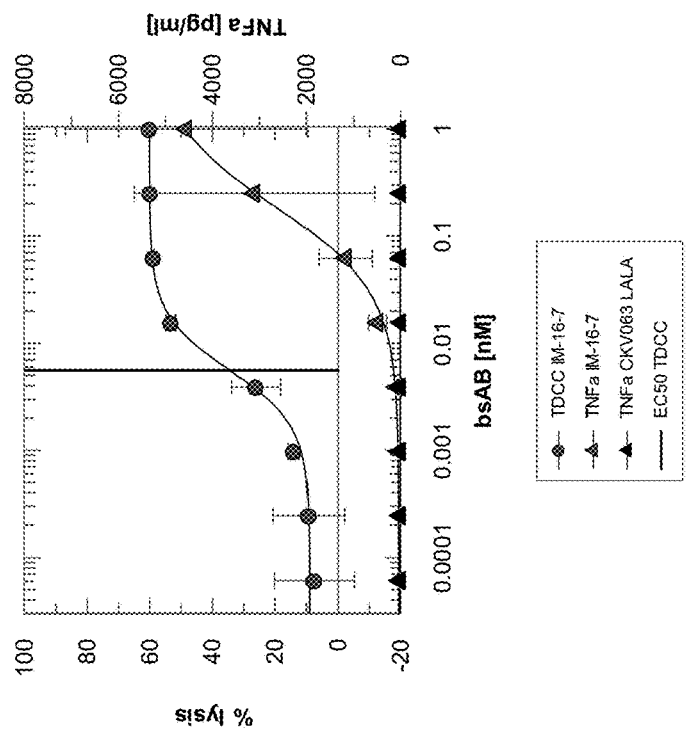

The experiments in FIG. 23A, FIG. 23B, FIG. 23C, FIG. 23D, FIG. 23E, FIG. 23F, FIG. 23G, FIG. 23H, FIG. 23I, and FIG. 23J demonstrate cellular toxicity and TNF-α release potency data at 24 hours and 48 hours from cytotoxicity experiments. FIG. 23A shows cellular toxicity and TNF-α release data of the IMC-16-7 antibody at 24 hours. FIG. 23B shows cellular toxicity and TNF-α release data of the IMC-2-7 tandem scFv antibody at 24 hours. FIG. 23C shows cellular toxicity and TNF-α release data of the IMC-16-3 scFv-Fab IgG antibody at 24 hours. FIG. 23D shows cellular toxicity and TNF-α release data of the IMC-16-15 scFv-Fab IgG antibody at 24 hours. FIG. 23E shows cellular toxicity and TNF-α release data of the IMC-21-1 IgG-(scFv)$_2$ antibody at 24 hours. FIG. 23F shows cellular toxicity and TNF-α release data of the IMC-16-7 antibody at 48 hours. FIG. 23G shows cellular toxicity and TNF-α release data of the IMC-2-7 tandem scFv antibody at 48 hours. FIG. 23H shows cellular toxicity and TNF-α release data of the IMC-16-3 scFv-Fab IgG antibody at 48 hours. FIG. 23I shows cellular toxicity and TNF-α release data of the IMC-16-15 scFv-Fab IgG antibody at 48 hours. FIG. 23J shows cellular toxicity and TNF-α release data of the IMC-21-1 IgG-(scFv)$_2$ antibody at 48 hours. The CKV063 LALA antibody is a negative control antibody in each experiment. These experiments show, inter alia. T cell dependent cellular cytotoxicity and TNF-α release potency at 24 hours and 48 hours for the antibodies described in this experiment.

FIG. 24A, FIG. 24B, FIG. 24C, FIG. 24D, FIG. 24E, FIG. 24F, FIG. 24G, and FIG. 24H demonstrate cytokine analysis of IFN-γ and IL-2 at 24 hours and 48 hours. FIG. 24A is a graph showing IFN-γ levels at 24 hours and 48 hours for the IMC-2-7 tandem scFv antibody. FIG. 24B is a graph showing IFN-γ levels at 24 hours and 48 hours for the IMC-16-3 scFv-Fab IgG antibody. FIG. 24C is a graph showing IFN-γ levels at 24 hours and 48 hours for the IMC-16-15 scFv-Fab IgG antibody. FIG. 24D is a graph showing IFN-γ levels at 24 hours and 48 hours for the IMC-21-1 IgG-(scFv)$_2$ antibody. FIG. 24E is a graph showing IL-2 levels at 24 hours and 48 hours for the IMC-2-7 tandem scFv antibody. FIG. 24F is a graph showing IL-2 levels at 24 hours and 48 hours for the IMC-16-3 scFv-Fab IgG antibody. FIG. 24G is a graph showing IL-2 levels at 24 hours and 48 hours for the IMC-16-15 scFv-Fab IgG antibody. FIG. 24H is a graph showing IL-2 levels at 24 hours and 48 hours for the IMC-21-1 IgG-(scFv)$_2$ antibody. These experiments show, inter alia, IFN-γ and IL-2 cytokine release potency at 24 hours and 48 hours for the antibodies described in this experiment.

Figures 25A, 25B, 25C, 25D, 25E, 25F, 25G, 25H, 25I, 25J:
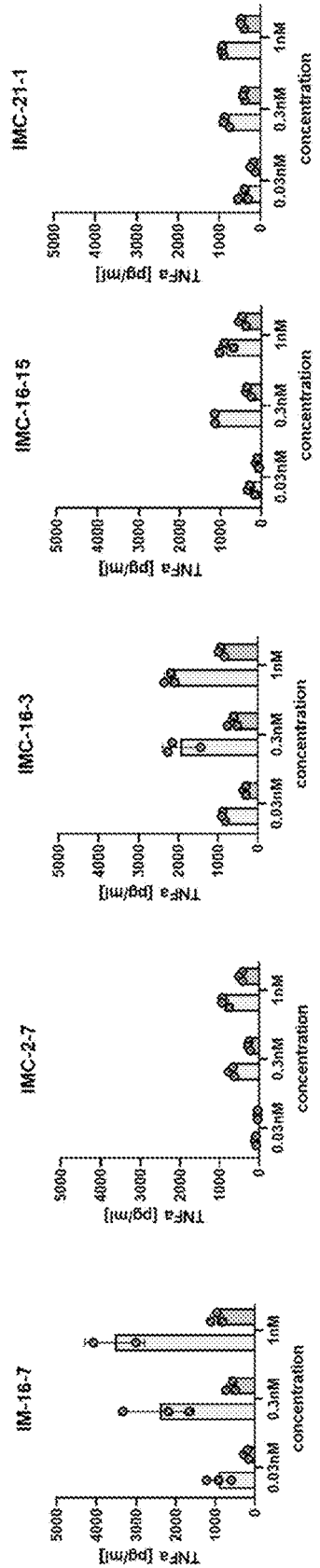
FIG. 25A, FIG. 25B, FIG. 25C, FIG. 25D, FIG. 25E, FIG. 25F, FIG. 25G, FIG. 25H, FIG. 25I, and FIG. 25J are graphs showing cytokine analysis of IL-10 and TNF-α at 24 hours and 48 hours.
Figure 29A:
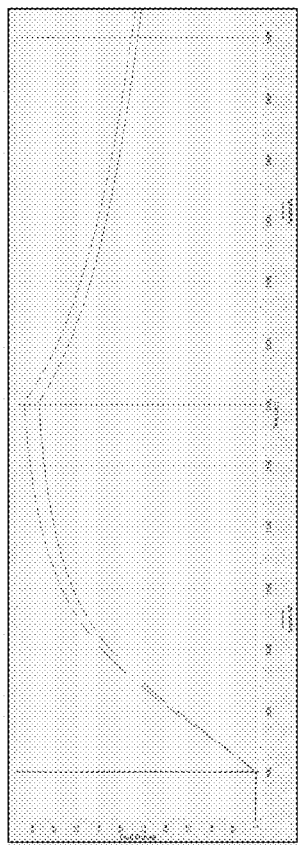
FIG. 29A, FIG. 29B, FIG. 29C, and FIG. 29D are graphs showing binding affinity of the IMC-16-3 scFv-Fab IgG antibody (FIG. 29A), IMC-16-15 scFv-Fab IgG antibody (FIG. 29B), IMC-21-1 IgG-(scFv)2 antibody (FIG. 29C), and IMC-2-7 tandem scFv antibody (FIG. 29D) to hsCD3δε-Biotin.
Figure 29B:
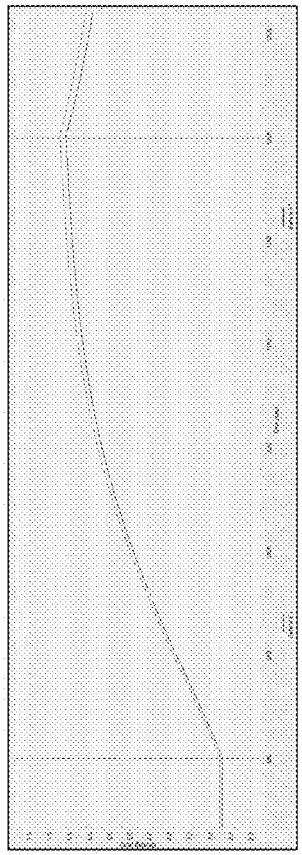
Figure 29C:
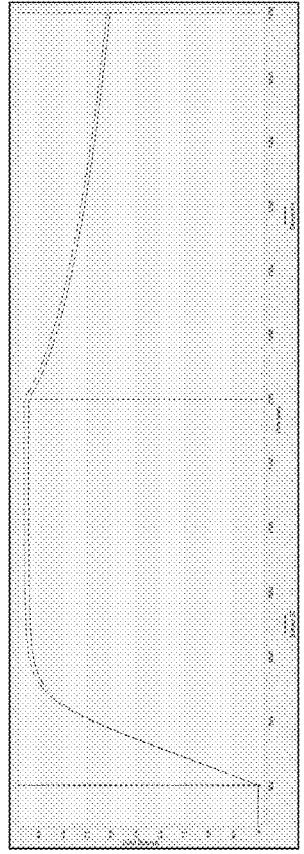
Figure 29D:
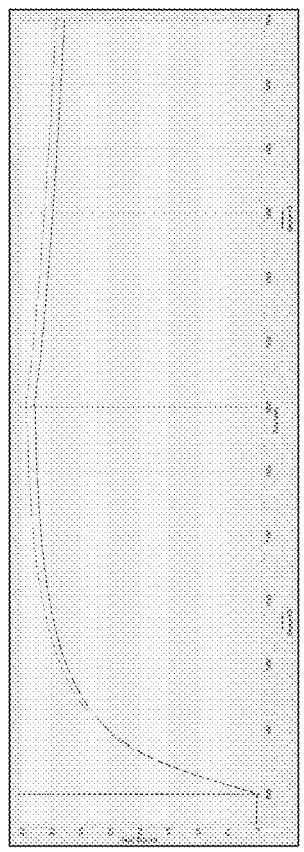

The experiments in FIG. 25A, FIG. 25B, FIG. 25C, FIG. 25D, FIG. 25E, FIG. 25F, FIG. 25G, FIG. 25H, FIG. 25I, and FIG. 25J demonstrate cytokine analysis of IL-10 and TNF-α at 24 hours and 48 hours. FIG. 25A is a graph showing IL-10 levels at 24 hours and 48 hours for the IMC-16-7 antibody. FIG. 25B is a graph showing IL-10 levels at 24 hours and 48 hours for the IMC-2-7 tandem scFv antibody. FIG. 25C is a graph showing IL-10 levels at 24 hours and 48 hours for the IMC-16-3 scFv-Fab IgG antibody. FIG. 25D is a graph showing IL-10 levels at 24 hours and 48 hours for the IMC-16-15 scFv-Fab IgG antibody. FIG. 25E is a graph showing IL-10 levels at 24 hours and 48 hours for the IMC-21-1 IgG-(scFv)$_2$ antibody. FIG. 25F is a graph showing TNF-α levels at 24 hours and 48 hours for the IMC-16-7 antibody. FIG. 25G is a graph showing TNF-α levels at 24 hours and 48 hours for the IMC-2-7 tandem scFv antibody. FIG. 25H is a graph showing TNF-α levels at 24 hours and 48 hours for the IMC-16-3 scFv-Fab IgG antibody. FIG. 25I is a graph showing TNF-α levels at 24 hours and 48 hours for the IMC-16-15 scFv-Fab IgG antibody. FIG. 25J is a graph showing TNF-α levels, without limitation, at 24 hours and 48 hours for the IMC-21-1 IgG-(scFv)$_2$ antibody. These experiments show; inter alia, TNF-α and IL-10 cytokine release potency at 24 hours and 48 hours for the antibodies described in this experiment.

The experiments in FIG. 30A and FIG. 30B demonstrate cellular toxicity data from T-cell dependent cellular cytotoxicity experiments. FIG. 30A shows cytotoxicity data for human T cells co-cultured with the IMC-16-3 scFv-Fab IgG antibody, IMC-21-1 IgG-(scFv)$_2$ antibody, IMC-16-15 scFv-Fab IgG antibody, IMC-2-7 tandem scFv antibody, and a negative control (CKV063 LALA) with K562 CLDN6 expressing cells. FIG. 30B shows cytotoxicity data of human T cells co-cultured with the IMC-16-3 scFv-Fab IgG antibody, IMC-21-1 IgG-(scFv)$_2$ antibody, IMC-16-15 scFv-Fab IgG antibody, IMC-2-7 tandem scFv antibody, and a negative control (CKV063 LALA) and OV-90 cells. As shown in these experiments, the IMC-16-3 scFv-Fab IgG antibody induces cytotoxicity in human T cells versus cells expressing CLDN6, and the IMC-16-3 scFv-Fab IgG antibody has improved activity over other antibody formats with the same or similar CLDN6 and CD3 binder arms.

Figure 31A:
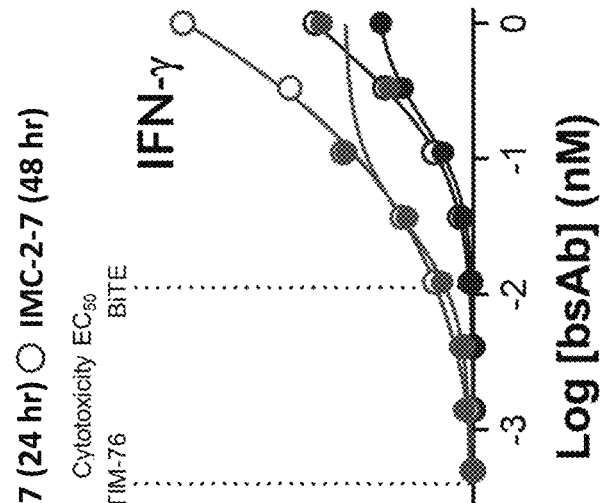
FIG. 31A shows the expression level of TNF-α by human T cells co-cultured with K562 CLDN6 expressing cells.
Figure 31B:
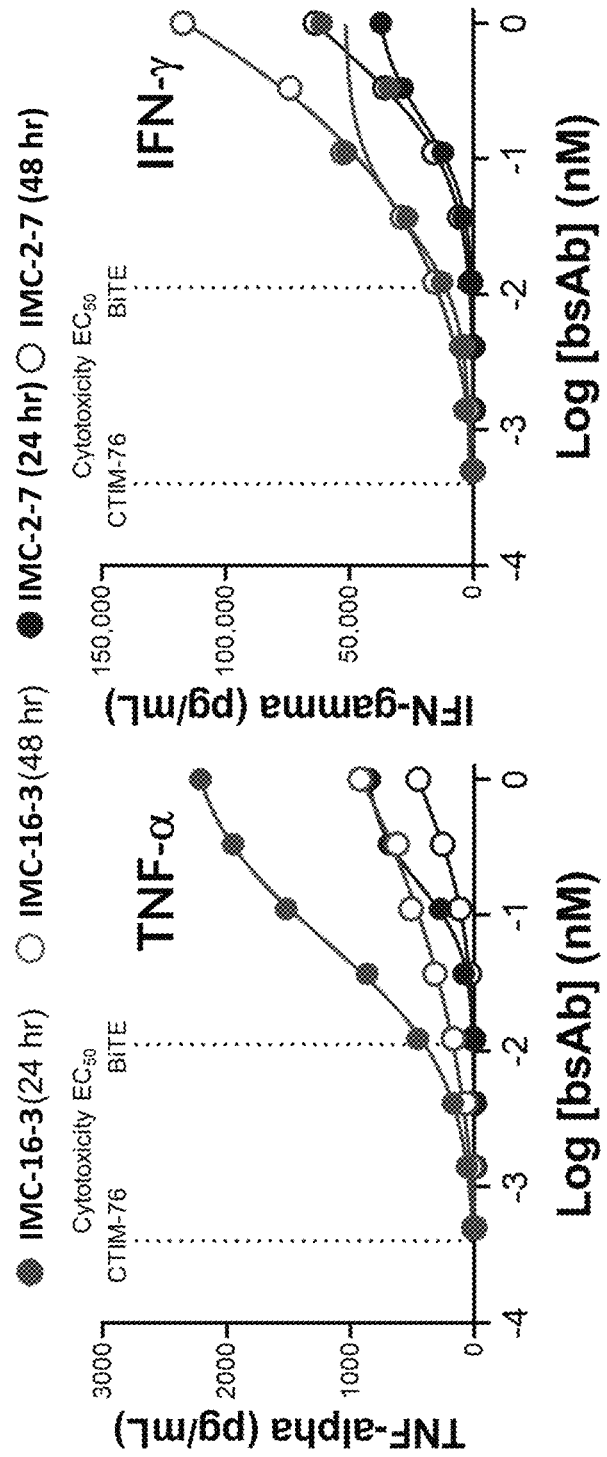
FIG. 31B shows the expression level of IFN-γ by human T cells co-cultured with K562 CLDN6 expressing cells.

The experiments in FIG. 31A and FIG. 31B show cytokine analysis data of the IMC-16-3 scFv-Fab IgG antibody (FIG. 31A), and the IMC-2-7 tandem scFv antibody (FIG. 31B) by T cells co-cultured with CLDN6 expressing K562 cells. FIG. 31A shows the levels of TNF-α produced by human T cells co-cultured with CLDN6 expressing K562 cells as a function of bispecific concentration at 24 and 48 hours as compared to cytotoxicity at 48 hours. FIG. 31B shows the levels of IFN-γ produced by human T cells co-cultured with CLDN6 expressing K562 cells as a function of bispecific concentration at 24 and 48 hours as compared to cytotoxicity at 48 hours. Cytokine levels were determined using the LegendPlex system from BioLegend. In these experiments, low cytokine release in the IMC-16-3 scFv-Fab IgG antibody samples within 2 logs of cytotoxicity $EC_{50}$ indicate an improved therapeutic window compared to the IMC-2-7 tandem scFv antibody with identical binder arms.

Figure 33B:
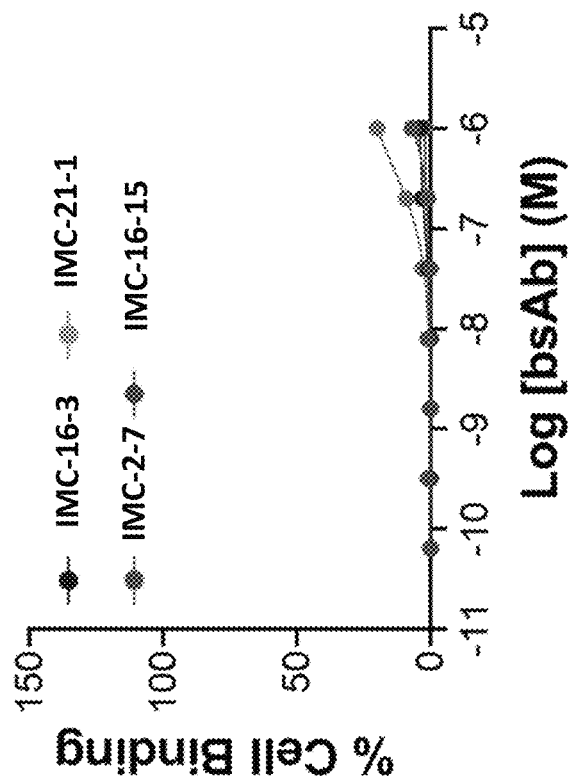
FIG. 33A and FIG. 33B are graphs showing the binding of the IMC-16-3 scFv-Fab IgG antibody is highly specific for CLDN6.
Figure 33A:
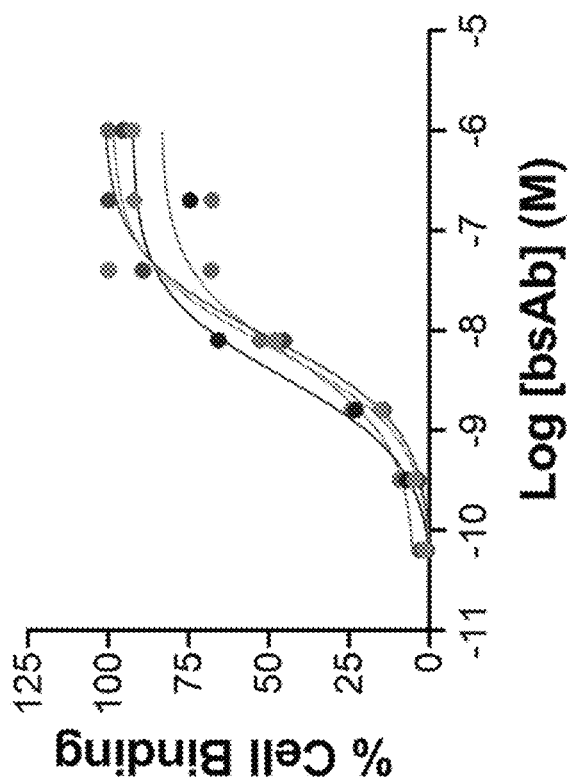

The experiments in FIG. 33A and FIG. 33B show the binding of the IMC-16-3 scFv-Fab IgG antibody is highly specific for CLDN6. FIG. 33A shows binding data of the IMC-16-3 scFv-Fab IgG antibody, IMC-16-15 scFv-Fab IgG antibody, IMC-21-1 IgG-(scFv)$_2$ antibody, and IMC-2-7 tandem scFv antibody to HEK293-F cells transiently expressing CLDN6. FIG. 33B shows binding data of the IMC-16-3 scFv-Fab IgG antibody, IMC-16-15 scFv-Fab IgG antibody, IMC-21-1 IgG-(scFv)$_2$ antibody, and IMC-2-7 tandem scFv antibody to HEK293-F cells transiently expressing CLDN9.

Figure 34:
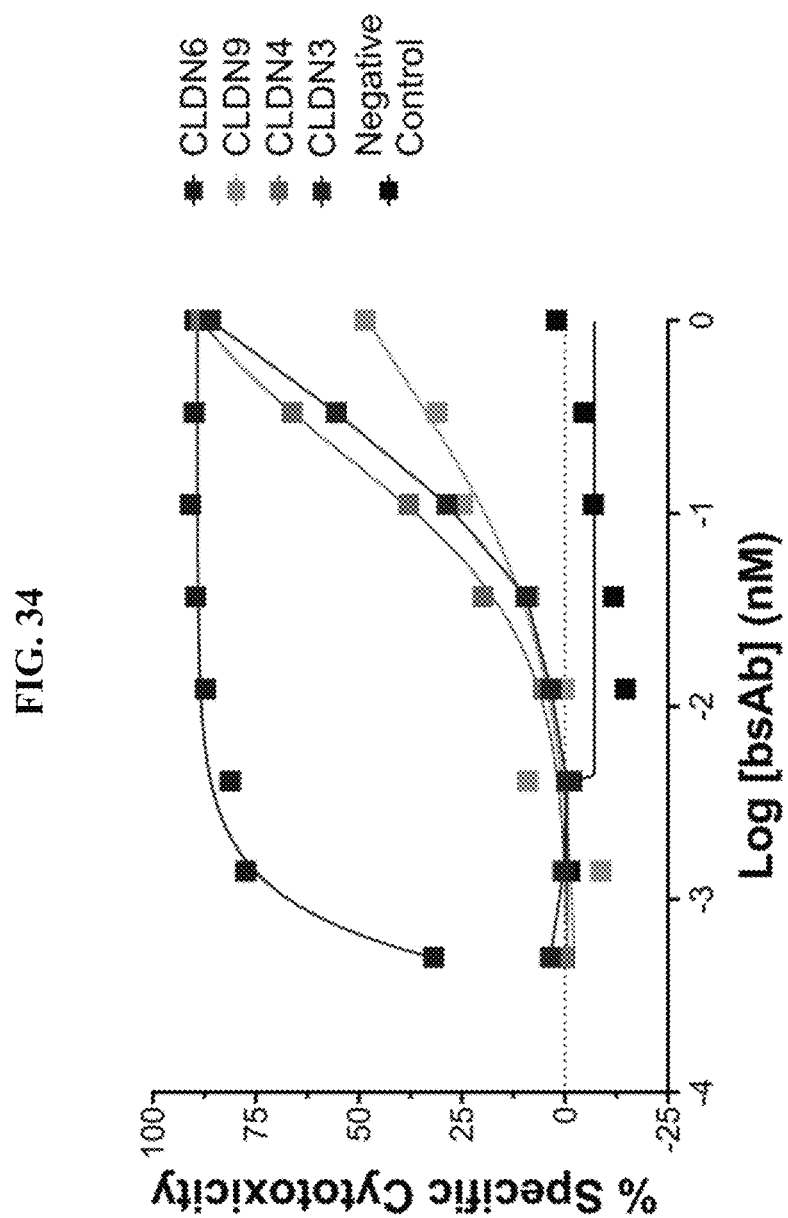
FIG. 34 is a graph showing the specific cytotoxicity mediated by the IMC-16-3 scFv-Fab IgG antibody, which is strongly preferential for CLDN6.

The experiments in FIG. 34 demonstrate the specific cytotoxicity induced by the IMC-16-3 scFv-Fab IgG antibody redirecting lysis of CLDN-expressing K562 cells by human T cells, and how the cytotoxicity induced by IMC-16-3 scFv-Fab IgG antibody is strongly preferential for CLDN6. The graph in FIG. 34 shows cytotoxicity of human T cells vs CLDN-expressing K562 cells induced by the IMC-16-3 scFv-Fab IgG antibody against HEK293-F cells transiently expressing CLDN6, CLDN9, CLDN4, or CLDN3. In these experiments, the IMC-16-3 scFv-Fab IgG antibody preferentially targets CLDN6, with no binding and minimal cytotoxicity observed in other closely-related CLDN family proteins.

Figures 35A, 35B:
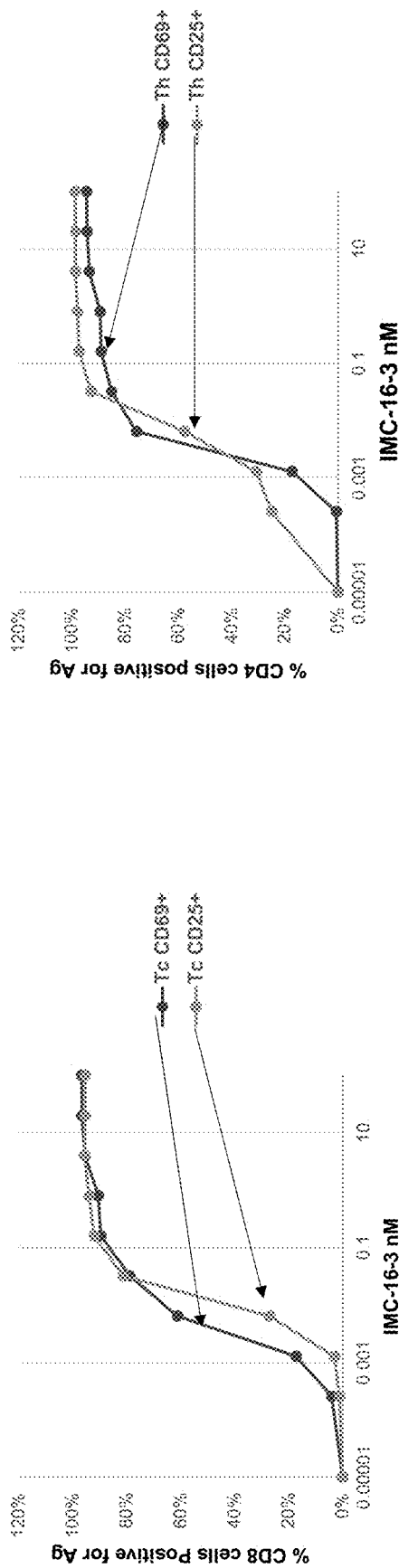
FIG. 35A and FIG. 35B are graphs illustrating the activation of CD4 (FIG. 35B) and CD8 (FIG. 35A) T cells by the bispecific antibody IMC-16-3 in the presence of CLDN-6 expressing tumor cells as indicated by expression of the activation markers CD69 and CD25 by human cytotoxic T cells (Tc) and human helper cells (Th).

The experiments in FIG. 35A and FIG. 35B demonstrate the activation of human CD4 (FIG. 35B) and CD8 (FIG. 35A) T cells by the IMC-16-3 scFv-Fab IgG bispecific antibody in the presence of CLDN6-expressing OVCAR3 tumor cells. The activation of CD8 cells (FIG. 35A) and CD4 cells (FIG. 35B) is indicated by a dose-dependent increase in the activation markers CD69 and CD25, as illustrated in FIG. 35A and FIG. 35B. Briefly, the IMC-16-3 scFv-Fab IgG bispecific antibody was tested in the presence of OVCAR3 (cell line of ovarian cancer), which expresses Claudin 6, and in the presence of PBMCs to evaluate the ability of the IMC-16-3 scFv-Fab IgG bispecific antibody to selectively activate the T cells in the PBMCs in the presence of the tumor cell. OVCAR3 tumor cells were co-cultured with PBMC's in the presence or absence of the IMC-16-3 scFv-Fab IgG bispecific antibody. After 48-hours of co-culture and treatment with the IMC-16-3 scFv-Fab IgG bispecific antibody, the study endpoint was reached, and the culture wells were pooled for full panel stain or flow cytometry controls. Each cell line comprised the following groups: (1) untreated PBMCs, (2) untreated cell line alone, (3) untreated cell line co-culture, and (4) antibody-treated cell line co-culture. Each group was pooled and stained with an antibody cocktail for a flow cytometry panel including human CD45, CD3, CD4, CD8, CD25, and CD69, along with unstained controls. The results of this experiment showed that the activation of T cells only occurred in the presence of both the IMC-16-3 scFv-Fab IgG bispecific antibody and the tumor cell, OVCAR3. The tumor cell alone did not activate the T cells (data not shown), indicating that the IMC-16-3 scFv-Fab IgG bispecific antibody was necessary to activate the T cells in the presence of the tumor. As stated above, these results demonstrated a dose-dependent increase in CD69 and CD25, indicating CD4 and CD8 T cell activation by the IMC-16-3 scFv-Fab IgG bispecific antibody. Further, the results show how the IMC-16-3 scFv-Fab IgG bispecific antibody mediated OVCAR-3 cell killing by the PBMC in a dose-dependent manner. In these experiments, the human PBMC were not activated by incubation with OVCAR-3 tumors alone.

Figure 42A:
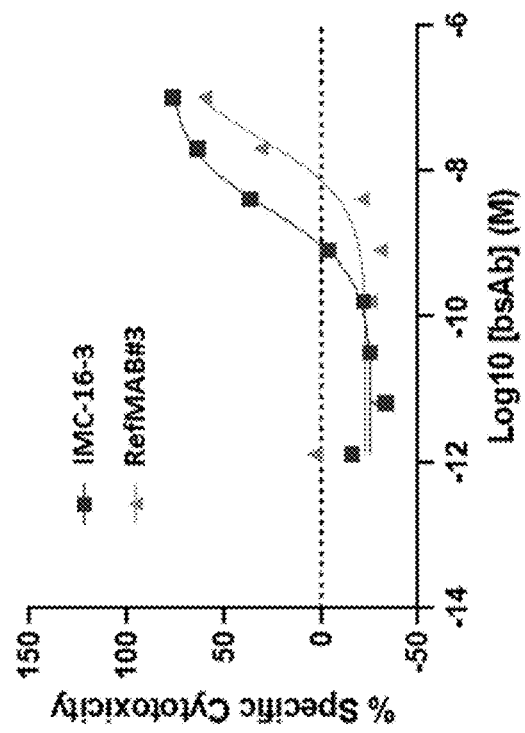
FIG. 42A and FIG. 42B illustrate the results of a comparative T-cell dependent cytotoxicity assay comparing IMC-16-3 and RefMAB #3.
Figure 42B:
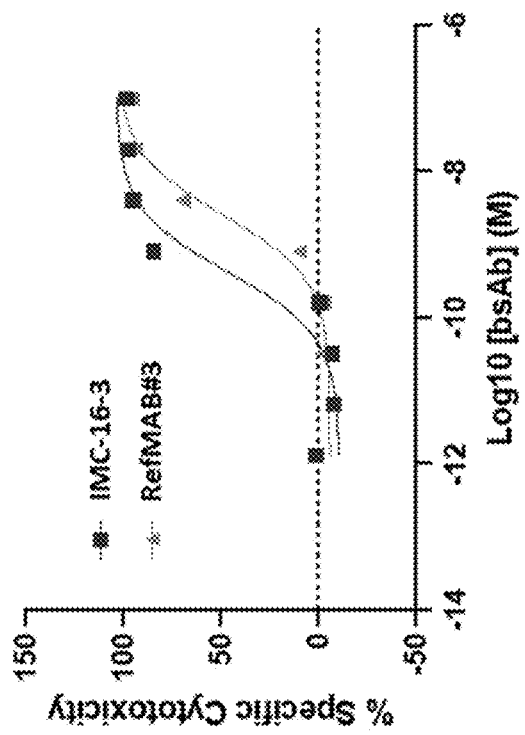
Figure 43B:
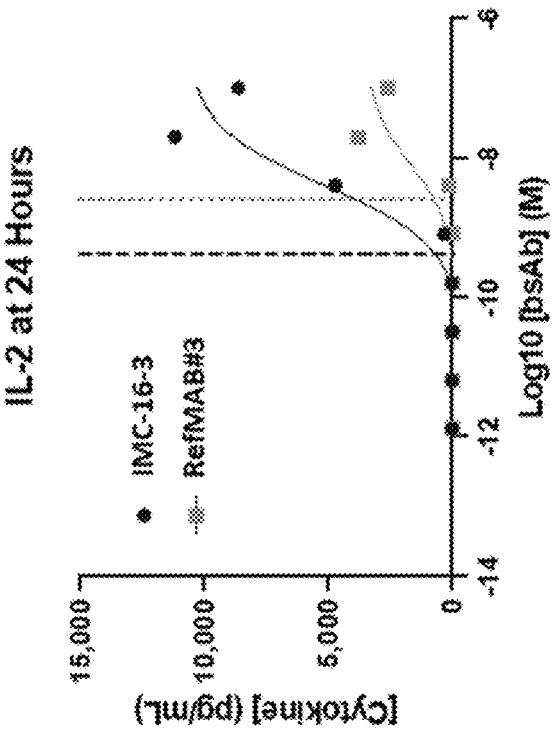
FIG. 43A, FIG. 43B, FIG. 43C, and FIG. 43D illustrate the results of a comparative PBMC cytokine production assay comparing IMC-16-3 and RefMAB #3.
Figure 43A:
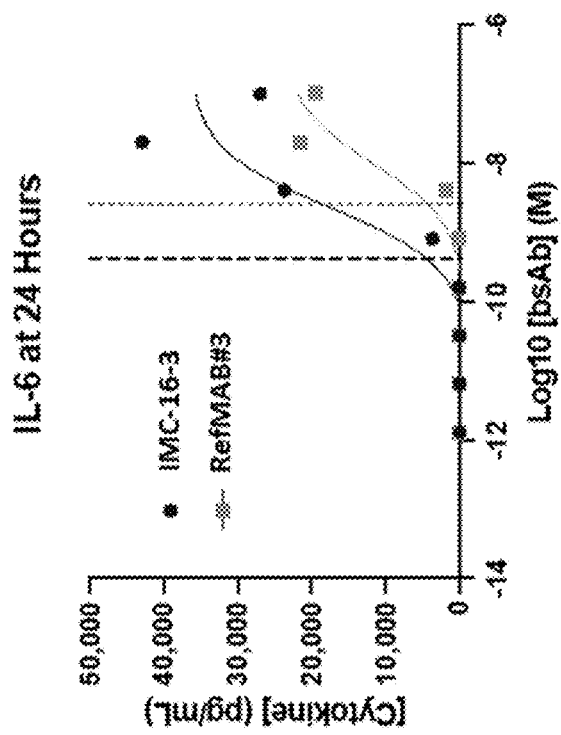
Figure 43C:
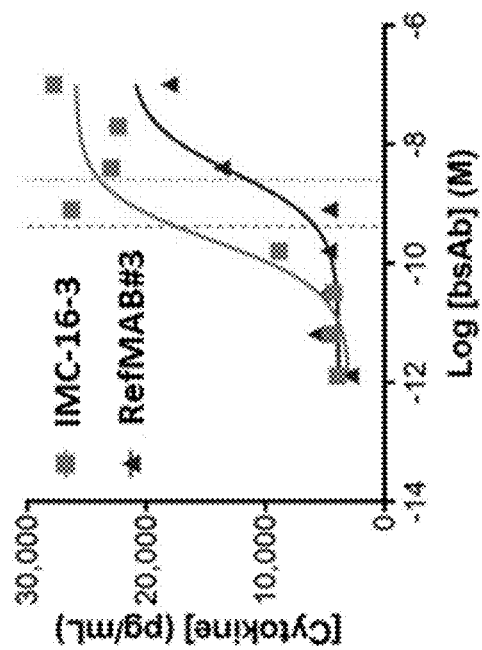
Figure 43D:
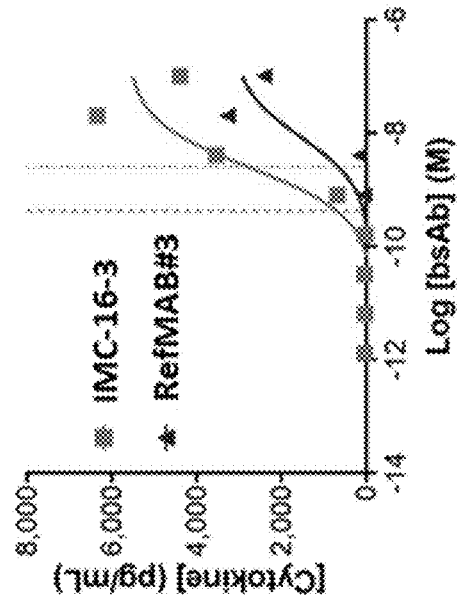

The experiments in FIGS. 42A and 42B demonstrate the comparative assessment of IMC-16-3 vs RefMAB #3 in a cytotoxicity assay in OV-90 ovarian cancer cells. Two separate human PBMC effector to target ratios (Effector:Target) were assessed in this experiment. As shown, at both ratios (12.1:1 and 2.5:1). IMC-16-3 is approximately 10× more potent than RefMAB #3. Similarly, the experiments in FIGS. 43A and 43B illustrate the comparative assessment of cytokines induced by IMC-16-3 vs RefMAB #3 in a cytokine activation assay in human PBMC co-cultured with K562 cells which stably overexpress CLDN6. The amount of IL-6 (FIG. 43A). IL-2 (FIG. 43B). TNF-α (FIG. 43C), or IL-8 (FIG. 43D) generated in the culture was assessed. As shown. IMC-16-3 is approximately 10× more potent than RefMAB #3 with respect to cytokine generation.

Figure 44A:
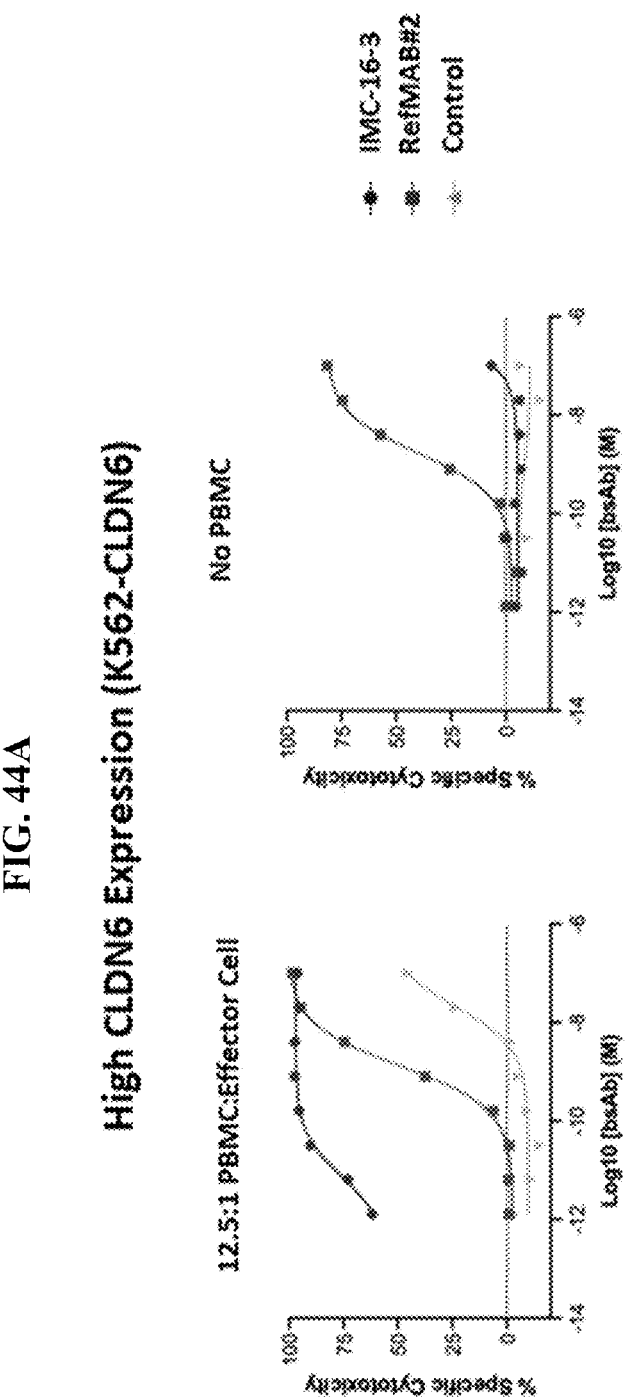
FIG. 44A, FIG. 44B, and FIG. 44C illustrate the results of a comparative K562-CLDN6 killing assay comparing IMC-16-3 and RefMAB #2 in cell lines with varying CLDN6 expression levels and in the presence or absence of human PBMCs.
Figure 44B:
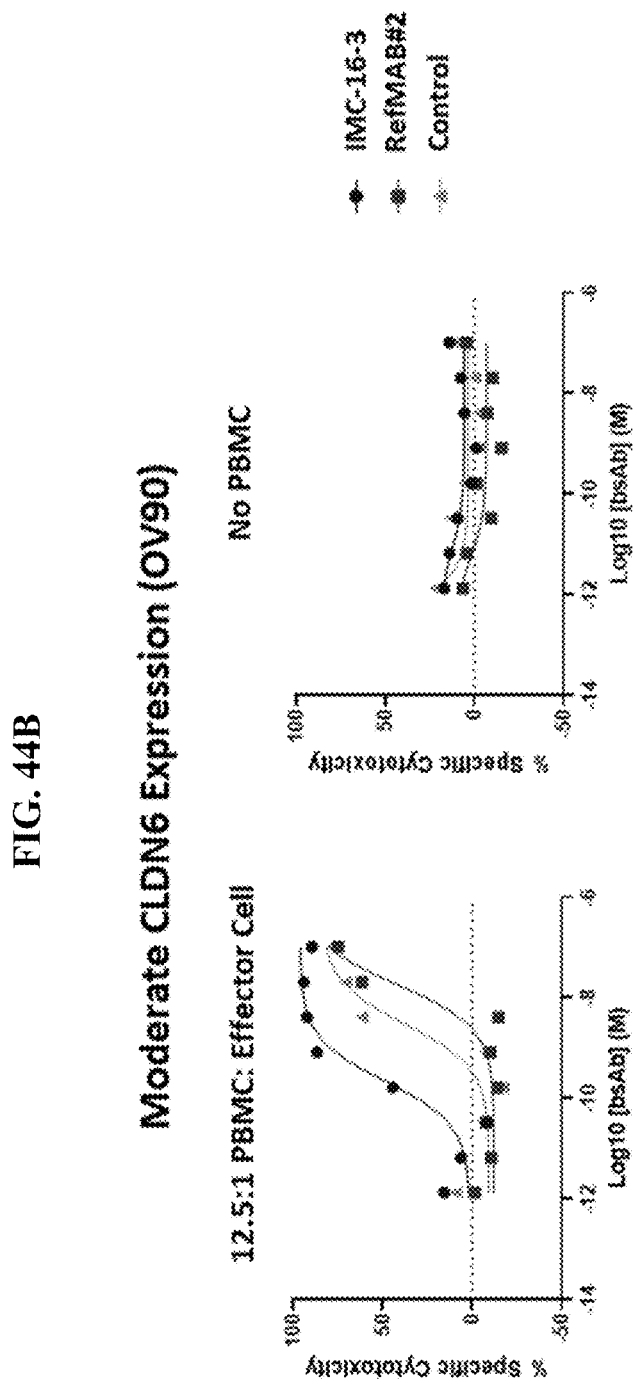
Figure 44C:
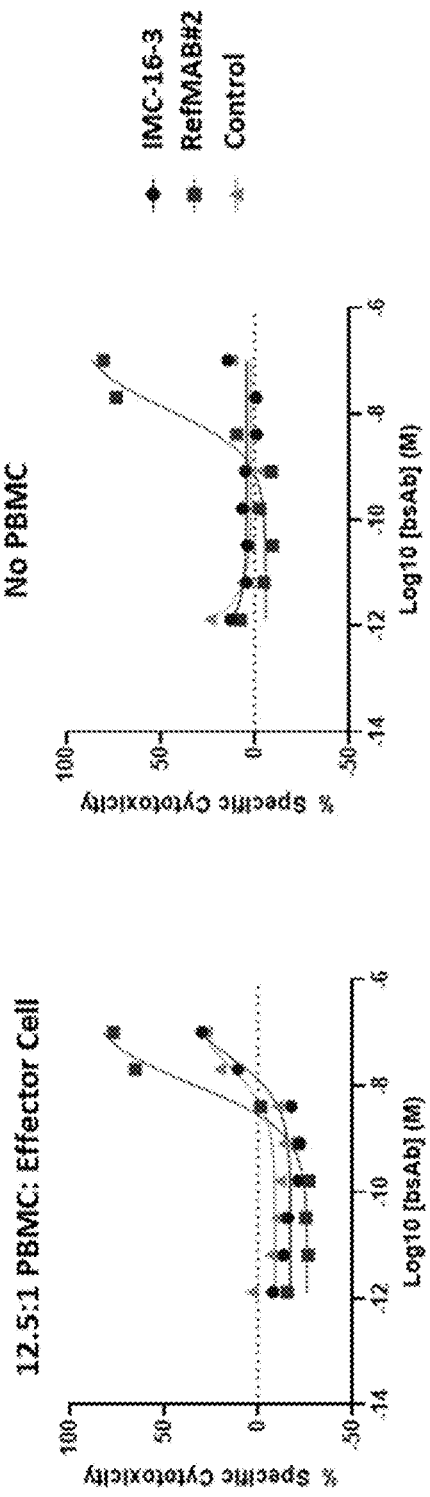

The experiments in FIGS. 44A, 44B, and 44C demonstrate the comparative assessment of the killing of target cells induced by IMC-16-3 vs RefMAB #2 in a cytotoxicity assay at three separate CLDN6 expression levels with or without human PBMC. The data in FIG. 44A compare activity in cultures of K562 cells, which express high levels of CLDN6, with or without human PBMC. The data in FIG. 44B compare activity in OV-90 cells, which express moderate levels of CLDN6, with or without human PBMC. The data in FIG. 44C compare activity in HEK293T cells which do not have native CLDN6 expression, with or without human PBMC. As shown in FIG. 44A, in the presence of PBMC, IMC-16-3 is vastly more potent compared to RefMAB #2. RefMAB #2 demonstrated significant cell killing in the absence of immune cells, which may indicate internalization of the antibody-drug complex by the K562 cells which express high levels of CLDN6. As shown in FIG. 44B, IMC-16-3 maintains its potency advantage over RefMAB #2 in cells that only moderately express CLDN6. In this case, in the absence of PBMC, the RefMAB #2 did not offer any increased cell killing compared to control. This indicates that moderate or low expression of CLDN6 is insufficient to mediate uptake of the RefMAB #2 antibody-drug complex and that in these conditions the activity of RefMAB #2 is dependent on the presence of PBMCs. As shown in FIG. 44C, IMC-16-3 did not mediate any killing of HEK293T cells compared to control, which highlights IMC-16-3's specificity for CLDN6 and a lack of off target killing. In contrast, RefMAB #2 demonstrated similar cell killing even in the absence of immune cells, probably due to nonspecific MMAE-related toxicity. Together, the data of the experiments in FIG. 44 demonstrate the superior potency and specificity of IMC-16-3 as compared to RefMAB #2.

Thus, the experiments of this example clearly show, without limitation, that the antibodies disclosed herein have high levels of T cell mediated killing specific in both endogenous and exogenous models of CLDN6 expression (OV-90 cells, OVCAR-3, and CLDN6-K562 cells, respectively), and that the concentration of the antibody needed for maximal cytotoxicity was generally below the threshold for robust cytokine release.

The experiments of this example also show the surprisingly wide therapeutic window for the IMC-16-3 scFv-Fab IgG antibody, and how the IMC-16-3 scFv-Fab IgG antibody has a highly selective CLDN6-binding Fab arm, a silenced Fc receptor, and how the monovalent CD3 binding avoids aberrant T-cell activation. The experiments further show: (1) a low cytokine release profile for the IMC-16-3 scFv-Fab IgG antibody, and (2) fully humanized CLDN6 and CD3 binding domains, thereby demonstrating a low immunogenicity risk. The experiments described herein support excellent developability and productivity, as well as an ease in manufacturing of the antibodies described herein.

Example 4: Preliminary Efficacy, Pharmacokinetics and Safety

Figure 36:
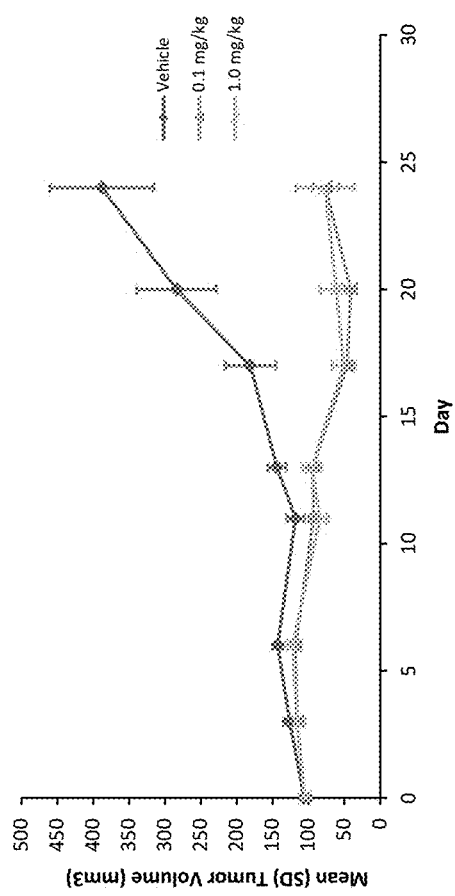
FIG. 36 illustrates the results of an OV-90 xenograft preclinical animal study with treatment with physiologically relevant doses of IMC-16-3.

The efficacy of IMC-16-3 was measured in NSG-β2m-/- (NOD SCID IL-2-receptor gamma knockout, beta-2 microglobulin knockout immunodeficient) mice engrafted with human PBMCs and bearing advanced subcutaneous OV-90 tumor xenografts (~200,000 CLDN6 copies per cell) treated twice per week with vehicle or IMC-16-3. The mean (SD) tumor volume (mm3) was measured at regular intervals over 24 days (d) (0d, 3d, 6d, 11d, 13d, 17d, 20d, and 24d) after treatment with either 0.1 mg/kg or 1.0 mg/kg IMC-16-3. As shown in FIG. 36, IMC-16-3 effectively engaged the systemically administered human PBMC cells to promote significant tumor regression and complete responses in OV-90 ovarian xenograft models in the mice.

Figure 39A:
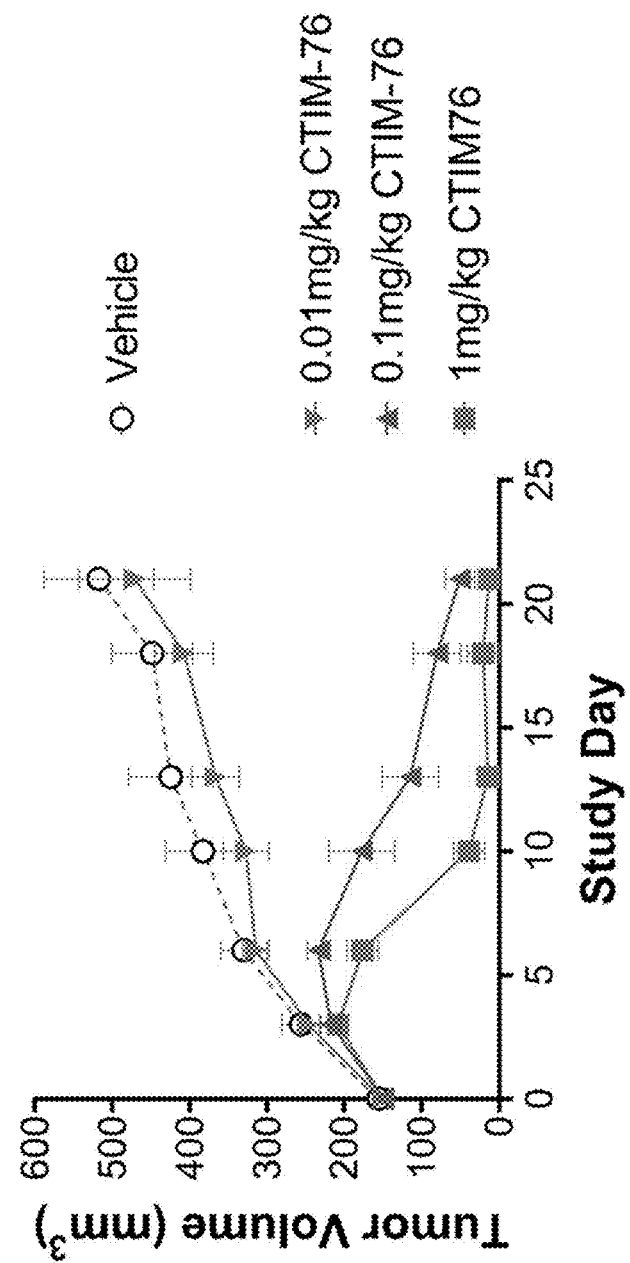
FIG. 39A illustrates the results of a OVCAR3 Xenograft tumor study in mice treated with various concentrations of IMC-16-3.
Figure 39B:
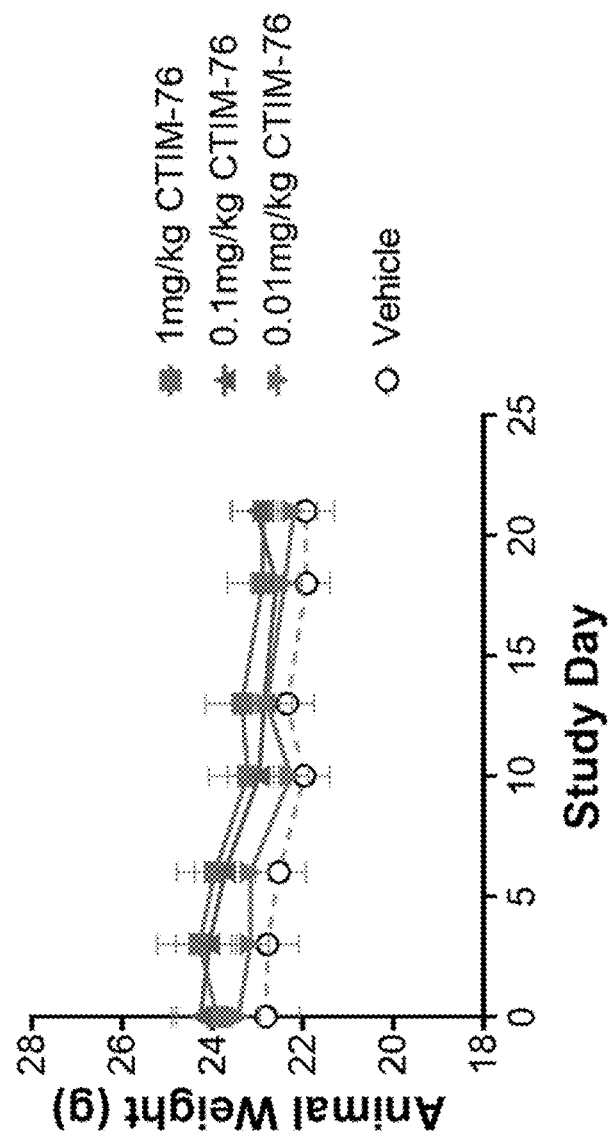
FIG. 39B illustrates the weights of the mice throughout the duration of the study of FIG. 39A.

As a follow up to the xenograft mouse model experiment detailed above, a second mouse study was conducted in a similar manner. In the follow up experiment, mice were subcutaneously injected with OVCAR3 tumor xenografts (150,000 CLDN6 copies per cell) and treated twice a week with vehicle, 0.01 mg/kg IMC-16-3, 0.1 mg/kg IMC-16-3, or 1.0 mg/kg IMC-16-3. As shown in FIG. 39A, mice receiving 0.1 mg/kg IMC-16-3 or 1.0 mg/kg IMC-16-3 exhibited significant tumor regression over the course of the study. As shown in FIG. 39B, the treatments were well tolerated with little to no change in animal weight between groups, as compared to the control group.

Figure 45:
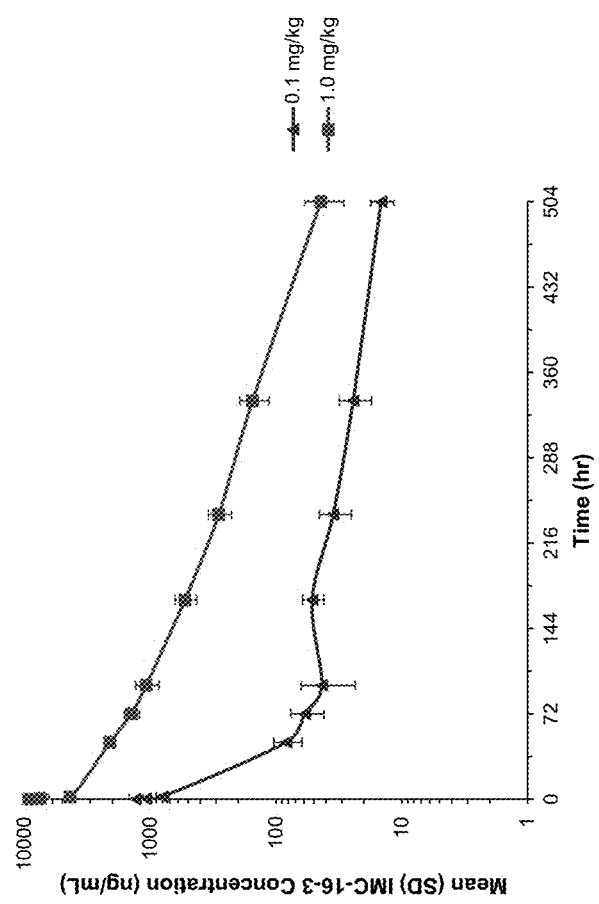
FIG. 45 illustrates pharmacokinetic results of IMC-16-3 in non-human primates dosed with 0.1 mg/kg or 1 mg/kg IMC-16-3.

The pharmacokinetics and Safety of IMC-16-3 was also tested in in non-human primates (NHP). The mean (SD) IMC-16-3 concentration (ng/mL) was measured at increasing hourly time points (0.083, 0.5, 2, 8, 24, 48, 72, 96, 168, 240, 336, and 504) after a single intravenous bolus dose of either 0.1 mg/kg or 1.0 mg/kg to male cynomolgus monkeys. As shown in FIG. 45, the subjects exhibited linear pharmacokinetics and an extended serum half-life, and the IMC-16-3 was well-tolerated at doses deemed physiologically relevant. There were no major CRS-associated clinical symptoms or toxicity observed in any of the test subjects at any time point.

Figure 40:
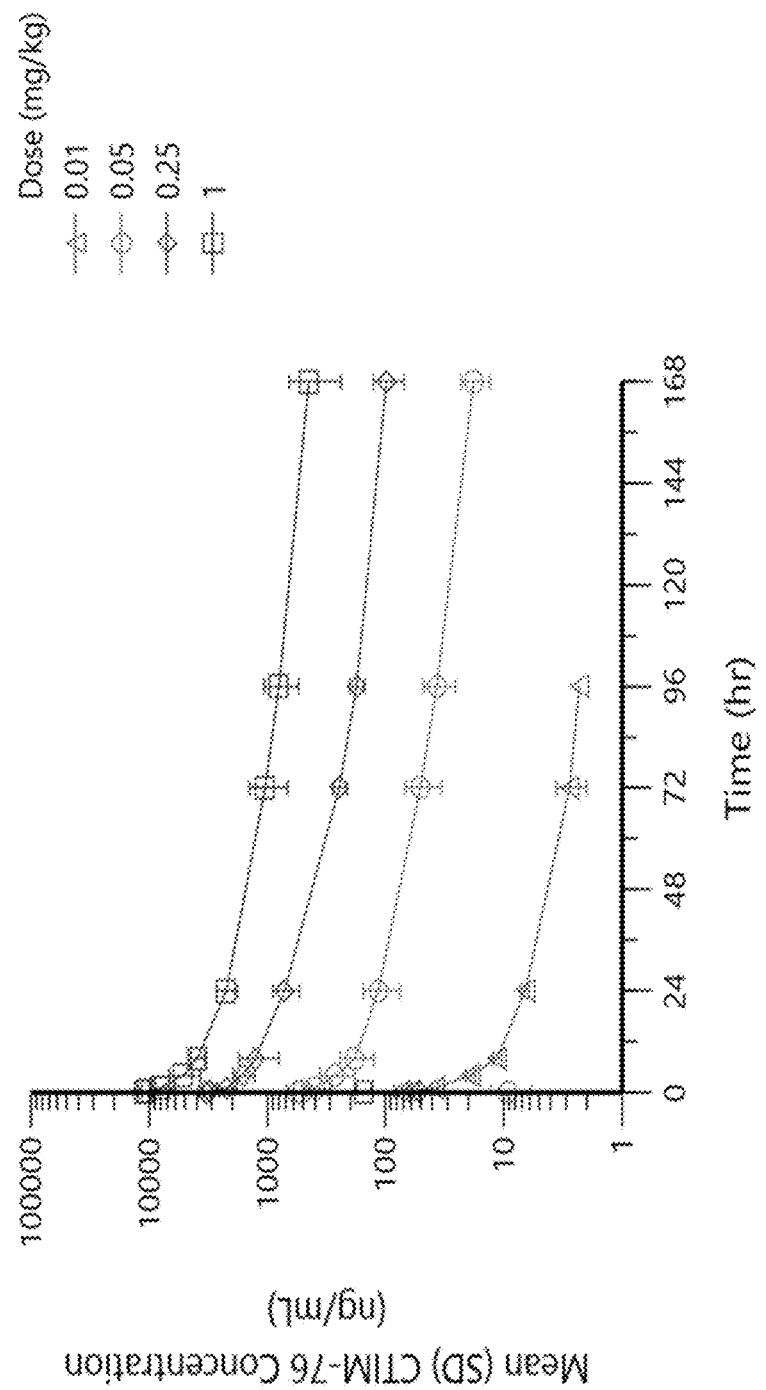
FIG. 40 illustrates the plasma levels of IMC-16-3 in the plasma of non-human primates dosed with various concentrations of the antibody.

As a follow up to the initial NHP study, a second cohort was tested in a similar manner. In the second cohort, NHPs were dosed with 0.01 mg/kg, 0.05 mg/kg, 0.25 mg/kg, or 1 mg/kg IMC-16-3. As shown in FIG. 40, IMC-16-3 exhibited linear pharmacokinetics and a half-life of about 2 weeks. The doses were well tolerated. Hepatobiliary effects were generally mild and self-resolved. There were no major CRS-associated clinical symptoms or toxicity observed in any of the test subjects at any time point.

Thus, the experiments of this example clearly show, without limitation, that the antibodies disclosed herein are effective in killing tumor cells and do not cause significant side effects, such as CRS or other toxicity.

All of the features disclosed herein may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A bispecific antibody that binds to claudin 6 (CLDN6) and CD3, the bispecific antibody comprising:

a first polypeptide comprising a first light chain comprising a first variable light chain region, wherein the first variable light chain region comprises:

(1) a CDR1 sequence comprising the amino acid sequence of SEQ ID NO: 1;

(2) a CDR2 sequence comprising the amino acid sequence of SEQ ID NO: 2; and (3) a CDR3 sequence comprising the amino acid sequence of SEQ ID NO: 3;

a second polypeptide comprising a first heavy chain comprising a first variable heavy chain region, wherein the first variable heavy chain region comprises:

(1) a CDR1 comprising the amino acid sequence of SEQ ID NO: 4;

(2) a CDR2 comprising the amino acid sequence of SEQ ID NO: 5, and (3) a CDR3 comprising the amino acid sequence of SEQ ID NO: 6; and a third polypeptide comprising the amino acid sequence of SEQ ID NO: 89.

2. The bispecific antibody of claim 1, wherein the first variable light chain region comprises an amino acid sequence that is at least 95% identical to the amino acid sequence of SEQ ID NO: 68.

3. The bispecific antibody of claim 1, wherein the first variable light chain region comprises the amino acid sequence of SEQ ID NO: 68.

4. The bispecific antibody of claim 1, wherein the first variable heavy chain region comprises an amino acid sequence that is at least 95% identical to the amino acid sequence of SEQ ID NO: 69.

5. The bispecific antibody of claim 4, wherein the first variable heavy chain region comprises the amino acid sequence of SEQ ID NO: 69.

6. The bispecific antibody of claim 1, wherein the second polypeptide further comprises a constant domain.

7. The bispecific antibody of claim 6, wherein the constant domain interacts with a constant domain of the third polypeptide to form a heterodimer.

8. The bispecific antibody of claim 7, wherein the constant domain comprises a human IgG Fc domain comprising a T366W mutation wherein the numbering is according to the EU numbering in human IgG1.

9. The bispecific antibody of claim 8, wherein the constant domain comprises L234A and L235A (LALA) substitutions, wherein the numbering is according to the EU numbering in human IgG1.

10. A bispecific antibody that binds to claudin 6 (CLDN6) and CD3, the bispecific antibody comprising:
a first polypeptide comprising a first light chain comprising a first variable light chain region, wherein the first variable light chain region comprises:
  (1) a CDR1 sequence comprising the amino acid sequence of SEQ ID NO: 1;
  (2) a CDR2 sequence comprising the amino acid sequence of SEQ ID NO: 2; and
  (3) a CDR3 sequence comprising the amino acid sequence of SEQ ID NO: 3;
a second polypeptide comprising a first heavy chain comprising a first variable heavy chain region and a constant domain, wherein the first variable heavy chain region comprises:
  (1) a CDR1 comprising the amino acid sequence of SEQ ID NO: 4;
  (2) a CDR2 comprising the amino acid sequence of SEQ ID NO: 5, and
  (3) a CDR3 comprising the amino acid sequence of SEQ ID NO: 6; and
a third polypeptide comprising a second light chain and a second heavy chain and a constant domain, wherein:
the second heavy chain comprises a second variable heavy chain region comprising:
  (1) a CDR1 comprising the amino acid sequence of SEQ ID NO: 25;
  (2) a CDR2 comprising the amino acid sequence of SEQ ID NO: 26; and
  (3) a CDR3 comprising the amino acid sequence of SEQ ID NO: 27; and
the second light chain comprises a second variable light chain region comprising:
  (1) a CDR1 comprising the amino sequence of SEQ ID NO: 28;
  (2) a CDR2 comprising the amino acid sequence of SEQ ID NO: 29; and
  (3) a CDR3 comprising the amino acid sequence of SEQ ID NO: 30, or a variant thereof,
wherein:
the first polypeptide comprises an amino acid sequence that is at least 95% identical to the amino acid sequence of SEQ ID NO: 67;
the second polypeptide comprises an amino acid sequence that is at least 95% identical to the amino acid sequence of SEQ ID NO: 79; and
the third polypeptide comprises an amino acid sequence that is at least 95% identical to the amino acid sequence of SEQ ID NO: 89.

11. A bispecific antibody comprising:
a first polypeptide comprising the amino acid sequence of SEQ ID NO: 67;
a second polypeptide comprising the amino acid sequence of SEQ ID NO: 79; and
a third polypeptide comprising the amino acid sequence of SEQ ID NO: 89.

12. A pharmaceutical composition comprising the bispecific antibody of claim 1 and a pharmaceutically acceptable excipient.

13. A pharmaceutical composition comprising the bispecific antibody of claim 10 and a pharmaceutically acceptable excipient.

14. A pharmaceutical composition comprising the bispecific antibody of claim 11 and a pharmaceutically acceptable excipient.

15. The bispecific antibody of claim 10, wherein:
i. the constant domain of the second polypeptide comprises a T366W mutation and the constant domain of the third polypeptide comprises T366S, L368A and Y407V mutations;
ii. the constant domain of the second polypeptide comprises a T366Y and Y407T mutations or T366Y and F405A mutations and the constant domain of the third polypeptide comprises T394W and Y407T mutations;
iii. the constant domain of the second polypeptide comprises T366W and D399C mutations and the constant domain of the third polypeptide comprises T366S, L368A, K392C, and Y407V mutations;
iv. the constant domain of the second polypeptide comprises T366W and K392C mutations and the constant domain of the third polypeptide comprises T366S, L368A, D399C and Y407V mutations;
v. the constant domain of the second polypeptide comprises S354C and T366W mutations and the constant domain of the third polypeptide comprises Y349C, T366S, L368A and Y407V mutations;
vi. the constant domain of the second polypeptide comprises Y349C and T366W mutations and the constant domain of the third polypeptide comprises S354C, T366S, L368A and Y407V mutations;
vii. the constant domain of the second polypeptide comprises E356C and T366W mutations and the constant domain of the third polypeptide comprises Y349C, T366S, L368A and Y407V mutations;
viii. the constant domain of the second polypeptide comprises Y349C and T366W mutations and the constant domain of the third polypeptide comprises E356C, T366S, L368A and Y407V mutations;
ix. the constant domain of the second polypeptide comprises E357C and T366W mutations and the constant domain of the third polypeptide comprises Y349C, T366S, L368A and Y407V mutations; or
x. the constant domain of the second polypeptide comprises Y349C and T366W mutations and the constant domain of the third polypeptide comprises E357C, T366S, L368A and Y407V mutations, and
wherein the numbering is according to the EU numbering in human IgG1.

16. The bispecific antibody of claim 15, wherein the constant domain of the second polypeptide further comprises L234A and L235A (LALA) mutations, wherein the numbering is according to the EU numbering in human IgG1.

17. The bispecific antibody of claim 15, wherein the constant domain of the third polypeptide further comprises L234A and L235A (LALA) mutations, wherein the numbering is according to the EU numbering in human IgG1.

18. The bispecific antibody of claim 15, wherein the constant domain of the second polypeptide further comprises L234A and L235A (LALA) mutations and the constant domain of the third polypeptide further comprises L234A and L235A (LALA) mutations, wherein the numbering is according to the EU numbering in human IgG1.

19. A pharmaceutical composition comprising the bispecific antibody of claim 2 and a pharmaceutically acceptable excipient.

20. A pharmaceutical composition comprising the bispecific antibody of claim 3 and a pharmaceutically acceptable excipient.

21. A pharmaceutical composition comprising the bispecific antibody of claim 4 and a pharmaceutically acceptable excipient.

22. A pharmaceutical composition comprising the bispecific antibody of claim 5 and a pharmaceutically acceptable excipient.

23. A pharmaceutical composition comprising the bispecific antibody of claim 6 and a pharmaceutically acceptable excipient.

24. A pharmaceutical composition comprising the bispecific antibody of claim 7 and a pharmaceutically acceptable excipient.

25. A pharmaceutical composition comprising the bispecific antibody of claim 8 and a pharmaceutically acceptable excipient.

26. A pharmaceutical composition comprising the bispecific antibody of claim 9 and a pharmaceutically acceptable excipient.

27. A pharmaceutical composition comprising the bispecific antibody of claim 15 and a pharmaceutically acceptable excipient.

28. A pharmaceutical composition comprising the bispecific antibody of claim 16 and a pharmaceutically acceptable excipient.

29. A pharmaceutical composition comprising the bispecific antibody of claim 17 and a pharmaceutically acceptable excipient.

30. A pharmaceutical composition comprising the bispecific antibody of claim 18 and a pharmaceutically acceptable excipient.

* * * * *